(12) United States Patent
Li et al.

(10) Patent No.: US 10,611,780 B2
(45) Date of Patent: Apr. 7, 2020

(54) BORON-CONTAINING SMALL MOLECULES

(71) Applicants: ANACOR PHARMACEUTICALS, INC., Palo Alto, CA (US); BILL AND MELINDA GATES FOUNDATION, Seattle, WA (US); Yong-kang Zhang, San Jose, CA (US); Matthew Perry, San Jose, CA (US); Xianfeng Li, Cupertino, CA (US); Christopher S. Lunde, Belmont, CA (US); Robert T. Jacobs, Wake Forrest, NC (US); Vincent S. Hernandez, Watsonville, CA (US); Yi Xia, Palo Alto, CA (US); Jacob J. Plattner, Berkeley, CA (US); Kathy Jingyuan Cao, Sunnyvalle, CA (US)

(72) Inventors: Xianfeng Li, Cupertino, CA (US); Christopher S. Lunde, Belmont, CA (US); Robert T. Jacobs, Wake Forest, NC (US); Vincent S. Hernandez, Watsonville, CA (US); Yi Xia, Palo Alto, CA (US); Jacob J. Plattner, Berkeley, CA (US); Kathy Jingyuan Cao, Sunnyvale, CA (US); Yong-Kang Zhang, San Jose, CA (US); Matthew Perry, San Jose, CA (US)

(73) Assignee: Bill and Melinda Gates Foundation, Seattle, WA (US)

(*) Notice: Subject to any disclaimer, the term of this patent is extended or adjusted under 35 U.S.C. 154(b) by 0 days.

(21) Appl. No.: 16/081,902

(22) PCT Filed: Feb. 27, 2017

(86) PCT No.: PCT/US2017/019650
§ 371 (c)(1),
(2) Date: Sep. 1, 2018

(87) PCT Pub. No.: WO2017/151489
PCT Pub. Date: Sep. 8, 2017

(65) Prior Publication Data
US 2019/0077814 A1  Mar. 14, 2019

Related U.S. Application Data

(60) Provisional application No. 62/302,564, filed on Mar. 2, 2016.

(51) Int. Cl.
C07F 5/02 (2006.01)
A61K 31/69 (2006.01)
A61K 45/06 (2006.01)
A61P 31/04 (2006.01)

(52) U.S. Cl.
CPC ............. *C07F 5/025* (2013.01); *A61K 31/69* (2013.01); *A61K 45/06* (2013.01); *A61P 31/04* (2018.01); *C07F 5/02* (2013.01); *Y02A 50/422* (2018.01)

(58) Field of Classification Search
CPC .................................. C07F 5/025; C07F 5/02
USPC ............................................................ 514/64
See application file for complete search history.

(56) References Cited

U.S. PATENT DOCUMENTS

| | | | |
|---|---|---|---|
| 5,880,188 A | 3/1999 | Austin et al. | |
| 6,239,175 B1* | 5/2001 | Hinks | C07C 271/32 514/480 |
| 6,248,305 B1 | 6/2001 | Groziak | |
| 2006/0234981 A1 | 10/2006 | Baker et al. | |
| 2007/0155699 A1 | 7/2007 | Baker et al. | |
| 2007/0293457 A1 | 12/2007 | Baker et al. | |
| 2009/0227541 A1 | 9/2009 | Baker et al. | |
| 2011/0212918 A1 | 9/2011 | Hernandez et al. | |
| 2014/0142064 A1 | 5/2014 | Baker et al. | |

FOREIGN PATENT DOCUMENTS

WO  9921855 A1  5/1999

OTHER PUBLICATIONS

Bailey, PJ et al. "Boron-Containing Antibacterial Agents: Effects on Growth and Morphology of Bacteria Under Various Culture Conditions" Antimicrobial Agents and Chemotherapy, 1980; vol. 17, No. 4; pp. 549-553.
Berge, S. et al. "Pharmaceutical Salts" Journal of Pharmaceutical Sciences, Jan. 1977; vol. 66, No. 1; 19 pages.
Clare, R. et al. "Development and Validation of a High-Throughput Anti-Wolbachia Whole-Cell Screen: A Route to Macrofilaricidal Drugs against Onchocerciasis and Lymphatic Filariasi" Journal of Biomolecular Screening, 2015; vol. 20, No. 1; pp. 64-69.
Eccleston, J. et al. "Fluorescence—Based Assays" Progress in Medicinal Chemistry, Jan. 2005; vol. 43; pp. 19-48.
EPO, Extended European Search Report for European Application No. 17760538.3. dated Aug. 20, 2019. 8 pages.
ISA, International Search Report and Written Opinion for International Application No. PCT/US2017/19650. dated Apr. 25, 2017. 13 pages.
Kanichar, D. et al. "Synthesis, Characterization, and Antibacterial Activity of Structurally Complex 2-Acylated 2,3,1-Benzodiazaborines and Related Compounds" Chemistry & Biodiversity, 2014; vol. 11; pp. 1381-1397.
Maehr, H. "A proposed new convention for graphic presentation of molecular geometry and topography" Journal of Chemical Education, 1985; vol. 62, No. 2, pp. 114-120.
Hunt, E. "Pleuromutilin antibiotics" Drugs of the Future, Jan. 2000, vol. 25, No. 11, pp. 1163-1168.

* cited by examiner

*Primary Examiner* — Kahsay Habte
(74) *Attorney, Agent, or Firm* — Perkins Coie LLP

(57) ABSTRACT

Compounds, pharmaceutical formulations, and methods of treating bacterial infections are disclosed.

13 Claims, No Drawings

BORON-CONTAINING SMALL MOLECULES

CROSS-REFERENCE TO RELATED APPLICATIONS

This application is a U.S. National Phase application of PCT/US2017/019650, filed Feb. 27, 2017, which claims the benefit of U.S. Provisional Patent Application No. 62/302,564, filed Mar. 2, 2016, both of which are incorporated by reference in their entirety for all purposes.

BACKGROUND OF THE INVENTION

The present invention relates to organic compounds, such as pleuromutilins. Pleuromutilin, a compound having the following formula:

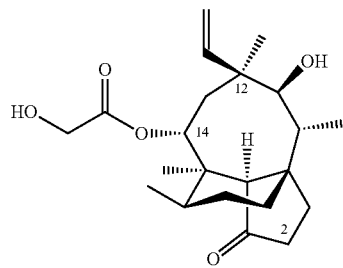

is a naturally occurring antibacterial, e.g. produced by the basidomycetes *Pleurotus mutilus* and *P. passeckerianus*, see e.g. The Merck Index, 13th edition, item 7617. Further modified pleuromutilins are also known.

Surprisingly, it has now been discovered that certain classes of pleuromutilins modified with boron are surprisingly effective antibacterials. This, and other uses of these compounds, are described herein.

SUMMARY OF THE INVENTION

In a first aspect, the invention provides a compound having a structure which is a salt or a hydrate or a solvate thereof, having a structure which is:

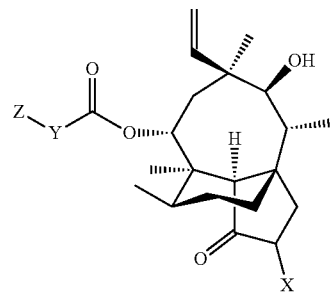

wherein X is H or F or OH; Y is selected from the group consisting of a bond, —O—, —S—, —NH—, substituted or unsubstituted alkylene, and substituted or unsubstituted heteroalkylene; and Z is a substituted or unsubstituted heterocyclic ring or ring system containing at least one endocyclic boron.

In a second aspect, the invention provides a combination comprising a compound of the invention together with at least one other therapeutically active agent.

In a third aspect, the invention provides a pharmaceutical formulation comprising: a) a compound of the invention; and b) a pharmaceutically acceptable excipient.

In a fourth aspect, the invention provides a method of inhibiting protein synthesis in a bacteria, the method comprising contacting the bacteria with a compound of the invention, thereby inhibiting protein synthesis in the bacteria.

In a fifth aspect, the invention provides a method of inhibiting the growth and/or killing a bacteria, the method comprising contacting the bacteria with the compound of the invention, thereby inhibiting the growth and/or killing the bacteria.

In a sixth aspect, the invention provides a method of treating a microbial disease and/or a worm disease in an animal, the method comprising administering to the animal a therapeutically effective amount of a compound of the invention, thereby treating the microbial disease and/or the worm disease.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; MgSO$_4$ is magnesium sulfate; mins or min is minutes; Mp or MP is melting point; NaCNBH$_3$ is sodium cyanoborohydride; NaOH is sodium hydroxide; Na$_2$SO$_4$ is sodium sulfate; NBS is N-bromosuccinimide; NH$_4$Cl is ammonium chloride; NIS is N-iodosuccinimide; N$_2$ is nitrogen; NMM is N-methylmorpholine; n-BuLi is n-butyllithium; overnight is O/N; PdCl$_2$(pddf) is 1,1'-Bis (diphenylphosphino) ferrocene]dichloropalladium(II); Pd/C is the catalyst known as palladium on carbon; Pd$_2$(dba)$_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; POCl$_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—NH$_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein, refers to the compounds discussed herein, salts (e.g. pharmaceutically acceptable salts), prodrugs, solvates and hydrates of these compounds.

"Combination of the invention," as used herein, refers to the compounds and antiinflammatories discussed herein as well as acids, bases, salt forms (such as pharmaceutically acceptable salts), prodrugs, solvates and hydrates of these compounds and antiinflammatories.

"Boron containing compounds", as used herein, refers to the compounds of the invention that contain boron as part of their chemical formula.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR''''-C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R''', R'''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''', R'''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR''''-C(NR' R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', R'''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''', R'''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—

(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted $C_1$ or $C_2$ or $C_3$ or $C_4$ or $C_5$ or $C_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N), sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the animal. Representative carriers include water, oils, both vegetable and mineral, cream bases, lotion bases, ointment bases and the like. These bases include suspending agents, thickeners, penetration enhancers, and the like. Their formulation is well known to those in the pharmaceutical arts. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents, vehicles, and or additives used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a topical formulation, such as a cream or an ointment, for example. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more amenable to the animal, by minimizing the frequency (e.g., once daily) or route of dosing (e.g., oral), or to improve the taste or odor if given orally, or to minimize pain if given parenterally.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase or a phosphodiesterase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include H$^+$, H$_3$O+, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include H+, H$_3$O, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The invention provides novel boron compounds and methods for the preparation of these molecules. The invention further provides methods of treating bacterial infections, killing and/or inhibiting the growth of bacteria in part or wholly through the use of the compounds described herein. In another aspect, the invention is a combination of a compound of the invention and an antibacterial. In another aspect, the invention is a pharmaceutical formulation comprising a pharmaceutically acceptable excipient and a compound of the invention. In another aspect, the invention is a pharmaceutical formulation comprising a compound of the invention, an antibacterial, and a pharmaceutically acceptable excipient.

III. a) Compounds

In one aspect the invention provides a compound of the invention. In an exemplary embodiment, the invention provides a compound described herein, or a salt or a hydrate or a solvate thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

In an exemplary embodiment, the compound has a structure which is

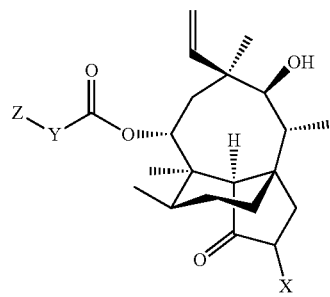

(I)

wherein X is H or F or OH; Y is selected from the group consisting of a bond, —O—, —S—, —NH—, substituted or unsubstituted alkylene, and substituted or unsubstituted heteroalkylene; and Z is a substituted or unsubstituted heterocyclic ring or ring system containing at least one endocyclic boron.

In an exemplary embodiment, the compound is Formula (I), Y and Z are as described herein, and X is H. In an exemplary embodiment, the compound is Formula (I), Y and Z are as described herein, and X is F. In an exemplary embodiment, the compound is Formula (I), Y and Z are as described herein, and X is OH.

In an exemplary embodiment, the compound is Formula (I), X and Z are as described herein, and Y is substituted alkylene. In an exemplary embodiment, the compound is Formula (I), X and Z are as described herein, and Y is unsubstituted alkylene. In an exemplary embodiment, the compound is Formula (I), X and Z are as described herein, and Y is methylene. In an exemplary embodiment, the compound is Formula (I), X and Z are as described herein, and Y is ethylene. In an exemplary embodiment, the compound is Formula (I), X and Z are as described herein, and Y is propylene. In an exemplary embodiment, the compound is Formula (I), X and Z are as described herein, and Y is substituted heteroalkylene. In an exemplary embodiment, the compound is Formula (I), X and Z are as described herein, and Y is unsubstituted heteroalkylene. In an exemplary embodiment, the compound is Formula (I), X and Z are as described herein, and Y is *—OCH$_2$—. In an exemplary embodiment, the compound is Formula (I), X and Z are as described herein, and Y is *—SCH$_2$—. In an exemplary embodiment, the compound is Formula (I), X and Z are as described herein, and Y is *—NHCH$_2$—. In an exemplary embodiment, the compound is Formula (I), X and Z are as described herein, and Y is *—CH$_2$NH—. In an exemplary embodiment, the compound is Formula (I), X and Z are as described herein, and Y is *—C(O)NH—. In an exemplary embodiment, the compound is Formula (I), X and Z are as described herein, and Y is *—CH$_2$NHCH$_2$— or 1-piperazinyl or *—S(O)CH$_2$— or *—S(O)$_2$—. In an exemplary embodiment, the compound is Formula (I), X and Z are as described herein, and Y is 1-piperazinyl. In an exemplary embodiment, the compound is Formula (I), X and Z are as described herein, and Y is *—S(O)CH$_2$—. In an exemplary embodiment, the compound is Formula (I), X and Z are as described herein, and Y is *—S(O)$_2$—. In an exemplary embodiment, the compound is Formula (I), X and Z are as described herein, and Y is *—NHC(O)OCH$_2$—. In this paragraph, * represents the point of attachment to Z.

In an exemplary embodiment, the compound is Formula (I), X and Y are as described herein, and Z is substituted or unsubstituted heteroaryl, wherein said heteroaryl comprises an endocyclic boron. In an exemplary embodiment, the compound is Formula (I), X and Y are as described herein, and Z is substituted or unsubstituted heteroaryl, wherein said heteroaryl has one ring, and said ring comprises an endocyclic boron. In an exemplary embodiment, the compound is Formula (I), X and Y are as described herein, and Z is substituted or unsubstituted heteroaryl, wherein said heteroaryl has two rings, and one of the two rings comprises an endocyclic boron.

In an exemplary embodiment, the compound is Formula (I), X and Y are as described herein, and Z is substituted or unsubstituted heterocycloalkyl, wherein said heterocycloalkyl comprises an endocyclic boron. In an exemplary embodiment, the compound is Formula (I), X and Y are as described herein, and Z is substituted or 5 unsubstituted heterocycloalkyl, wherein said heterocycloalkyl has one ring, and said ring comprises an endocyclic boron. In an exemplary embodiment, the compound is Formula (I), X and Y are as described herein, and Z is substituted or unsubstituted heterocycloalkyl, wherein said heterocycloalkyl has two rings, and one of the two rings comprises an endocyclic boron.

In an exemplary embodiment, the compound is Formula (I), X and Y are as described herein, and Z is substituted or unsubstituted benzoxaborole. In an exemplary embodiment, the compound is Formula (I), X and Y are as described herein, and Z is substituted or unsubstituted pyridinyloxaborole. In an exemplary embodiment, the compound is Formula (I), X and Y are as described herein, and Z is substituted or unsubstituted benzoxaborininol. In an exemplary embodiment, the compound is Formula (I), X and Y are as described herein, and Z is substituted or unsubstituted benzoxazaborininol. In an exemplary embodiment, the compound is Formula (I), X and Y are as described herein, and Z is substituted or unsubstituted benzodiazaborininol. In an exemplary embodiment, the compound is Formula (I), X and Y are as described herein, and Z is substituted or unsubstituted oxaborole. In an exemplary embodiment, the compound is Formula (I), X and Y are as described herein, and Z is substituted or unsubstituted dihydrobenzoazaborinine.

In an exemplary embodiment, the compound is Formula (I), X and Y are as described herein, and said Z is

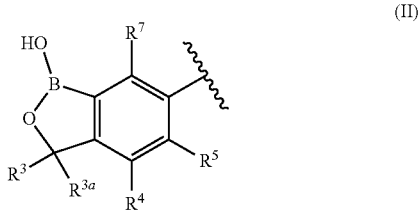

(II)

wherein $R^3$, $R^{3a}$, $R^4$, $R^5$, and $R^1$ are each independently selected from the group consisting of $R^{10}$, $-OR^{10}$, $-NR^{10}R^{11}$, $-SR^{10}$, $-S(O)R^{10}$, $-S(O)_2R^{10}$, $-S(O)_2NR^{10}R^{11}$, $-C(O)R^{10}$, $-C(O)OR^{10}$, and $-C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), X and Y are as described herein, and said Z is

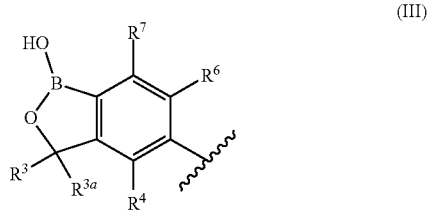

(III)

wherein $R^3$, $R^{3a}$, $R^4$, $R^6$, and $R^7$ are each independently selected from the group consisting of $R^{10}$, $-OR^{10}$, $-NR^{10}R^{11}$, $-SR^{10}$, $-S(O)R^{10}$, $-S(O)_2R^{10}$, $-S(O)_2NR^{10}R^{11}$, $-C(O)R^{10}$, $-C(O)OR^{10}$, and $-C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), $R^4$, $R^5$, $R^6$, $R^7$, X and Y are as described herein, Z is Formula (II) or (III), and $R^3$ is H and $R^{3a}$ is H. In an exemplary embodiment, the compound is Formula (I), $R^4$, $R^5$, $R^6$, $R^7$, X and Y are as described herein, Z is Formula (II) or (III), and $R^3$ is unsubstituted $C_1$-$C_3$ alkyl and $R^{3a}$ is unsubstituted $C_1$-$C_3$ alkyl. In an exemplary embodiment, the compound is Formula (I), $R^4$, $R^5$, $R^6$, $R^7$, X and Y are as described herein, Z is Formula (II) or (III), and $R^3$ is unsubstituted $C_1$-$C_3$ alkyl and $R^{3a}$ is H. In an exemplary embodiment, the compound is Formula (I), $R^4$, $R^5$, $R^6$, $R^7$, X and Y are as described herein, Z is Formula (II) or (III), and $R^3$ is methyl and $R^{3a}$ is methyl. In an exemplary embodiment, the compound is Formula (I), $R^4$, $R^5$, $R^6$, $R^7$, X and Y are as described herein, Z is Formula (II) or (III), and $R^3$ is methyl and $R^{3a}$ is H. In an exemplary embodiment, the compound is Formula (I), $R^4$, $R^5$, $R^6$, $R^7$, X and Y are as described herein, Z is Formula (II) or (III), and $R^3$ is $C_1$-$C_3$ alkyl substituted with substituted or unsubstituted amino and $R^{3a}$ is H. In an exemplary embodiment, the compound is Formula (I), $R^4$, $R^5$, $R^6$, $R^7$, X and Y are as described herein, Z is Formula (II) or (III), and $R^3$ is $-CH_2NH_2$ and $R^{3a}$ is H.

In an exemplary embodiment, the compound is Formula (I), $R^3$, $R^{3a}$, X and Y are as described herein, Z is Formula (II), $R^4$ is H or halogen, $R^5$ is H or halogen, and $R^7$ is H or halogen. In an exemplary embodiment, the compound is Formula (I), $R^3$, $R^{3a}$, X and Y are as described herein, Z is Formula (II), $R^4$ is halogen, $R^5$ is H, and $R^7$ is H. In an exemplary embodiment, the compound is Formula (I), $R^3$, $R^{3a}$, X and Y are as described herein, Z is Formula (II), $R^4$ is Cl, $R^5$ is H, and $R^7$ is H. In an exemplary embodiment, the compound is Formula (I), $R^3$, $R^{3a}$, X and Y are as described herein, Z is Formula (II), $R^4$ is F, $R^5$ is H, and $R^7$ is H. In an exemplary embodiment, the compound is Formula (I), $R^3$, $R^{3a}$, X and Y are as described herein, Z is Formula (II), $R^4$ is H, $R^5$ is halogen, and $R^7$ is H. In an exemplary embodiment, the compound is Formula (I), $R^3$, $R^{3a}$, X and Y are as described herein, Z is Formula (II), $R^4$ is H, $R^5$ is Cl, and $R^7$ is H. In an exemplary embodiment, the compound is Formula (I), $R^3$, $R^{3a}$, X and Y are as described herein, Z is Formula (II), $R^4$ is H, $R^5$ is F, and $R^7$ is H. In an exemplary embodiment, the compound is Formula (I), $R^3$, $R^{3a}$, X and Y are as described herein, Z is Formula (II), $R^4$ is H, $R^5$ is H, and $R^7$ is halogen. In an exemplary embodiment, the compound is Formula (I), $R^3$, $R^{3a}$, X and Y are as described herein, Z is Formula (II), $R^4$ is H, $R^5$ is H, and $R^7$ is Cl. In an exemplary embodiment, the compound is Formula (I), $R^3$, $R^{3a}$, X and Y are as described herein, Z is Formula (II), $R^4$ is H, $R^5$ is H, and $R^7$ is F. In an exemplary embodiment, the compound is Formula (I), $R^3$, $R^{3a}$, X and Y are as described herein, Z is Formula (II), $R^4$ is H, $R^5$ is halogen, and $R^7$ is halogen. In an exemplary embodiment, the compound is Formula (I), $R^3$, $R^{3a}$, X and Y are as described herein, Z is Formula (II), $R^4$ is H, $R^5$ is Cl, and $R^7$ is Cl. In an exemplary embodiment, the compound is Formula (I), $R^3$, $R^{3a}$, X and Y are as described herein, Z is Formula (II), $R^4$ is H, $R^5$ is F, and $R^7$ is F.

In an exemplary embodiment, the compound is Formula (I), $R^3$, $R^{3a}$, X and Y are as described herein, Z is Formula (III), $R^4$ is H or halogen, $R^6$ is H or halogen, and $R^7$ is H or halogen. In an exemplary embodiment, the compound is Formula (I), $R^3$, $R^{3a}$, X and Y are as described herein, Z is Formula (III), $R^4$ is halogen, $R^6$ is H, and $R^7$ is H. In an exemplary embodiment, the compound is Formula (I), $R^3$, $R^{3a}$, X and Y are as described herein, Z is Formula (III), $R^4$ is Cl, $R^6$ is H, and $R^7$ is H. In an exemplary embodiment, the compound is Formula (I), $R^3$, $R^{3a}$, X and Y are as described herein, Z is Formula (III), $R^4$ is F, $R^6$ is H, and $R^7$ is H. In an exemplary embodiment, the compound is Formula (I), $R^3$, $R^{3a}$, X and Y are as described herein, Z is Formula (III), $R^4$ is H, $R^6$ is halogen, and $R^7$ is H. In an exemplary embodiment, the compound is Formula (I), $R^3$, $R^{3a}$, X and Y are as described herein, Z is Formula (III), $R^4$ is H, $R^6$ is Cl, and $R^7$ is H. In an exemplary embodiment, the compound is Formula (I), $R^3$, $R^{3a}$, X and Y are as described herein, Z is Formula (III), $R^4$ is H, $R^6$ is F, and $R^7$ is H. In an exemplary embodiment, the compound is Formula (I), $R^3$, $R^{3a}$, X and Y are as described herein, Z is Formula (III), $R^4$ is H, $R^6$ is H, and $R^7$ is halogen. In an exemplary embodiment, the compound is Formula (I), $R^3$, $R^{3a}$, X and Y are as described herein, Z is Formula (III), $R^4$ is H, $R^6$ is H, and $R^7$ is Cl. In an exemplary embodiment, the compound is Formula (I), $R^3$, $R^{3a}$, X and Y are as described herein, Z is Formula (III), $R^4$ is H, $R^6$ is H, and $R^7$ is F. In an exemplary embodiment, the compound is Formula (I), $R^3$, $R^{3a}$, X and Y are as described herein, Z is Formula (III), $R^4$ is H, $R^6$ is halogen, and $R^7$ is halogen. In an exemplary embodiment, the compound is Formula (I), $R^3$, $R^{3a}$, X and Y are as described herein, Z is Formula (III), $R^4$ is H, $R^6$ is Cl, and $R^7$ is Cl. In an exemplary embodiment, the compound is Formula (I), $R^3$, $R^{3a}$, X and Y are as described herein, Z is Formula (III), $R^4$ is H, $R^6$ is F, and $R^7$ is F.

In an exemplary embodiment, the compound is Formula (I), $R^3$, $R^{3a}$, X and Y are as described herein, Z is Formula (II), $R^4$ is H or cyano, $R^5$ is H or cyano, and $R^7$ is H or cyano. In an exemplary embodiment, the compound is Formula (I), $R^3$, $R^{3a}$, X and Y are as described herein, Z is Formula (II), $R^4$ is cyano, $R^5$ is H, and $R^7$ is H. In an exemplary embodiment, the compound is Formula (I), $R^3$, $R^{3a}$, X and Y are as described herein, Z is Formula (II), $R^4$ is H, $R^5$ is cyano, and $R^7$ is H. In an exemplary embodiment, the compound is Formula (I), $R^3$, $R^{3a}$, X and Y are as described herein, Z is Formula (II), $R^4$ is H, $R^5$ is H, and $R^7$ is cyano.

In an exemplary embodiment, the compound is Formula (I), $R^3$, $R^{3a}$, X and Y are as described herein, Z is Formula (III), $R^4$ is H or cyano, $R^6$ is H or cyano, and $R^7$ is H or cyano. In an exemplary embodiment, the compound is Formula (I), $R^3$, $R^{3a}$, X and Y are as described herein, Z is Formula (III), $R^4$ is cyano, $R^6$ is H, and $R^7$ is H. In an exemplary embodiment, the compound is Formula (I), $R^3$, $R^{3a}$, X and Y are as described herein, Z is Formula (III), $R^4$ is H, $R^6$ is cyano, and $R^7$ is H. In an exemplary embodiment, the compound is Formula (I), $R^3$, $R^{3a}$, X and Y are as described herein, Z is Formula (III), $R^4$ is H, $R^6$ is H, and $R^7$ is cyano.

In an exemplary embodiment, the compound is Formula (I), $R^3$, $R^{3a}$, X and Y are as described herein, Z is Formula (II), $R^4$, $R^5$, and $R^7$ are each independently selected from H or $C_1$-$C_3$ alkyl substituted with amino. In an exemplary embodiment, the compound is Formula (I), $R^3$, $R^{3a}$, X and Y are as described herein, Z is Formula (II), $R^4$, $R^5$, and $R^7$ are each independently selected from H or —$CH_2NH_2$. In an exemplary embodiment, the compound is Formula (I), $R^3$, $R^{3a}$, X and Y are as described herein, Z is Formula (II), $R^4$ is —$CH_2NH_2$, $R^5$ is H, and $R^7$ is H. In an exemplary embodiment, the compound is Formula (I), $R^3$, $R^{3a}$, X and Y are as described herein, Z is Formula (II), $R^4$ is H, $R^5$ is —$CH_2NH_2$, and $R^7$ is H. In an exemplary embodiment, the compound is Formula (I), $R^3$, $R^{3a}$, X and Y are as described herein, Z is Formula (II), $R^4$ is H, $R^5$ is H, and $R^7$ is —$CH_2NH_2$.

In an exemplary embodiment, the compound is Formula (I), $R^3$, $R^{3a}$, X and Y are as described herein, Z is Formula (III), $R^4$, $R^6$, and $R^7$ are each independently selected from H or $C_1$-$C_3$ alkyl substituted with amino. In an exemplary embodiment, the compound is Formula (I), $R^3$, $R^{3a}$, X and Y are as described herein, Z is Formula (III), $R^4$, $R^6$, and $R^7$ are each independently selected from H or —$CH_2NH_2$. In an exemplary embodiment, the compound is Formula (I), $R^3$, $R^{3a}$, X and Y are as described herein, Z is Formula (III), $R^4$ is —$CH_2NH_2$, $R^6$ is H, and $R^7$ is H. In an exemplary embodiment, the compound is Formula (I), $R^3$, $R^{3a}$, X and Y are as described herein, Z is Formula (III), $R^4$ is H, $R^6$ is —$CH_2NH_2$, and $R^7$ is H. In an exemplary embodiment, the compound is Formula (I), $R^3$, $R^{3a}$, X and Y are as described herein, Z is Formula (III), $R^4$ is H, $R^6$ is H, and $R^7$ is —$CH_2NH_2$.

In an exemplary embodiment, the compound is Formula (I), $R^3$, $R^{3a}$, X and Y are as described herein, Z is Formula (II), $R^4$, $R^5$, and $R^7$ are each independently selected from H or $C_1$-$C_3$ alkoxy. In an exemplary embodiment, the compound is Formula (I), $R^3$, $R^{3a}$, X and Y are as described herein, Z is Formula (II), $R^4$, $R^5$, and $R^7$ are each independently selected from H or —$OCH_3$. In an exemplary embodiment, the compound is Formula (I), $R^3$, $R^{3a}$, X and Y are as described herein, Z is Formula (II), $R^4$ is —$OCH_3$, $R^5$ is H, and $R^7$ is H. In an exemplary embodiment, the compound is Formula (I), $R^3$, $R^{3a}$, X and Y are as described herein, Z is Formula (II), $R^4$ is H, $R^5$ is —$OCH_3$, and $R^7$ is H. In an exemplary embodiment, the compound is Formula (I), $R^3$, $R^{3a}$, X and Y are as described herein, Z is Formula (II), $R^4$ is H, $R^5$ is H, and $R^7$ is —$OCH_3$.

In an exemplary embodiment, the compound is Formula (I), $R^3$, $R^{3a}$, X and Y are as described herein, Z is Formula (III), $R^4$, $R^6$, and $R^7$ are each independently selected from H or $C_1$-$C_3$ alkoxy. In an exemplary embodiment, the compound is Formula (I), $R^3$, $R^{3a}$, X and Y are as described herein, Z is Formula (III), $R^4$, $R^6$, and $R^7$ are each independently selected from H or —$OCH_3$.

In an exemplary embodiment, the compound is Formula (I), $R^3$, $R^{3a}$, X and Y are as described herein, Z is Formula (II), $R^4$ is —$OCH_3$, $R^6$ is H, and $R^7$ is H. In an exemplary embodiment, the compound is Formula (I), X and Y are as described herein, Z is Formula (II), $R^3$ is H, $R^{3a}$ is H, $R^4$ is —$OCH_3$, $R^6$ is H, and $R^7$ is H. In an exemplary embodiment, the compound is Formula (I), Y is as described herein, X is H, Z is Formula (II), $R^3$ is H, $R^{3a}$ is H, $R^4$ is —$OCH_3$, $R^6$ is H, and $R^7$ is H. In an exemplary embodiment, the compound is Formula (I), Y is as described herein, X is F, Z is Formula (II), $R^3$ is H, $R^{3a}$ is H, $R^4$ is —$OCH_3$, $R^6$ is H, and $R^7$ is H. In an exemplary embodiment, the compound is Formula (I), Y is as described herein, X is OH, Z is Formula (II), $R^3$ is H, $R^{3a}$ is H, $R^4$ is —$OCH_3$, $R^6$ is H, and $R^7$ is H. In an exemplary embodiment, the compound is Formula (I), X and Y are as described herein, Z is Formula (II), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is —$OCH_3$, $R^6$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is —$OCH_3$, $R^6$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is —$OCH_3$, $R^6$ is H, and $R^7$ is H.

In an exemplary embodiment, the compound is Formula (I), $R^3$, $R^{3a}$, X and Y are as described herein, Z is Formula (III), $R^4$ is —$OCH_3$, $R^6$ is H, and $R^7$ is H. In an exemplary embodiment, the compound is Formula (I), X and Y are as described herein, Z is Formula (III), $R^3$ is H, $R^{3a}$ is H, $R^4$ is —$OCH_3$, $R^6$ is H, and $R^7$ is H. In an exemplary embodiment, the compound is Formula (I), Y is as described herein, X is H, Z is Formula (III), $R^3$ is H, $R^{3a}$ is H, $R^4$ is —$OCH_3$, $R^6$ is H, and $R^7$ is H. In an exemplary embodiment, the compound is Formula (I), Y is as described herein, X is F, Z is Formula (III), $R^3$ is H, $R^{3a}$ is H, $R^4$ is —$OCH_3$, $R^6$ is H, and $R^7$ is H. In an exemplary embodiment, the compound is Formula (I), Y is as described herein, X is OH, Z is Formula (III), $R^3$ is H, $R^{3a}$ is H, $R^4$ is —$OCH_3$, $R^6$ is H, and $R^7$ is H. In an exemplary embodiment, the compound is Formula (I), X and Y are as described herein, Z is Formula (III), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is H, Z is Formula (III), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is F, Z is Formula (III), $R^3$ is $CH_3$, $R^{3a}$ is H, $R^4$ is —$OCH_3$, $R^6$ is H, and $R^7$ is H. In an exemplary embodiment, the compound is Formula (I), Y is as described herein, X is OH, Z is Formula (III), $R^3$ is $CH_3$, $R^{3a}$ is H, $R^4$ is —$OCH_3$, $R^6$ is H, and $R^7$ is H. In an exemplary embodiment, the compound is Formula (I), X and Y are as described herein, Z is Formula (III), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is —$OCH_3$, $R^6$ is H, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is —$OCH_3$, $R^6$ is H, and $R^7$ is H. In an exemplary embodiment, the compound is Formula (I), X and Y are as described herein, Z is Formula (III), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is —$OCH_3$, $R^6$ is H, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is —$OCH_3$, $R^6$ is H, and $R^7$ is H.

In an exemplary embodiment, the compound is Formula (I), $R^3$, $R^{3a}$, X and Y are as described herein, Z is Formula (II), $R^4$ is H, $R^6$ is —$OCH_3$, and $R^7$ is H. In an exemplary embodiment, the compound is Formula (I), X and Y are as described herein, Z is Formula (II), $R^3$ is H, $R^{3a}$ is H, $R^4$ is H, $R^6$ is —$OCH_3$, and $R^7$ is H. In an exemplary embodiment, the compound is Formula (I), Y is as described herein, X is H, Z is Formula (II), $R^3$ is H, $R^{3a}$ is H, $R^4$ is H, $R^6$ is —$OCH_3$, and $R^7$ is H. In an exemplary embodiment, the compound is Formula (I), Y is as described herein, X is F, Z is Formula (II), $R^3$ is H, $R^{3a}$ is H, $R^4$ is H, $R^6$ is —$OCH_3$, and $R^7$ is H. In an exemplary embodiment, the compound is Formula (I), Y is as described herein, X is OH, Z is Formula (II), $R^3$ is H, $R^{3a}$ is H, $R^4$ is H, $R^6$ is —$OCH_3$, and $R^7$ is H. In an exemplary embodiment, the compound is Formula (I), X and Y are as described herein, Z is Formula (II), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^6$ is —$OCH_3$, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^6$ is —$OCH_3$, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^6$ is —$OCH_3$, and $R^7$ is H.

In an exemplary embodiment, the compound is Formula (I), $R^3$, $R^{3a}$, X and Y are as described herein, Z is Formula (III), $R^4$ is H, $R^6$ is —$OCH_3$, and $R^7$ is H. In an exemplary embodiment, the compound is Formula (I), X and Y are as described herein, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is —$OCH_3$, and $R^7$ is H.

In an exemplary embodiment, the compound is Formula (I), X and Y are as described herein, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is —$OCH_3$, and $R^7$ is H.

In an exemplary embodiment, the compound is Formula (I), $R^3$, $R^{3a}$, X and Y are as described herein, Z is Formula (II), $R^4$ is H, $R^6$ is H, and $R^7$ is —$OCH_3$. In an exemplary embodiment, the compound is Formula (I), X and Y are as described herein, Z is Formula (II), $R^3$ is H, $R^{3a}$ is H, $R^4$ is H, $R^6$ is H, and $R^7$ is —$OCH_3$. In an exemplary embodiment, the compound is Formula (I), Y is as described herein, X is H, Z is Formula (II), $R^3$ is H, $R^{3a}$ is H, $R^4$ is H, $R^6$ is H, and $R^7$ is —$OCH_3$. In an exemplary embodiment, the compound is Formula (I), Y is as described herein, X is F, Z is Formula (II), $R^3$ is H, $R^{3a}$ is H, $R^4$ is H, $R^6$ is H, and $R^7$ is —$OCH_3$. In an exemplary embodiment, the compound is Formula (I), Y is as described herein, X is OH, Z is Formula (II), $R^3$ is H, $R^{3a}$ is H, $R^4$ is H, $R^6$ is H, and $R^7$ is —$OCH_3$. In an exemplary embodiment, the compound is Formula (I), X and Y are as described herein, Z is Formula (II), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is H, Z is Formula (II), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is F, Z is Formula (II), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is OH, Z is Formula (II), $R^3$ is $CH_3$, $R^{3a}$ is H, $R^4$ is H, $R^6$ is H, and $R^7$ is —$OCH_3$. In an exemplary embodiment, the compound is Formula (I), X and Y are as described herein, Z is Formula (II), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is H, Z is Formula (II), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is F, Z is Formula (II), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is OH, Z is Formula (II), $R^3$ is $CH_3$, $R^{3a}$ is $CH_3$, $R^4$ is H, $R^6$ is H, and $R^7$ is —$OCH_3$. In an exemplary embodiment, the compound is Formula (I), X and Y are as described herein, Z is Formula (II), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is H, Z is Formula (II), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is F, Z is Formula (II), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is OH, Z is Formula (II), $R^3$ is —$CH_2NH_2$, $R^{3a}$ is H, $R^4$ is H, $R^6$ is H, and $R^7$ is —$OCH_3$.

In an exemplary embodiment, the compound is Formula (I), $R^3$, $R^{3a}$, X and Y are as described herein, Z is Formula (III), $R^4$ is H, $R^6$ is H, and $R^7$ is —$OCH_3$. In an exemplary embodiment, the compound is Formula (I), X and Y are as described herein, Z is Formula (III), $R^3$ is H, $R^{3a}$ is H, $R^4$ is H, $R^6$ is H, and $R^7$ is —$OCH_3$. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is —$OCH_3$. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is —$OCH_3$. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is —$OCH_3$. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is —$OCH_3$. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is —$OCH_3$. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is —$OCH_3$. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is —$OCH_3$. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is —$OCH_3$. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is —$OCH_3$.

In an exemplary embodiment, the compound is Formula (I), $R^3$, $R^{3a}$, X and Y are as described herein, Z is Formula (II), $R^4$ is H, $R^5$ is H, and $R^7$ is H. In an exemplary embodiment, the compound is Formula (I), X and Y are as described herein, Z is Formula (II), $R^3$ is H, $R^{3a}$ is H, $R^4$ is H, $R^5$ is H, and $R^7$ is H. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is H. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is H. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is H. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is H.

In an exemplary embodiment, the compound is Formula (I), $R^3$, $R^{3a}$, X and Y are as described herein, Z is Formula (III), $R^4$ is H, $R^6$ is H, and $R^7$ is H. In an exemplary embodiment, the compound is Formula (I), X and Y are as described herein, Z is Formula (III), $R^3$ is H, $R^{3a}$ is H, $R^4$ is H, $R^6$ is H, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is H. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is H.

In an exemplary embodiment, the compound is Formula (I), $R^3$, $R^{3a}$, X and Y are as described herein, Z is Formula (II), $R^4$ is H, $R^5$ is H, and $R^7$ is F. In an exemplary embodiment, the compound is Formula (I), X and Y are as described herein, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is F. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is F. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is F.

In an exemplary embodiment, the compound is Formula (I), $R^3$, $R^{3a}$, X and Y are as described herein, Z is Formula (III), $R^4$ is H, $R^6$ is H, and $R^7$ is F. In an exemplary embodiment, the compound is Formula (I), X and Y are as described herein, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is F. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is F. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is F.

In an exemplary embodiment, the compound is Formula (I), $R^3$, $R^{3a}$, X and Y are as described herein, Z is Formula (II), $R^4$ is H, $R^5$ is F, and $R^7$ is H. In an exemplary embodiment, the compound is Formula (I), X and Y are as described herein, Z is Formula (II), $R^3$ is H, $R^{3a}$ is H, $R^4$ is H, $R^5$ is F, and $R^7$ is H. In an exemplary embodiment, the compound is Formula (I), Y is as described herein, X is H, Z is Formula (II), $R^3$ is H, $R^{3a}$ is H, $R^4$ is H, $R^5$ is F, and $R^7$ is H. In an exemplary embodiment, the compound is Formula (I), Y is as described herein, X is F, Z is Formula (II), $R^3$ is H, $R^{3a}$ is H, $R^4$ is H, $R^5$ is F, and $R^7$ is H. In an exemplary embodiment, the compound is Formula (I), Y is as described herein, X is OH, Z is Formula (II), $R^3$ is H, $R^{3a}$ is H, $R^4$ is H, $R^5$ is F, and $R^7$ is H. In an exemplary embodiment, the compound is Formula (I), X and Y are as described herein, Z is Formula (II), $R^3$ is $CH_3$, $R^{3a}$ is H, $R^4$ is H, $R^5$ is F, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^5$ is F, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^5$ is F, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^5$ is F, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^5$ is F, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is F, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is F, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is F, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^5$ is F, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is F, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is F, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is F, and $R^7$ is H.

In an exemplary embodiment, the compound is Formula (I), $R^3$, $R^{3a}$, X and Y are as described herein, Z is Formula (III), $R^4$ is H, $R^6$ is F, and $R^7$ is H. In an exemplary embodiment, the compound is Formula (I), X and Y are as described herein, Z is Formula (III), $R^3$ is H, $R^{3a}$ is H, $R^4$ is H, $R^6$ is F, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is F, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is F, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is F, and $R^7$ is H. In an exemplary embodiment, the compound is Formula (I), X and Y are as described herein, Z is Formula (III), $R^3$ is $CH_3$, $R^{3a}$ is H, $R^4$ is H, $R^6$ is F, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is F, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is F, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is F, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is F, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is F, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is F, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is F, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is F, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is F, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is F, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is F, and $R^7$ is H.

In an exemplary embodiment, the compound is Formula (I), $R^3$, $R^{3a}$, X and Y are as described herein, Z is Formula (II), $R^4$ is F, $R^5$ is H, and $R^7$ is H. In an exemplary embodiment, the compound is Formula (I), X and Y are as described herein, Z is Formula (II), $R^3$ is H, $R^{3a}$ is H, $R^4$ is F, $R^5$ is H, and $R^7$ is H. In an exemplary embodiment, the compound is Formula (I), Y is as described herein, X is H, Z is Formula (II), $R^3$ is H, $R^{3a}$ is H, $R^4$ is F, $R^5$ is H, and $R^7$ is H. In an exemplary embodiment, the compound is Formula (I), Y is as described herein, X is F, Z is Formula (II), $R^3$ is H, $R^{3a}$ is H, $R^4$ is F, $R^5$ is H, and $R^7$ is H. In an exemplary embodiment, the compound is Formula (I), Y is as described herein, X is OH, Z is Formula (II), $R^3$ is H, $R^{3a}$ is H, $R^4$ is F, $R^5$ is H, and $R^7$ is H. In an exemplary embodiment, the compound is Formula (I), X and Y are as described herein, Z is Formula (II), $R^3$ is $CH_3$, $R^{3a}$ is H, $R^4$ is F, $R^5$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is F, $R^5$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is F, $R^5$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is F, $R^5$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is F, $R^5$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is F, $R^5$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is F, $R^5$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is F, $R^5$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is F, $R^5$ is H, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is F, $R^5$ is H, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is F, $R^5$ is H, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is F, $R^5$ is H, and $R^7$ is H.

In an exemplary embodiment, the compound is Formula (I), $R^3$, $R^{3a}$, X and Y are as described herein, Z is Formula (III), $R^4$ is F, $R^6$ is H, and $R^7$ is H. In an exemplary embodiment, the compound is Formula (I), X and Y are as described herein, Z is Formula (III), $R^3$ is H, $R^{3a}$ is H, $R^4$ is F, $R^6$ is H, and $R^7$ is H. In an exemplary embodiment, the compound is Formula (I), Y is as described herein, X is H, Z is Formula (III), $R^3$ is H, $R^{3a}$ is H, $R^4$ is F, $R^6$ is H, and $R^7$ is H. In an exemplary embodiment, the compound is Formula (I), Y is as described herein, X is F, Z is Formula (III), $R^3$ is H, $R^{3a}$ is H, $R^4$ is F, $R^6$ is H, and $R^7$ is H. In an exemplary embodiment, the compound is Formula (I), Y is as described herein, X is OH, Z is Formula (III), $R^3$ is H, $R^{3a}$ is H, $R^4$ is F, $R^6$ is H, and $R^7$ is H. In an exemplary embodiment, the compound is Formula (I), X and Y are as described herein, Z is Formula (III), $R^3$ is $CH_3$, $R^{3a}$ is H, $R^4$ is F, $R^6$ is H, and $R^7$ is H. In an exemplary embodiment, the compound is Formula (I), Y is as described herein, X is H, Z is Formula (III), $R^3$ is $CH_3$, $R^{3a}$ is H, $R^4$ is F, $R^6$ is H, and $R^7$ is H. In an exemplary embodiment, the compound is Formula (I), Y is as described herein, X is F, Z is Formula (III), $R^3$ is $CH_3$, $R^{3a}$ is H, $R^4$ is F, $R^6$ is H, and $R^7$ is H. In an exemplary embodiment, the compound is Formula (I), Y is as described herein, X is OH, Z is Formula (III), $R^3$ is $CH_3$, $R^{3a}$ is H, $R^4$ is F, $R^6$ is H, and $R^7$ is H. In an exemplary embodiment, the compound is Formula (I), X and Y are as described herein, Z is Formula (III), $R^3$ is $CH_3$, $R^{3a}$ is $CH_3$, $R^4$ is F, $R^6$ is H, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is F, $R^6$ is H, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is F, $R^6$ is H, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is F, $R^6$ is H, and $R^7$ is H. In an exemplary embodiment, the compound is Formula (I), X and Y are as described herein, Z is Formula (III), $R^3$ is —$CH_2NH_2$, $R^{3a}$ is H, $R^4$ is F, $R^6$ is H, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is F, $R^6$ is H, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is F, $R^6$ is H, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is F, $R^6$ is H, and $R^7$ is H.

In an exemplary embodiment, the compound is Formula (I), $R^3$, $R^{3a}$, X and Y are as described herein, Z is Formula (II), one of $R^4$, $R^5$, and $R^7$ is H, and each of the remaining $R^4$, $R^5$, and $R^7$ is halogen. In an exemplary embodiment, the compound is Formula (I), $R^3$, $R^{3a}$, X and Y are as described herein, Z is Formula (II), one of $R^4$, $R^5$, and $R^7$ is H, and each of the remaining $R^4$, $R^5$, and $R^7$ is F. In an exemplary embodiment, the compound is Formula (I), $R^3$, $R^{3a}$, X and Y are as described herein, Z is Formula (II), one of $R^4$, $R^5$, and $R^7$ is H, and each of the remaining $R^4$, $R^5$, and $R^7$ is Cl. In an exemplary embodiment, the compound is Formula (I), $R^3$, $R^{3a}$, X and Y are as described herein, Z is Formula (II), one of $R^4$, $R^5$, and $R^7$ is H, one of $R^4$, $R^5$, and $R^7$ is Cl and one of $R^4$, $R^5$, and $R^7$ is F.

In an exemplary embodiment, the compound is Formula (I), X and Y are as described herein, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is F. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is F. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is F. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is F.

In an exemplary embodiment, the compound is Formula (I), $R^3$, $R^{3a}$, X and Y are as described herein, Z is Formula (III), $R^4$ is H, $R^6$ is H, and $R^7$ is F. In an exemplary embodiment, the compound is Formula (I), X and Y are as described herein, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is F. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is F. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is F. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is F.

In an exemplary embodiment, the compound is Formula (I), $R^3$, $R^{3a}$, X and Y are as described herein, Z is Formula (II), $R^4$ is H, $R^5$ is H, and $R^7$ is Cl. In an exemplary embodiment, the compound is Formula (I), X and Y are as described herein, Z is Formula (II), $R^3$ is H, $R^{3a}$ is H, $R^4$ is H, $R^5$ is H, and $R^7$ is Cl. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is Cl. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is Cl. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is Cl. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is Cl. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is Cl. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is Cl. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is Cl. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is Cl. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is Cl. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is Cl. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is Cl. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is Cl. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is Cl. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is Cl. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is Cl.

In an exemplary embodiment, the compound is Formula (I), $R^3$, $R^{3a}$, X and Y are as described herein, Z is Formula (III), $R^4$ is H, $R^6$ is H, and $R^7$ is Cl. In an exemplary embodiment, the compound is Formula (I), X and Y are as described herein, Z is Formula (III), $R^3$ is H, $R^{3a}$ is H, $R^4$ is H, $R^6$ is H, and $R^7$ is Cl. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is Cl. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is Cl. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is Cl. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is Cl. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is Cl. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is Cl. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is Cl. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is Cl. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is Cl. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is Cl. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is Cl. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is Cl. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is Cl. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is Cl. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is Cl.

In an exemplary embodiment, the compound is Formula (I), $R^3$, $R^{3a}$, X and Y are as described herein, Z is Formula (II), $R^4$ is H, $R^5$ is Cl, and $R^7$ is H. In an exemplary embodiment, the compound is Formula (I), X and Y are as described herein, Z is Formula (II), $R^3$ is H, $R^{3a}$ is H, $R^4$ is H, $R^5$ is Cl, and $R^7$ is H. In an exemplary embodiment, the compound is Formula (I), Y is as described herein, X is H, Z is Formula (II), $R^3$ is H, $R^{3a}$ is H, $R^4$ is H, $R^5$ is Cl, and $R^7$ is H. In an exemplary embodiment, the compound is Formula (I), Y is as described herein, X is F, Z is Formula (II), $R^3$ is H, $R^{3a}$ is H, $R^4$ is H, $R^5$ is Cl, and $R^7$ is H. In an exemplary embodiment, the compound is Formula (I), Y is as described herein, X is OH, Z is Formula (II), $R^3$ is H, $R^{3a}$ is H, $R^4$ is H, $R^5$ is Cl, and $R^7$ is H. In an exemplary embodiment, the compound is Formula (I), X and Y are as described herein, Z is Formula (II), $R^3$ is $CH_3$, $R^{3a}$ is H, $R^4$ is H, $R^5$ is Cl, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^5$ is Cl, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^5$ is Cl, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^5$ is Cl, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^5$ is Cl, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is Cl, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is Cl, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is Cl, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^5$ is Cl, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is Cl, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is Cl, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is Cl, and $R^7$ is H.

In an exemplary embodiment, the compound is Formula (I), $R^3$, $R^{3a}$, X and Y are as described herein, Z is Formula (III), $R^4$ is H, $R^6$ is Cl, and $R^7$ is H. In an exemplary embodiment, the compound is Formula (I), X and Y are as described herein, Z is Formula (III), $R^3$ is H, $R^{3a}$ is H, $R^4$ is H, $R^6$ is Cl, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is Cl, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is Cl, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is Cl, and $R^7$ is H. In an exemplary embodiment, the compound is Formula (I), X and Y are as described herein, Z is Formula (III), $R^3$ is $CH_3$, $R^{3a}$ is H, $R^4$ is H, $R^6$ is Cl, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is Cl, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is Cl, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is Cl, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is Cl, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is Cl, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is Cl, and $R^7$ is H.

In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is Cl, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is Cl, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is Cl, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is Cl, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is Cl, and $R^7$ is H.

In an exemplary embodiment, the compound is Formula (I), $R^3$, $R^{3a}$, X and Y are as described herein, Z is Formula (II), $R^4$ is Cl, $R^5$ is H, and $R^7$ is H. In an exemplary embodiment, the compound is Formula (I), X and Y are as described herein, Z is Formula (II), $R^3$ is H, $R^{3a}$ is H, $R^4$ is Cl, $R^5$ is H, and $R^7$ is H. In an exemplary embodiment, the compound is Formula (I), Y is as described herein, X is H, Z is Formula (II), $R^3$ is H, $R^{3a}$ is H, $R^4$ is Cl, $R^5$ is H, and $R^7$ is H. In an exemplary embodiment, the compound is Formula (I), Y is as described herein, X is F, Z is Formula (II), $R^3$ is H, $R^{3a}$ is H, $R^4$ is Cl, $R^5$ is H, and $R^7$ is H. In an exemplary embodiment, the compound is Formula (I), Y is as described herein, X is OH, Z is Formula (II), $R^3$ is H, $R^{3a}$ is H, $R^4$ is Cl, $R^5$ is H, and $R^7$ is H. In an exemplary embodiment, the compound is Formula (I), X and Y are as described herein, Z is Formula (II), $R^3$ is $CH_3$, $R^{3a}$ is H, $R^4$ is Cl, $R^5$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is Cl, $R^5$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is Cl, $R^5$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is Cl, $R^5$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is Cl, $R^5$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is Cl, $R^5$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is Cl, $R^5$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is Cl, $R^5$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is Cl, $R^5$ is H, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is Cl, $R^5$ is H, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is Cl, $R^5$ is H, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is Cl, $R^5$ is H, and $R^7$ is H.

In an exemplary embodiment, the compound is Formula (I), $R^3$, $R^{3a}$, X and Y are as described herein, Z is Formula (III), $R^4$ is Cl, $R^6$ is H, and $R^7$ is H. In an exemplary embodiment, the compound is Formula (I), X and Y are as described herein, Z is Formula (III), $R^3$ is H, $R^{3a}$ is H, $R^4$ is Cl, $R^6$ is H, and $R^7$ is H. In an exemplary embodiment, the compound is Formula (I), Y is as described herein, X is H, Z is Formula (III), $R^3$ is H, $R^{3a}$ is H, $R^4$ is Cl, $R^6$ is H, and $R^7$ is H. In an exemplary embodiment, the compound is Formula (I), Y is as described herein, X is F, Z is Formula (III), $R^3$ is H, $R^{3a}$ is H, $R^4$ is Cl, $R^6$ is H, and $R^7$ is H. In an exemplary embodiment, the compound is Formula (I), Y is as described herein, X is OH, Z is Formula (III), $R^3$ is H, $R^{3a}$ is H, $R^4$ is Cl, $R^6$ is H, and $R^7$ is H. In an exemplary embodiment, the compound is Formula (I), X and Y are as described herein, Z is Formula (III), $R^3$ is $CH_3$, $R^{3a}$ is H, $R^4$ is Cl, $R^6$ is H, and $R^7$ is H. In an exemplary embodiment, the compound is Formula (I), Y is as described herein, X is H, Z is Formula (III), $R^3$ is $CH_3$, $R^{3a}$ is H, $R^4$ is Cl, $R^6$ is H, and $R^7$ is H. In an exemplary embodiment, the compound is Formula (I), Y is as described herein, X is F, Z is Formula (III), $R^3$ is $CH_3$, $R^{3a}$ is H, $R^4$ is Cl, $R^6$ is H, and $R^7$ is H. In an exemplary embodiment, the compound is Formula (I), Y is as described herein, X is OH, Z is Formula (III), $R^3$ is $CH_3$, $R^{3a}$ is H, $R^4$ is Cl, $R^6$ is H, and $R^7$ is H. In an exemplary embodiment, the compound is Formula (I), X and Y are as described herein, Z is Formula (III), $R^3$ is $CH_3$, $R^{3a}$ is $CH_3$, $R^4$ is Cl, $R^6$ is H, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is Cl, $R^6$ is H, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is Cl, $R^6$ is H, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is Cl, $R^6$ is H, and $R^7$ is H. In an exemplary embodiment, the compound is Formula (I), X and Y are as described herein, Z is Formula (III), $R^3$ is —$CH_2NH_2$, $R^{3a}$ is H, $R^4$ is Cl, $R^6$ is H, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is Cl, $R^6$ is H, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is Cl, $R^6$ is H, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is Cl, $R^6$ is H, and $R^7$ is H.

In an exemplary embodiment, the compound is Formula (I), $R^3$, $R^{3a}$, X and Y are as described herein, Z is Formula (II), $R^4$ is H, $R^5$ is H, and $R^7$ is $CH_3$. In an exemplary embodiment, the compound is Formula (I), X and Y are as described herein, Z is Formula (II), $R^3$ is H, $R^{3a}$ is H, $R^4$ is H, $R^5$ is H, and $R^7$ is $CH_3$. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is $CH_3$. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is $CH_3$. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is $CH_3$. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is $CH_3$. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is $CH_3$. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is $CH_3$. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is $CH_3$. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is $CH_3$. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is $CH_3$. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is $CH_3$. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is $CH_3$. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is $CH_3$. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is $CH_3$. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is $CH_3$. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is $CH_3$.

In an exemplary embodiment, the compound is Formula (I), $R^3$, $R^{3a}$, X and Y are as described herein, Z is Formula (III), $R^4$ is H, $R^6$ is H, and $R^7$ is $CH_3$. In an exemplary embodiment, the compound is Formula (I), X and Y are as described herein, Z is Formula (III), $R^3$ is H, $R^{3a}$ is H, $R^4$ is H, $R^6$ is H, and $R^7$ is $CH_3$. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is $CH_3$. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is $CH_3$. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is $CH_3$. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is $CH_3$. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is $CH_3$. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is $CH_3$. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is $CH_3$. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is $CH_3$. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is $CH_3$. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is $CH_3$. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is $CH_3$. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is $CH_3$. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is $CH_3$. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is $CH_3$. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is $CH_3$.

In an exemplary embodiment, the compound is Formula (I), $R^3$, $R^{3a}$, X and Y are as described herein, Z is Formula (II), $R^4$ is H, $R^5$ is $CH_3$, and $R^7$ is H. In an exemplary embodiment, the compound is Formula (I), X and Y are as described herein, Z is Formula (II), $R^3$ is H, $R^{3a}$ is H, $R^4$ is H, $R^5$ is $CH_3$, and $R^7$ is H. In an exemplary embodiment, the compound is Formula (I), Y is as described herein, X is H, Z is Formula (II), $R^3$ is H, $R^{3a}$ is H, $R^4$ is H, $R^5$ is $CH_3$, and $R^7$ is H. In an exemplary embodiment, the compound is Formula (I), Y is as described herein, X is F, Z is Formula (II), $R^3$ is H, $R^{3a}$ is H, $R^4$ is H, $R^5$ is $CH_3$, and $R^7$ is H. In an exemplary embodiment, the compound is Formula (I), Y is as described herein, X is OH, Z is Formula (II), $R^3$ is H, $R^{3a}$ is H, $R^4$ is H, $R^5$ is $CH_3$, and $R^7$ is H. In an exemplary embodiment, the compound is Formula (I), X and Y are as described herein, Z is Formula (II), $R^3$ is $CH_3$, $R^{3a}$ is H, $R^4$ is H, $R^5$ is $CH_3$, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^5$ is $CH_3$, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^5$ is $CH_3$, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^5$ is $CH_3$, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^5$ is $CH_3$, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is $CH_3$, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is $CH_3$, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is $CH_3$, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^5$ is $CH_3$, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is $CH_3$, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is $CH_3$, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is $CH_3$, and $R^7$ is H.

In an exemplary embodiment, the compound is Formula (I), $R^3$, $R^{3a}$, X and Y are as described herein, Z is Formula (III), $R^4$ is H, $R^6$ is $CH_3$, and $R^7$ is H. In an exemplary embodiment, the compound is Formula (I), X and Y are as described herein, Z is Formula (III), $R^3$ is H, $R^{3a}$ is H, $R^4$ is H, $R^6$ is $CH_3$, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is $CH_3$, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is $CH_3$, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is $CH_3$, and $R^7$ is H. In an exemplary embodiment, the compound is Formula (I), X and Y are as described herein, Z is Formula (III), $R^3$ is $CH_3$, $R^{3a}$ is H, $R^4$ is H, $R^6$ is $CH_3$, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is $CH_3$, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is $CH_3$, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is $CH_3$, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is $CH_3$, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is $CH_3$, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is $CH_3$, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is $CH_3$, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is $CH_3$, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is $CH_3$, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is $CH_3$, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is $CH_3$, and $R^7$ is H.

In an exemplary embodiment, the compound is Formula (I), $R^3$, $R^{3a}$, X and Y are as described herein, Z is Formula (II), $R^4$ is $CH_3$, $R^5$ is H, and $R^7$ is H. In an exemplary embodiment, the compound is Formula (I), X and Y are as described herein, Z is Formula (II), $R^3$ is H, $R^{3a}$ is H, $R^4$ is $CH_3$, $R^5$ is H, and $R^7$ is H. In an exemplary embodiment, the compound is Formula (I), Y is as described herein, X is H, Z is Formula (II), $R^3$ is H, $R^{3a}$ is H, $R^4$ is $CH_3$, $R^5$ is H, and $R^7$ is H. In an exemplary embodiment, the compound is Formula (I), Y is as described herein, X is F, Z is Formula (II), $R^3$ is H, $R^{3a}$ is H, $R^4$ is $CH_3$, $R^5$ is H, and $R^7$ is H. In an exemplary embodiment, the compound is Formula (I), Y is as described herein, X is OH, Z is Formula (II), $R^3$ is H, $R^{3a}$ is H, $R^4$ is $CH_3$, $R^5$ is H, and $R^7$ is H. In an exemplary embodiment, the compound is Formula (I), X and Y are as described herein, Z is Formula (II), $R^3$ is $CH_3$, $R^{3a}$ is H, $R^4$ is $CH_3$, $R^5$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is $CH_3$, $R^5$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is $CH_3$, $R^5$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is $CH_3$, $R^5$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is $CH_3$, $R^5$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is $CH_3$, $R^5$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is $CH_3$, $R^5$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is $CH_3$, $R^5$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is $CH_3$, $R^5$ is H, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is $CH_3$, $R^5$ is H, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is $CH_3$, $R^5$ is H, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is $CH_3$, $R^5$ is H, and $R^7$ is H.

In an exemplary embodiment, the compound is Formula (I), $R^3$, $R^{3a}$, X and Y are as described herein, Z is Formula (III), $R^4$ is $CH_3$, $R^6$ is H, and $R^7$ is H. In an exemplary embodiment, the compound is Formula (I), X and Y are as described herein, Z is Formula (III), $R^3$ is H, $R^{3a}$ is H, $R^4$ is $CH_3$, $R^6$ is H, and $R^7$ is H. In an exemplary embodiment, the compound is Formula (I), Y is as described herein, X is H, Z is Formula (III), $R^3$ is H, $R^{3a}$ is H, $R^4$ is $CH_3$, $R^6$ is H, and $R^7$ is H. In an exemplary embodiment, the compound is Formula (I), Y is as described herein, X is F, Z is Formula (III), $R^3$ is H, $R^{3a}$ is H, $R^4$ is $CH_3$, $R^6$ is H, and $R^7$ is H. In an exemplary embodiment, the compound is Formula (I), Y is as described herein, X is OH, Z is Formula (III), $R^3$ is H, $R^{3a}$ is H, $R^4$ is $CH_3$, $R^6$ is H, and $R^7$ is H. In an exemplary embodiment, the compound is Formula (I), X and Y are as described herein, Z is Formula (III), $R^3$ is $CH_3$, $R^{3a}$ is H, $R^4$ is $CH_3$, $R^6$ is H, and $R^7$ is H. In an exemplary embodiment, the compound is Formula (I), Y is as described herein, X is H, Z is Formula (III), $R^3$ is $CH_3$, $R^{3a}$ is H, $R^4$ is $CH_3$, $R^6$ is H, and $R^7$ is H. In an exemplary embodiment, the compound is Formula (I), Y is as described herein, X is F, Z is Formula (III), $R^3$ is $CH_3$, $R^{3a}$ is H, $R^4$ is $CH_3$, $R^6$ is H, and $R^7$ is H. In an exemplary embodiment, the compound is Formula (I), Y is as described herein, X is OH, Z is Formula (III), $R^3$ is $CH_3$, $R^{3a}$ is H, $R^4$ is $CH_3$, $R^6$ is H, and $R^7$ is H. In an exemplary embodiment, the compound is Formula (I), X and Y are as described herein, Z is Formula (III), $R^3$ is $CH_3$, $R^{3a}$ is $CH_3$, $R^4$ is $CH_3$, $R^6$ is H, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is $CH_3$, $R^6$ is H, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is $CH_3$, $R^6$ is H, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is $CH_3$, $R^6$ is H, and $R^7$ is H. In an exemplary embodiment, the compound is Formula (I), X and Y are as described herein, Z is Formula (III), $R^3$ is —$CH_2NH_2$, $R^{3a}$ is H, $R^4$ is $CH_3$, $R^6$ is H, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is $CH_3$, $R^6$ is H, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is $CH_3$, $R^6$ is H, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is $CH_3$, $R^6$ is H, and $R^7$ is H.

In an exemplary embodiment, the compound is Formula (I), $R^3$, $R^{3a}$, X and Y are as described herein, Z is Formula (II), $R^4$ is H, $R^5$ is H, and $R^7$ is CN. In an exemplary embodiment, the compound is Formula (I), $R^3$, $R^{3a}$, X and Y are as described herein, Z is Formula (II), $R^4$ is H, $R^5$ is H, and $R^7$ is CN. In an exemplary embodiment, the compound is Formula (I), $R^3$, $R^{3a}$, X and Y are as described herein, Z is Formula (II), $R^4$ is H, $R^5$ is H, and $R^7$ is CN. In an exemplary embodiment, the compound is Formula (I), $R^3$, $R^{3a}$, X and Y are as described herein, Z is Formula (II), $R^4$ is H, $R^5$ is H, and $R^7$ is CN. In an exemplary embodiment, the compound is Formula (I), X and Y are as described herein, Z is Formula (II), $R^3$ is H, $R^{3a}$ is H, $R^4$ is H, $R^5$ is H, and $R^7$ is CN. In an exemplary embodiment, the compound is Formula (I), Y is as described herein, X is H, Z is Formula (II), $R^3$ is H, $R^{3a}$ is H, $R^4$ is H, $R^5$ is H, and $R^7$ is CN. In an exemplary embodiment, the compound is Formula (I), Y is as described herein, X is F, Z is Formula (II), $R^3$ is H, $R^{3a}$ is H, $R^4$ is H, $R^5$ is H, and $R^7$ is CN. In an exemplary embodiment, the compound is Formula (I), Y is as described herein, X is OH, Z is Formula (II), $R^3$ is H, $R^{3a}$ is H, $R^4$ is H, $R^5$ is H, and $R^7$ is CN. In an exemplary embodiment, the compound is Formula (I), X and Y are as described herein, Z is Formula (II), $R^3$ is $CH_3$, $R^{3a}$ is H, $R^4$ is H, $R^5$ is H, and $R^7$ is CN. In an exemplary embodiment, the compound is Formula (I), Y is as described herein, X is H, Z is Formula (II), $R^3$ is $CH_3$, $R^{3a}$ is H, $R^4$ is H, $R^5$ is H, and $R^7$ is CN. In an exemplary embodiment, the compound is Formula (I), Y is as described herein, X is F, Z is Formula (II), $R^3$ is $CH_3$, $R^{3a}$ is H, $R^4$ is H, $R^5$ is H, and $R^7$ is CN. In an exemplary embodiment, the compound is Formula (I), Y is as described herein, X is OH, Z is Formula (II), $R^3$ is $CH_3$, $R^{3a}$ is H, $R^4$ is H, $R^5$ is H, and $R^7$ is CN. In an exemplary embodiment, the compound is Formula (I), X and Y are as described herein, Z is Formula (II), $R^3$ is $CH_3$, $R^{3a}$ is $CH_3$, $R^4$ is H, $R^5$ is H, and $R^7$ is CN. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is H, and $R^7$ is CN. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is H, and $R^7$ is CN. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is H, and $R^7$ is CN. In an exemplary embodiment, the compound is Formula (I), X and Y are as described herein, Z is Formula (II), $R^3$ is —$CH_2NH_2$, $R^{3a}$ is H, $R^4$ is H, $R^5$ is H, and $R^7$ is CN. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is H, and $R^7$ is CN. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is H, and $R^7$ is CN. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is H, and $R^7$ is CN.

In an exemplary embodiment, the compound is Formula (I), $R^3$, $R^{3a}$, X and Y are as described herein, Z is Formula (III), $R^4$ is H, $R^6$ is H, and $R^7$ is CN. In an exemplary embodiment, the compound is Formula (I), $R^3$, $R^{3a}$, and Y are as described herein, X is H, Z is Formula (III), $R^4$ is H, $R^6$ is H, and $R^7$ is CN. In an exemplary embodiment, the compound is Formula (I), $R^3$, $R^{3a}$, Y is as described herein, X is F, Z is Formula (III), $R^4$ is H, $R^6$ is H, and $R^7$ is CN. In an exemplary embodiment, the compound is Formula (I), $R^3$, $R^{3a}$, and Y are as described herein, X is OH, Z is Formula (III), $R^4$ is H, $R^6$ is H, and $R^7$ is CN. In an exemplary embodiment, the compound is Formula (I), X and Y are as described herein, Z is Formula (III), $R^3$ is H, $R^{3a}$ is H, $R^4$ is H, $R^6$ is H, and $R^7$ is CN. In an exemplary embodiment, the compound is Formula (I), Y is as described herein, X is H, Z is Formula (III), $R^3$ is H, $R^{3a}$ is H, $R^4$ is H, $R^6$ is H, and $R^7$ is CN. In an exemplary embodiment, the compound is Formula (I), Y is as described herein, X is F, Z is Formula (III), $R^3$ is H, $R^{3a}$ is H, $R^4$ is H, $R^6$ is H, and $R^7$ is CN. In an exemplary embodiment, the compound is Formula (I), Y is as described herein, X is OH, Z is Formula (III), $R^3$ is H, $R^{3a}$ is H, $R^4$ is H, $R^6$ is H, and $R^7$ is CN. In an exemplary embodiment, the compound is Formula (I), X and Y are as described herein, Z is Formula (III), $R^3$ is $CH_3$, $R^{3a}$ is H, $R^4$ is H, $R^6$ is H, and $R^7$ is CN. In an exemplary embodiment, the compound is Formula (I), Y is as described herein, X is H, Z is Formula (III), $R^3$ is $CH_3$, $R^{3a}$ is H, $R^4$ is H, $R^6$ is H, and $R^7$ is CN. In an exemplary embodiment, the compound is Formula (I), Y is as described herein, X is F, Z is Formula (III), $R^3$ is $CH_3$, $R^{3a}$ is H, $R^4$ is H, $R^6$ is H, and $R^7$ is CN. In an exemplary embodiment, the compound is Formula (I), Y is as described herein, X is OH, Z is Formula (III), $R^3$ is $CH_3$, $R^{3a}$ is H, $R^4$ is H, $R^6$ is H, and $R^7$ is CN. In an exemplary embodiment, the compound is Formula (I), X and Y are as described herein, Z is Formula (III), $R^3$ is $CH_3$, $R^{3a}$ is $CH_3$, $R^4$ is H, $R^6$ is H, and $R^7$ is CN. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is H, and $R^7$ is CN. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is H, and $R^7$ is CN. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is H, and $R^7$ is CN. In an exemplary embodiment, the compound is Formula (I), X and Y are as described herein, Z is Formula (III), $R^3$ is —$CH_2NH_2$, $R^{3a}$ is H, $R^4$ is H, $R^6$ is H, and $R^7$ is CN. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is H, and $R^7$ is CN. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is H, and $R^7$ is CN. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is H, and $R^7$ is CN.

In an exemplary embodiment, the compound is Formula (I), $R^3$, $R^{3a}$, X and Y are as described herein, Z is Formula (II), $R^4$ is H, $R^5$ is —$OCH_3$, and $R^7$ is H. In an exemplary embodiment, the compound is Formula (I), $R^3$, $R^{3a}$, Y is as described herein, X is H, Z is Formula (II), $R^4$ is H, $R^5$ is —$OCH_3$, and $R^7$ is H. In an exemplary embodiment, the compound is Formula (I), $R^3$, $R^{3a}$, Y is as described herein, X is F, Z is Formula (II), $R^4$ is H, $R^5$ is —$OCH_3$, and $R^7$ is H. In an exemplary embodiment, the compound is Formula (I), $R^3$, $R^{3a}$, Y is as described herein, X is OH, Z is Formula (II), $R^4$ is H, $R^5$ is —$OCH_3$, and $R^7$ is H. In an exemplary embodiment, the compound is Formula (I), X and Y are as described herein, Z is Formula (II), $R^3$ is H, $R^{3a}$ is H, $R^4$ is H, $R^5$ is —$OCH_3$, and $R^7$ is H. In an exemplary embodiment, the compound is Formula (I), Y is as described herein, X is H, Z is Formula (II), $R^3$ is H, $R^{3a}$ is H, $R^4$ is H, $R^5$ is —$OCH_3$, and $R^7$ is H. In an exemplary embodiment, the compound is Formula (I), Y is as described herein, X is F, Z is Formula (II), $R^3$ is H, $R^{3a}$ is H, $R^4$ is H, $R^5$ is —$OCH_3$, and $R^7$ is H. In an exemplary embodiment, the compound is Formula (I), Y is as described herein, X is OH, Z is Formula (II), $R^3$ is H, $R^{3a}$ is H, $R^4$ is H, $R^5$ is —$OCH_3$, and $R^7$ is H. In an exemplary embodiment, the compound is Formula (I), X and Y are as described herein, Z is Formula (II), $R^3$ is $CH_3$, $R^{3a}$ is H, $R^4$ is H, $R^5$ is —$OCH_3$, and $R^7$ is H. In an exemplary embodiment, the compound is Formula (I), Y is as described herein, X is H, Z is Formula (II), $R^3$ is $CH_3$, $R^{3a}$ is H, $R^4$ is H, $R^5$ is —$OCH_3$, and $R^7$ is H. In an exemplary embodiment, the compound is Formula (I), Y is as described herein, X is F, Z is Formula (II), $R^3$ is $CH_3$, $R^{3a}$ is H, $R^4$ is H, $R^5$ is —$OCH_3$, and $R^7$ is H. In an exemplary embodiment, the compound is Formula (I), Y is as described herein, X is OH, Z is Formula (II), $R^3$ is $CH_3$, $R^{3a}$ is H, $R^4$ is H, $R^5$ is —$OCH_3$, and $R^7$ is H. In an exemplary embodiment, the compound is Formula (I), X and Y are as described herein, Z is Formula (II), $R^3$ is $CH_3$, $R^{3a}$ is $CH_3$, $R^4$ is H, $R^5$ is —$OCH_3$, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is H, $R^5$ is —$OCH_3$, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is H, $R^5$ is —$OCH_3$, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is H, $R^5$ is —$OCH_3$, and $R^7$ is H. In an exemplary embodiment, the compound is Formula (I), X and Y are as described herein, Z is Formula (II), $R^3$ is —$CH_2NH_2$, $R^{3a}$ is H, $R^4$ is H, $R^5$ is —$OCH_3$, and $R^7$ is H. In an exemplary embodiment, the compound is Formula (I), Y is as described herein, X is H, Z is Formula (II), $R^3$ is —$CH_2NH_2$, $R^{3a}$ is H, $R^4$ is H, $R^5$ is —$OCH_3$, and $R^7$ is H. In an exemplary embodiment, the compound is Formula (I), Y is as described herein, X is F, Z is Formula (II), $R^3$ is —$CH_2NH_2$, $R^{3a}$ is H, $R^4$ is H, $R^5$ is —$OCH_3$, and $R^7$ is H. In an exemplary embodiment, the compound is Formula (I), Y is as described herein, X is OH, Z is Formula (II), $R^3$ is —$CH_2NH_2$, $R^{3a}$ is H, $R^4$ is H, $R^5$ is —$OCH_3$, and $R^7$ is H.

In an exemplary embodiment, the compound is Formula (I), $R^3$, $R^{3a}$, X and Y are as described herein, Z is Formula (III), $R^4$ is H, $R^6$ is —$OCH_3$, and $R^7$ is H. In an exemplary embodiment, the compound is Formula (I), $R^3$, $R^{3a}$, Y is as described herein, X is H, Z is Formula (III), $R^4$ is H, $R^6$ is —$OCH_3$, and $R^7$ is H. In an exemplary embodiment, the compound is Formula (I), $R^3$, $R^{3a}$, Y is as described herein, X is F, Z is Formula (III), $R^4$ is H, $R^6$ is —$OCH_3$, and $R^7$ is H. In an exemplary embodiment, the compound is Formula (I), $R^3$, $R^{3a}$, Y is as described herein, X is OH, Z is Formula (III), $R^4$ is H, $R^6$ is —$OCH_3$, and $R^7$ is H. In an exemplary embodiment, the compound is Formula (I), X and Y are as described herein, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is H, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is H, $R^{3a}$ is H, $R^4$ is H, $R^6$ is —$OCH_3$, and $R^7$ is H. In an exemplary embodiment, the compound is Formula (I), X and Y are as described herein, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), X and Y are as described herein, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is H, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is F, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), Y is as described herein, X is OH, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), X and Y are as described herein, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is H, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is F, Z is Formula (III), $R^3$ is —$CH_2NH_2$, $R^{3a}$ is H, $R^4$ is H, $R^6$ is —$OCH_3$, and $R^7$ is H. In an exemplary embodiment, the compound is Formula (I), Y is as described herein, X is OH, Z is Formula (III), $R^3$ is —$CH_2NH_2$, $R^{3a}$ is H, $R^4$ is H, $R^6$ is —$OCH_3$, and $R^7$ is H.

In an exemplary embodiment, the compound is Formula (I), $R^3$, $R^{3a}$, X and Y are as described herein, Z is Formula (II), $R^4$ is —$CH_2NH_2$, $R^5$ is H, and $R^7$ is H. In an exemplary embodiment, the compound is Formula (I), X and Y are as described herein, Z is Formula (II), $R^3$ is H, $R^{3a}$ is H, $R^4$ is —$CH_2NH_2$, $R^5$ is H, and $R^7$ is H. In an exemplary embodiment, the compound is Formula (I), Y is as described herein, X is H, Z is Formula (II), $R^3$ is H, $R^{3a}$ is H, $R^4$ is —$CH_2NH_2$, $R^5$ is H, and $R^7$ is H. In an exemplary embodiment, the compound is Formula (I), Y is as described herein, X is F, Z is Formula (II), $R^3$ is H, $R^{3a}$ is H, $R^4$ is —$CH_2NH_2$, $R^5$ is H, and $R^7$ is H. In an exemplary embodiment, the compound is Formula (I), Y is as described herein, X is OH, Z is Formula (II), $R^3$ is H, $R^{3a}$ is H, $R^4$ is —$CH_2NH_2$, $R^5$ is H, and $R^7$ is H. In an exemplary embodiment, the compound is Formula (I), X and Y are as described herein, Z is Formula (II), $R^3$ is $CH_3$, $R^{3a}$ is H, $R^4$ is —$CH_2NH_2$, $R^5$ is H, and $R^7$ is H. In an exemplary embodiment, the compound is Formula (I), Y is as described herein, X is H, Z is Formula (II), $R^3$ is $CH_3$, $R^{3a}$ is H, $R^4$ is —$CH_2NH_2$, $R^5$ is H, and $R^7$ is H. In an exemplary embodiment, the compound is Formula (I), Y is as described herein, X is F, Z is Formula (II), $R^3$ is $CH_3$, $R^{3a}$ is H, $R^4$ is —$CH_2NH_2$, $R^5$ is H, and $R^7$ is H. In an exemplary embodiment, the compound is Formula (I), Y is as described herein, X is OH, Z is Formula (II), $R^3$ is $CH_3$, $R^{3a}$ is H, $R^4$ is —$CH_2NH_2$, $R^5$ is H, and $R^7$ is H. In an exemplary embodiment, the compound is Formula (I), X and Y are as described herein, Z is Formula (II), $R^3$ is $CH_3$, $R^{3a}$ is $CH_3$, $R^4$ is —$CH_2NH_2$, $R^5$ is H, and $R^7$ is H. In an exemplary embodiment, the compound is Formula (I), Y is as described herein, X is H, Z is Formula (II), $R^3$ is $CH_3$, $R^{3a}$ is $CH_3$, $R^4$ is —$CH_2NH_2$, $R^5$ is H, and $R^7$ is H. In an exemplary embodiment, the compound is Formula (I), Y is as described herein, X is F, Z is Formula (II), $R^3$ is $CH_3$, $R^{3a}$ is $CH_3$, $R^4$ is —$CH_2NH_2$, $R^5$ is H, and $R^7$ is H. In an exemplary embodiment, the compound is Formula (I), Y is as described herein, X is OH, Z is Formula (II), $R^3$ is $CH_3$, $R^{3a}$ is $CH_3$, $R^4$ is —$CH_2NH_2$, $R^5$ is H, and $R^7$ is H. In an exemplary embodiment, the compound is Formula (I), X and Y are as described herein, Z is Formula (II), $R^3$ is —$CH_2NH_2$, $R^{3a}$ is H, $R^4$ is —$CH_2NH_2$, $R^5$ is H, and $R^7$ is H. In an exemplary embodiment, the compound is Formula (I), Y is as described herein, X is H, Z is Formula (II), R³ is —CH₂NH₂, R³ᵃ is H, R⁴ is —CH₂NH₂, R⁵ is H, and R⁷ is H. In an exemplary embodiment, the compound is Formula (I), Y is as described herein, X is F, Z is Formula (II), R³ is —CH₂NH₂, R³ᵃ is H, R⁴ is —CH₂NH₂, R⁵ is H, and R⁷ is H. In an exemplary embodiment, the compound is Formula (I), Y is as described herein, X is OH, Z is Formula (II), R³ is —CH₂NH₂, R³ᵃ is H, R⁴ is —CH₂NH₂, R⁵ is H, and R⁷ is H.

In an exemplary embodiment, the compound is Formula (I), R³, R³ᵃ, X and Y are as described herein, Z is Formula (III), R⁴ is —CH₂NH₂, R⁶ is H, and R⁷ is H. In an exemplary embodiment, the compound is Formula (I), R³, R³ᵃ, Y is as described herein, X is H, Z is Formula (III), R⁴ is —CH₂NH₂, R⁶ is H, and R⁷ is H. In an exemplary embodiment, the compound is Formula (I), R³, R³ᵃ, Y is as described herein, X is F, Z is Formula (III), R⁴ is —CH₂NH₂, R⁶ is H, and R⁷ is H. In an exemplary embodiment, the compound is Formula (I), R³, R³ᵃ, Y is as described herein, X is OH, Z is Formula (III), R⁴ is —CH₂NH₂, R⁶ is H, and R⁷ is H. In an exemplary embodiment, the compound is Formula (I), X and Y are as described herein, Z is Formula (III), R³ is H, R³ᵃ is H, R⁴ is —CH₂NH₂, R⁶ is H, and R⁷ is H. In an exemplary embodiment, the compound is Formula (I), Y is as described herein, X is H, Z is Formula (III), R³ is H, R³ᵃ is H, R⁴ is —CH₂NH₂, R⁶ is H, and R⁷ is H. In an exemplary embodiment, the compound is Formula (I), Y is as described herein, X is F, Z is Formula (III), R³ is H, R³ᵃ is H, R⁴ is —CH₂NH₂, R⁶ is H, and R⁷ is H. In an exemplary embodiment, the compound is Formula (I), Y is as described herein, X is OH, Z is Formula (III), R³ is H, R³ᵃ is H, R⁴ is —CH₂NH₂, R⁶ is H, and R⁷ is H. In an exemplary embodiment, the compound is Formula (I), X and Y are as described herein, Z is Formula (III), R³ is CH₃, R³ᵃ is H, R⁴ is —CH₂NH₂, R⁶ is H, and R⁷ is H. In an exemplary embodiment, the compound is Formula (I), Y is as described herein, X is H, Z is Formula (III), R³ is CH₃, R³ᵃ is H, R⁴ is —CH₂NH₂, R⁶ is H, and R⁷ is H. In an exemplary embodiment, the compound is Formula (I), Y is as described herein, X is F, Z is Formula (III), R³ is CH₃, R³ᵃ is H, R⁴ is —CH₂NH₂, R⁶ is H, and R⁷ is H. In an exemplary embodiment, the compound is Formula (I), Y is as described herein, X is OH, Z is Formula (III), R³ is CH₃, R³ᵃ is H, R⁴ is —CH₂NH₂, R⁶ is H, and R⁷ is H. In an exemplary embodiment, the compound is Formula (I), X and Y are as described herein, Z is Formula (III), R³ is CH₃, R³ᵃ is CH₃, R⁴ is —CH₂NH₂, R⁶ is H, and R⁷ is H. In an exemplary embodiment, the compound is Formula (I), Y is as described herein, X is H, Z is Formula (III), R³ is CH₃, R³ᵃ is CH₃, R⁴ is —CH₂NH₂, R⁶ is H, and R⁷ is H. In an exemplary embodiment, the compound is Formula (I), Y is as described herein, X is F, Z is Formula (III), R³ is CH₃, R³ᵃ is CH₃, R⁴ is —CH₂NH₂, R⁶ is H, and R⁷ is H. In an exemplary embodiment, the compound is Formula (I), Y is as described herein, X is OH, Z is Formula (III), R³ is CH₃, R³ᵃ is CH₃, R⁴ is —CH₂NH₂, R⁶ is H, and R⁷ is H. In an exemplary embodiment, the compound is Formula (I), X and Y are as described herein, Z is Formula (III), R³ is —CH₂NH₂, R³ᵃ is H, R⁴ is —CH₂NH₂, R⁶ is H, and R⁷ is H. In an exemplary embodiment, the compound is Formula (I), Y is as described herein, X is H, Z is Formula (III), R³ is —CH₂NH₂, R³ᵃ is H, R⁴ is —CH₂NH₂, R⁶ is H, and R⁷ is H. In an exemplary embodiment, the compound is Formula (I), Y is as described herein, X is F, Z is Formula (III), R³ is —CH₂NH₂, R³ᵃ is H, R⁴ is —CH₂NH₂, R⁶ is H, and R⁷ is H. In an exemplary embodiment, the compound is Formula (I), Y is as described herein, X is OH, Z is Formula (III), R³ is —CH₂NH₂, R³ᵃ is H, R⁴ is —CH₂NH₂, R⁶ is H, and R⁷ is H.

In an exemplary embodiment, the compound is Formula (I), X and Y are as described herein, and said Z is

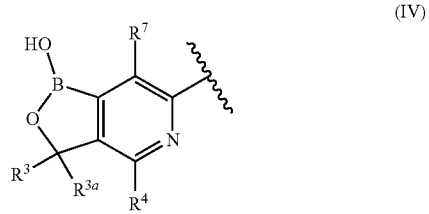

(IV)

wherein R³, R³ᵃ, R⁴, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R³ᵃ, R⁴, R⁷, X and Y are as described herein, and said Z is according to Formula (IV). In an exemplary embodiment, the compound is Formula (I), X and Y are as described herein, Z is according to Formula (IV), R³ is H, R³ᵃ is H, R⁴ is H, and R⁷ is F. In an exemplary embodiment, the compound is Formula (I), X and Y are as described herein, Z is according to Formula (IV), R³ is H, R³ᵃ is H, R⁴ is H, and R⁷ is Cl or CH₃. In an exemplary embodiment, the compound is Formula (I), X and Y are as described herein, Z is according to Formula (IV), R³ is H, R³ᵃ is H, R⁴ is F or Cl or CH₃, and R⁷ is H.

In an exemplary embodiment, the compound is Formula (I), X and Y are as described herein, and said Z is

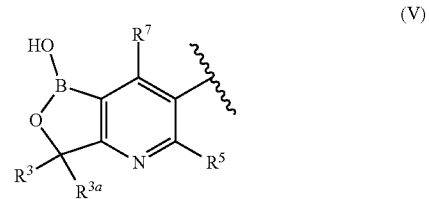

(V)

wherein R³, R³ᵃ, R⁵, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R³ᵃ, R⁵, and R⁷, X and Y are as described herein, and said Z is according to Formula (V). In an exemplary embodiment, the compound is Formula (I), X and Y are as described herein, Z is according to Formula (V), R³ is H, R³ᵃ is H, R⁵ is H, and R⁷ is F. In an exemplary embodiment, the compound is Formula (I), X and Y are as described herein, Z is according to Formula (V), R³ is H, R³ᵃ is H, R⁵ is H, and R⁷ is Cl or CH₃. In an exemplary embodiment, the compound is Formula (I), X and Y are as described herein, Z is according to Formula (V), R³ is H, R³ᵃ is H, R⁵ is F or Cl or CH₃, and R⁷ is H.

In an exemplary embodiment, the compound is Formula (I), X and Y are as described herein, and said Z is

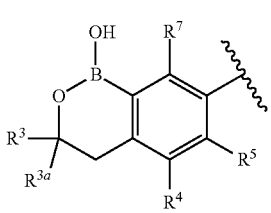

(VI)

wherein R³, R³ᵃ, R⁴, R⁵, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R³ᵃ, R⁴, R⁵, and R⁷, X and Y are as described herein, and said Z is according to Formula (VI). In an exemplary embodiment, the compound is Formula (I), X and Y are as described herein, Z is according to Formula (VI), R³ is H, R³ᵃ is H, R⁴ is H, R⁵ is H, and R⁷ is F. In an exemplary embodiment, the compound is Formula (I), X and Y are as described herein, Z is according to Formula (VI), R³ is H, R³ᵃ is H, R⁴ is H, R⁵ is H, and R⁷ is Cl or CH₃. In an exemplary embodiment, the compound is Formula (I), X and Y are as described herein, Z is according to Formula (VI), R³ is H, R³ᵃ is H, R⁴ is H, R⁵ is F or Cl or CH₃, and R⁷ is H. In an exemplary embodiment, the compound is Formula (I), X and Y are as described herein, Z is according to Formula (VI), R³ is H, R³ᵃ is H, R⁴ is F or Cl or CH₃, R⁵ is H, and R⁷ is H.

In an exemplary embodiment, the compound is Formula (I), X and Y are as described herein, and said Z is

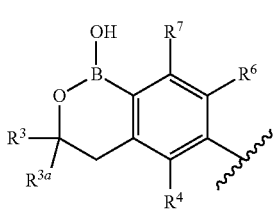

(VII)

wherein R³, R³ᵃ, R⁴, R⁶, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R³ᵃ, R⁴, R⁶, and R⁷, X and Y are as described herein, and said Z is according to Formula (VII). In an exemplary embodiment, the compound is Formula (I), X and Y are as described herein, Z is according to Formula (VII), R³ is H, R³ᵃ is H, R⁴ is H, R⁶ is H, and R⁷ is F. In an exemplary embodiment, the compound is Formula (I), X and Y are as described herein, Z is according to Formula (VII), R³ is H, R³ᵃ is H, R⁴ is H, R⁶ is H, and R⁷ is Cl or CH₃. In an exemplary embodiment, the compound is Formula (I), X and Y are as described herein, Z is according to Formula (VII), R³ is H, R³ᵃ is H, R⁴ is H, R⁶ is F or Cl or CH₃, and R⁷ is H. In an exemplary embodiment, the compound is Formula (I), X and Y are as described herein, Z is according to Formula (VII), R³ is H, R³ᵃ is H, R⁴ is F or Cl or CH₃, R⁶ is H, and R⁷ is H.

In an exemplary embodiment, the compound is Formula (I), X and Y are as described herein, and said Z is

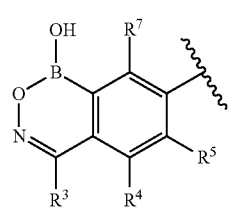

(VIII)

wherein R³, R⁴, R⁵, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R⁴, R⁵, and R⁷, X and Y are as described herein, and said Z is according to Formula (VIII). In an exemplary embodiment, the compound is Formula (I), X and Y are as described herein, Z is according to Formula (VIII), R³ is H, R⁴ is H, R⁵ is H, and R⁷ is F. In an exemplary embodiment, the compound is Formula (I), X and Y are as described herein, Z is according to Formula (VIII), R³ is H, R⁴ is H, R⁵ is H, and R⁷ is Cl or CH₃. In an exemplary embodiment, the compound is Formula (I), X and Y are as described herein, Z is according to Formula (VIII), R³ is H, R⁴ is H, R⁵ is F or Cl or CH₃, and R⁷ is H. In an exemplary embodiment, the compound is Formula (I), X and Y are as described herein, Z is according to Formula (VIII), R³ is H, R⁴ is F or Cl or CH₃, R⁵ is H, and R⁷ is H.

In an exemplary embodiment, the compound is Formula (I), X and Y are as described herein, and said Z is

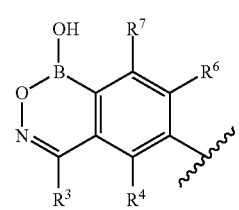

(IX)

wherein R³, R⁴, R⁶, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R⁴, R⁶, and R⁷, X and Y are as described herein, and said Z is according to Formula (IX). In an exemplary embodiment, the compound is Formula (I), X and Y are as described herein, Z is according to Formula (IX), R³ is H, R⁴ is H, R⁶ is H, and R⁷ is F. In an exemplary embodiment, the compound is Formula (I), X and Y are as described herein, Z is according to Formula (IX), R³ is H, R⁴ is H, R⁶ is H, and R⁷ is Cl or CH₃. In an exemplary embodiment, the compound is Formula (I), X and Y are as described herein, Z is according to Formula (IX), R³ is H, R⁴ is H, R⁶ is F or Cl or CH₃, and R⁷ is H. In an exemplary embodiment, the compound is Formula (I), X and Y are as described herein, Z is according to Formula (IX), R³ is H, R⁴ is F or Cl or CH₃, R⁶ is H, and R⁷ is H.

In an exemplary embodiment, the compound is Formula (I), X and Y are as described herein, and said Z is $$\text{(X)}$$

wherein R¹, R⁴, R⁵, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R¹, R⁴, R⁵, and R⁷, X and Y are as described herein, and said Z is according to Formula (X). In an exemplary embodiment, the compound is Formula (I), X, Y, R⁴, R⁵, and R⁷ are as described herein, Z is according to Formula (X), and R¹ is H. In an exemplary embodiment, the compound is Formula (I), X, Y, R⁴, R⁵, and R⁷ are as described herein, Z is according to Formula (X), and R¹ is an ester. In an exemplary embodiment, the compound is Formula (I), X, Y, R⁴, R⁵, and R⁷ are as described herein, Z is according to Formula (X), and R¹ is a ketone. In an exemplary embodiment, the compound is Formula (I), X, Y, R⁴, R⁵, and R⁷ are as described herein, Z is according to Formula (X), and R¹ is —C(O)OC(CH₃)₃. In an exemplary embodiment, the compound is Formula (I), X, Y, R⁴, R⁵, and R⁷ are as described herein, Z is according to Formula (X), and R¹ is —S(O)₂R¹ᵃ, wherein R¹ᵃ is substituted or unsubstituted C₁-C₆ alkyl. In an exemplary embodiment, the compound is Formula (I), X, Y, R⁴, R⁵, and R⁷ are as described herein, Z is according to Formula (X), and R¹ is —S(O)₂CH₃. In an exemplary embodiment, the compound is Formula (I), X, Y, R⁴, R⁵, and R⁷ are as described herein, Z is according to Formula (X), and R¹ is —CH₃. In an exemplary embodiment, the compound is Formula (I), X, Y, R⁴, R⁵, and R⁷ are as described herein, Z is according to Formula (X), and R¹ is —CH₂CH₃. In an exemplary embodiment, the compound is Formula (I), X, Y, R⁴, R⁵, and R⁷ are as described herein, Z is according to Formula (X), and R¹ is C₃-C₆ alkyl. In an exemplary embodiment, the compound is Formula (I), X, Y, R⁴, R⁵, and R⁷ are as described herein, Z is according to Formula (X), and R¹ is —C(O)R¹ᵃ, wherein R¹ᵃ is substituted or unsubstituted C₁-C₆ alkyl. In an exemplary embodiment, the compound is Formula (I), X, Y, R⁴, R⁵, and R⁷ are as described herein, Z is according to Formula (X), and R¹ is —C(O)CH₃. In an exemplary embodiment, the compound is Formula (I), X, Y, R⁴, R⁵, and R⁷ are as described herein, Z is according to Formula (X), and R¹ is —C(O)OR¹ᵃ, wherein R¹ᵃ is substituted or unsubstituted C₁-C₆ alkyl. In an exemplary embodiment, the compound is Formula (I), X, Y, R⁴, R⁵, and R⁷ are as described herein, Z is according to Formula (X), and R¹ is —C(O)OCH₃. In an exemplary embodiment, the compound is Formula (I), R¹, X and Y are as described herein, Z is according to Formula (X), R⁴ is H, R⁵ is H, and R⁷ is F. In an exemplary embodiment, the compound is Formula (I), R¹, X and Y are as described herein, Z is according to Formula (X), R⁴ is H, R⁵ is H, and R⁷ is Cl or CH₃. In an exemplary embodiment, the compound is Formula (I), R¹, X and Y are as described herein, Z is according to Formula (X), R⁴ is H, R⁵ is F or Cl or CH₃, and R⁷ is H. In an exemplary embodiment, the compound is Formula (I), R¹, X and Y are as described herein, Z is according to Formula (X), R⁴ is F or Cl or CH₃, R⁵ is H, and R⁷ is H.

In an exemplary embodiment, the compound is Formula (I), X and Y are as described herein, and said Z is $$\text{(XI)}$$

wherein R¹, R⁴, R⁶, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R¹, R⁴, R⁶, and R⁷, X and Y are as described herein, and said Z is according to Formula (XI). In an exemplary embodiment, the compound is Formula (I), X, Y, R⁴, R⁶, and R⁷ are as described herein, Z is according to Formula (XI), and R¹ is H. In an exemplary embodiment, the compound is Formula (I), X, Y, R⁴, R⁶, and R⁷ are as described herein, Z is according to Formula (XI), and R¹ is an ester. In an exemplary embodiment, the compound is Formula (I), X, Y, R⁴, R⁶, and R⁷ are as described herein, Z is according to Formula (XI), and R¹ is a ketone.

In an exemplary embodiment, the compound is Formula (I), X, Y, R⁴, R⁶, and R⁷ are as described herein, Z is according to Formula (XI), and R¹ is —C(O)OC(CH₃)₃. In an exemplary embodiment, the compound is Formula (I), X, Y, R⁴, R⁶, and R⁷ are as described herein, Z is according to Formula (XI), and R¹ is —S(O)₂R¹ᵃ, wherein R¹ᵃ is substituted or unsubstituted C₁-C₆ alkyl. In an exemplary embodiment, the compound is Formula (I), X, Y, R⁴, R⁶, and R⁷ are as described herein, Z is according to Formula (XI), and R¹ is —S(O)₂CH₃. In an exemplary embodiment, the compound is Formula (I), X, Y, R⁴, R⁶, and R⁷ are as described herein, Z is according to Formula (XI), and R¹ is —CH₃. In an exemplary embodiment, the compound is Formula (I), X, Y, R⁴, R⁶, and R⁷ are as described herein, Z is according to Formula (XI), and R¹ is —CH₂CH₃. In an exemplary embodiment, the compound is Formula (I), X, Y, R⁴, R⁶, and R⁷ are as described herein, Z is according to Formula (XI), and R¹ is C₃-C₆ alkyl. In an exemplary embodiment, the compound is Formula (I), X, Y, R⁴, R⁶, and R⁷ are as described herein, Z is according to Formula (XI), and R¹ is —C(O)R¹ᵃ, wherein R¹ᵃ is substituted or unsubstituted C₁-C₆ alkyl. In an exemplary embodiment, the compound is Formula (I), X, Y, R⁴, R⁶, and R⁷ are as described herein, Z is according to Formula (XI), and R¹ is —C(O)CH₃. In an exemplary embodiment, the compound is Formula (I), X, Y, R⁴, R⁶, and R⁷ are as described herein, Z is according to Formula (XI), and R¹ is —C(O)OR¹ᵃ, wherein R¹ᵃ is substituted or unsubstituted C₁-C₆ alkyl. In an exemplary embodiment, the compound is Formula (I), X, Y, R⁴, R⁶, and R⁷ are as described herein, Z is according to Formula (XI), and R¹ is —C(O)OCH₃. In an exemplary embodiment, the compound is Formula (I), R¹, X and Y are as described herein, Z is according to Formula (XI), R⁴ is H, R⁶ is H, and R⁷ is F. In an exemplary embodiment, R¹, X and Y are as described herein, Z is according to Formula (XI), R⁴ is H, R⁶ is H, and R⁷ is Cl or CH₃. In an exemplary embodiment, the compound is Formula (I), R¹, X and Y are as described herein, Z is according to Formula (XI), R⁴ is H, R⁶ is F or Cl or CH₃, and R⁷ is H. In an exemplary embodiment, the compound is Formula (I), R¹, X and Y are as described herein, Z is according to Formula (XI), R⁴ is F or Cl or CH₃, R⁶ is H, and R⁷ is H.

In an exemplary embodiment, the compound is Formula (I), X and Y are as described herein, and said Z is

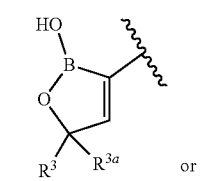

(XII)

or

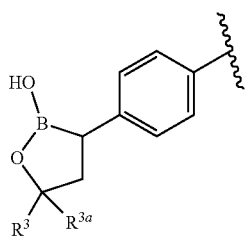

(XIII)

wherein R³ and R³ᵃ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R³, R³ᵃ, X and Y are as described herein, and said Z is according to Formula (XII) or (XIII). In an exemplary embodiment, the compound is Formula (I), X and Y are as described herein, and said Z is according to Formula (XII) or (XIII), wherein R³ is H, and R³ᵃ is H.

In an exemplary embodiment, the compound is Formula (I), X and Y are as described herein, and said Z is

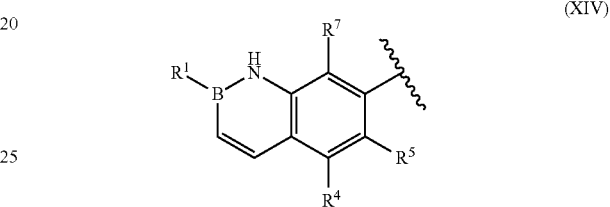

(XIV)

wherein R¹, R⁴, R⁵, and R⁷ are each independently selected from the group consisting of R¹⁰, —OR¹⁰, —NR¹⁰R¹¹, —SR¹⁰, —S(O)R¹⁰, —S(O)₂R¹⁰, —S(O)₂NR¹⁰R¹¹, —C(O)R¹⁰, —C(O)OR¹⁰, and —C(O)NR¹⁰R¹¹ wherein R¹⁰ and R¹¹ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), R¹, R⁴, R⁵, R⁷, X and Y are as described herein, and said Z is according to Formula (XIV). In an exemplary embodiment, the compound is Formula (I), X, Y, R⁴, R⁵, and R⁷ are as described herein, and said Z is according to Formula (XIV), and R¹ is H. In an exemplary embodiment, the compound is Formula (I), X, Y, R⁴, R⁵, and R⁷ are as described herein, and said Z is according to Formula (XIV), and R¹ is an ester. the compound is Formula (I), X, Y, R⁴, R⁵, and R⁷ are as described herein, and said Z is according to Formula (XIV), and R¹ is a ketone. the compound is Formula (I), X, Y, R⁴, R⁵, and R⁷ are as described herein, and said Z is according to Formula (XIV), and R¹ is —C(O)OC(CH₃)₃. the compound is Formula (I), X, Y, R⁴, R⁵, and R⁷ are as described herein, and said Z is according to Formula (XIV), and R¹ is —S(O)₂R¹ᵃ, wherein R¹ᵃ is substituted or unsubstituted C₁-C₆ alkyl. the compound is Formula (I), X, Y, R⁴, R⁵, and R⁷ are as described herein, and said Z is according to Formula (XIV), and R¹ is —S(O)₂CH₃. the compound is Formula (I), X, Y, R⁴, R⁵, and R⁷ are as described herein, and said Z is according to Formula (XIV), and R¹ is —CH₃. the compound is Formula (I), X, Y, R⁴, R⁵, and R⁷ are as described herein, and said Z is according to Formula (XIV), and R¹ is —CH₂CH₃. the compound is Formula (I), X, Y, R⁴, R⁵, and R⁷ are as described herein, and said Z is according to Formula (XIV), and R¹ is C₃-C₆ alkyl. the compound is Formula (I), X, Y, R⁴, R⁵, and R⁷ are as described herein, and said Z is according to Formula (XIV), and R¹ is —C(O)R¹ᵃ, wherein R¹ᵃ is substituted or unsubstituted C₁-C₆ alkyl. the compound is Formula (I), X, Y, $R^4$, $R^5$, and $R^7$ are as described herein, and said Z is according to Formula (XIV), and $R^1$ is —C(O)CH$_3$. the compound is Formula (I), X, Y, $R^4$, $R^5$, and $R^7$ are as described herein, and said Z is according to Formula (XIV), and $R^1$ is —C(O)OR$^{1a}$, wherein $R^{1a}$ is substituted or unsubstituted $C_1$-$C_6$ alkyl. the compound is Formula (I), X, Y, $R^4$, $R^5$, and $R^7$ are as described herein, and said Z is according to Formula (XIV), and $R^1$ is —C(O)OCH$_3$. the compound is Formula (I), X, Y, $R^4$, $R^5$, and $R^7$ are as described herein, and said Z is according to Formula (XIV), and $R^4$ is H, $R^5$ is H, and $R^7$ is F. the compound is Formula (I), X, Y, $R^4$, $R^5$, and $R^7$ are as described herein, and said Z is according to Formula (XIV), and $R^4$ is H, $R^5$ is H, and $R^7$ is Cl or CH$_3$. the compound is Formula (I), X, Y, $R^4$, $R^5$, and $R^7$ are as described herein, and said Z is according to Formula (XIV), and $R^4$ is H, $R^5$ is F or Cl or CH$_3$, and $R^7$ is H. the compound is Formula (I), X, Y, $R^4$, $R^5$, and $R^7$ are as described herein, and said Z is according to Formula (XIV), and $R^4$ is F or Cl or CH$_3$, $R^5$ is H, and $R^7$ is H.

In an exemplary embodiment, the compound is Formula (I), Z is as described herein, X is H, and Y is a bond. In an exemplary embodiment, the compound is Formula (I), Z is as described herein, X is H, and Y is —O—. In an exemplary embodiment, the compound is Formula (I), Z is as described herein, X is H, and Y is —S—. In an exemplary embodiment, the compound is Formula (I), Z is as described herein, X is H, and Y is —NH—. In an exemplary embodiment, the compound is Formula (I), Z is as described herein, X is H, and Y is substituted alkylene. In an exemplary embodiment, the compound is Formula (I), Z is as described herein, X is H, and Y is unsubstituted alkylene. In an exemplary embodiment, the compound is Formula (I), Z is as described herein, X is H, and Y is substituted heteroalkylene. In an exemplary embodiment, the compound is Formula (I), Z is as described herein, X is H, and Y is unsubstituted heteroalkylene. In an exemplary embodiment, the compound is Formula (I), Z is as described herein, X is H, and Y is methylene. In an exemplary embodiment, the compound is Formula (I), Z is as described herein, X is H, and Y is ethylene. In an exemplary embodiment, the compound is Formula (I), Z is as described herein, X is H, and Y is propylene. In an exemplary embodiment, the compound is Formula (I), Z is as described herein, X is H, and Y is substituted heteroalkylene. In an exemplary embodiment, the compound is Formula (I), Z is as described herein, X is H, and Y is unsubstituted heteroalkylene. In an exemplary embodiment, the compound is Formula (I), Z is as described herein, X is H, and Y is *—OCH$_2$—. In an exemplary embodiment, the compound is Formula (I), Z is as described herein, X is H, and Y is *—SCH$_2$—. In an exemplary embodiment, the compound is Formula (I), Z is as described herein, X is H, and Y is *—NHCH$_2$—. In an exemplary embodiment, the compound is Formula (I), Z is as described herein, X is H, and Y is *—CH$_2$NH—. In an exemplary embodiment, the compound is Formula (I), Z is as described herein, X is H, and Y is *—C(O)NH—. In an exemplary embodiment, the compound is Formula (I), Z is as described herein, X is H, and Y is *—CH$_2$NHCH$_2$— or 1-piperazinyl or *—S(O)CH$_2$— or *—S(O)$_2$— or —S(O)$_2$CH$_2$—. In an exemplary embodiment, the compound is Formula (I), Z is as described herein, X is H, and Y is 1-piperazinyl. In an exemplary embodiment, the compound is Formula (I), Z is as described herein, X is H, and Y is *—S(O)CH$_2$—. In an exemplary embodiment, the compound is Formula (I), Z is as described herein, X is H, and Y is *—S(O)$_2$—. In an exemplary embodiment, the compound is Formula (I), Z is as described herein, X is H, and Y is *—S(O)$_2$CH$_2$—. In an exemplary embodiment, the compound is Formula (I), Z is as described herein, X is H, and Y is *—NHC(O)OCH$_2$—. In this paragraph, * represents the point of attachment to Z.

In an exemplary embodiment, the compound is Formula (I), Z is as described herein, X is F, and Y is a bond. In an exemplary embodiment, the compound is Formula (I), Z is as described herein, X is F, and Y is —O—. In an exemplary embodiment, the compound is Formula (I), Z is as described herein, X is F, and Y is —S—. In an exemplary embodiment, the compound is Formula (I), Z is as described herein, X is F, and Y is —NH—. In an exemplary embodiment, the compound is Formula (I), Z is as described herein, X is F, and Y is substituted alkylene. In an exemplary embodiment, the compound is Formula (I), Z is as described herein, X is F, and Y is unsubstituted alkylene. In an exemplary embodiment, the compound is Formula (I), Z is as described herein, X is F, and Y is substituted heteroalkylene. In an exemplary embodiment, the compound is Formula (I), Z is as described herein, X is F, and Y is unsubstituted heteroalkylene. In an exemplary embodiment, the compound is Formula (I), Z is as described herein, X is F, and Y is methylene. In an exemplary embodiment, the compound is Formula (I), Z is as described herein, X is F, and Y is ethylene. In an exemplary embodiment, the compound is Formula (I), Z is as described herein, X is F, and Y is propylene. In an exemplary embodiment, the compound is Formula (I), Z is as described herein, X is F, and Y is substituted heteroalkylene. In an exemplary embodiment, the compound is Formula (I), Z is as described herein, X is F, and Y is unsubstituted heteroalkylene. In an exemplary embodiment, the compound is Formula (I), Z is as described herein, X is F, and Y is *—OCH$_2$—. In an exemplary embodiment, the compound is Formula (I), Z is as described herein, X is F, and Y is *—SCH$_2$—. In an exemplary embodiment, the compound is Formula (I), Z is as described herein, X is F, and Y is *—NHCH$_2$—. In an exemplary embodiment, the compound is Formula (I), Z is as described herein, X is F, and Y is *—CH$_2$NH—. In an exemplary embodiment, the compound is Formula (I), Z is as described herein, X is F, and Y is *—C(O)NH—. In an exemplary embodiment, the compound is Formula (I), Z is as described herein, X is F, and Y is *—CH$_2$NHCH$_2$— or 1-piperazinyl or *—S(O)CH$_2$— or *—S(O)$_2$— or *—S(O)$_2$CH$_2$—. In an exemplary embodiment, the compound is Formula (I), Z is as described herein, X is F, and Y is 1-piperazinyl. In an exemplary embodiment, the compound is Formula (I), Z is as described herein, X is F, and Y is *—S(O)CH$_2$—. In an exemplary embodiment, the compound is Formula (I), Z is as described herein, X is F, and Y is *—S(O)$_2$—. In an exemplary embodiment, the compound is Formula (I), Z is as described herein, X is F, and Y is *—S(O)$_2$CH$_2$—. In an exemplary embodiment, the compound is Formula (I), Z is as described herein, X is F, and Y is *—NHC(O)OCH$_2$—. In this paragraph, * represents the point of attachment to Z.

In an exemplary embodiment, the compound is Formula (I), Z is as described herein, X is OH, and Y is a bond. In an exemplary embodiment, the compound is Formula (I), Z is as described herein, X is OH, and Y is —O—. In an exemplary embodiment, the compound is Formula (I), Z is as described herein, X is OH, and Y is —S—. In an exemplary embodiment, the compound is Formula (I), Z is as described herein, X is OH, and Y is —NH—. In an exemplary embodiment, the compound is Formula (I), Z is as described herein, X is OH, and Y is substituted alkylene. In an exemplary embodiment, the compound is Formula (I), Z is as described herein, X is OH, and Y is unsubstituted alkylene. In an exemplary embodiment, the compound is Formula (I), Z is as described herein, X is OH, and Y is substituted heteroalkylene. In an exemplary embodiment, the compound is Formula (I), Z is as described herein, X is OH, and Y is unsubstituted heteroalkylene. In an exemplary embodiment, the compound is Formula (I), Z is as described herein, X is OH, and Y is methylene. In an exemplary embodiment, the compound is Formula (I), Z is as described herein, X is OH, and Y is ethylene. In an exemplary embodiment, the compound is Formula (I), Z is as described herein, X is OH, and Y is propylene. In an exemplary embodiment, the compound is Formula (I), Z is as described herein, X is OH, and Y is substituted heteroalkylene. In an exemplary embodiment, the compound is Formula (I), Z is as described herein, X is OH, and Y is unsubstituted heteroalkylene. In an exemplary embodiment, the compound is Formula (I), Z is as described herein, X is OH, and Y is *—OCH$_2$—. In an exemplary embodiment, the compound is Formula (I), Z is as described herein, X is OH, and Y is *—SCH$_2$—. In an exemplary embodiment, the compound is Formula (I), Z is as described herein, X is OH, and Y is *—NHCH$_2$—. In an exemplary embodiment, the compound is Formula (I), Z is as described herein, X is OH, and Y is *—CH$_2$NH—. In an exemplary embodiment, the compound is Formula (I), Z is as described herein, X is OH, and Y is *—C(O)NH—. In an exemplary embodiment, the compound is Formula (I), Z is as described herein, X is OH, and Y is *—CH$_2$NHCH$_2$— or 1-piperazinyl or *—S(O)CH$_2$— or *—S(O)$_2$— or *—S(O)$_2$CH$_2$—. In an exemplary embodiment, the compound is Formula (I), Z is as described herein, X is OH, and Y is 1-piperazinyl. In an exemplary embodiment, the compound is Formula (I), Z is as described herein, X is OH, and Y is *—S(O)CH$_2$—. In an exemplary embodiment, the compound is Formula (I), Z is as described herein, X is OH, and Y is *—S(O)$_2$—. In an exemplary embodiment, the compound is Formula (I), Z is as described herein, X is OH, and Y is *—S(O)$_2$CH$_2$—. In an exemplary embodiment, the compound is Formula (I), Z is as described herein, X is OH, and Y is *—NHC(O)OCH$_2$—. In this paragraph, * represents the point of attachment to Z.

In an exemplary embodiment, the compound is Formula (I), Z is substituted or unsubstituted heteroaryl, wherein said heteroaryl comprises an endocyclic boron, X is H, and Y is a bond. In an exemplary embodiment, the compound is Formula (I), and Z is substituted or unsubstituted heteroaryl, wherein said heteroaryl has one ring, and said ring comprises an endocyclic boron, X is H, and Y is a bond. In an exemplary embodiment, the compound is Formula (I), Z is substituted or unsubstituted heteroaryl, wherein said heteroaryl has two rings, and one of the two rings comprises an endocyclic boron, X is H, and Y is a bond. In an exemplary embodiment, the compound is Formula (I), Z is substituted or unsubstituted heterocycloalkyl, wherein said heterocycloalkyl comprises an endocyclic boron, X is H, and Y is a bond. In an exemplary embodiment, the compound is Formula (I), and Z is substituted or unsubstituted heterocycloalkyl, wherein said heterocycloalkyl has one ring, and said ring comprises an endocyclic boron, X is H, and Y is a bond. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is a bond. In an exemplary embodiment, the compound is Formula (I), Z substituted or unsubstituted benzoxaborole, X is H, and Y is a bond. In an exemplary embodiment, the compound is Formula (I), Z substituted or unsubstituted pyridinyloxaborole, X is H, and Y is a bond. In an exemplary embodiment, the compound is Formula (I), Z substituted or unsubstituted benzoxaborininol, X is H, and Y is a bond. In an exemplary embodiment, the compound is Formula (I), Z substituted or unsubstituted benzoxazaborininol, X is H, and Y is a bond. In an exemplary embodiment, the compound is Formula (I), Z substituted or unsubstituted benzodiazaborininol, X is H, and Y is a bond. In an exemplary embodiment, the compound is Formula (I), Z substituted or unsubstituted oxaborole, X is H, and Y is a bond. In an exemplary embodiment, the compound is Formula (I), Z substituted or unsubstituted dihydrobenzoazaborinine, X is H, and Y is a bond.

In an exemplary embodiment, the compound is Formula (I), Z is substituted or unsubstituted heteroaryl, wherein said heteroaryl comprises an endocyclic boron, X is H, and Y is —NH—. In an exemplary embodiment, the compound is Formula (I), and Z is substituted or unsubstituted heteroaryl, wherein said heteroaryl has one ring, and said ring comprises an endocyclic boron, X is H, and Y is —NH—. In an exemplary embodiment, the compound is Formula (I), Z is substituted or unsubstituted heteroaryl, wherein said heteroaryl has two rings, and one of the two rings comprises an endocyclic boron, X is H, and Y is —NH—. In an exemplary embodiment, the compound is Formula (I), Z is substituted or unsubstituted heterocycloalkyl, wherein said heterocycloalkyl comprises an endocyclic boron, X is H, and Y is —NH—. In an exemplary embodiment, the compound is Formula (I), and Z is substituted or unsubstituted heterocycloalkyl, wherein said heterocycloalkyl has one ring, and said ring comprises an endocyclic boron, X is H, and Y is —NH—. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is —NH—. In an exemplary embodiment, the compound is Formula (I), Z substituted or unsubstituted benzoxaborole, X is H, and Y is —NH—. In an exemplary embodiment, the compound is Formula (I), Z substituted or unsubstituted pyridinyloxaborole, X is H, and Y is —NH—. In an exemplary embodiment, the compound is Formula (I), Z substituted or unsubstituted benzoxaborininol, X is H, and Y is —NH—. In an exemplary embodiment, the compound is Formula (I), Z substituted or unsubstituted benzoxazaborininol, X is H, and Y is —NH—. In an exemplary embodiment, the compound is Formula (I), Z substituted or unsubstituted benzodiazaborininol, X is H, and Y is —NH—. In an exemplary embodiment, the compound is Formula (I), Z substituted or unsubstituted oxaborole, X is H, and Y is —NH—. In an exemplary embodiment, the compound is Formula (I), Z substituted or unsubstituted dihydrobenzoazaborinine, X is H, and Y is —NH—.

In an exemplary embodiment, the compound is Formula (I), Z is substituted or unsubstituted heteroaryl, wherein said heteroaryl comprises an endocyclic boron, X is H, and Y is *—OCH$_2$—. In an exemplary embodiment, the compound is Formula (I), and Z is substituted or unsubstituted heteroaryl, wherein said heteroaryl has one ring, and said ring comprises an endocyclic boron, X is H, and Y is *—OCH$_2$—. In an exemplary embodiment, the compound is Formula (I), Z is substituted or unsubstituted heteroaryl, wherein said heteroaryl has two rings, and one of the two rings comprises an endocyclic boron, X is H, and Y is *—OCH$_2$—. In an exemplary embodiment, the compound is Formula (I), Z is substituted or unsubstituted heterocycloalkyl, wherein said heterocycloalkyl comprises an endocyclic boron, X is H, and Y is *—OCH$_2$—. In an exemplary embodiment, the compound is Formula (I), and Z is substituted or unsubstituted heterocycloalkyl, wherein said heterocycloalkyl has one ring, and said ring comprises an endocyclic boron, X is H, and Y is *—OCH₂—. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is *—OCH₂—. In an exemplary embodiment, the compound is Formula (I), Z substituted or unsubstituted benzoxaborole, X is H, and Y is *—OCH₂—. In an exemplary embodiment, the compound is Formula (I), Z substituted or unsubstituted pyridinyloxaborole, X is H, and Y is *—OCH₂—. In an exemplary embodiment, the compound is Formula (I), Z substituted or unsubstituted benzoxaborininol, X is H, and Y is *—OCH₂—. In an exemplary embodiment, the compound is Formula (I), Z substituted or unsubstituted benzoxazaborininol, X is H, and Y is *—OCH₂—. In an exemplary embodiment, the compound is Formula (I), Z substituted or unsubstituted benzodiazaborininol, X is H, and Y is *—OCH₂—. In an exemplary embodiment, the compound is Formula (I), Z substituted or unsubstituted oxaborole, X is H, and Y is *—OCH₂—. In an exemplary embodiment, the compound is Formula (I), Z substituted or unsubstituted dihydrobenzoazaborinine, X is H, and Y is *—OCH₂—. In this paragraph, * represents the point of attachment to Z.

In an exemplary embodiment, the compound is Formula (I), Z is substituted or unsubstituted heteroaryl, wherein said heteroaryl comprises an endocyclic boron, X is H, and Y is *—SCH₂—. In an exemplary embodiment, the compound is Formula (I), and Z is substituted or unsubstituted heteroaryl, wherein said heteroaryl has one ring, and said ring comprises an endocyclic boron, X is H, and Y is *—SCH₂—. In an exemplary embodiment, the compound is Formula (I), Z is substituted or unsubstituted heteroaryl, wherein said heteroaryl has two rings, and one of the two rings comprises an endocyclic boron, X is H, and Y is *—SCH₂—. In an exemplary embodiment, the compound is Formula (I), Z is substituted or unsubstituted heterocycloalkyl, wherein said heterocycloalkyl comprises an endocyclic boron, X is H, and Y is *—SCH₂—. In an exemplary embodiment, the compound is Formula (I), and Z is substituted or unsubstituted heterocycloalkyl, wherein said heterocycloalkyl has one ring, and said ring comprises an endocyclic boron, X is H, and Y is *—SCH₂—. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is *—SCH₂—. In an exemplary embodiment, the compound is Formula (I), Z substituted or unsubstituted benzoxaborole, X is H, and Y is *—SCH₂—. In an exemplary embodiment, the compound is Formula (I), Z substituted or unsubstituted pyridinyloxaborole, X is H, and Y is *—SCH₂—. In an exemplary embodiment, the compound is Formula (I), Z substituted or unsubstituted benzoxaborininol, X is H, and Y is *—SCH₂—. In an exemplary embodiment, the compound is Formula (I), Z substituted or unsubstituted benzoxazaborininol, X is H, and Y is *—SCH₂—. In an exemplary embodiment, the compound is Formula (I), Z substituted or unsubstituted benzodiazaborininol, X is H, and Y is *—SCH₂—. In an exemplary embodiment, the compound is Formula (I), Z substituted or unsubstituted oxaborole, X is H, and Y is *—SCH₂—. In an exemplary embodiment, the compound is Formula (I), Z substituted or unsubstituted dihydrobenzoazaborinine, X is H, and Y is *—SCH₂—. In this paragraph, * represents the point of attachment to Z.

In an exemplary embodiment, the compound is Formula (I), Z is substituted or unsubstituted heteroaryl, wherein said heteroaryl comprises an endocyclic boron, X is H, and Y is *—NHCH₂— or *—CH₂NH—. In an exemplary embodiment, the compound is Formula (I), and Z is substituted or unsubstituted heteroaryl, wherein said heteroaryl has one ring, and said ring comprises an endocyclic boron, X is H, and Y is *—NHCH₂— or *—CH₂NH—. In an exemplary embodiment, the compound is Formula (I), Z is substituted or unsubstituted heteroaryl, wherein said heteroaryl has two rings, and one of the two rings comprises an endocyclic boron, X is H, and Y is *—NHCH₂— or *—CH₂NH—. In an exemplary embodiment, the compound is Formula (I), Z is substituted or unsubstituted heterocycloalkyl, wherein said heterocycloalkyl comprises an endocyclic boron, X is H, and Y is *—NHCH₂— or *—CH₂NH—. In an exemplary embodiment, the compound is Formula (I), and Z is substituted or unsubstituted heterocycloalkyl, wherein said heterocycloalkyl has one ring, and said ring comprises an endocyclic boron, X is H, and Y is *—NHCH₂— or *—CH₂NH—. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is *—NHCH₂— or *—CH₂NH—. In an exemplary embodiment, the compound is Formula (I), Z substituted or unsubstituted benzoxaborole, X is H, and Y is *—NHCH₂— or *—CH₂NH—. In an exemplary embodiment, the compound is Formula (I), Z substituted or unsubstituted pyridinyloxaborole, X is H, and Y is *—NHCH₂— or *—CH₂NH—. In an exemplary embodiment, the compound is Formula (I), Z substituted or unsubstituted benzoxaborininol, X is H, and Y is *—NHCH₂— or *—CH₂NH—. In an exemplary embodiment, the compound is Formula (I), Z substituted or unsubstituted benzoxazaborininol, X is H, and Y is *—NHCH₂— or *—CH₂NH—. In an exemplary embodiment, the compound is Formula (I), Z substituted or unsubstituted benzodiazaborininol, X is H, and Y is *—NHCH₂— or *—CH₂NH—. In an exemplary embodiment, the compound is Formula (I), Z substituted or unsubstituted oxaborole, X is H, and Y is *—NHCH₂— or *—CH₂NH—. In an exemplary embodiment, the compound is Formula (I), Z substituted or unsubstituted dihydrobenzoazaborinine, X is H, and Y is *—NHCH₂— or *—CH₂NH—. In this paragraph, * represents the point of attachment to Z.

In an exemplary embodiment, the compound is Formula (I), Z is substituted or unsubstituted heteroaryl, wherein said heteroaryl comprises an endocyclic boron, X is H, and Y is *—C(O)NH— or *—S(O)CH₂— or *—S(O)₂CH₂—. In an exemplary embodiment, the compound is Formula (I), and Z is substituted or unsubstituted heteroaryl, wherein said heteroaryl has one ring, and said ring comprises an endocyclic boron, X is H, and Y is *—C(O)NH— or *—S(O)CH₂— or *—S(O)₂CH₂—. In an exemplary embodiment, the compound is Formula (I), Z is substituted or unsubstituted heteroaryl, wherein said heteroaryl has two rings, and one of the two rings comprises an endocyclic boron, X is H, and Y is *—C(O)NH— or *—S(O)CH₂— or *—S(O)₂CH₂—. In an exemplary embodiment, the compound is Formula (I), Z is substituted or unsubstituted heterocycloalkyl, wherein said heterocycloalkyl comprises an endocyclic boron, X is H, and Y is *—C(O)NH— or *—S(O)CH₂— or —S(O)₂CH₂—. In an exemplary embodiment, the compound is Formula (I), and Z is substituted or unsubstituted heterocycloalkyl, wherein said heterocycloalkyl has one ring, and said ring comprises an endocyclic boron, X is H, and Y is

*—C(O)NH— or *—S(O)CH$_2$— or *—S(O)$_2$CH$_2$—. In an exemplary embodiment, the compound is Formula (I), Z is substituted or unsubstituted heterocycloalkyl, wherein said heterocycloalkyl has two rings, and one of the two rings comprises an endocyclic boron, X is H, and Y is *—C(O)NH— or *—S(O)CH$_2$— or *—S(O)$_2$CH$_2$—. In an exemplary embodiment, the compound is Formula (I), Z substituted or unsubstituted benzoxaborole, X is H, and Y 5 is *—C(O)NH— or *—S(O)CH$_2$— or *—S(O)$_2$CH$_2$—. In an exemplary embodiment, the compound is Formula (I), Z substituted or unsubstituted pyridinyloxaborole, X is H, and Y is *—C(O)NH— or *—S(O)CH$_2$— or *—S(O)$_2$CH$_2$—. In an exemplary embodiment, the compound is Formula (I), Z substituted or unsubstituted benzoxaborininol, X is H, and Y is *—C(O)NH— or *—S(O)CH$_2$— or *—S(O)$_2$CH$_2$—. In an exemplary embodiment, the compound is Formula (I), Z substituted or unsubstituted benzoxazaborininol, X is H, and Y is *—C(O)NH— or *—S(O)CH$_2$— or * S(O)$_2$CH$_2$—. In an exemplary embodiment, the compound is Formula (I), Z substituted or unsubstituted benzodiazaborininol, X is H, and Y is *—C(O)NH— or *—S(O)CH$_2$— or *—S(O)$_2$CH$_2$—. In an exemplary embodiment, the compound is Formula (I), Z substituted or unsubstituted oxaborole, X is H, and Y is *—C(O)NH— or *—S(O)CH$_2$— or *—S(O)$_2$CH$_2$—. In an exemplary embodiment, the compound is Formula (I), Z substituted or unsubstituted dihydrobenzoazaborinine, X is H, and Y is *—C(O)NH— or *—S(O)CH$_2$— or *—S(O)$_2$CH$_2$—. In this paragraph, * represents the point of attachment to Z.

In an exemplary embodiment, the compound is Formula (I), Z is substituted or unsubstituted heteroaryl, wherein said heteroaryl comprises an endocyclic boron, X is F, and Y is a bond. In an exemplary embodiment, the compound is Formula (I), and Z is substituted or unsubstituted heteroaryl, wherein said heteroaryl has one ring, and said ring comprises an endocyclic boron, X is F, and Y is a bond. In an exemplary embodiment, the compound is Formula (I), Z is substituted or unsubstituted heteroaryl, wherein said heteroaryl has two rings, and one of the two rings comprises an endocyclic boron, X is F, and Y is a bond. In an exemplary embodiment, the compound is Formula (I), Z is substituted or unsubstituted heterocycloalkyl, wherein said heterocycloalkyl comprises an endocyclic boron, X is F, and Y is a bond. In an exemplary embodiment, the compound is Formula (I), and Z is substituted or unsubstituted heterocycloalkyl, wherein said heterocycloalkyl has one ring, and said ring comprises an endocyclic boron, X is F, and Y is a bond. In an exemplary embodiment, the compound is Formula (I), Z substituted or unsubstituted heterocycloalkyl, wherein said heterocycloalkyl has two rings, and one of the two rings comprises an endocyclic boron, X is F, and Y is a bond. In an exemplary embodiment, the compound is Formula (I), Z substituted or unsubstituted benzoxaborole, X is F, and Y is a bond. In an exemplary embodiment, the compound is Formula (I), Z substituted or unsubstituted pyridinyloxaborole, X is F, and Y is a bond. In an exemplary embodiment, the compound is Formula (I), Z substituted or unsubstituted benzoxaborininol, X is F, and Y is a bond. In an exemplary embodiment, the compound is Formula (I), Z substituted or unsubstituted benzoxazaborininol, X is F, and Y is a bond. In an exemplary embodiment, the compound is Formula (I), Z substituted or unsubstituted benzodiazaborininol, X is F, and Y is a bond. In an exemplary embodiment, the compound is Formula (I), Z substituted or unsubstituted oxaborole, X is F, and Y is a bond. In an exemplary embodiment, the compound is Formula (I), Z substituted or unsubstituted dihydrobenzoazaborinine, X is F, and Y is a bond.

In an exemplary embodiment, the compound is Formula (I), Z is substituted or unsubstituted heteroaryl, wherein said heteroaryl comprises an endocyclic boron, X is F, and Y is —NH—. In an exemplary embodiment, the compound is Formula (I), and Z is substituted or unsubstituted heteroaryl, wherein said heteroaryl has one ring, and said ring comprises an endocyclic boron, X is F, and Y is —NH—. In an exemplary embodiment, the compound is Formula (I), Z is substituted or unsubstituted heteroaryl, wherein said heteroaryl has two rings, and one of the two rings comprises an endocyclic boron, X is F, and Y is —NH—. In an exemplary embodiment, the compound is Formula (I), Z is substituted or unsubstituted heterocycloalkyl, wherein said heterocycloalkyl comprises an endocyclic boron, X is F, and Y is —NH—. In an exemplary embodiment, the compound is Formula (I), and Z is substituted or unsubstituted heterocycloalkyl, wherein said heterocycloalkyl has one ring, and said ring comprises an endocyclic boron, X is F, and Y is —NH—. In an exemplary embodiment, the compound is Formula (I), Z is substituted or unsubstituted heterocycloalkyl, wherein said heterocycloalkyl has two rings, and one of the two rings comprises an endocyclic boron, X is F, and Y is —NH—. In an exemplary embodiment, the compound is Formula (I), Z substituted or unsubstituted benzoxaborole, X is F, and Y is —NH—. In an exemplary embodiment, the compound is Formula (I), Z substituted or unsubstituted pyridinyloxaborole, X is F, and Y is —NH—. In an exemplary embodiment, the compound is Formula (I), Z substituted or unsubstituted benzoxaborininol, X is F, and Y is —NH—. In an exemplary embodiment, the compound is Formula (I), Z substituted or unsubstituted benzoxazaborininol, X is F, and Y is —NH—. In an exemplary embodiment, the 5 compound is Formula (I), Z substituted or unsubstituted benzodiazaborininol, X is F, and Y is —NH—. In an exemplary embodiment, the compound is Formula (I), Z substituted or unsubstituted oxaborole, X is F, and Y is —NH—. In an exemplary embodiment, the compound is Formula (I), Z substituted or unsubstituted dihydrobenzoazaborinine, X is F, and Y is —NH—.

In an exemplary embodiment, the compound is Formula (I), Z is substituted or unsubstituted heteroaryl, wherein said heteroaryl comprises an endocyclic boron, X is F, and Y is *—OCH$_2$—. In an exemplary embodiment, the compound is Formula (I), and Z is substituted or unsubstituted heteroaryl, wherein said heteroaryl has one ring, and said ring comprises an endocyclic boron, X is F, and Y is *—OCH$_2$—. In an exemplary embodiment, the compound is Formula (I), Z is substituted or unsubstituted heteroaryl, wherein said heteroaryl has two rings, and one of the two rings comprises an endocyclic boron, X is F, and Y is *—OCH$_2$—. In an exemplary embodiment, the compound is Formula (I), Z is substituted or unsubstituted heterocycloalkyl, wherein said heterocycloalkyl comprises an endocyclic boron, X is F, and Y is *—OCH$_2$—. In an exemplary embodiment, the compound is Formula (I), and Z is substituted or unsubstituted heterocycloalkyl, wherein said heterocycloalkyl has one ring, and said ring comprises an endocyclic boron, X is F, and Y is *—OCH$_2$—. In an exemplary embodiment, the compound is Formula (I), Z is substituted or unsubstituted heterocycloalkyl, wherein said heterocycloalkyl has two rings, and one of the two rings comprises an endocyclic boron, X is F, and Y is *—OCH$_2$—. In an exemplary embodiment, the compound is Formula (I), Z substituted or unsubstituted benzoxaborole, X is F, and Y is *—OCH$_2$—. In an exemplary embodiment, the compound is Formula (I), Z substituted or unsubstituted pyridinyloxaborole, X is F, and Y is *—OCH$_2$—. In an exemplary embodiment, the compound is Formula (I), Z substituted or unsubstituted benzoxaborininol, X is F, and Y is *—OCH$_2$—. In an exemplary embodiment, the compound is Formula (I), Z substituted or unsubstituted benzoxazaborininol, X is F, and Y is *—OCH$_2$—. In an exemplary embodiment, the compound is Formula (I), Z substituted or unsubstituted benzodiazaborininol, X is F, and Y is *—OCH$_2$—. In an exemplary embodiment, the compound is Formula (I), Z substituted or unsubstituted oxaborole, X is F, and Y is *—OCH$_2$—. In an exemplary embodiment, the compound is Formula (I), Z substituted or unsubstituted dihydrobenzoazaborinine, X is F, and Y is *—OCH$_2$—. In this paragraph, * represents 5 the point of attachment to Z.

In an exemplary embodiment, the compound is Formula (I), Z is substituted or unsubstituted heteroaryl, wherein said heteroaryl comprises an endocyclic boron, X is F, and Y is *—SCH$_2$—. In an exemplary embodiment, the compound is Formula (I), and Z is substituted or unsubstituted heteroaryl, wherein said heteroaryl has one ring, and said ring comprises an endocyclic boron, X is F, and Y is *—SCH$_2$—. In an exemplary embodiment, the compound is Formula (I), Z is substituted or unsubstituted heteroaryl, wherein said heteroaryl has two rings, and one of the two rings comprises an endocyclic boron, X is F, and Y is *—SCH$_2$—. In an exemplary embodiment, the compound is Formula (I), Z is substituted or unsubstituted heterocycloalkyl, wherein said heterocycloalkyl comprises an endocyclic boron, X is F, and Y is *—SCH$_2$—. In an exemplary embodiment, the compound is Formula (I), and Z is substituted or unsubstituted heterocycloalkyl, wherein said heterocycloalkyl has one ring, and said ring comprises an endocyclic boron, X is F, and Y is *—SCH$_2$—. In an exemplary embodiment, the compound is Formula (I), Z is substituted or unsubstituted heterocycloalkyl, wherein said heterocycloalkyl has two rings, and one of the two rings comprises an endocyclic boron, X is F, and Y is *—SCH$_2$—. In an exemplary embodiment, the compound is Formula (I), Z substituted or unsubstituted benzoxaborole, X is F, and Y is *—SCH$_2$—. In an exemplary embodiment, the compound is Formula (I), Z substituted or unsubstituted pyridinyloxaborole, X is F, and Y is *—SCH$_2$—. In an exemplary embodiment, the compound is Formula (I), Z substituted or unsubstituted benzoxaborininol, X is F, and Y is *—SCH$_2$—. In an exemplary embodiment, the compound is Formula (I), Z substituted or unsubstituted benzoxazaborininol, X is F, and Y is *—SCH$_2$—. In an exemplary embodiment, the compound is Formula (I), Z substituted or unsubstituted benzodiazaborininol, X is F, and Y is *—SCH$_2$—. In an exemplary embodiment, the compound is Formula (I), Z substituted or unsubstituted oxaborole, X is F, and Y is *—SCH$_2$—. In an exemplary embodiment, the compound is Formula (I), Z substituted or unsubstituted dihydrobenzoazaborinine, X is F, and Y is *—SCH$_2$—. In this paragraph, * represents the point of attachment to Z.

In an exemplary embodiment, the compound is Formula (I), Z is substituted or unsubstituted heteroaryl, wherein said heteroaryl comprises an endocyclic boron, X is F, and Y is *—NHCH$_2$— or *—CH$_2$NH—. In an exemplary embodiment, the compound is Formula (I), and Z is substituted or unsubstituted heteroaryl, wherein said heteroaryl has one ring, and said ring comprises an endocyclic boron, X is F, and Y is *—NHCH$_2$— or *—CH$_2$NH—. In an exemplary embodiment, the compound is Formula (I), Z is substituted or unsubstituted heteroaryl, wherein said heteroaryl has two rings, and one of the two rings comprises an endocyclic boron, X is F, and Y is *—NHCH$_2$— or *—CH$_2$NH—. In an exemplary embodiment, the compound is Formula (I), Z is substituted or unsubstituted heterocycloalkyl, wherein said heterocycloalkyl comprises an endocyclic boron, X is F, and Y is *—NHCH$_2$— or *—CH$_2$NH—. In an exemplary embodiment, the compound is Formula (I), and Z is substituted or unsubstituted heterocycloalkyl, wherein said heterocycloalkyl has one ring, and said ring comprises an endocyclic boron, X is F, and Y is *—NHCH$_2$— or *—CH$_2$NH—. In an exemplary embodiment, the compound is Formula (I), Z is substituted or unsubstituted heterocycloalkyl, wherein said heterocycloalkyl has two rings, and one of the two rings comprises an endocyclic boron, X is F, and Y is *—NHCH$_2$— or *—CH$_2$NH—. In an exemplary embodiment, the compound is Formula (I), Z substituted or unsubstituted benzoxaborole, X is F, and Y is *—NHCH$_2$— or *—CH$_2$NH—. In an exemplary embodiment, the compound is Formula (I), Z substituted or unsubstituted pyridinyloxaborole, X is F, and Y is *—NHCH$_2$— or *—CH$_2$NH—. In an exemplary embodiment, the compound is Formula (I), Z substituted or unsubstituted benzoxaborininol, X is F, and Y is *—NHCH$_2$— or *—CH$_2$NH—. In an exemplary embodiment, the compound is Formula (I), Z substituted or unsubstituted benzoxazaborininol, X is F, and Y is *—NHCH$_2$— or *—CH$_2$NH—. In an exemplary embodiment, the compound is Formula (I), Z substituted or unsubstituted benzodiazaborininol, X is F, and Y is *—NHCH$_2$— or *—CH$_2$NH—. In an exemplary embodiment, the compound is Formula (I), Z substituted or unsubstituted oxaborole, X is F, and Y is *—NHCH$_2$— or *—CH$_2$NH—. In an exemplary embodiment, the compound is Formula (I), Z substituted or unsubstituted dihydrobenzoazaborinine, X is F, and Y is *—NHCH$_2$— or *—CH$_2$NH—. In this paragraph, * represents the point of attachment to Z.

In an exemplary embodiment, the compound is Formula (I), Z is substituted or unsubstituted heteroaryl, wherein said heteroaryl comprises an endocyclic boron, X is F, and Y is *—C(O)NH— or *—S(O)CH$_2$— or *—S(O)$_2$CH$_2$—. In an exemplary embodiment, the compound is Formula (I), and Z is substituted or unsubstituted heteroaryl, wherein said heteroaryl has one ring, and said ring comprises an endocyclic boron, X is F, and Y is *—C(O)NH— or *—S(O)CH$_2$— or *—S(O)$_2$CH$_2$—. In an exemplary embodiment, the compound is Formula (I), Z is substituted or unsubstituted heteroaryl, wherein said heteroaryl has two rings, and one of the two rings comprises an endocyclic boron, X is F, and Y is *—C(O)NH— or *—S(O)CH$_2$— or *—S(O)$_2$CH$_2$—. In an exemplary embodiment, the compound is Formula (I), Z is substituted or unsubstituted heterocycloalkyl, wherein said heterocycloalkyl comprises an endocyclic boron, X is F, and Y is *—C(O)NH— or *—S(O)CH$_2$— or —S(O)$_2$CH$_2$—. In an exemplary embodiment, the compound is Formula (I), and Z is substituted or unsubstituted heterocycloalkyl, wherein said heterocycloalkyl has one ring, and said ring comprises an endocyclic boron, X is F, and Y is *—C(O)NH— or *—S(O)CH$_2$— or *—S(O)$_2$CH$_2$—. In an exemplary embodiment, the compound is Formula (I), Z is substituted or unsubstituted heterocycloalkyl, wherein said heterocycloalkyl has two rings, and one of the two rings comprises an endocyclic boron, X is F, and Y is *—C(O)NH— or *—S(O)CH$_2$— or *—S(O)$_2$CH$_2$—. In an exemplary embodiment, the compound is Formula (I), Z substituted or unsubstituted benzoxaborole, X is F, and Y is *—C(O)NH— or *—S(O)CH$_2$— or *—S(O)$_2$CH$_2$—. In an exemplary embodiment, the compound is Formula (I), Z substituted or unsubstituted pyridinyloxaborole, X is F, and Y is *—C(O)NH— or *—S(O)CH$_2$— or *—S(O)$_2$CH$_2$—. In an exemplary embodiment, the compound is Formula (I), Z substituted or unsubstituted benzoxaborininol, X is F, and Y is *—C(O)NH— or *—S(O)CH$_2$— or *—S(O)$_2$CH$_2$—. In an exemplary embodiment, the compound is Formula (I), Z substituted or unsubstituted benzoxazaborininol, X is F, and Y is *—C(O)NH— or *—S(O)CH$_2$— or * S(O)$_2$CH$_2$—. In an exemplary embodiment, the compound is Formula (I), Z substituted or unsubstituted benzodiazaborininol, X is F, and Y is *—C(O)NH— or *—S(O)CH$_2$— or *—S(O)$_2$CH$_2$—. In an exemplary embodiment, the compound is Formula (I), Z substituted or unsubstituted oxaborole, X is F, and Y is *—C(O)NH— or *—S(O)CH$_2$— or *—S(O)$_2$CH$_2$—. In an exemplary embodiment, the compound is Formula (I), Z substituted or unsubstituted dihydrobenzoazaborinine, X is F, and Y is *—C(O)NH— or *—S(O)CH$_2$— or *—S(O)$_2$CH$_2$—. In this paragraph, * represents the point of attachment to Z.

In an exemplary embodiment, the compound is Formula (I), Z is substituted or unsubstituted heteroaryl, wherein said heteroaryl comprises an endocyclic boron, X is OH, and Y is a bond. In an exemplary embodiment, the compound is Formula (I), and Z is substituted or unsubstituted heteroaryl, wherein said heteroaryl has one ring, and said ring comprises an endocyclic boron, X is OH, and Y is a bond. In an exemplary embodiment, the compound is Formula (I), Z is substituted or unsubstituted heteroaryl, wherein said heteroaryl has two rings, and one of the two rings comprises an endocyclic boron, X is OH, and Y is a bond. In an exemplary embodiment, the compound is Formula (I), Z is substituted or unsubstituted heterocycloalkyl, wherein said heterocycloalkyl comprises an endocyclic boron, X is OH, and Y is a bond. In an exemplary embodiment, the compound is Formula (I), and Z is substituted or unsubstituted heterocycloalkyl, wherein said heterocycloalkyl has one ring, and said ring comprises an endocyclic boron, X is OH, and Y is a bond. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is a bond. In an exemplary embodiment, the compound is Formula (I), Z substituted or unsubstituted benzoxaborole, X is OH, and Y is a bond. In an exemplary embodiment, the compound is Formula (I), Z substituted or unsubstituted pyridinyloxaborole, X is OH, and Y is a bond. In an exemplary embodiment, the compound is Formula (I), Z substituted or unsubstituted benzoxaborininol, X is OH, and Y is a bond. In an exemplary embodiment, the compound is Formula (I), Z substituted or unsubstituted benzoxazaborininol, X is OH, and Y is a bond. In an exemplary embodiment, the compound is Formula (I), Z substituted or unsubstituted benzodiazaborininol, X is OH, and Y is a bond. In an exemplary embodiment, the compound is Formula (I), Z substituted or unsubstituted oxaborole, X is OH, and Y is a bond. In an exemplary embodiment, the compound is Formula (I), Z substituted or unsubstituted dihydrobenzoazaborinine, X is OH, and Y is a bond.

In an exemplary embodiment, the compound is Formula (I), Z is substituted or unsubstituted heteroaryl, wherein said heteroaryl comprises an endocyclic boron, X is OH, and Y is —NH—. In an exemplary embodiment, the compound is Formula (I), and Z is substituted or unsubstituted heteroaryl, wherein said heteroaryl has one ring, and said ring comprises an endocyclic boron, X is OH, and Y is —NH—. In an exemplary embodiment, the compound is Formula (I), Z is substituted or unsubstituted heteroaryl, wherein said heteroaryl has two rings, and one of the two rings comprises an endocyclic boron, X is OH, and Y is —NH—. In an exemplary embodiment, the compound is Formula (I), Z is substituted or unsubstituted heterocycloalkyl, wherein said heterocycloalkyl comprises an endocyclic boron, X is OH, and Y is —NH—. In an exemplary embodiment, the compound is Formula (I), and Z is substituted or unsubstituted heterocycloalkyl, wherein said heterocycloalkyl has one ring, and said ring comprises an endocyclic boron, X is OH, and Y is —NH—. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is —NH—. In an exemplary embodiment, the compound is Formula (I), Z substituted or unsubstituted benzoxaborole, X is OH, and Y is —NH—. In an exemplary embodiment, the compound is Formula (I), Z substituted or unsubstituted pyridinyloxaborole, X is OH, and Y is —NH—. In an exemplary embodiment, the compound is Formula (I), Z substituted or unsubstituted benzoxaborininol, X is OH, and Y is —NH—. In an exemplary embodiment, the compound is Formula (I), Z substituted or unsubstituted benzoxazaborininol, X is OH, and Y is —NH—. In an exemplary embodiment, the compound is Formula (I), Z substituted or unsubstituted benzodiazaborininol, X is OH, and Y is —NH—. In an exemplary embodiment, the compound is Formula (I), Z substituted or unsubstituted oxaborole, X is OH, and Y is —NH—. In an exemplary embodiment, the compound is Formula (I), Z substituted or unsubstituted dihydrobenzoazaborinine, X is OH, and Y is —NH—.

In an exemplary embodiment, the compound is Formula (I), Z is substituted or unsubstituted heteroaryl, wherein said heteroaryl comprises an endocyclic boron, X is OH, and Y is *—OCH$_2$—. In an exemplary embodiment, the compound is Formula (I), and Z is substituted or unsubstituted heteroaryl, wherein said heteroaryl has one ring, and said ring comprises an endocyclic boron, X is OH, and Y is *—OCH$_2$—. In an exemplary embodiment, the compound is Formula (I), Z is substituted or unsubstituted heteroaryl, wherein said heteroaryl has two rings, and one of the two rings comprises an endocyclic boron, X is OH, and Y is *—OCH$_2$—. In an exemplary embodiment, the compound is Formula (I), Z is substituted or unsubstituted 5 heterocycloalkyl, wherein said heterocycloalkyl comprises an endocyclic boron, X is OH, and Y is *—OCH$_2$—. In an exemplary embodiment, the compound is Formula (I), and Z is substituted or unsubstituted heterocycloalkyl, wherein said heterocycloalkyl has one ring, and said ring comprises an endocyclic boron, X is OH, and Y is *—OCH$_2$—. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is *—OCH$_2$—. In an exemplary embodiment, the compound is Formula (I), Z substituted or unsubstituted benzoxaborole, X is OH, and Y is *—OCH$_2$—. In an exemplary embodiment, the compound is Formula (I), Z substituted or unsubstituted pyridinyloxaborole, X is OH, and Y is *—OCH$_2$—. In an exemplary embodiment, the compound is Formula (I), Z substituted or unsubstituted benzoxaborininol, X is OH, and Y is *—OCH$_2$—. In an exemplary embodiment, the compound is Formula (I), Z substituted or unsubstituted benzoxazaborininol, X is OH, and Y is *—OCH$_2$—. In an exemplary embodiment, the compound is Formula (I), Z substituted or unsubstituted benzodiazaborininol, X is OH, and Y is *—OCH$_2$—. In an exemplary embodiment, the compound is Formula (I), Z substituted or unsubstituted oxaborole, X is OH, and Y is *—OCH₂—. In an exemplary embodiment, the compound is Formula (I), Z substituted or unsubstituted dihydrobenzoazaborinine, X is OH, and Y is *—OCH₂—. In this paragraph, * represents the point of attachment to Z.

In an exemplary embodiment, the compound is Formula (I), Z is substituted or unsubstituted heteroaryl, wherein said heteroaryl comprises an endocyclic boron, X is OH, and Y is *—SCH₂—. In an exemplary embodiment, the compound is Formula (I), and Z is substituted or unsubstituted heteroaryl, wherein said heteroaryl has one ring, and said ring comprises an endocyclic boron, X is OH, and Y is *—SCH₂—. In an exemplary embodiment, the compound is Formula (I), Z is substituted or unsubstituted heteroaryl, wherein said heteroaryl has two rings, and one of the two rings comprises an endocyclic boron, X is OH, and Y is *—SCH₂—. In an exemplary embodiment, the compound is Formula (I), Z is substituted or unsubstituted heterocycloalkyl, wherein said heterocycloalkyl comprises an endocyclic boron, X is OH, and Y is *—SCH₂—. In an exemplary embodiment, the compound is Formula (I), and Z is substituted or unsubstituted heterocycloalkyl, wherein said heterocycloalkyl has one ring, and said ring comprises an endocyclic boron, X is OH, and Y is *—SCH₂—. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is *—SCH₂—. In an exemplary embodiment, the compound is Formula (I), Z substituted or unsubstituted benzoxaborole, X is OH, and Y is *—SCH₂—. In an exemplary embodiment, the compound is Formula (I), Z substituted or unsubstituted pyridinyloxaborole, X is OH, and Y is *—SCH₂—. In an exemplary embodiment, the compound is Formula (I), Z substituted or unsubstituted benzoxaborininol, X is OH, and Y is *—SCH₂—. In an exemplary embodiment, the compound is Formula (I), Z substituted or unsubstituted benzoxazaborininol, X is OH, and Y is *—SCH₂—. In an exemplary embodiment, the compound is Formula (I), Z substituted or unsubstituted benzodiazaborininol, X is OH, and Y is *—SCH₂—. In an exemplary embodiment, the compound is Formula (I), Z substituted or unsubstituted oxaborole, X is OH, and Y is *—SCH₂—. In an exemplary embodiment, the compound is Formula (I), Z substituted or unsubstituted dihydrobenzoazaborinine, X is OH, and Y is *—SCH₂—. In this paragraph, * represents the point of attachment to Z.

In an exemplary embodiment, the compound is Formula (I), Z is substituted or unsubstituted heteroaryl, wherein said heteroaryl comprises an endocyclic boron, X is OH, and Y is *—NHCH₂— or *—CH₂NH—. In an exemplary embodiment, the compound is Formula (I), and Z is substituted or unsubstituted heteroaryl, wherein said heteroaryl has one ring, and said ring comprises an endocyclic boron, X is OH, and Y is *—NHCH₂— or *—CH₂NH—. In an exemplary embodiment, the compound is Formula (I), Z is substituted or unsubstituted heteroaryl, wherein said heteroaryl has two rings, and one of the two rings comprises an endocyclic boron, X is OH, and Y is *—NHCH₂— or *—CH₂NH—. In an exemplary embodiment, the compound is Formula (I), Z is substituted or unsubstituted heterocycloalkyl, wherein said heterocycloalkyl comprises an endocyclic boron, X is OH, and Y is *—NHCH₂— or *—CH₂NH—. In an exemplary embodiment, the compound is Formula (I), and Z is substituted or unsubstituted heterocycloalkyl, wherein said heterocycloalkyl has one ring, and said ring comprises an endocyclic boron, X is OH, and Y is *—NHCH₂— or *—CH₂NH—. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is *—NHCH₂— or *—CH₂NH—. In an exemplary embodiment, the compound is Formula (I), Z substituted or unsubstituted benzoxaborole, X is OH, and Y is *—NHCH₂— or *—CH₂NH—. In an exemplary embodiment, the compound is Formula (I), Z substituted or unsubstituted pyridinyloxaborole, X is OH, and Y is *—NHCH₂— or *—CH₂NH—. In an exemplary embodiment, the compound is Formula (I), Z substituted or unsubstituted benzoxaborininol, X is OH, and Y is *—NHCH₂— or *—CH₂NH—. In an exemplary embodiment, the compound is Formula (I), Z substituted or unsubstituted benzoxazaborininol, X is OH, and Y is *—NHCH₂— or *—CH₂NH—. In an exemplary embodiment, the compound is Formula (I), Z substituted or unsubstituted benzodiazaborininol, X is OH, and Y is *—NHCH₂— or *—CH₂NH—. In an exemplary embodiment, the compound is Formula (I), Z substituted or unsubstituted oxaborole, X is OH, and Y is *—NHCH₂— or *—CH₂NH—. In an exemplary embodiment, the compound is Formula (I), Z substituted or unsubstituted dihydrobenzoazaborinine, X is OH, and Y is *—NHCH₂— or *—CH₂NH—. In this paragraph, * represents the point of attachment to Z.

In an exemplary embodiment, the compound is Formula (I), Z is substituted or unsubstituted heteroaryl, wherein said heteroaryl comprises an endocyclic boron, X is OH, and Y is *—C(O)NH— or *—S(O)CH₂— or *—S(O)₂CH₂—. In an exemplary embodiment, the compound is Formula (I), and Z is substituted or unsubstituted heteroaryl, wherein said heteroaryl has one ring, and said ring comprises an endocyclic boron, X is OH, and Y is *—C(O)NH— or *—S(O)CH₂— or *—S(O)₂CH₂—. In an exemplary embodiment, the compound is Formula (I), Z is substituted or unsubstituted heteroaryl, wherein said heteroaryl has two rings, and one of the two rings comprises an endocyclic boron, X is OH, and Y is *—C(O)NH— or *—S(O)CH₂— or *—S(O)₂CH₂—. In an exemplary embodiment, the compound is Formula (I), Z is substituted or unsubstituted heterocycloalkyl, wherein said heterocycloalkyl comprises an endocyclic boron, X is OH, and Y is *—C(O)NH— or *—S(O)CH₂— or —S(O)₂CH₂—. In an exemplary embodiment, the compound is Formula (I), and Z is substituted or unsubstituted heterocycloalkyl, wherein said heterocycloalkyl has one ring, and said ring comprises an endocyclic boron, X is OH, and Y is *—C(O)NH— or *—S(O)CH₂— or *—S(O)₂CH₂—. In an exemplary embodiment, the compound is Formula (I), Z is substituted or unsubstituted heterocycloalkyl, wherein said heterocycloalkyl has two rings, and one of the two rings comprises an endocyclic boron, X is OH, and Y is *—C(O)NH— or *—S(O)CH₂— or *—S(O)₂CH₂—. In an exemplary embodiment, the compound is Formula (I), Z substituted or unsubstituted benzoxaborole, X is OH, and Y is *—C(O)NH— or *—S(O)CH₂— or *—S(O)₂CH₂—. In an exemplary embodiment, the compound is Formula (I), Z substituted or unsubstituted pyridinyloxaborole, X is OH, and Y is *—C(O)NH— or *—S(O)CH₂— or *—S(O)₂CH₂—. In an exemplary embodiment, the compound is Formula (I), Z substituted or unsubstituted benzoxaborininol, X is OH, and Y is *—C(O)NH— or *—S(O)CH₂— or *—S(O)₂CH₂—. In an exemplary embodiment, the compound is Formula (I), Z substituted or unsubstituted benzoxazaborininol, X is OH, and Y is *—C(O)NH— or *—S(O)CH₂— or *—S(O)₂CH₂—. In an exemplary embodiment, the compound is Formula (I), Z substituted or unsubstituted benzodiazaborininol, X is OH, and Y is *—C(O)NH— or *—S(O)CH$_2$— or *—S(O)$_2$CH$_2$—. In an exemplary embodiment, the compound is Formula (I), Z substituted or unsubstituted oxaborole, X is OH, and Y is *—C(O)NH— or *—S(O)CH$_2$— or *—S(O)$_2$CH$_2$—. In an exemplary embodiment, the compound is Formula (I), Z substituted or unsubstituted dihydrobenzoazaborinine, X is OH, and Y is *—C(O)NH— or *—S(O)CH$_2$— or *—S(O)$_2$CH$_2$—. In this paragraph, * represents the point of attachment to Z.

The compounds of the invention can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Combinations Comprising Additional Therapeutically Active Agents

The compounds of the invention may also be used in combination with at least one other therapeutically active agent. The invention thus provides, in a further aspect, a combination comprising a compound of the invention together with at least one other therapeutically active agent, or a salt, prodrug, hydrate or solvate thereof. In an exemplary embodiment, the compound of the invention is a compound described herein, or a salt thereof. In an exemplary embodiment, the additional therapeutically active agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in section III a).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (for example, a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a single unit dosage form which includes a compound of the invention; an antibacterial and a pharmaceutically acceptable excipient. In an exemplary embodiment, the pharmaceutical formulation is a single unit dosage form which includes a compound of the invention; an antibacterial and at least one pharmaceutically acceptable excipient. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an antibacterial and d) a second pharmaceutically acceptable excipient.

III. c) Preparation of Compounds of the Invention

Compounds of the invention can be prepared using commercially available starting materials, known intermediates, or by using the synthetic methods published in references described and incorporated by reference herein, such as U.S. patent application Ser. No. 12/142,692 and U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues. Benzoxaborole, benzoxaborininol, and benzodiazaborininol are shown below for exemplary purposes. The procedures are adaptable to any of the boron ring systems described herein.

General Procedure 1:

A general method of creating a modified pleuromutilin is provided below:

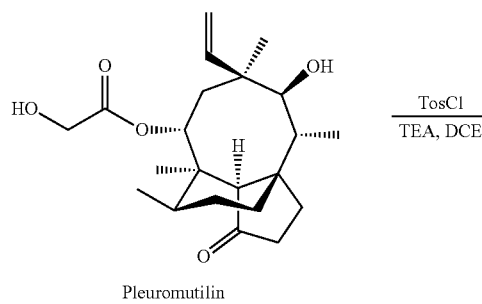

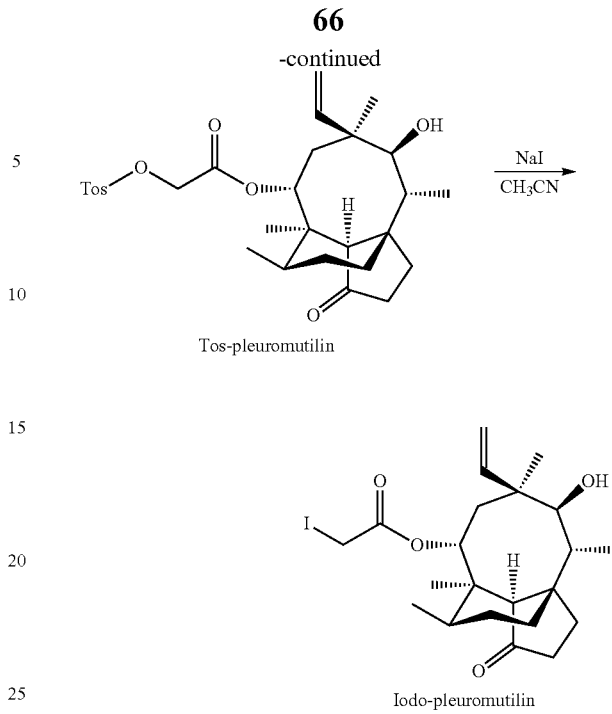

A general method of attaching a modified pleuromutilin to a ring system containing at least one endocyclic boron is provided below.

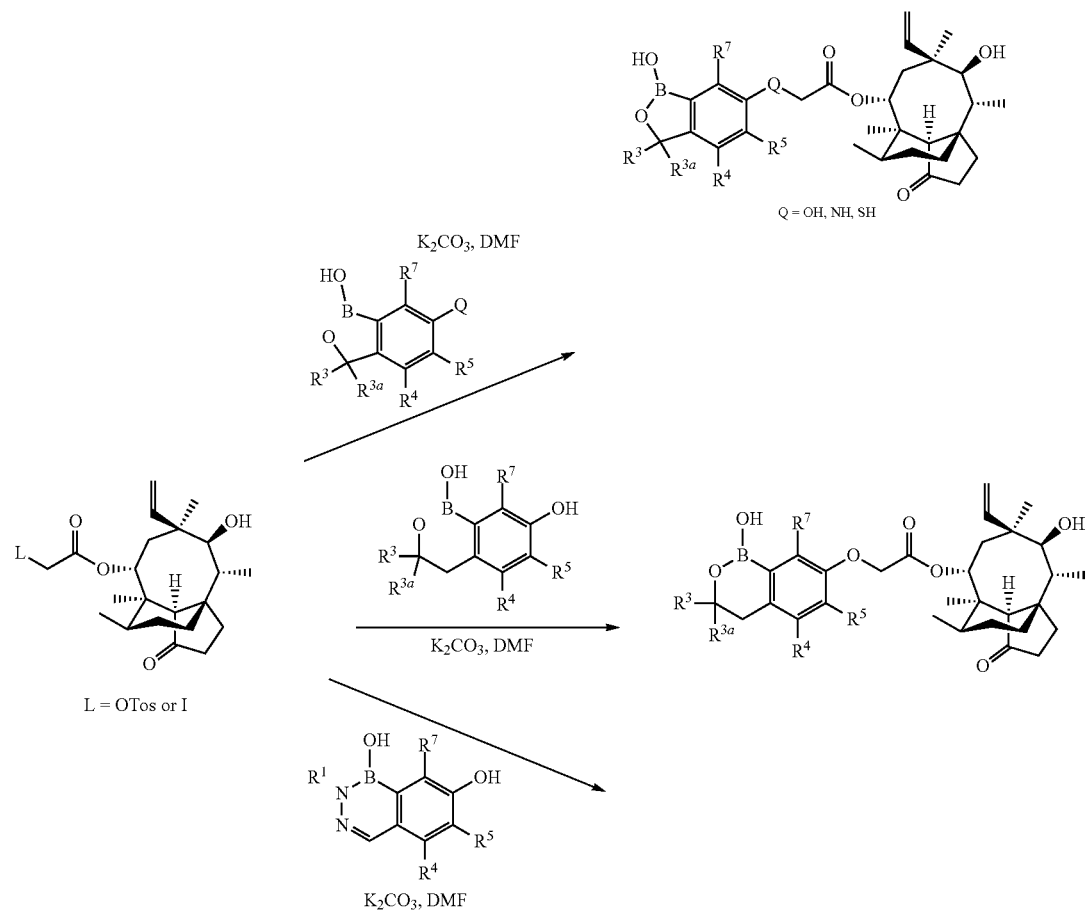

-continued

General Procedure 2:
A general method of creating a modified pleuromutilin is provided below:

A general method of attaching a modified pleuromutilin to a ring system containing at least one endocyclic boron is provided below.

General Procedure 3:

A general method of creating a modified pleuromutilin is provided below:

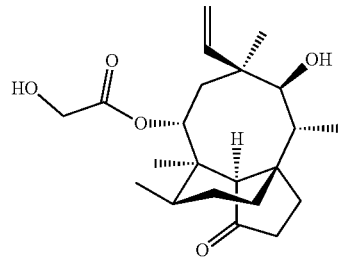

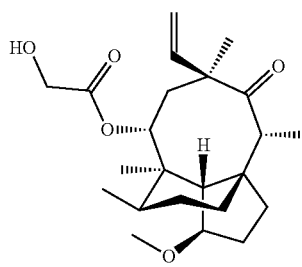

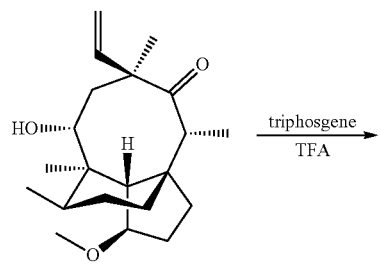

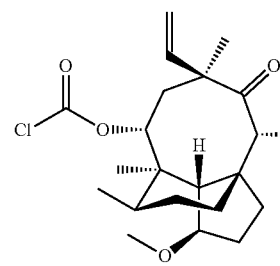

A general method of attaching a modified pleuromutilin to a ring system containing at least one endocyclic boron is provided below:

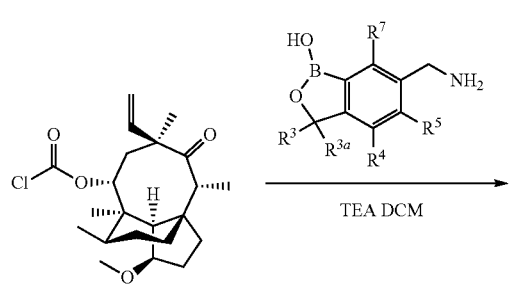

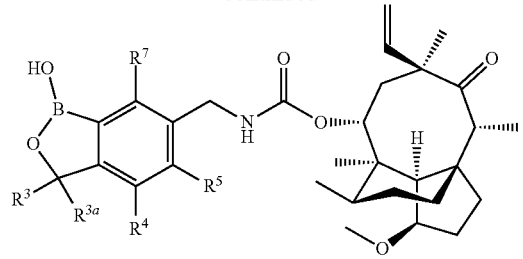

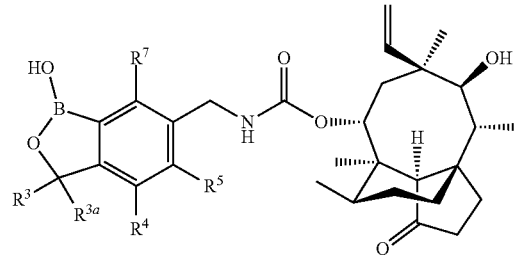

General Procedure 4: Synthesis of Pleuromutilins with C2 Modified with OH

A general method of attaching a C2-modified pleuromutilin to a ring system containing at least one endocyclic boron is provided below:

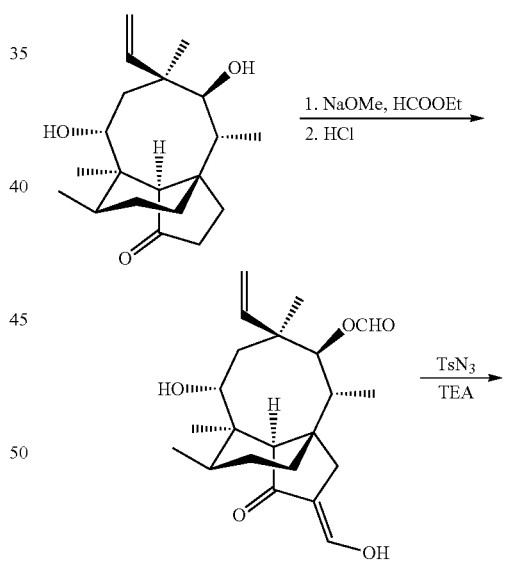

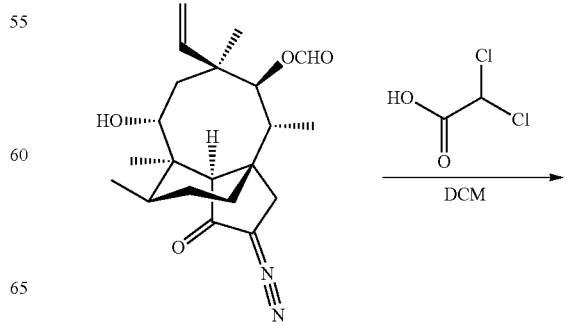

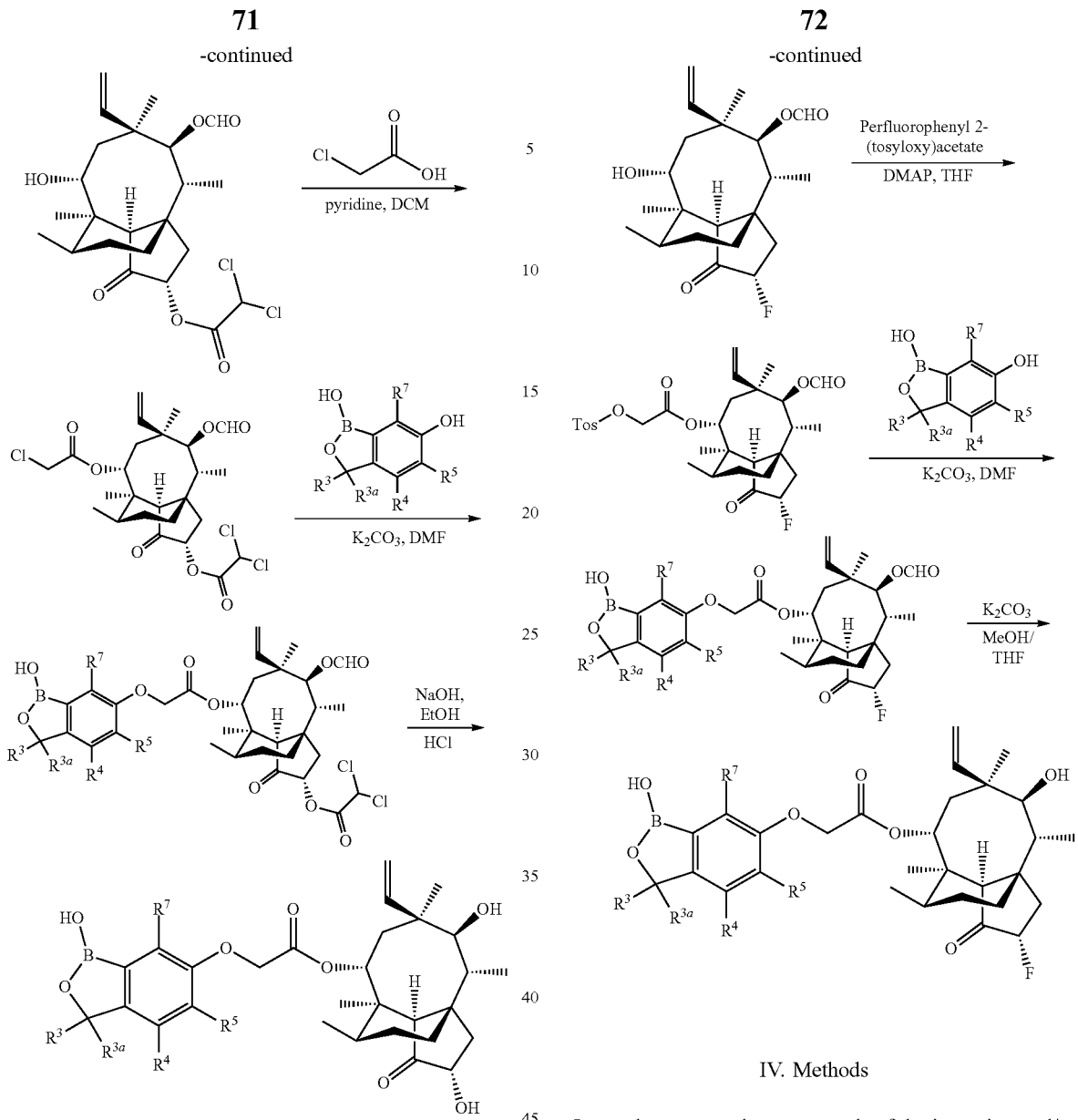

General Procedure 5: Synthesis of Pleuromutilins with C2 Modified with F

A general method of attaching a C2-modified pleuromutilin to a ring system containing at least one endocyclic boron is provided below:

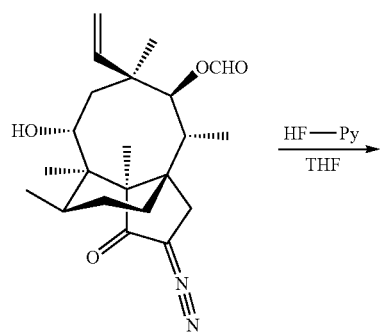

IV. Methods

In another aspect, the compounds of the invention and/or combinations of the invention can be utilized to inhibit protein synthesis in a bacteria. In another aspect, the compounds of the invention and/or combinations of the invention exhibit potency against microorganisms, such as bacteria, and worms, and therefore have the potential to kill and/or inhibit the growth of them. In another aspect, the compounds of the invention and/or combinations of the invention exhibit potency against microorganisms, such as bacteria, and worms, and therefore have the potential to achieve therapeutic efficacy in infections by these microorganisms and/or worms in the animals described herein. In an exemplary embodiment, the bacteria is Gram-positive. In another exemplary embodiment, the bacteria is a symbiont with another organism. In another exemplary embodiment, the bacteria is a symbiont with a worm. In another exemplary embodiment, the bacteria is a symbiont with an arthropod.

IV. A) Inhibiting Microorganism Growth or Killing Microorganisms

The compounds of the invention and/or combinations of the invention exhibit potency against microorganisms, such as bacteria, and therefore have the potential to treat, and/or prevent a microorganism infection, or kill and/or inhibit the growth of microorganisms.

In a further aspect, the invention provides a method of inhibiting the growth of and/or killing a bacteria, the method comprising contacting the bacteria with a compound of the invention, or a pharmaceutically acceptable salt or a hydrate or a solvate thereof, thereby inhibiting the growth of and/or killing the bacteria. In an exemplary embodiment, the bacteria is contacting with a therapeutically effective amount of the compound of the invention. In an exemplary embodiment, the bacteria is contacting with a prophylactically effective amount of the compound of the invention.

In a further aspect, the invention provides a method of treating and/or preventing a microorganism infection, or a method of killing and/or inhibiting the growth of a microorganism, said method comprising contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising contacting said microorganism with an effective amount of a combination of the invention, thereby killing and/or inhibiting the growth of the microorganism.

In a further aspect, the invention provides a method of treating and/or preventing a microorganism infection, or a method of killing and/or inhibiting the growth of a microorganism, said method comprising contacting said microorganism with a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising: contacting said microorganism with an effective amount of a combination of the invention, thereby killing and/or inhibiting the growth of the microorganism.

In a further aspect, the invention provides a method of treating a bacterial infection comprising administering to an animal suffering from the infection an effective amount of a compound of the invention or a combination of the invention, or a pharmaceutically acceptable salt thereof, thereby treating the bacterial infection. In an exemplary embodiment, the invention provides a method of treating a bacterial infection comprising administering to an animal suffering from the infection an effective amount of a compound of the invention, or a pharmaceutically acceptable salt thereof, and an effective amount of an antibacterial, or a pharmaceutically acceptable salt thereof, thereby treating the bacterial infection.

In a further aspect, the invention provides a method of preventing a bacterial infection comprising administering to an animal a prophylactic amount of a compound of the invention or a combination of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof.

In an exemplary embodiment, the microorganism is a bacteria. In an exemplary embodiment, the compound or combination is described herein, or a salt, prodrug, hydrate or solvate thereof, or a combination thereof. In an exemplary embodiment, the invention provides a compound or combination described herein, or a salt, hydrate or solvate thereof. In an exemplary embodiment, the invention provides a compound or combination described herein, or a prodrug thereof. In an exemplary embodiment, the invention provides a compound or combination described herein, or a salt thereof. In another exemplary embodiment, the compound or combination of the invention is a compound or combination described herein, or a pharmaceutically acceptable salt thereof. In another exemplary embodiment, the compound or compound of the combination is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the contacting occurs under conditions which permit entry of the compound into the organism. Such conditions are known to one skilled in the art and are described herein.

In another aspect, the microorganism is inside, and/or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism infection is treated and or prevented, and/or the microorganism is killed or its growth is inhibited, through oral administration of the compound of the invention and/or the combination of the invention. In an exemplary embodiment, the microorganism infection is treated and or prevented, and/or the microorganism is killed or its growth is inhibited through intravenous administration of the compound of the invention and/or the combination of the invention.

In an exemplary embodiment, the microorganism is a bacteria. In an exemplary embodiment, an infection is caused by and/or associated with a microorganism, particularly a bacteria. In an exemplary embodiment, the bacteria is a Gram-positive bacteria. In another exemplary embodiment, the Gram-positive bacteria is selected from the group consisting of *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species, *Streptomyces* species, *Listeria* species. In another exemplary embodiment, the Gram-positive bacteria is selected from the group consisting of *Propionibacterium acnes, Staphylococcus aureus, Staphylococcus epidermidis, Staphylococcus saprophyticus, Staphylococcus haemolyticus, Streptococcus pyogenes, Streptococcus agalactiae, Streptococcus pneumoniae, Enterococcus faecalis, Enterococcus faecium, Bacillus anthracis, Mycobacterium avium-intracellulare, Mycobacterium tuberculosis, Corynebacterium diphtheria, Clostridium perfringens, Clostridium botulinum, Clostridium tetani, Clostridium difficile*, and *Listeria monocytogenes*. In another exemplary embodiment, the Gram-positive bacteria is selected from the group consisting of *Staphylococcus aureus, Staphylococcus epidermidis, Streptococcus pneumoniae, Streptococcus pyogenes, Enterococcus faecalis, Enterococcus faecium, Clostridium difficile* and *Propionibacter acnes*. In an exemplary embodiment, the bacteria is a coagulase positive Staphylococci. In an exemplary embodiment, the bacteria is a coagulase negative Staphylococci. In another exemplary embodiment, the bacteria is *Staphylococcus aureus*. In another exemplary embodiment, the bacteria is methicillin-resistant *Staphylococcus aureus*. In another exemplary embodiment, the bacteria is health care-associated methicillin-resistant *Staphylococcus aureus*. In another exemplary embodiment, the bacteria is community-associated methicillin-resistant *Staphylococcus aureus*. In another exemplary embodiment, the bacteria is *Staphylococcus epidermidis*. In another exemplary embodiment, the bacteria is *Streptococcus pneumoniae*. In another exemplary embodiment, the bacteria is *Streptococcus pyogenes*. In another exemplary embodiment, the bacteria is *Streptococcus agalactiae*. In another exemplary embodiment, the bacteria is a beta-hemolytic Streptococci. In another exemplary embodiment, the bacteria is a beta-hemolytic *Streptococcus pyogenes*. In another exemplary embodiment, the bacteria is a beta-hemolytic *Streptococcus agalactiae*. In another exemplary embodiment, the bacteria is a group A Streptococci. In another exemplary embodiment, the bacteria is a group A *Streptococcus pyogenes*. In another exemplary embodiment, the bacteria is a group B Streptococci. In another exemplary embodiment, the bacteria is a group B *Streptococcus agalactiae*. In another exemplary embodiment, the bacteria is *Enterococcus faecalis*. In another exemplary embodiment, the bacteria is *Enterococcus faecium*.

In an exemplary embodiment, the microorganism is a bacteria, and the bacteria is a Gram-negative bacteria. In an exemplary embodiment, the bacteria is a *Haemophilus* species. In an exemplary embodiment, the bacteria is *Haemophilus influenzae*. In an exemplary embodiment, the bacteria is a *Moraxella* species. In an exemplary embodiment, the bacteria is *Moraxella catarrhalis*.

In an exemplary embodiment, the compounds of the invention exhibit potency against bacteria which are associated with worms. In an exemplary embodiment, the compounds of the invention exhibit potency against bacteria which live inside of worms. In an exemplary embodiment, the compounds of the invention exhibit potency against bacteria which are essential for worm survival. In an exemplary embodiment, the compounds of the invention exhibit potency against bacteria which are a symbiont for a worm. In an exemplary embodiment, the invention provides a method of killing and/or inhibiting the growth of a bacteria which is associated with a worm, comprising contacting the bacteria with an effective amount of the compound of the invention, thereby killing and/or inhibiting the growth of the bacteria. In an exemplary embodiment, the bacteria is of the *Wolbachia* genus. In an exemplary embodiment, the bacteria is *Wolbachia pipientis*.

IV. b) Inhibiting Worm Growth or Killing Worms

The compounds of the present invention exhibit potency against certain worms as a consequence of their ability to kill the endosymbiotic bacteria of the *Wolbachia* genus, and therefore have the potential to kill and/or inhibit the growth of such worms. The invention therefore provides a method of killing a worm, comprising contacting the worm with an effective amount of the compound of the invention, thereby killing the worm. The invention provides a method of inhibiting the growth of a worm, comprising contacting the worm with an effective amount of the compound of the invention, thereby inhibiting the growth of the worm. In an exemplary embodiment, the worm is female. In an exemplary embodiment, the worm is male. In an exemplary embodiment, the worm is a hermaphrotide. In an exemplary embodiment, the worm is an egg. In an exemplary embodiment, the worm is an unfertilized egg. In an exemplary embodiment, the worm is fertilized egg. In an exemplary embodiment, the worm is a larvae. In an exemplary embodiment, the worm is mature. In an exemplary embodiment, the worm is fully mature. In an exemplary embodiment, the worm is contacted with the compound of the invention inside an animal. In an exemplary embodiment, the worm is contacted with the compound of the invention outside of an animal.

In an exemplary embodiment, the worm is a parasitic worm. In an exemplary embodiment, the worm is a helminth. In an exemplary embodiment, the worm is a nematode. In an exemplary embodiment, the nematode is a filarid. In an exemplary embodiment, the nematode is a member of Filarioidea. In an exemplary embodiment, the nematode is a member of Onchocercinae. In an exemplary embodiment, the nematode is a member of Dirofilariinae. In an exemplary embodiment, the nematode is a filarid. In an exemplary embodiment, the nematode is a filarial worm. In an exemplary embodiment, the nematode is a member of the genus *Wuchereria*. In an exemplary embodiment, the nematode is *Wuchereria bancrofti*. In an exemplary embodiment, the nematode is a member of the genus *Brugia*. In an exemplary embodiment, the nematode is *Brugia malayi*. In an exemplary embodiment, the nematode is *Brugia timori*. In an exemplary embodiment, the *Brugia* is a microfilariae. In an exemplary embodiment, the *Brugia* is a larvae. In an exemplary embodiment, the *Brugia* is mature. In an exemplary embodiment, the *Brugia* is contacted by the compound of the invention in the skin of the animal. In an exemplary embodiment, the *Brugia* is contacted by the compound of the invention in the lymphatic system of the animal. In an exemplary embodiment, the *Brugia* is contacted by the compound of the invention in the blood of the animal. In an exemplary embodiment, the *Brugia* is contacted by the compound of the invention in the muscle of the animal. In an exemplary embodiment, the *Brugia* is contacted by the compound of the invention in the salivary gland of the animal.

In an exemplary embodiment, the nematode is a member of the genus *Mansonella*. In an exemplary embodiment, the nematode is selected from the group consisting of *Mansonella streptocerca*, *Mansonella perstans*, and *Mansonella ozzardi*. In an exemplary embodiment, the nematode is a member of the genus *Onchocerca*. In an exemplary embodiment, the nematode is *Onchocerca volvulus*. In an exemplary embodiment, the nematode is *Onchocerca ochengi*.

In an exemplary embodiment, the nematode is a heartworm. In an exemplary embodiment, the nematode is a member of the genus *Dirofilaria*. In an exemplary embodiment, the nematode is *Dirofilaria immitis*. In an exemplary embodiment, the nematode is *Dirofilaria tenuis* or *Dirofilaria repens*.

IV. c) Diseases

The compounds of the invention and/or combinations of the invention exhibit potency against microorganisms, such as bacteria, and therefore have the potential to achieve therapeutic efficacy in the animals described herein. The compounds of the invention and/or combinations of the invention exhibit potency against worms, and therefore have the potential to achieve therapeutic efficacy in the animals described herein.

In another aspect, the invention provides a method of treating and/or preventing a disease. In an exemplary embodiment, the method includes administering to the animal a therapeutically and/or prophylactically effective amount of a compound of the invention, sufficient to treat and/or prevent the disease. In an exemplary embodiment, the method includes administering to the animal a therapeutically and/or prophylactically effective amount of a combination of the invention, sufficient to treat and/or prevent the disease. In an exemplary embodiment, the animal being administered the compound is not otherwise in need of treatment with a compound of the invention.

In an exemplary embodiment, the compound of the invention or the combination of the invention can be used in human or veterinary medical therapy, particularly in the treatment or prophylaxis of bacterial-associated disease. In an exemplary embodiment, the compound of the invention or the combination of the invention can be used in human or veterinary medical therapy, particularly in the treatment of a Gram-positive bacterial-associated disease. In an exemplary embodiment, the compound of the invention or the combination of the invention can be used in human or veterinary medical therapy, particularly in the prophylaxis of a Gram-positive bacterial-associated disease. In an exemplary embodiment, the compound of the invention or the combination of the invention can be used in human or veterinary medical therapy, particularly in the treatment of a *Wolbachia*-associated disease. In an exemplary embodiment, the compound of the invention or the combination of the invention can be used in human or veterinary medical therapy, particularly in the prophylaxis of a *Wolbachia*-associated disease. In another exemplary embodiment, the disease is pneumonia. In another exemplary embodiment, the disease is hospital-acquired pneumonia. In another exemplary embodiment, the disease is hospital-associated pneumonia. In another exemplary embodiment, the disease is community-acquired pneumonia. In another exemplary embodiment, the disease is a acute bacterial skin and skin-structure infection (ABSSSI). In another exemplary embodiment, the disease is bacteremia. In another exemplary embodiment, the disease is endocarditis. In another exemplary embodiment, the disease is osteomyelitis. In an exemplary embodiment, the disease is associated with a *Staphylococcus* species. In another exemplary embodiment, the disease is selected from the group consisting of pneumonia, gastroenteritis, toxic shock syndrome, community acquired pneumonia (CAP), meningitis, septic arthritis, urinary tract infection, bacteremia, endocarditis, osteomylitis, skin and skin-structure infection. In an exemplary embodiment, the disease is associated with a *Streptococcus* species. In another exemplary embodiment, the disease is selected from the group consisting of strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diptheria. In an exemplary embodiment, the disease is associated with a *Listeria* species. In an exemplary embodiment, the disease is meningitis. In an exemplary embodiment, the disease is associated with a *Bacillus* species. In another exemplary embodiment, the disease is anthrax or food poisoning. In an exemplary embodiment, the disease is associated with a *Clostridium* species. In another exemplary embodiment, the disease is selected from the group consisting of botulism, tetanus, gas gangrene and diarrhea. In an exemplary embodiment, the disease is associated with a *Mycobacterium* species. In another exemplary embodiment, the disease is tuberculosis or leprosy. In an exemplary embodiment, the disease is associated with a *Listeria* species. In an exemplary embodiment, the disease is associated with a *Wolbachia* species. In an exemplary embodiment, the disease is associated with *Wolbachia pipientis*. In an exemplary embodiment, the disease is selected from the group consisting of candidiasis, aspergillosis, coccidioidomycosis, cryptococcosis, histoplasmosis, blastomycosis, paracoccidioidomycosis, zygomycosis, phaeohyphomycosis and rhinosporidiosis.

In an exemplary embodiment, the compound of the invention can be used in human medical therapy, particularly in the treatment of worm-associated disease. In an exemplary embodiment, the compound of the invention can be used in human medical therapy, particularly in the prophylaxis of worm-associated disease. In an exemplary embodiment, the compound of the invention can be used in veterinary medical therapy, particularly in the treatment of worm-associated disease. In an exemplary embodiment, the compound of the invention can be used in veterinary medical therapy, particularly in the prophylaxis of worm-associated disease. In an exemplary embodiment, the compound of the invention can be used in human medical therapy, particularly in the treatment of helminth-associated disease. In an exemplary embodiment, the compound of the invention can be used in human medical therapy, particularly in the prophylaxis of helminth-associated disease. In an exemplary embodiment, the compound of the invention can be used in veterinary medical therapy, particularly in the treatment of helminth-associated disease. In an exemplary embodiment, the compound of the invention can be used in veterinary medical therapy, particularly in the prophylaxis of helminth-associated disease. In an exemplary embodiment, the disease is associated with a worm. In an exemplary embodiment, the disease is caused by a worm. In an exemplary embodiment, the disease is associated with a worm described herein. In an exemplary embodiment, the disease is associated with a nematode. In an exemplary embodiment, the disease is associated with a nematode described herein. In an exemplary embodiment, the nematode is *Wuchereria bancrofti*. In an exemplary embodiment, the nematode is *Brugia malayi*. In an exemplary embodiment, the nematode is *Brugia timori*. In an exemplary embodiment, the nematode is *Dirofilaria immitis*. In an exemplary embodiment, the disease is a member selected from enterobiasis, filariasis, and onchocerciasis. In an exemplary embodiment, the disease is lymphatic filariasis. In an exemplary embodiment, the disease is bancroftian filariasis. In an exemplary embodiment, the disease is lymphadenitis. In an exemplary embodiment, the disease is lymphangitis. In an exemplary embodiment, the disease is lymphedema. In an exemplary embodiment, the disease is subcutaneous filariasis. In an exemplary embodiment, the disease is serious cavity filariasis. In an exemplary embodiment, the disease is elephantiasis. In an exemplary embodiment, the disease is elephantiasis *tropica*. In an exemplary embodiment, the disease is onchocerciasis.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the disease is a systemic disease. In another exemplary embodiment, the disease is a topical disease.

In an exemplary embodiment, the disease is treated through oral administration of a compound of the invention and/or a combination of the invention. In an exemplary embodiment, the disease is treated through intravenous administration of a compound of the invention and/or a combination of the invention. In an exemplary embodiment, the disease is treated through intramuscular administration of a compound of the invention and/or a combination of the invention. In an exemplary embodiment, the disease is treated through topical administration of a compound of the invention and/or a combination of the invention.

In an exemplary embodiment, for any of the methods described herein, a compound of the invention, a combination of the invention, a compound described herein or a pharmaceutically acceptable salt thereof, or combination described herein, and/or a pharmaceutical formulation described herein can be used.

V. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

Information regarding excipients of use in the formulations of the invention can be found in *Remington: The Science and Practice of Pharmacy*, 21st Ed., Pharmaceutical Press (2011) which is incorporated herein by reference.

Exemplary embodiments are summarized herein below.

In an exemplary embodiment, the invention provides a compound, or a salt or a hydrate or a solvate thereof, having a structure according to the following formula:

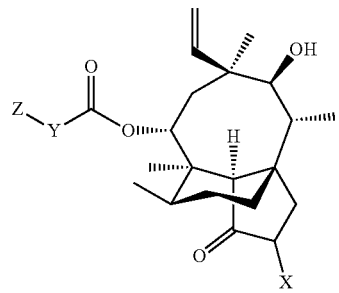

wherein X is H or F or OH; Y is selected from the group consisting of a bond, —O—, —S—, —NH—, substituted or unsubstituted alkylene, and substituted or unsubstituted heteroalkylene; and Z is a substituted or unsubstituted heterocyclic ring or ring system containing at least one endocyclic boron.

In an exemplary embodiment, according to the above paragraph, the compound, or a salt or a hydrate or a solvate thereof, wherein said Y is *—OCH$_2$— or *—SCH$_2$— or *—NHCH$_2$— or *—CH$_2$NH— or *—C(O)NH—, wherein * represents the point of attachment to said Z.

In an exemplary embodiment, according to any of the above paragraphs, for the compound, or a salt or a hydrate or a solvate thereof, wherein said Z is selected from the group consisting of substituted or unsubstituted benzoxaborole, substituted or unsubstituted pyridinyloxaborole, substituted or unsubstituted benzoxaborininol, substituted or unsubstituted benzoxazaborininol, substituted or unsubstituted benzodiazaborininol, substituted or unsubstituted oxaborole, and substituted or unsubstituted dihydrobenzoazaborinine.

In an exemplary embodiment, according to any of the above paragraphs, for the compound, or a salt or a hydrate or a solvate thereof, wherein said Z is

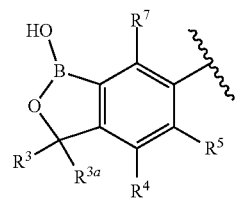

wherein $R^3$, $R^{3a}$, $R^4$, $R^5$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$, wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, the compound, or a salt or a hydrate or a solvate thereof, which is (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate.

In an exemplary embodiment, according to any of the above paragraphs, the compound, or a salt or a hydrate or a solvate thereof, which is (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-fluoro-1-hydroxy-1,3-dihydrobenzo[c][1,2]oxaborol-6-yl)glycinate.

In an exemplary embodiment, according to any of the above paragraphs, the compound, or a salt or a hydrate or a solvate thereof, which is (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((7-fluoro-1-hydroxy-1,3-dihydrobenzo[c][1,2]oxaborol-6-yl)methyl) carbamate.

In an exemplary embodiment, according to any of the above paragraphs, the compound, or a salt or a hydrate or a solvate thereof, wherein said Z is

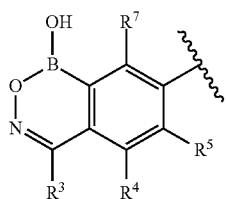

wherein $R^3$, $R^4$, $R^5$, and $R^7$ are each independently selected from the group consisting 5 of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$, wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, the compound, or a salt or a hydrate or a solvate thereof, which is (3aR,4R,5R,7S,8S,9R,9aS,12R)-8-hydroxy-4,7,9,12-tetramethyl-3-oxo-7-vinyldecahydro-4, 9a-propanocyclopenta[8]annulen-5-yl 2-((1-hydroxy-1H-benzo[d][1,2,6]oxazaborinin-7-yl)oxy)acetate.

In an exemplary embodiment, according to any of the above paragraphs, the compound, or a salt or a hydrate or a solvate thereof, wherein said Z is

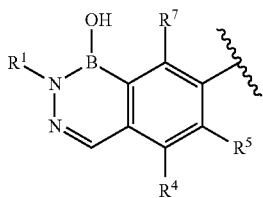

wherein $R^1$, $R^4$, $R^5$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, the compound, or a salt or a hydrate or a solvate thereof, which is methyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate.

In an exemplary embodiment, the invention provides a combination comprising: the compound of a preceding claim, or a pharmaceutically acceptable salt thereof, together with at least one other therapeutically active agent.

In an exemplary embodiment, according to the above combination paragraph, wherein the other therapeutically active agent is an anti-bacterial agent.

In an exemplary embodiment, the invention provides a pharmaceutical formulation comprising: a) the compound of a preceding claim, or a pharmaceutically acceptable salt or a hydrate or a solvate thereof; and b) a pharmaceutically acceptable excipient.

In an exemplary embodiment, according to the above pharmaceutical formulation paragraph, the pharmaceutical formulation is an oral formulation or an intravenous formulation.

In an exemplary embodiment, according to any of the above paragraphs, the salt of the compound according to any of the above paragraphs is a pharmaceutically acceptable salt.

In an exemplary embodiment, the invention is a method of inhibiting protein synthesis in a bacteria, the method comprising contacting the bacteria with the compound in any of the above paragraphs, or a pharmaceutically acceptable salt or a hydrate or a solvate thereof, thereby inhibiting protein synthesis in the bacteria.

In an exemplary embodiment, the invention is a method of inhibiting the growth of and/or killing a bacteria, the method comprising contacting the bacteria with the compound in any of the above paragraphs, or a pharmaceutically acceptable salt or a hydrate or a solvate thereof, thereby inhibiting the growth of and/or killing the bacteria.

In an exemplary embodiment, according to any of the above method paragraphs, wherein the bacteria is Gram-positive.

In an exemplary embodiment, according to any of the above method paragraphs, wherein the bacteria is *Staphylococcus aureus* or *Streptococcus pneumoniae*.

In an exemplary embodiment, according to any of the above method paragraphs, wherein the bacteria is methicillin-resistant *Staphylococcus aureus*.

In an exemplary embodiment, according to any of the above method paragraphs, wherein the bacteria is of the *Wolbachia* genus.

In an exemplary embodiment, according to any of the above method paragraphs, wherein the bacteria is *Wolbachia pipientis*.

In an exemplary embodiment, the invention is a method of treating a disease in an animal in need of the treatment, the method comprising administering to the animal a therapeutically effective amount of the compound in any of the above paragraphs, or a pharmaceutically acceptable salt or a hydrate or a solvate thereof, thereby treating the disease.

In an exemplary embodiment, according to the above method paragraph, wherein the disease is associated with a Gram-positive bacteria.

In an exemplary embodiment, according to any of the above method paragraphs, wherein the disease is pneumonia.

In an exemplary embodiment, according to any of the above method paragraphs, wherein the disease is onchocerciasis.

In an exemplary embodiment, according to any of the above method paragraphs, the animal is a human.

In an exemplary embodiment, according to any of the above method paragraphs, there is a proviso that the animal is not otherwise in need of treatment with a compound of the invention.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

1. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate

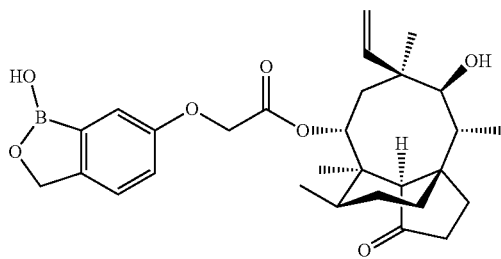

TosCl (19.1 g, 0.1 mol) in 1,2-dichloroethane (100 mL) was slowly added to a mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-hydroxyacetate (35.4 g, 0.1 mol), triethylamine (12.0 g, 0.1 mol) and pyridine (1 mL) in 1,2-dichloroethane (100 mL). The mixture was stirred at 10-15° C. for 20 hrs, washed with water (3×100 mL), then concentrated to dryness. Purification was achieved by recrystallization from DCM/Petroleum ether (1:100) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate as a white solid (45.0 g, yield 90.0%). $^1$H NMR (DMSO-d$_6$, 400 MHz) δ 7.80 (d, J=8.0 Hz, 1H), 7.47 (d, J=8.0 Hz, 1H), 6.05 (dd, J=17.8, 11.2 Hz, 1H), 5.53 (d, J=8.4 Hz, 1H), 5.09-4.96 (m, 2H), 4.81-4.59 (m, 2H), 3.40 (d, J=5.6 Hz, 1H), 2.41 (s, 2H), 2.39 (br. s., 1H), 2.24-1.95 (m, 5H), 1.75-1.41 (m, 4H), 1.30 (s, 4H), 1.27-1.18 (m, 4H), 1.03 (s, 3H), 0.99-0.92 (m, 2H), 0.81 (d, J=7.2 Hz, 3H), 0.50 (d, J=7.2 Hz, 3H).

Tos-pleuromutilin (1.8 g, 3.3 mmol), benzo[c][1,2]oxaborole-1,6(3H)-diol (0.5 g, 3.3 mmol) and K$_2$CO$_3$ (0.7 g, 5.0 mmol) in 20 mL of DMF was heated to 50° C. overnight. Main peak was product in LCMS. Water was added and the mixture was adjust pH<4 with 2N HCl. The solid was filtered and the crude product was purified by Pre-HPLC (column: Luna C18 250×30 mm, 10 μm; liquid phase: [A-TFA/H$_2$O=0.1% v/v; B-ACN] B %: 35%-65%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-1,3-dihydrobenzo[c][1,2]oxaborol-6-yl)oxy) acetate (1.0 g, yield 57.0%). $^1$H NMR (DMSO-d$_6$, 400 MHz) δ 7.30 (d, J=8.4 Hz, 1H), 7.19 (d, J=2.0 Hz, 1H), 7.04 (dd, J=8.4, 2.4 Hz, 1H) 6.10 (dd, J=17.6, 11.2 Hz, 1H), 5.59 (d, J=8.4 Hz, 1H), 5.11-4.97 (m, 2H), 4.91 (s, 2H), 4.76-4.63 (m, 2H), 3.41 (d, J=5.6 Hz, 1H), 2.40 (br. s., 1H), 2.26-1.99 (m, 4H), 1.72-1.43 (m, 4H), 1.38 (d, J=13.2 Hz, 1H), 1.34 (s, 3H), 1.29-1.15 (m, 4H), 1.03 (s, 3H), 1.01 (br. s., 1H), 0.81 (d, J=6.8 Hz, 3H), 0.63 (d, J=6.8 Hz, 3H).

2. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate

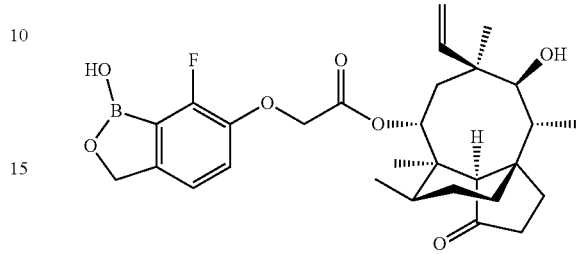

To a solution of Tos-pleuromutilin (51.5 g, 96.7 mmol, 1.0 eq.) in CH$_3$CN (600.0 mL) was added NaI (87.0 g, 580.1 mmol, 6.0 eq.). The mixture was stirred at 90° C. for 16 hours. HPLC indicated the reaction was completed. The reaction mixture was concentrated under reduced pressure to remove CH$_3$CN. The residue was diluted with H$_2$O (500 mL) and extracted with DCM (500 mL×3). The combined organic layers were concentrated under reduced pressure to give a residue. The residue was washed with petroleum ether (200 mL). (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-iodoacetate (40.0 g, 81.9 mmol, 84.7% yield) was obtained as a yellow solid. $^1$H NMR (DMSO-d$_6$, 400 MHz) δ 6.11 (dd, J=11.2, 17.9 Hz, 1H), 5.52 (d, J=7.9 Hz, 1H), 5.13-5.01 (m, 2H), 4.55 (d, J=5.7 Hz, 1H), 3.82-3.75 (m, 1H), 3.73-3.66 (m, 1H), 3.43 (t, J=5.3 Hz, 1H), 2.45-2.39 (m, 1H), 2.25-2.00 (m, 4H), 1.72-1.57 (m, 2H), 1.53-1.21 (m, 9H), 1.11-0.97 (m, 4H), 0.83 (d, J=6.6 Hz, 3H), 0.64 (d, J=7.1 Hz, 3H).

To a solution of 2,3-difluorophenol (300.0 g, 2.3 mol, 1.0 eq) in DCM (1.5 L) was added MOM-Cl (278.9 g, 3.5 mol, 1.5 eq) and DIEA (597.1 g, 4.6 mol, 2.0 eq). The mixture was stirred at 0° C. for 2 hours. TLC indicated that STM was consumed. The reaction mixture was quenched by addition of H$_2$O (1500 mL) at 0° C., and then was adjusted to pH=6. The combined organic layers were washed with saturation NH$_4$Cl (500 mL×3), dried over Na$_2$SO$_4$, filtered and concentrated under reduced pressure to give a residue. 1,2-difluoro-3-(methoxymethoxy)benzene (400.0 g, 2.3 mol, 99.4% yield) was obtained as yellow oil which was used into the next step without further purification. $^1$H NMR (CDCl$_3$, 400 MHz) δ 7.03-6.93 (m, 1H), 6.89-6.78 (m, 1H), 5.28-5.20 (m, 2H), 3.58-3.50 (m, 3H)

To a solution of 1,2-difluoro-3-(methoxymethoxy)benzene (100.0 g, 574.3 mmol, 1.0 eq.) in THF (1.5 L) was added BuLi (2.5 M, 298.6 mL, 1.3 eq.). The mixture was stirred at −78° C. for 7 hours. Then ethylformate (85.1 g, 1150 mmol, 2.0 eq.) was added and the mixture was stirred for another 1 hour. TLC indicated that STM was consumed completely. The reaction mixture was quenched by addition of H$_2$O (1000 mL) at 0° C., and then was extracted with EtOAc (800 mL×3). The combined organic layers were washed with brine 1000 mL, dried over Na$_2$SO$_4$, filtered and concentrated under reduced pressure to give a residue. The 3,4-difluoro-2-(methoxymethoxy)benzaldehyde (492.0 g, crude) as a yellow oil was used into the next step without further purification. ¹H NMR (CDCl₃, 400 MHz) δ 10.40-10.29 (m, 1H), 7.73-7.57 (m, 1H), 7.11-6.98 (m, 1H), 5.33 (s, 2H), 3.63-3.58 (m, 3H).

To a solution of 3,4-difluoro-2-(methoxymethoxy)benzaldehyde (256.0 g, 1.27 mol, 1.0 eq.) in DMF (1.5 L) was added Cs₂CO₃ (618.9 g, 1.90 mol, 1.5 eq.) and phenylmethanol (136.9 g, 1.3 mol, 1.0 eq.). The mixture was stirred at 70° C. for 10 hours. TLC indicated that STM was consumed completely. The reaction mixture was quenched by addition of H₂O (1000 mL) at 0° C., and then diluted with EtOAc (1200 mL) and extracted with EtOAc (1200 mL×2). The combined organic layers were washed with H₂O (1000 mL×2), dried over Na₂SO₄, filtered and concentrated under reduced pressure to give a residue. 4-(benzyloxy)-3-fluoro-2-(methoxymethoxy)benzaldehyde (400.0 g, crude) as a yellow oil, which was used into the next step without further purification.

To a solution of 4-(benzyloxy)-3-fluoro-2-(methoxymethoxy)benzaldehyde (760.0 g, 2.6 mol, 1.0 eq.) in CH₃OH (600.0 mL) was added aq. HCl (2 M, 200.0 mL). The mixture was stirred at 40° C. for 4 hours. TLC indicated that STM was consumed completely. The reaction was quenched by addition of H₂O (300 mL) and the mixture was concentrated under reduced pressure to remove CH₃OH. The residue was diluted with DCM 500 mL and extracted with DCM 1000 mL (500 mL×2). The combined organic layers were washed with brine (500 mL×3), dried over Na₂SO₄, filtered and concentrated under reduced pressure to give a residue. The residue was purified by column chromatography (SiO₂, petroleum ether/ethyl acetate=20:1 to 5:1). 4-(benzyloxy)-3-fluoro-2-hydroxybenzaldehyde (225.0 g, 913.8 mmol, 34.9% yield) was obtained as a black-brown solid. ¹H NMR (DMSO-d₆, 400 MHz) δ 10.97 (s, 1H), 10.06 (s, 1H), 7.34-7.52 (m, 6H), 6.90-6.98 (m, 1H), 5.28 (s, 2H).

To a solution of 4-(benzyloxy)-3-fluoro-2-hydroxybenzaldehyde (117.0 g, 475.2 mmol, 1.0 eq.), pyridine (75.2 g, 950.3 mmol, 2.0 eq.) and DMAP (5.8 g, 47.5 mmol, 0.1 eq.) in DCM (1.5 L) was added Tf₂O (201.1 g, 712.8 mmol, 1.5 eq.) dropwise. The mixture was stirred at 0° C. for 2 hours. HPLC indicated that STM was consumed completely. The reaction mixture was quenched by addition of H₂O (1000 mL), and extracted with DCM (1000 mL×2). The combined organic layers were washed with brine (500 mL), dried over Na₂SO₄, filtered and concentrated under reduced pressure to give a residue. The residue was purified by column chromatography (SiO₂, petroleum ether/ethyl acetate=20:1 to 2:1). 3-(benzyloxy)-2-fluoro-6-formylphenyl trifluoromethanesulfonate (150.0 g, 396.5 mmol, 83.5% yield) was obtained as a yellow oil. ¹H NMR (CDCl₃, 400 MHz) δ 10.08 (s, 1H), 7.71 (d, J=7.8 Hz, 1H), 7.49-7.36 (m, 5H), 7.19-7.13 (m, 1H), 5.28 (s, 2H).

To a solution of 3-(benzyloxy)-2-fluoro-6-formylphenyl trifluoromethanesulfonate (52.0 g, 137.5 mmol, 1.00 eq.), KOAc (40.5 g, 412.4 mmol, 3.0 eq.) and Pin₂B₂(104.7 g, 412.4 mmol, 3.0 eq.) in dioxane (1.0 L) was added Pd (dppf) Cl₂ (2.0 g, 2.75 mmol, 0.02 eq.). The mixture was stirred at 70° C. for 16 hours. HPLC indicated that STM was consumed completely. The reaction mixture was filtered and concentrated under reduced pressure to give a residue. The residue was purified by column chromatography (SiO₂, petroleum ether/ethyl acetate=50:1 to 5:1). 4-(benzyloxy)-3-fluoro-2-(4,4,5,5-tetramethyl-1,3,2-dioxaborolan-2-yl) benzaldehyde (37.0 g, 103.9 mmol, 75.6% yield) was obtained as a white solid. ¹H NMR (DMSO-d₆, 400 MHz) δ 9.81 (d, J=3.0 Hz, 1H), 7.81 (d, J=8.3 Hz, 1H), 7.54-7.33 (m, 7H), 5.31 (s, 2H), 1.39-1.28 (m, 12H).

To a solution of 4-(benzyloxy)-3-fluoro-2-(4,4,5,5-tetramethyl-1,3,2-dioxaborolan-2-yl)benzaldehyde (20.0 g, 56.2 mmol, 1.00 eq) in THF (50.0 mL) was added NaBH₄ (3.2 g, 84.2 mmol, 1.5 eq). The mixture was stirred at 0° C. for 1 hour. TLC indicated that STM was consumed completely. The reaction mixture was quenched by addition H₂O 100 mL at 0° C., and then adjusted pH=5, removed the THF and the desired product was dissolved out, filtered and concentrated under reduced pressure to give a residue. 6-(benzyloxy)-7-fluorobenzo[c][1,2]oxaborol-1(3H)-ol (43.0 g, 166.6 mmol, 98.9% yield) was obtained as a white solid. ¹H NMR (DMSO-d₆, 400 MHz) δ 7.31-7.48 (m, 5H), 7.17 (t, J=7.78 Hz, 1H), 7.01 (d, J=8.03 Hz, 1H), 5.18 (s, 2H), 5.04 (s, 2H), 4.89 (s, 1H).

To a solution of 6-(benzyloxy)-7-fluorobenzo[c][1,2]oxaborol-1 (3H)-ol (15.0 g, 58.1 mmol, 1.0 eq) in EtOAc (400.0 mL) was added Pd/C (2.0 g). The mixture was stirred at 25° C. for 2 hours under H₂ atmosphere (50 Psi). TLC indicated that STM was consumed completely. The reaction mixture was filtered and concentrated under reduced pressure to give a residue. 7-fluorobenzo[c][1,2]oxaborole-1,6(3H)-diol (7.0 g, 41.7 mmol, 71.7% yield) was obtained as a white solid. ¹H NMR (DMSO-d₆, 400 MHz) δ 9.59 (s, 1H), 9.14 (s, 1H), 7.05-7.12 (m, 1H), 6.97-7.03 (m, 1H), 4.88 (s, 2H). MS (ESI): mass calcd. for C₇H₆BFO₃ 168.04, m/z found 167.1 [M−H]⁻. HPLC: 92.5% (220 nm), 94.4% (254 nm).

To a solution of 7-fluorobenzo[c][1,2]oxaborole-1,6(3H)-diol (5.0 g, 29.77 mmol, 1.0 eq) and Iodo-pleuromutilin (18.9 g, 38.71 mmol, 1.3 eq) in DMSO (60.00 mL) was added Na₂CO₃ (9.5 g, 89.32 mmol, 3.0 eq). The mixture was stirred at 35° C. for 14 hours under N₂ atmosphere. HPLC indicated that STM was consumed completely. The reaction mixture was quenched by addition H₂O (200 mL) at 0° C., and then was adjusted to pH=7, solid was dissolved out and then filtered to give crude product. Combined four batches together, and the crude product was purified by prep-HPLC (column: Phenomenex luna C18 250×50 mm×10 μm; liquid phase: [A-TFA/H₂O=0.075% v/v; B-ACN] B %: 35%-65%, 20 min]), then removed the CH₃CN, resulting aqueous phase was extracted by DCM (1500 mL×3). The combined organic layers were concentrated under reduced pressure to give the product as a light yellow solid. This product was dissolved in DCM, then MTBE and petroleum ether was added until the viscidity was appeared, filtered and the filtrate was concentrated under reduced pressure to give the product as a white solid. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate (15.0 g, 28.2 mmol, 24% yield, 99.0% purity) was obtained as a white solid. ¹H NMR (DMSO-d₆, 400 MHz) δ 9.26 (br. s., 1H), 7.25-7.17 (m, 1H), 7.09 (d, J=7.9 Hz, 1H), 6.11 (dd, J=11.2, 17.9 Hz, 1H), 5.60 (d, J=7.9 Hz, 1H), 5.10-4.98 (m, 2H), 4.92 (s, 2H), 4.86-4.74 (m, 2H), 4.52 (br. s., 1H), 3.41 (br. s., 1H), 2.41 (br. s., 1H), 2.25-2.01 (m, 4H), 1.70-1.57 (m, 2H), 1.48-1.20 (m, 8H), 1.15-0.91 (m, 4H), 0.82 (d, J=6.6 Hz, 3H), 0.62 (d, J=7.1 Hz, 3H). MS (ESI): mass calcd. for C₂₉H₃₈BFO₇ 528.27, m/z found 527.3[M−H]⁻. HPLC: 99.0% (220 nm), 100.0% (254 nm).

3. (3aR,4R,5R,7S,8S,9R,9aS,12R)-8-hydroxy-4,7,9,
12-tetramethyl-3-oxo-7-vinyldecahydro-4,9a-propanocyclopenta[8]annulen-5-yl 2-((5-fluoro-1-hydroxy-1,3-dihydrobenzo[c][1,2]oxaborol-6-yl)oxy)acetate

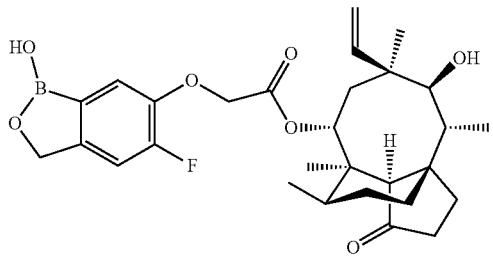

1,2-difluoro-4-nitrobenzene (7.1 g, 44.6 mmol), PMBOH (6.2 g, 44.6 mmol) and potassium hydroxide (3.8 g, 67.0 mmol) in 50 mL acetonitrile were stirred at room temperature overnight. Water was added to the mixture, the mixture was filtered, washed with water and dried to give 2-fluoro-1-((4-methoxybenzyl)oxy)-4-nitrobenzene (11.4 g, yield 92.0%). $^1$H NMR (CDCl$_3$, 400 MHz) δ 7.96-8.08 (m, 2H), 7.37 (d, J=8.8 Hz, 2H), 7.05-7.15 (m, 1H), 6.90-6.99 (m, 2H), 5.19 (s, 2H), 3.83 (s, 3H).

A mixture of 2-fluoro-1-((4-methoxybenzyl)oxy)-4-nitrobenzene (45 g, 162 mmol), iron powder (27 g, 487 mmol) and ammonium chloride (26 g, 487.0 mmol) in 300 mL ethanol and 50 mL water was stirred at reflux for 2 hours. The mixture was filtered and washed with ethanol and the filtrate was evaporated, to the residue was added brine (200 mL) and extracted with ethyl acetate (200 mL×3), the combined organic layers were concentrated to give 3-fluoro-4-((4-methoxybenzyl)oxy)aniline (29.0 g, yield 72.5%). $^1$H NMR (CDCl$_3$, 400 MHz) δ 7.40-7.31 (m, 2H), 6.93-6.87 (m, 2H), 6.81 (t, J=8.8 Hz, 1H), 6.46 (dd, J=12.8, 2.4 Hz, 1H), 6.33 (ddd, J=8.4, 2.8, 1.3 Hz, 1H), 4.96 (s, 2H), 3.82 (s, 3H), 3.51 (br. s., 2H).

NBS (14.4 g, 81.0 mmol) was added in portions to a solution of 3-fluoro-4-((4-methoxybenzyl)oxy)aniline (20 g, 81 mmol) in 500 mL of DCM at −15° C., five minutes later, new spot formed and STM consumed. Water was added to the mixture and the aqueous layer was treated with DCM, the crude product was purified by silica column to give 2-bromo-5-fluoro-4-((4-methoxybenzyl)oxy)aniline (28.0 g, quantitative). $^1$H NMR (CDCl$_3$, 400 MHz) δ 7.34 (d, J=8.8 Hz, 2H), 7.09 (d, J=8.4 Hz, 1H), 6.91 (d, J=8.8 Hz, 2H), 6.58 (s, 1H), 4.95 (s, 2H), 3.89 (br. s., 2H), 3.82 (s, 3H).

2-bromo-5-fluoro-4-((4-methoxybenzyl)oxy)aniline (28.0 g, 86.0 mmol) in aqueous hydrochloric acid solution (1.0 N, 1400 mL) at 0° C. was treated with a solution of sodium nitrite (7.1 g, 103.0 mmol) in water (20 mL). The solution was stirred at 0° C. for 30 min. A solution of potassium iodide (42.9 g, 258.0 mmol) in water (50 mL) was added and the solution was stirred for 30 mins at room temperature. The solution was diluted with ethyl acetate (200 mL) and quenched with an aqueous sodium thiosulfate solution (1.0 N, 500 mL), and the organic phase was separated. The organic layer was washed with aqueous hydrochloric acid solution (1.0 N, 100 mL), brine (100 mL), dried over sodium sulfate, and concentrated to give 5-bromo-2-fluoro-4-iodophenol (20.0 g, yield 50.0%) as a white solid. $^1$H NMR (CDCl$_3$, 400 MHz) δ 7.54 (d, J=9.6 Hz, 1H), 7.32 (d, J=8.4 Hz, 1H), 5.33 (br. s., 1H).

MOMCl (7.3 g, 88.8 mmol) was added to a solution of 5-bromo-2-fluoro-4-iodophenol (14.0 g, 44.4 mmol) and potassium carbonate (24.0 g, 177.0 mmol) in acetonitrile (150 mL) at 0° C. The mixture was stirred at room temperature for one hour. Water was added to mixture, and the aqueous was treated with EtOAc. The crude product was purified by flash column chromatography (Petroleum ether:EtOAc=20: 1-10:1) to give 1-bromo-4-fluoro-2-iodo-5-(methoxymethoxy)benzene (10.0 g, yield 62.5%). $^1$H NMR (CDCl$_3$, 400 MHz) δ 7.55 (d, J=10.0 Hz, 1H), 7.48 (d, J=7.6 Hz, 1H), 5.20 (s, 2H), 3.52 (s, 3H).

A solution of 1-bromo-4-fluoro-2-iodo-5-(methoxymethoxy)benzene (9.3 g, 25.7 mmol) in toluene (50 mL) was cooled to −40° C., then i-PrMgCl (19.3 mL, 38.6 mmol) was added dropwise. An hour later DMF (5.6 g, 77.0 mmol) was added dropwise. The mixture was quenched by addition of water. And the organic phase was separated. The organic layer was washed with brine (100 mL), dried over sodium sulfate, and concentrated to give 2-bromo-5-fluoro-4-(methoxymethoxy)benzaldehyde (5.6 g, yield 83.5%) as a white solid. $^1$H NMR (CDCl$_3$, 400 MHz) δ. 10.19 (d, J=3.6 Hz, 1H), 7.67 (d, J=10.6 Hz, 1H), 7.47 (d, J=7.2 Hz, 1H), 5.31 (s, 2H), 3.54 (s, 3H).

2-bromo-5-fluoro-4-(methoxymethoxy)benzaldehyde (2.6 g, 10.0 mmol), Pd(dppf)Cl$_2$ (0.4 g, 0.5 mmol), Pin$_2$B$_2$ (3.0 g, 12.0 mmol) and KOAc (2.9 g, 30.0 mmol) in dioxane (30 mL) were stirred at 80° C. overnight. LCMS showed main peak as TM. The solvent was evaporated and the residue was purified by flash column chromatography (Petroleum ether:EtOAc=20:1-10:1) to give 5-fluoro-4-(methoxymethoxy)-2-(4,4,5,5-tetramethyl-1,3,2-dioxaborolan-2-yl)benzaldehyde (2.4 g, yield 77.0%). $^1$H NMR (CDCl$_3$, 400 MHz) δ 10.51 (d, J=3.2 Hz, 1H), 7.73 (d, J=11.6 Hz, 1H), 7.64 (d, J=8.4 Hz, 1H), 5.35 (s, 2H), 3.54 (s, 3H), 1.38 (s, 12H).

Anhydrous MeOH was added to a solution of 5-fluoro-4-(methoxymethoxy)-2-(4,4,5,5-tetramethyl-1,3,2-dioxaborolan-2-yl)benzaldehyde (2.4 g, 7.7 mmol) and NaBH$_4$ (0.6 g, 15.5 mmol) in THF (50 mL) at 0° C. The mixture was stirred at ambient temperature for 2 hours, TLC shown that 5-fluoro-4-(methoxymethoxy)-2-(4,4,5,5-tetramethyl-1,3,2-dioxaborolan-2-yl)benzaldehyde consumed. 1 N HCl was added to the mixture until pH=4, the aqueous layer was treated with EtOAc, the organic layer was concentrated to give 5-fluoro-6-(methoxymethoxy)benzo[c][1,2]oxaborol-1 (3H)-ol (2.0 g crude) and used directly.

5-fluoro-6-(methoxymethoxy)benzo[c][1,2]oxaborol-1 (3H)-ol (2.0 g, crude) was dissolved in THF (20 mL) and 2N HCl (20 mL). The mixture was stirred at room temperature for 3 hours. LCMS showed main peak as TM. The crude product was recrystallized from DCM/Petroleum ether (~1:10) to give 5-fluorobenzo[c][1,2]oxaborole-1,6(3H)-diol (300.0 mg, yield 20.0%) and 257.0 mg delivered. $^1$H NMR (DMSO-d$_6$, 400 MHz) δ 9.75 (s, 1H), 9.10 (s, 1H), 7.27 (d, J=9.2 Hz, 1H), 7.18 (d, J=11.2 Hz, 1H), 4.85 (s, 2H). MS: 167 (M−1)$^-$ Tos-pleuromutilin (0.4 g, 0.8 mmol), 5-fluorobenzo[c][1,2]oxaborole-1,6(3H)-diol (0.1 g, 0.8 mmol) and K$_2$CO$_3$ (0.2 g, 1.2 mmol) in 10 mL DMF was heated at 50° C. overnight. Main peak on LCMS was desired product. Water was added and the mixture was adjust to pH<4 with 2N aqueous HCl. White solid precipitated and the mixture was filtered, the crude product was purified by Prep-HPLC (column: Luna C18 250×30 mm, 10 μm; liquid phase: [A-TFA/H$_2$O=0.1% v/v; B-ACN] B %: 40%-65%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((5-fluoro-1-hydroxy-1,3-dihydrobenzo[c][1,2]oxaborol-6-yl)oxy)acetate (255.0 mg, yield 57.0%) as white solid. $^1$H NMR (DMSO-d$_6$, 400 MHz) δ 9.10 (s, 1H), 7.35-7.26 (m, 2H), 6.08 (dd, J=18.0, 11.2 Hz, 1H), 5.58 (d, J=7.6 Hz, 1H), 5.09-4.96 (m, 2H), 4.90 (s, 2H), 4.85-4.74 (m, 2H), 4.52 (d, J=6.0 Hz, 1H), 3.43-3.38 (m, 1H), 2.41 (s, 1H), 2.25-1.96 (m, 6H), 1.73-1.20 (m, 9H), 1.03 (s, 3H), 0.81 (d, J=6.8 Hz, 3H), 0.61 (d, J=6.8 Hz, 3H). MS: 527 (M-1)$^-$ 4. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-fluoro-1-hydroxy-1,3-dihydrobenzo[c][1,2]oxaborol-6-yl)oxy)acetate

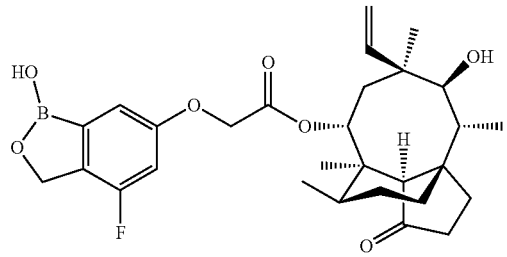

To a stirred suspension of 1-bromo-3-fluoro-5-methoxybenzene (5.0 g, 25 mmol) in DCM (50 mL) was added BBr$_3$ (12.2 g, 50 mmol) at −78° C. The resulting mixture was stirred at −78° C. to r.t for 3 hrs, then the mixture was poured into ice-water and extracted with EtOAc. The organics was dried and concentrated to give 3-bromo-5-fluorophenol (4 g, 85% yield) as yellow oil. $^1$H NMR: (CDCl3 400 MHz) δ 6.82-6.80 (m, 2H), 6.53-6.51 (m, 1H), 6.20-6.15 (m, 1H).

To a stirred suspension of 3-bromo-5-fluorophenol (4.5 g, 23.7 mmol) was added Cs$_2$CO$_3$ (15.5 g, 47.4 mmol) and BnBr (4.5 g, 26 mmol) in dry CH$_3$CN (50 mL). The resulting mixture was stirred at 80° C. 3 h, and then, the mixture was poured into water and extracted with EtOAc. The organics was dried and concentrated to give a residue, which was purified by silica gel chromatography (petroleum ether:EtOAc=100:1 to 6:1) to give 1-(benzyloxy)-3-bromo-5-fluorobenzene (4 g, 61.6% yield) as a white oil.

To a stirred suspension of 1-(benzyloxy)-3-bromo-5-fluorobenzene (15 g, 54 mmol) in THF (500 mL) was added LDA (64 mL, 0.13 mol) at −78° C. The mixture was stirred at −78° C. 2 hrs, and then DMF (11.7 g, 0.16 mol) was added to the solution. The resulting mixture was stirred at −78° C. to r.t for 2 hrs, and then, the mixture was poured into ice-water and extracted with EtOAc. The organics was dried and concentrated to give a residue, which was purified by silica gel chromatography (petroleum ether:EtOAc=100:1 to 5:1) to give 4-(benzyloxy)-2-bromo-6-fluorobenzaldehyde (6 g, 36.1% yield) as yellow oil.

A stirred mixture of 4-(benzyloxy)-2-bromo-6-fluorobenzaldehyde (2.5 g, 8.0 mmol) and NaBH$_4$ (0.58 g, 14.6 mmol) in MeOH (20 mL) was stirred at 0° C. for 1 h. The mixture was adjusted pH to 6-7, extracted with EtOAc. The organic layers were dried and concentrated to give (4-(benzyloxy)-2-bromo-6-fluorophenyl) methanol (2.3 g, 88%).

To a stirred suspension of (4-(benzyloxy)-2-bromo-6-fluorophenyl) methanol (2.3 g, 6.7 mmol) and DIEA (1.7 g, 13.5 mmol) in dry DCM (20 mL) was added MOMCl (0.68 g, 8.5 mmol) dropwise at 0° C. The resulting mixture was stirred at 0° C. for 2 hrs, and then, the mixture was poured into water and extracted with EtOAc. The organics was dried and concentrated to give a residue, which was purified by silica gel chromatography (petroleum ether:EtOAc=100:1 to 3:1) to give 5-(benzyloxy)-1-bromo-3-fluoro-2-((methoxymethoxy)methyl)benzene (1.6 g, 67.6% yield) as white oil. $^1$H NMR (CDCl$_3$, 400 MHz) δ 7.41-7.34 (m, 5H), 7.06 (s, 1H), 6.69-6.66 (m, 1H), 5.03 (s, 2H), 4.71 (s, 2H), 4.68 (s, 2H), 3.42 (s, 3H).

To a stirred suspension of 5-(benzyloxy)-1-bromo-3-fluoro-2-((methoxymethoxy)methyl)benzene (2 g, 5.6 mmol), 4,4,4',4',5,5,5',5'-octamethyl-2,2'-bi(1,3,2-dioxaborolane) (2.2 g, 8.5 mmol) and KOAc (1.6 g, 16.8 mmol) in dry dioxane (20 mL), was added Pd(dppf)Cl$_2$ (0.41 g, 0.56 mmol) under N$_2$. The resulting mixture was stirred at 80° C. 5 h under N$_2$, and then, the mixture was poured into water and extracted with EtOAc. The organics was dried and concentrated to give a crude 2-(5-(benzyloxy)-3-fluoro-2-((methoxymethoxy)methyl)phenyl)-4,4,5,5-tetramethyl-1,3,2-dioxaborolane (1.9 g, 84% yield) as yellow oil.

A stirred suspension of 2-(5-(benzyloxy)-3-fluoro-2-((methoxymethoxy)methyl)phenyl)-4,4,5,5-tetramethyl-1,3,2-dioxaborolane (2 g, 4.9 mmol) in HCl/THF (2M/L, 10 mL) was stirred at 60° C. for 10 hrs, and then, the mixture was poured into water and extracted with EtOAc. The organics was dried and concentrated to give a crude product, which was purified with prep-HPLC to give 6-(benzyloxy)-4-fluorobenzo[c][1,2]oxaborol-1(3H)-ol (0.5 g, 39.6% yield) as a yellow solid. $^1$H NMR (DMSO-d$_6$, 400 MHz) δ 9.38 (s, 1H), 7.46-7.44 (m, 2H), 7.39-7.38 (m, 2H), 7.35-7.33 (m, 1H), 7.17 (s, 1H), 7.03-7.00 (m, 1H), 5.14 (s, 2H), 4.99 (s, 2H). MS (ESI): mass calcd. for C$_{14}$H$_{12}$BFO$_3$ 258.09, m/z found 257.0 [M-1]$^-$. HPLC: 95.1% (220 nm), 83.4% (254 nm).

To a stirred suspension of 6-(benzyloxy)-4-fluorobenzo[c][1,2]oxaborol-1(3H)-ol (0.5 g, 1.94 mmol) in propan-2-ol (10 mL) was added Pd/C (0.4 g). The resulting mixture was stirred at r.t for 15 hrs under H$_2$, and then, the mixture was filtered and concentrated to give 4-fluorobenzo[c][1,2]oxaborole-1,6(3H)-diol (0.3 g, 92% yield) as a yellow solid. $^1$H NMR (DMSO-d$_6$, 400 MHz) δ 9.79 (s, 1H), 9.28 (s, 1H), 6.96 (s, 1H), 6.67-6.64 (m, 2H), 4.94 (s, 2H). MS (ESI): mass calcd. for C$_7$H$_6$BFO$_3$ 168.04, m/z found 167.1 [M-1]$^-$. HPLC: 98.9% (220 nm), 100% (254 nm).

A stirred mixture of 4-fluorobenzo[c][1,2]oxaborole-1,6(3H)-diol (150 mg, 0.9 mmol) and Tos-pleuromutilin (570 mg, 1.1 mmol) and K₂CO₃ (370 mg, 2.7 mmol) in DMF (5 mL) was stirred at 50° C. for 3 hrs. The mixture was then diluted with water and extracted with EtOAc The combined organic layers were washed with brine, dried over anhydrous Na₂SO4 and concentrated to give the crude product which was purified with prep-HPLC (column: Luna C18 100×30 mm, 5 μm; liquid phase: [A-TFA/H₂O=0.075% v/v; B-ACN] B %: 40%-70%, 20 min]) to give (3aR,4R,5R,7S, 8S,9R,9aS,12R)-8-hydroxy-4,7,9,12-tetramethyl-3-oxo-7-vinyldecahydro-4,9a-propanocyclopenta[8]annulen-5-yl 2-((4-fluoro-1-hydroxy-1,3-dihydrobenzo[c][1,2]oxaborol-6-yl)oxy)acetate (63 mg, 13.4%) as white solid. $^1$H NMR (DMSO-d₆, 400 MHz) δ 9.29-9.24 (br. s., 1H), 7.08 (s, 1H), 6.93 (d, J=11.2 Hz, 1H), 6.15-6.05 (m, 1H), 5.60-5.56 (d, J=8.8 Hz, 1H), 5.05-4.99 (m, 4H), 4.77-4.75 (d, J=8.0 Hz, 2H), 2.41 (s, 1H), 2.41-2.04 (m, 4H), 1.63-1.41 (m, 4H), 1.33-1.28 (m, 7H), 1.04-0.85 (m, 4H), 0.81 (d, J=6.4 Hz, 3H), 0.63 (d, J=6.4 Hz, 3H). MS (ESI): mass calcd. for C₂₉H₃₈BFO₇ 528.27, m/z found 527.2 [M–1]⁻. HPLC: 96.0% (220 nm), 69.6% (254 nm).

5. (3aR,4R,5R,7S,8S,9R,9aS,12R)-8-hydroxy-4,7,9, 12-tetramethyl-3-oxo-7-vinyldecahydro-4,9a-propanocyclopenta[8]annulen-5-yl 2-((5,7-difluoro-1-hydroxy-1,3-dihydrobenzo[c][1,2]oxaborol-6-yl) oxy)acetate

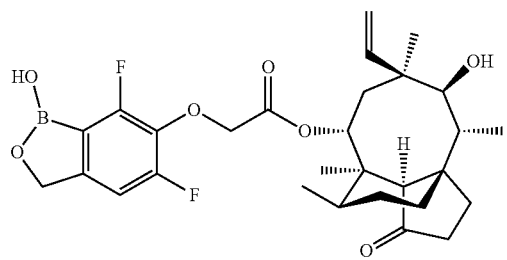

To a solution of 3,4,5-trifluorobenzoic acid (40.0 g, 227.2 mmol, 1.0 eq.) in THF (1 L) was added n-BuLi (2.5 M, 227.2 mL, 2.5 eq.). The mixture was stirred at −78° C. for 2.5 hrs, then I₂ (144.1 g, 567.9 mmol, 2.5 eq.) (in 500 mL THF) was added dropwise, the mixture was stirred at −78° C. for 0.5 hr. TLC indicated 3,4,5-trifluorobenzoic acid was consumed completely, one new spot formed. The reaction mixture was quenched by addition saturated Na₂S₂O₃ 500 mL, and then extracted with EtOAc 1500 mL (500 mL×3). The combined organic layers were washed with brine 600 mL, dried over Na₂SO₄, filtered and concentrated under reduced pressure to give a residue. 3,4,5-trifluoro-2-iodobenzoic acid (45.0 g, 149.0 mmol, 65.6% yield) was obtained as white solid. $^1$H NMR (CDCl₃, 400 MHz) δ 7.90-7.77 (m, 1H)

To a solution of 3,4,5-trifluoro-2-iodobenzoic acid (30.0 g, 99.3 mmol, 1.0 eq.) in EtOH (300.0 mL) was added con.H₂SO₄ (99.3 mmol, 1.0 eq.). The mixture was stirred at 90° C. for 16 hours. TLC indicated the 3,4,5-trifluoro-2-iodobenzoic acid was consumed completely. The reaction mixture was concentrated under reduced pressure to remove EtOH. The residue was diluted with H₂O 300 mL and extracted with DCM 600 mL (200 mL×3). The combined organic layers were washed with brine 300 mL, dried over Na₂SO₄, filtered and concentrated under reduced pressure to give a residue. The residue was purified by column chromatography (SiO₂, Petroleum ether/Ethyl acetate=10/1). ethyl 3,4,5-trifluoro-2-iodobenzoate (32.0 g, 96.9 mmol, 97.6% yield) was obtained as a colorless oil. $^1$H NMR (CDCl₃, 400 MHz) δ 7.64 (ddd, J=2.0, 7.5, 10.0 Hz, 1H), 4.44 (q, J=7.4 Hz, 2H), 1.44 (t, J=7.0 Hz, 3H).

To a solution of ethyl 3,4,5-trifluoro-2-iodobenzoate (13.0 g, 39.4 mmol, 1.0 eq.) and phenylmethanol (6.4 g, 59.1 mmol, 1.5 eq.) in DMF (10.00 mL) was added K₂CO₃ (6.5 g, 47.3 mmol, 1.2 eq.). The mixture was stirred at 25° C. for 18 hours. TLC indicated a main new pot was formed, but ethyl 3,4,5-trifluoro-2-iodobenzoate remained. The reaction mixture was quenched by addition H₂O 200 mL, and then extracted with EtOAc 600 mL (200 mL×3). The combined organic layers were washed with brine 200 mL, dried over Na₂SO₄, filtered and concentrated under reduced pressure to give a residue. The residue was purified by column chromatography (SiO₂, Petroleum ether/Ethyl acetate=50/1). ethyl 4-(benzyloxy)-3,5-difluoro-2-iodobenzoate (10.0 g, 23.9 mmol, 60.7% yield) was obtained as colorless oil. $^1$H NMR (CDCl₃, 400 MHz) δ 7.57-7.48 (m, 1H), 7.46-7.30 (m, 5H), 5.27 (s, 2H), 4.39 (q, J=7.4 Hz, 2H), 1.41 (t, J=7.0 Hz, 3H).

To a solution of ethyl 4-(benzyloxy)-3,5-difluoro-2-iodobenzoate (5.0 g, 11.9 mmol, 1.0 eq.), Pin₂B₂(24.3 g, 95.7 mmol, 8.0 eq.) and AcOK (2.7 g, 27.5 mmol, 2.3 eq.) in dioxane (50.0 mL) was added Pd(PPh₃)₂Cl₂ (167.9 mg, 239.4 umol, 0.02 eq.). The mixture was stirred at 120° C. for 40 hours. HPLC indicated ethyl 4-(benzyloxy)-3,5-difluoro-2-iodobenzoate was consumed completely. The reaction mixture was filtered to remove AcOK, then filtered and concentrated under reduced pressure to give a residue. The residue was purified by column chromatography (SiO₂, Petroleum ether/Ethyl acetate=100/1). ethyl 4-(benzyloxy)-3,5-difluoro-2-(4,4,5,5-tetramethyl-1,3,2-dioxaborolan-2-yl)benzoate (20.0 g, crude) (mixed Pin₂B₂) was obtained as a white solid. $^1$H NMR (CDCl₃, 400 MHz) δ 7.52-7.29 (m, 6H), 5.20 (s, 2H), 4.33 (q, J=7.4 Hz, 2H), 1.41 (s, 12H), 1.34 (t, J=7.3 Hz, 3H).

To a solution of ethyl 4-(benzyloxy)-3,5-difluoro-2-(4,4, 5,5-tetramethyl-1,3,2-dioxaborolan-2-yl)benzoate (20.0 g, 4.8 mmol, 1.0 eq.) in THF (150.0 mL) was added NaBH₄ (180.9 mg, 4.8 mmol, 1.0 eq). The mixture was stirred at 25° C. for 5 hours. TLC indicated ethyl 4-(benzyloxy)-3,5-difluoro-2-(4,4,5,5-tetramethyl-1,3,2-dioxaborolan-2-yl) benzoate was consumed completely. The reaction mixture was quenched by addition H₂O 100 mL, and then adjusted pH=6, removed THF, solid was dissolved out, filtered and concentrated under reduced pressure to give a residue. The residue was washed with Petroleum ether, then suspended with petroleum ether, filtrated to give desired product. 6-(benzyloxy)-5,7-difluorobenzo[c][1,2]oxaborol-1(3H)-ol (1.3 g, 4.7 mmol, 98.5% yield) was obtained as a white solid. $^1$H NMR (CDCl₃, 400 MHz) δ 7.46 (d, J=6.5 Hz, 2H), 7.41-7.33 (m, 3H), 6.89 (d, J=8.5 Hz, 1H), 5.17 (s, 2H), 5.01 (s, 2H).

To a solution of 6-(benzyloxy)-5,7-difluorobenzo[c][1,2] oxaborol-1(3H)-ol (100.0 mg, 362.3 umol, 1.0 eq.) in EtOAc (50.0 mL) was added Pd/C (200.0 mg). The mixture was stirred at 25° C. for 4 hours under H₂ atmosphere (50 psi). TLC indicated 6-(benzyloxy)-5,7-difluorobenzo[c][1,2]oxaborol-1(3H)-ol was consumed completely. The reaction mixture was filtered and concentrated under reduced pressure to give a desired. 5,7-difluorobenzo[c][1,2]oxaborole-1,6(3H)-diol (60.0 mg, 322.7 umol, 89.1% yield) was obtained as a white solid. $^1$H NMR (CDCl₃, 400 MHz) δ 9.92 (s, 1H), 9.23 (s, 1H), 7.10 (d, J=10.0 Hz, 1H), 4.88 (s, 2H)

To a solution of 5,7-difluorobenzo[c][1,2]oxaborole-1,6 (3H)-diol (300.0 mg, 1.6 mmol, 1.0 eq.) and pleur-tosylate (786.3 mg, 1.6 mmol, 1.0 eq) in DMSO (12.0 mL) was added Na$_2$CO$_3$ (341.3 mg, 3.2 mmol, 2.0 eq). The mixture was stirred at 30° C. for 16 hours. HPLC indicated 5,7-difluorobenzo[c][1,2]oxaborole-1,6(3H)-diol was consumed completely. The reaction mixture was quenched by addition H$_2$O 30 mL, and then adjusted pH=6. Solid was precipitated, and filtered to give a residue. The residue was purified by prep-HPLC column: Phenomenex luna (2) C18 250×50 mm, 10 μm; liquid phase: [A-TFA/H$_2$O=0.075% v/v; B-ACN] B %: 35%-65%, 20 min], removed CH$_3$CN, then freeze-drying to give the desired product. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((5,7-difluoro-1-hydroxy-1,3-dihydrobenzo[c][1,2]oxabor ol-6-yl)oxy)acetate (308.0 mg, 563.8 umol, 35.0% yield) was obtained as a light yellow solid. $^1$H NMR (DMSO-d$_6$, 400 MHz) δ7.16 (d, J=10.1 Hz, 1H), 6.05 (dd, J=11.5, 17.6 Hz, 1H), 5.57 (d, J=7.9 Hz, 1H), 4.97 (d, J=6.6 Hz, 1H), 4.93 (s, 1H), 4.89 (s, 2H), 4.71 (d, J=19.0 Hz, 2H), 3.36 (d, J=6.2 Hz, 1H), 2.34 (br. s., 1H), 2.20-2.09 (m, 1H), 2.08-1.94 (m, 3H), 1.67-1.51 (m, 3H), 1.41 (d, J=17.2 Hz, 1H), 1.36-1.14 (m, 6H), 1.03-0.90 (m, 4H), 0.78 (d, J=7.1 Hz, 3H), 0.53 (d, J=6.6 Hz, 3H). MS (ESI): mass calcd. For C$_{29}$H$_{37}$BF$_2$NO$_7$ 546.3, m/z found 545.2[M–H]$^-$. HPLC: 97.3% (220 nm), 94.0% (254 nm).

6. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-chloro-1-hydroxy-1,3-dihydrobenzo[c][1,2]oxaborol-6-yl)oxy)acetate

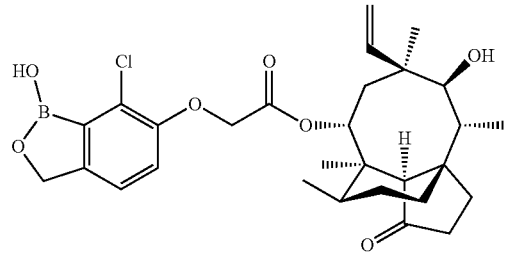

Sodium hydride (60% in oil, 190 mg, 4.76 mmol) was added to a solution of 7-chlorobenzo[c][1,2]oxaborole-1,5(3H)-diol (330 mg, 1.79 mmol) in 5 mL of DMF. After the suspension was stirred at 50° C. for two hours, a solution of Tos-pleuromutilin (634 mg, 1.19 mmol) in 5 mL DMF was added. The mixture was stirred at room temperature overnight. The crude was purified by prep HPLC (column: SunFire C18 OBD 100×30 mm, 5 μm) eluted with gradient water/acetonitrile (0.1% TFA) to afford (3aR,4R,5R,7S,8S, 9R,9aS,12R)-8-hydroxy-4,7,9,12-tetramethyl-3-oxo-7-vinyldecahydro-4,9a-propanocyclopenta[8]annulen-5-yl 2-((7-chloro-1-hydroxy-1,3-dihydrobenzo[c][1,2]oxaborol-6-yl)oxy)acetate as white flakes. $^1$H NMR (400 MHz, DMSO-d$_6$) δ 9.06 (s, 1H), 7.18 (d, J=8 Hz, 1H), 7.07 (d, J=8.4 Hz, 1H), 6.04 (dd, J=17.6, 11.2 Hz, 1H), 5.53 (d, J=7.2 Hz, 1H), 5.02 (m, 2H), 4.84 (s, 2H), 4.79 (s, 2H), 4.49 (d, J=6.4 Hz, 1H), 3.35 (m, 1H), 2.35 (s, 1H), 2.11-1.96 (m, 4H), 1.61-1.17 (m, 10H), 0.98-0.93 (m, 4H), 0.74 (d, J=6.8 Hz, 3H), 0.58 (d, J=6.8 Hz, 3H). MS (ESI): mass calcd. For C$_{29}$H$_{38}$BO$_7$Cl 544.87, m/z found 543.2 [M–H]$^-$. HPLC: 100% (220 nm), 100% (254 nm).

7. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-7-chloro-1-hydroxy-1,3-dihydrobenzo[c][1,2]oxaborol-6-yl)oxy)acetate 8. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-7-chloro-1-hydroxy-1,3-dihydrobenzo[c][1,2]oxaborol-6-yl)oxy)acetate

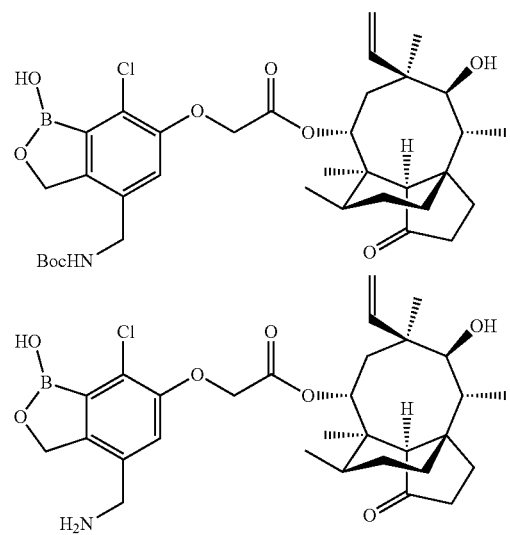

To a solution of 3,5-dibromo-4-methylphenol (10 g, 38 mmol) and DIPEA (14 mL, 76 mmol) in DCM (150 mL) was added (chloromethoxy)ethane (5.4 mL, 57 mmol). The reaction mixture was heated to reflux overnight. After cooled to r.t, water (150 mL) was added and the mixture was extracted with DCM (150 mL×2). The combined organic layers were washed with brine, dried over Na$_2$SO$_4$, filtered and concentrated under the reduced pressure. The residue was purified by silica gel column chromatography using petroleum ether:ethyl acetate=20:1 as eluent to give 1,3-dibromo-5-(ethoxymethoxy)-2-methylbenzene (10 g, yield 82%) as a colorless oil. $^1$H NMR (400 MHz, CDCl$_3$) δ 7.24 (s, 2H), 5.16 (s, 2H), 3.70 (q, J=7.2 Hz, 2H), 2.49 (s, 3H), 1.22 (t, J=6.8 Hz, 3H).

To a solution of 1,3-dibromo-5-(ethoxymethoxy)-2-methylbenzene (1.5 g, 4.66 mmol) in pyridine:DMF (1:2) (30 mL) was added CuCN (419 mg, 4.66 mmol). The reaction mixture was heated to 140° C. overnight. After cooled to room temperature, EA (150 mL) and ammonia water (50 mL) were added. The mixture was washed with water (100 mL×3). The solvent was removed and the residue was purified by silica gel column chromatography using petroleum ether:ethyl acetate=15:1 to give 3-bromo-5-(ethoxymethoxy)-2-methylbenzonitrile (520 mg, yield 41%) as a white solid. $^1$H NMR (400 MHz, CDCl$_3$) δ 7.48 (d, J=2.4 Hz, 1H), 7.26 (d, J=2.4 Hz, 1H), 5.19 (s, 2H), 3.71 (q, J=7.2 Hz, 2H), 2.55 (s, 3H), 1.22 (t, J=7.2 Hz, 3H).

To a solution of 3-bromo-5-(ethoxymethoxy)-2-methylbenzonitrile (1.72 g, 6.37 mmol) and NBS (1.1 g, 6.37 mmol) in CCl$_4$ (30 mL) was added AIBN (104 mg, 0.637 mmol). The reaction mixture was heated to reflux overnight.

The solvent was removed and the residue was purified by silica gel column chromatography using petroleum ether: ethyl acetate=15:1 to give 3-bromo-2-(bromomethyl)-5-(ethoxymethoxy)benzonitrile (1.2 g, yield 54%) as a colorless oil. It was used in next step without further purification.

To a solution of 3-bromo-2-(bromomethyl)-5-(ethoxymethoxy)benzonitrile (1.2 g, 3.44 mmol) in DMF (30 mL) was added NaOAc (564 mg, 6.88 mmol). The reaction mixture was heated to 50° C. for 1 h, then EA (150 mL) was added. The mixture was washed with water (50 mL×3). The solvent was removed and the residue was purified by silica gel column chromatography using petroleum ether: ethyl acetate=6:1 to give 2-bromo-6-cyano-4-(ethoxymethoxy)benzyl acetate (950 mg, yield 84%) as a white solid. $^1$H NMR (400 MHz, CDCl$_3$) δ 7.53 (s, 1H), 7.34 (s, 1H), 5.32 (s, 2H), 5.24 (s, 2H), 3.72 (q, J=7.2 Hz, 2H), 2.11 (s, 3H), 1.23 (t, J=7.2 Hz, 3H). MS (ESI): mass calcd. For $C_{13}H_{14}BrNO_4$ 327.01, m/z found 350.0 [M+Na]$^+$.

To a solution of 2-bromo-6-cyano-4-(ethoxymethoxy) benzyl acetate (200 mg, 0.61 mmol), Pin$_2$B$_2$(310 mg, 1.22 mmol) and KOAc (179 mg, 1.83 mmol) in 1,4-dioxane (5 mL) was added PdCl$_2$(dppf)$_2$ (22 mg, 0.03 mmol). The reaction mixture was stirred at 80° C. under argon atmosphere overnight. The solvent was removed and the residue was purified by column chromatography on silica gel by elution with petroleum ether:ethyl acetate=6:1 to give 2-cyano-4-(ethoxymethoxy)-6-(4,4,5,5-tetramethyl-1,3,2-dioxaborolan-2-yl)benzyl acetate (140 mg, yield 61%) as a colorless oil. MS (ESI): mass calcd. For $C_{19}H_{26}BNO_6$ 375.17, m/z found 398.2 [M+Na]$^+$.

A mixture of 2-cyano-4-(ethoxymethoxy)-6-(4,4,5,5-tetramethyl-1,3,2-dioxaborolan-2-yl)benzyl acetate (1 g, 2.67 mmol), NaOH (213 mg, 5.3 mmol) in H$_2$O (5 mL) and THF (20 mL) was stirred at r.t for 3 h, Then the mixture was added HCl (6N) to pH=3, the mixture was stirred r.t for 3 h. Water (20 mL) was added and the solution was extracted with EA (100 mL×2). The combined organic layers were dried over Na$_2$SO$_4$, filtered and concentrated under the reduced pressure. The residue was purified by Combiflash to give 6-(ethoxymethoxy)-1-hydroxy-1,3-dihydrobenzo[c][1,2]oxaborole-4-carbonitrile (280 mg, yield 45%) as a white solid. $^1$H NMR (400 MHz, DMSO-d$_6$) δ: 9.55 (s, 1H), 7.69 (d, J=2.0 Hz, 1H), 7.61 (d, J=2.0 Hz, 1H), 5.32 (s, 2H), 5.10 (s, 2H), 3.67 (q, J=6.0 Hz, 2H), 1.13 (t, J=6.0 Hz, 3H To a solution of tert-butyl (1,6-dihydroxy-1,3-dihydrobenzo[c][1,2]oxaborol-4-yl)methylcarbamate (75 mg, 0.27 mmol) in DMF (3 mL) was added NCS (36 mg, 0.27 mmol). The reaction mixture was heated to 50° C. for 2 h. Then the mixture was purified by prep-HPLC to give tert-butyl (7-chloro-1,6-dihydroxy-1,3-dihydrobenzo[c][1,2]oxaborol-4-yl)methylcarbamate (50 mg, yield 60%) as a white solid. MS (ESI): mass calcd. For $C_{13}H_{17}BClNO_5$ 313.54, m/z found 214.1 [M−99]$^+$.

To a solution of tert-butyl (7-chloro-1,6-dihydroxy-1,3-dihydrobenzo[c][1,2]oxaborol-4-yl)methylcarbamate (40 mg, 0.128 mmol), KI (4 mg, 0.026 mmol) and K$_2$CO$_3$ (35 mg, 0.255 mmol) in MeCN (3 mL) was added TsO-Pleu (82 mg, 0.153 mmol). The reaction mixture was heated to reflux overnight. After removed the solvent, the residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-7-chloro-1-hydroxy-1,3-dihydrobenzo[c][1,2]oxaborol-6-yl)oxy)acetate (42 mg, yield 47%) as a white solid. $^1$H NMR (400 MHz, DMSO-d$_6$) δ 9.11 (s, 1H), 7.28 (t, J=5.2 Hz, 1H), 7.03 (s, 1H), 6.13-6.09 (m, 1H), 5.60 (d, J=8.4 Hz, 1H), 5.11-5.02 (m, 2H), 4.94 (s, 2H), 4.78 (q, J=16.8 Hz, 2H), 4.02 (d, J=5.2 Hz, 2H), 2.43 (s, 1H), 2.20-2.04 (m, 4H), 1.68-0.97 (m, 24H), 0.82 (d, J=6.8 Hz, 3H), 0.65 (d, J=7.2 Hz, 3H). HPLC purity: 100% (214 nm); MS (ESI): mass calcd. For $C_{35}H_{49}BClNO_9$ 673.32, m/z found 695.8 [M+Na]$^+$.

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-7-chloro-1-hydroxy-1,3-dihydrobenzo[c][1,2]oxaborol-6-yl)oxy)acetate (42 mg, 0.062 mmol) in DCM (5 mL) was added HCl/1,4-dioxane (4 N, 2.5 mL). The reaction mixture was stirred at r.t for 3 h. The solvent was removed and the residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-7-chloro-1-hydroxy-1,3-dihydrobenzo[c][1,2]oxaborol-6-yl)oxy)acetate (22.2 mg, yield 62%) as a white solid. $^1$H NMR (400 MHz, DMSO-d$_6$) δ 9.04 (s, 1H), 7.17 (s, 1H), 6.16-6.13 (m, 1H), 5.61 (d, J=8.0 Hz, 1H), 5.11-5.01 (m, 2H), 4.97 (s, 2H), 4.822 (d, J=4.0 Hz, 2H), 4.54 (d, J=6.0 Hz, 1H), 4.46-4.44 (m, 2H), 3.62 (s, 2H), 2.43 (s, 1H), 2.23-2.04 (m, 4H), 1.68-0.97 (m, 14H), 0.81 (d, J=7.2 Hz, 3H), 0.66 (d, J=6.8 Hz, 3H). HPLC purity: 100% (214 nm); MS (ESI): mass calcd. For $C_{30}H_{41}BClNO_7$ 573.27, m/z found 573.8 [M+H]$^+$.

9. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-7-methyl-1,3-dihydrobenzo[c][1,2]oxaborol-6-yl)oxy)acetate

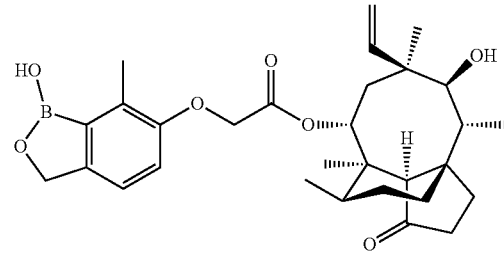

7-methylbenzo[c][1,2]oxaborole-1,6(3H)-diol (0.2 g, 1.5 mmol), (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (0.8 g, 1.5 mmol) and K$_2$CO$_3$ (0.6 g, 4.4 mmol) in 5 mL of DMF was heated at 50° C. overnight. Main peak on LCMS was desired product. Water was added and the mixture was adjust to pH<4 with 2N aqueous HCl. White solid precipitated and the mixture was filtered, the crude product was purified by prep-HPLC (column: Luna C18 250×30 mm, 10 μm; liquid phase: [A-TFA/H$_2$O=0.1% v/v; B-ACN] B %: 35%-65%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-7-methyl-1,3-dihydrobenzo[c][1,2]oxaborol-6-yl)oxy)acetate (0.4 g, 54.0%). $^1$H NMR (DMSO-d$_6$, 400 MHz) δ 7.09 (d, J=8.0 Hz, 1H), 6.95 (d, J=8.0 Hz, 1H), 6.11 (dd, J=17.6, 11.2 Hz, 1H), 5.61 (d, J=8.0 Hz, 1H), 5.09-4.98 (m, 2H), 4.87 (s, 2H), 4.72 (d, J=2.0 Hz, 2H), 3.41 (d, J=5.6 Hz, 2H), 2.36 (s, 1H), 2.33 (s, 3H), 2.20-2.10 (m, 1H), 2.10-1.95 (m, 4H), 1.72-

1.55 (m, 2H), 1.54-1.36 (m, 2H), 1.34 (s, 3H), 1.31-1.15 (m, 3H), 1.03 (s, 4H), 0.82 (d, J=6.8 Hz, 3H), 0.63 (d, J=6.8 Hz, 3H). MS: 523 (M−1)⁻.

10. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-5-methyl-1,3-dihydrobenzo[c][1,2]oxaborol-6-yl)oxy) acetate

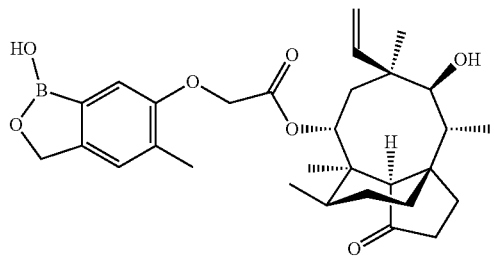

A mixture of 1-fluoro-2-methyl-4-nitrobenzene (20.0 g, 129.0 mmol), PMBOH (17.8 g, 129 mmol) and potassium hydroxide (10.8 g, 194.0 mmol) in 150 mL of acetonitrile were stirred overnight. Water was added to the mixture, the mixture was filtered, washed with water and dried to give 1-((4-methoxybenzyl)oxy)-2-methyl-4-nitrobenzene (32.1 g, yield 92.0%). $^1$H NMR (CDCl$_3$, 400 MHz) δ 8.10-8.07 (m, 2H), 7.37-7.35 (d, J=8.8 Hz, 2H), 6.95-6.92 (m, 3H), 5.11 (s, 2H), 3.83 (s, 3H), 2.31 (s, 3H).

To a mixture of 1-((4-methoxybenzyl)oxy)-2-methyl-4-nitrobenzene (43.5 g, 160.0 mmol), and ammonium chloride (25.6 g, 480.0 mmol) in 300 mL of ethanol and 50 mL of water was added iron powder (25.0 g, 450.0 mmol). The mixture was stirred at reflux for 2 hours. The mixture was filtered and washed with ethanol and the filtrate was evaporated, the crude product was added to brine and extracted with ethyl acetate three times, then concentrated to give 4-((4-methoxybenzyl)oxy)-3-methylaniline (31.0 g, yield 80.3%). $^1$H NMR (CDCl$_3$, 400 MHz) δ 7.35-7.34 (d, J=8.8 Hz, 2H), 6.92-6.90 (d, J=8.8 Hz, 2H), 6.74-6.72 (d, J=8.8 Hz, 1H), 6.56 (s, 1H), 6.50-6.48 (s, 1H), 4.92 (s, 2H), 3.82 (s, 3H), 2.19 (s, 3H).

NBS (13.0 g, 73.2 mmol) was added in portions to a solution of 4-((4-methoxybenzyl)oxy)-3-methylaniline (17.8 g, 73.2 mmol) in 500 mL DCM at −15° C., five minutes later, new spot formed and STM consumed. Water was added to the mixture and the aqueous layer was treated with DCM, the crude product was purified by silica column to give 2-bromo-4-((4-methoxybenzyl)oxy)-5-methylaniline (8.0 g, yield 23.5%). $^1$H NMR (CDCl$_3$, 400 MHz) δ7.35 (d, J=8.8 Hz, 2H), 7.27 (s, 1H), 6.98 (s, 2H), 6.92 (d, J=8.8 Hz, 2H), 6.63 (d, J=0.8 Hz, 1H), 4.90 (s, 2H), 3.84-3.82 (m, 3H), 2.15 (s, 3H).

To a solution of 2-bromo-4-((4-methoxybenzyl)oxy)-5-methylaniline (12.0 g, 37.2 mmol) in aqueous hydrochloric acid solution (1.0 N, 600 mL) was added a solution of sodium nitrite (3.4 g, 48.4 mmol) in water (10 mL) at 0° C. The solution was stirred at 0° C. for 30 min. A solution of potassium iodide (18.5 g, 111 mmol) in water (20 mL) was added and the solution stirred 30 min at room temperature. The solution was diluted with ethyl acetate (200 mL) and quenched with an aqueous sodium thiosulfate solution (1.0 N, 500 mL), and the organic phase was separated. The organic layer was washed with aqueous hydrochloric acid solution (1.0 N, 100 mL), brine (100 mL), dried over sodium sulfate, and concentrated to give 1-bromo-2-iodo-5-((4-methoxybenzyl)oxy)-4-methylbenzene as a white solid (8.0 g, yield 50.0%). $^1$H NMR (CDCl$_3$, 400 MHz) δ 7.59 (d, J=0.8 Hz, 1H), 7.34 (d, J=8.8 Hz, 2H), 7.15 (s, 1H), 6.95-6.90 (m, 2H), 4.96 (s, 2H), 3.84 (s, 3H), 2.15 (s, 3H).

A solution of 1-bromo-2-iodo-5-((4-methoxybenzyl)oxy)-4-methylbenzene (0.5 g, 1.6 mmol) in toluene (20 mL) was cooled to −40° C., then a solution of i-PrMgCl (1 mL, 2.0 mmol) was added dropwise. An hour later DMF (0.38 g, 5.3 mmol) was added to the mixture dropwise. After stirring for 2 hrs at 0° C., the mixture was quenched by addition of water. And the organic phase was separated. The organic layer was washed with brine (100 mL), dried over sodium sulfate, and concentrated to give 2-bromo-4-((4-methoxybenzyl)oxy)-5-methylbenzaldehyde as a white solid (0.2 g, yield 58.0%). $^1$H NMR (CDCl$_3$, 400 MHz) δ 10.20 (s, 1H), 7.75 (s, 1H), 7.77 (d, J=4.8 Hz, 1H), 7.11 (s, 1H), 6.95 (d, J=8.8 Hz, 1H), 5.08 (s, 2H), 3.84 (s, 3H), 2.22 (s, 3H).

A mixture of 2-bromo-4-((4-methoxybenzyl)oxy)-5-methylbenzaldehyde (2.5 g, 7.5 mmol), Pd(dppf)Cl$_2$ (0.3 g, 0.4 mmol), Pin$_2$B$_2$(2.8 g, 9.0 mmol) and KOAc (2.2 g, 22.4 mmol) in dioxane (30 mL) was stirred at 80° C. overnight. LCMS showed main peak as desired compound. The solvent was evaporated to give crude product, which was purified by flash column chromatography (Petroleum ether:EA=0-10:1) to give 4-((4-methoxybenzyl)oxy)-5-methyl-2-(4,4,5,5-tetramethyl-1,3,2-dioxaborolan-2-yl)benzaldehyde (1.7 g, yield 58.5%) as white solid. $^1$H NMR (CDCl$_3$, 400 MHz) δ10.47 (s, 1H), 7.83 (s, 1H), 7.43-7.33 (m, 3H), 6.98-6.91 (m, 2H), 5.13 (s, 2H), 3.84 (s, 3H), 2.29 (s, 3H), 1.40 (s, 12H).

Anhydrous MeOH (5 mL) was added to a solution of 4-((4-methoxybenzyl)oxy)-5-methyl-2-(4,4,5,5-tetramethyl-1,3,2-dioxaborolan-2-yl)benzaldehyde (1.7 g, 4.3 mmol) and NaBH$_4$ (0.3 g, 8.7 mmol) in THF (20 mL) at 0° C. The mixture was stirred at ambient temperature for 30 mins. 1 N aq. HCl was added to the mixture until pH=4, the aqueous layer was treated with EtOAc, the organic layer was concentrated to give 6-((4-methoxybenzyl)oxy)-5-methylbenzo[c][1,2]oxaborol-1(3H)-ol (0.7 g, yield 57.0%) and used directly into next step.

6-((4-methoxybenzyl)oxy)-5-methylbenzo[c][1,2]oxaborol-1(3H)-ol (1.7 g, 7.0 mmol) was dissolved in EtOAc (80 mL). To this solution under nitrogen was added Pd/C (0.5 g). The reaction mixture was vacuumed and backfilled hydrogen for 3 times, then hydrogenated at room temperature, 50 psi overnight. After filtration and rotary evaporation, the residue was purified by recrystallization (DCM/Petroleum Ether, 1:10) to give 5-methylbenzo[c][1,2]oxaborole-1,6(3H)-diol (300.0 mg, 31.5% yield) and 151.0 mg delivered. δ 9.22 (d, J=1.6 Hz, 1H), 8.94 (d, J=1.6 Hz, 1H), 7.08 (d, J=4.8 Hz, 1H), 4.82 (s, 2H), 2.15 (s, 3H). MS: 163 (M−1)⁻

Tos-pleuromutilin (420.0 mg, 0.8 mmol), 5-methylbenzo[c][1,2]oxaborole-1,6(3H)-diol (130.0 mg, 0.8 mmol) and K$_2$CO$_3$ (330.0 g, 2.3 mmol) in 20 mL DMF was heated at 50° C. overnight. Main peak on LCMS was desired product. Water was added and the mixture was adjust to pH<4 with 2N aqueous HCl. White solid precipitated and the mixture was filtered, the crude product was purified by prep-HPLC (column: Luna C18 250×30 mm, 5 μm; liquid phase: [A-TFA/H$_2$O=0.1% v/v; B-ACN] B %: 40%-70%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-5-methyl-1,3-dihydrobenzo[c][1,2]oxa borol-6-yl)oxy)acetate (78.0 mg, yield 19.0%). δ 8.93 (br. s., 1H), 7.19 (s, 1H), 7.09 (s, 1H), 6.08 (dd, J=17.6, 11.2 Hz, 1H), 5.59 (d, J=8.0 Hz, 1H), 5.12-4.95 (m, 2H), 4.87 (s, 2H), 4.71 (s, 2H), 3.40 (d, J=4.8 Hz, 1H), 2.40 (s, 1H), 2.25 (s, 3H), 2.20-1.96 (m, 3H), 1.74-1.55 (m, 2H), 1.50-1.45 (m, 1H), 1.37 (s, 3H), 1.45-1.17 (m, 6H), 1.10-0.94 (m, 4H), 0.82 (d, J=6.4 Hz, 3H), 0.62 (d, J=6.4 Hz, 3H). MS: 523 (M−1)⁻

11. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-4-methyl-1,3-dihydrobenzo[c][1,2]oxaborol-6-yl)oxy)acetate

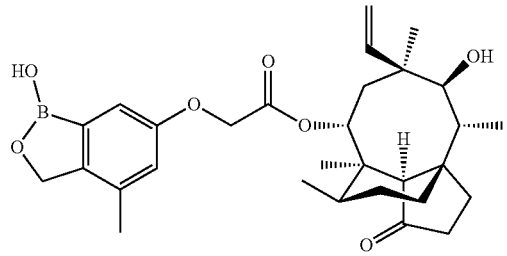

5-methylbenzene-1,3-diol (25.0 g, 0.2 mol) in DMF (100 mL) was added dropwise to a mixture of POCl₃ (44.0 g, 0.3 mol) in DMF (200 mL) at 0° C., the mixture was stirred at room temperature for 1 hr, then the reaction mixture was poured into ice water, solid precipitated and the mixture was filtered and washed with water three times, dried to give 2,4-dihydroxy-6-methylbenzaldehyde (21.0 g, 82.0%), which was used for next step directly.

BnBr (15.24 mL, 0.128 mol) was added to a mixture of 2,4-dihydroxy-6-methylbenzaldehyde (19.5 g, 0.1 mol) and NaHCO₃ (10.8 g, 0.1 mol) in MeCN (200 mL) at room temperature and the mixture was then refluxed at 90° C. for 48 hrs. The solvent was removed under reduced pressure and the residue was poured into cold water, extracted with EtOAc twice, the combined organic layers were dried over Na₂SO₄, concentrated and then purified by column chromatography (EtOAc/Petroleum ether, 1:10-1:5) to give 4-(benzyloxy)-2-hydroxy-6-methylbenzaldehyde (23.6 g, 76.0%). ¹H NMR (MeOD, 400 MHz) δ 10.13 (s, 1H), 7.24-7.59 (m, 5H), 6.26-6.51 (m, 2H), 5.13 (s, 2H), 2.54 (s, 3H).

To a solution of 4-(benzyloxy)-2-hydroxy-6-methylbenzaldehyde (13.6 g, 560.0 mmol) and TEA (19.0 mL) in dry DCM (200 mL) was added Tf₂O (14.2 mL, 840.0 mmol) dropwise at 0° C. The mixture was stirred at room temperature for 4 hrs. Then water was added, adjusted pH to 3-4, extracted with DCM, purified by column chromatography (EtOAc/Petroleum ether, 1:10~1:5) to give 5-(benzyloxy)-2-formyl-3-methylphenyl trifluoromethanesulfonate (15.0 g, 71.0%). ¹H NMR (CDCl₃, 400 MHz) δ 10.35 (s, 1H), 7.43-7.38 (m, 7H), 5.14 (s, 2H), 2.66 (s, 3H).

A mixture of 5-(benzyloxy)-2-formyl-3-methylphenyl trifluoromethanesulfonate (2.0 g, 5.3 mmol), Pin₂B₂(1.4 g, 5.6 mmol), Pd(dppf)Cl₂ (0.1 g, 0.2 mmol) and KOAc (1.6 g, 16.0 mmol) in dioxane (20 mL) was bubbled with nitrogen for 10 mins, then the mixture was stirred overnight at 80° C. under a N₂ balloon. The solvent was removed and the residue was purified by silica gel chromatography (EtOAc/Petroleum ether, 1:20-1:5) to give 4-(benzyloxy)-2-methyl-6-(4,4,5,5-tetramethyl-1,3,2-dioxaborolan-2-yl)benzaldehyde (1.0 g, 53.0%). ¹H NMR (CDCl₃, 400 MHz) δ 10.34 (s, 1H), 7.32-7.47 (m, 5H), 7.06 (d, J=2.0 Hz, 1H), 6.80 (d, J=2.0 Hz, 1H), 5.13 (s, 2H), 2.63 (s, 3H), 1.43 (s, 12H).

To a stirred solution of 4-(benzyloxy)-2-methyl-6-(4,4,5,5-tetramethyl-1,3,2-dioxaborolan-2-yl)benzaldehyde (1 g, 2.8 mmol) in dry THF (10 mL) was added NaBH₄ (0.2 g, 5.7 mmol), MeOH (0.5 mL). The mixture was stirred at room temperature for 2 hrs. Then water was added, the mixture was extracted with EtOAc, evaporated to give 6-(benzyloxy)-4-methylbenzo[c][1,2]oxaborol-1(3H)-ol (0.8 g crude). ¹H NMR (MeOD, 400 MHz) δ 7.46-7.33 (m, 5H), 7.14 (s, 1H), 6.96 (s, 1H), 5.10 (s, 2H), 4.00 (s, 2H), 2.25 (s, 3H).

To a stirred solution of 6-(benzyloxy)-4-methylbenzo[c][1,2]oxaborol-1(3H)-ol (0.8 g, 3.2 mmol) in EtOAc (50 mL) was added Pd/C (0.2 g) and the mixture was stirred under hydrogen atmospheres (50 psi) overnight. The mixture was filtered through celite and the filtrate was concentrated, recrystallized with DCM/petroleum ether (1:5) to give the desired product as white solid (0.4 g, 78.0% yield). ¹H NMR (DMSO-d₆, 400 MHz) δ 9.16 (s, 1H), 8.98 (s, 1H), 6.91 (s, 1H), 6.68 (s, 1H), 4.83 (s, 2H), 2.13 (s, 3H). MS: 163 (M−1)⁻

4-methylbenzo[c][1,2]oxaborole-1,6(3H)-diol (0.3 g, 1.8 mmol), (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (1.0 g, 1.8 mmol) and K₂CO₃ (0.8 g, 5.5 mmol) in 5 mL DMF was heated at 50° C. overnight. Main peak on LCMS was desired product. Water was added and the mixture was adjust to pH<4 with 2N HCl, White solid precipitated and filtered, the crude product was purified by prep-HPLC (column: Luna C18 250×30 mm, 10 m; liquid phase: [A-TFA/H₂O=0.1% v/v; B-ACN] B %: 35%-65%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-4-methyl-1,3-dihydrobenzo[c][1,2]oxaborol-6-yl)oxy)acetate (0.2 g, 22.0%). ¹H NMR (DMSO-d₆, 400 MHz) δ 7.02 (d, J=1.76 Hz, 1H), 6.83 (d, J=1.76 Hz, 1H), 6.10 (dd, J=17.6, 11.2 Hz, 1H), 5.60 (d, J=8.4 Hz, 1H), 5.12-4.96 (m, 2H), 4.87 (s, 2H), 4.75-4.60 (m, 2H), 2.41 (br. s., 1H), 2.17 (s, 3H), 2.00-2.13 (m, 5H), 1.72-1.55 (m, 2H), 1.54-1.39 (m, 2H), 1.35 (s, 3H), 1.32-1.20 (m, 3H), 1.04 (m, 4H), 0.82 (d, J=6.4 Hz, 3H), 0.64 (d, J=7.2 Hz, 3H). MS: 523 (M−1)⁻

12. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy)acetate Hydrochloride

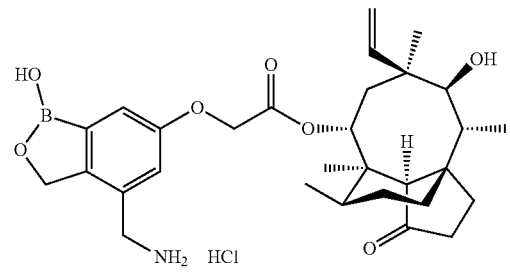

A mixture of tert-butyl ((1,6-dihydroxy-1,3-dihydrobenzo[c][1,2]oxaborol-4-yl) methyl)carbamate (1.6 g, 5.8 mmol, 1.0 equiv), pleuromutilintosylate (3.4 g, 7.0 mmol, 1.2 equiv) and $K_2CO_3$ (2.4 g, 17.5 mmol, 3.0 equiv) in DMSO (50.0 mL) was degassed and purged with $N_2$ for 3 times, and then the mixture was stirred at 80° C. for 12 hours under $N_2$ atmosphere. The mixture was poured into ice-water and the solid was filtered, which was purified by prep-HPLC (column: Luna 250×50.0 mm, 5 m; liquid phase: [A-$H_2O$+ 0.075% TFA; B-ACN] B %: 35%-65%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-1-hydroxy-1,3-dihydrobenzo [c][1,2]oxaborol-6-yl)oxy)acetate (1.3 g, 2.0 mmol, 34.8% yield) as a white solid. $^1$H NMR (DMSO-$d_6$, 400 MHz) δ 9.08 (s, 1H), 7.36 (s, 1H), 7.06 (s, 1H), 6.90 (s, 1H), 6.13-6.06 (m, 1H), 5.58 (d, J=10.8 Hz, 1H), 5.10-4.99 (m, 2H), 4.93 (s, 2H), 4.68 (q, J=16.8 Hz, 2H), 4.06-4.04 (m, 2H), 3.42-3.41 (m, 2H), 2.41 (s, 1H), 2.18-1.05 (m, 27H), 0.82 (d, J=6.8 Hz, 3H), 0.63 (d, J=6.4 Hz, 3H).

A mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(((tert-butoxycarbonyl) amino)methyl)-1-hydroxy-1,3-dihydrobenzo[c][1,2] oxaborol-6-yl)oxy)acetate (1.6 g, 2.5 mmol, 1.0 equiv) in HCl/EtOAc (20.0 mL) was stirred at 25° C. for 4 hours then solid precipitated. The mixture was filtered to collect the solid. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy)acetate (1.18 g, 2.05 mmol, 81.95% yield) was obtained as an off-white solid. $^1$H NMR (DMSO-$d_6$, 400 MHz) δ 9.19 (s, 1H), 8.30 (br. s., 3H), 7.26-7.17 (m, 2H), 6.11 (dd, J=11.2, 17.9 Hz, 1H), 5.62 (d, J=8.8 Hz, 1H), 5.15-4.95 (m, 4H), 4.79-4.65 (m, 2H), 4.55 (br. s., 1H), 3.93 (d, J=5.3 Hz, 2H), 3.43 (br. s., 2H), 2.44 (d, J=7.9 Hz, 1H), 2.26-2.01 (m, 4H), 1.73-1.19 (m, 10H), 1.12-0.94 (m, 4H), 0.82 (d, J=7.1 Hz, 3H), 0.65 (d, J=7.1 Hz, 3H). MS (ESI): mass calcd. for $C_{30}H_{43}BClNO_7$ 575.3, m/z found 540.4 [M+H]$^+$. HPLC: 96.1% (220 nm), 91.0% (weak absorption at 254 nm).

13. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-((dimethylamino)methyl)-1-hydroxy-1,3-dihydrobenzo[c][1,2]oxaborol-6-yl)oxy)acetate Hydrochloride

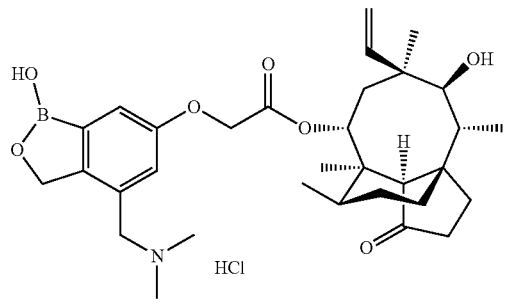

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy) acetate hydrochloride salt (125.0 mg, 231.7 umol, 1.0 eq.) in $CH_3CN$ (10.0 mL) was added formaldehyde (188.1 mg, 2.3 mmol, 172.5 uL, 37% purity, 10.0 eq.), sodium cyanoboranuide (21.8 mg, 347.6 umol, 1.5 eq.) and AcOH (1.4 mg, 23.2 umol, 1.3 uL, 0.1 eq). The mixture was stirred at 25° C. for 6 hours. HPLC and LCMS indicated the reaction was completed. The reaction mixture was concentrated under reduced pressure to remove $CH_3CN$. The residue purified by pre-HPLC (column: Luna C18 100×30 mm, 5 m; liquid phase: [A-TFA/$H_2O$=0.075% v/v; B-ACN] B %: 20%-50%, 12 min]). Freeze-dry after added two drops of 2N HCl (aq.), (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-((dimethylamino)methyl)-1-hydroxy-1,3-dihydrobenzo[c][1,2]oxaborol-6-yl)oxy)acetate hydrochloride (80.0 mg, 141.0 umol, 60.8% yield) was obtained as a white solid. $^1$H NMR (DMSO-$d_6$, 400 MHz) δ 10.52 (br. s., 1H), 7.40 (s, 1H), 7.31 (d, J=1.6 Hz, 1H), 6.11 (dd, J=11.2, 18.0 Hz, 1H), 5.61 (d, J=8.0 Hz, 1H), 5.13-4.98 (m, 4H), 4.75 (d, J=11.2 Hz, 2H), 4.18 (d, J=4.8 Hz, 2H), 3.42 (d, J=5.6 Hz, 1H), 2.73 (s, 6H), 2.42 (s, 1H), 2.26-2.01 (m, 4H), 1.72-1.57 (m, 3H), 1.55-1.20 (m, 9H), 1.09-0.95 (m, 4H), 0.82 (d, J=6.4 Hz, 3H), 0.64 (d, J=6.4 Hz, 3H). MS (ESI): mass calcd. for $C_{32}H_{46}BNO_7$ 567.3, m/z found 568.5 [M+H]$^+$. HPLC: 98.0% (220 nm), 99.2% (254 nm).

14. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-7-methoxy-1,3-dihydrobenzo[c][1,2]oxaborol-6-yl)oxy)acetate

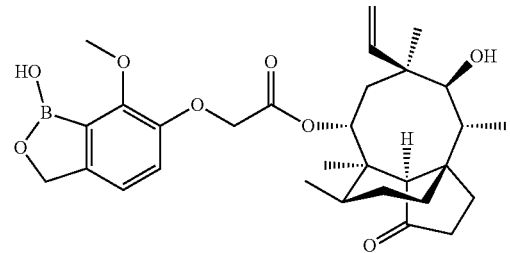

To a solution of 4-hydroxy-3-methoxybenzaldehyde (40.0 g, 262.9 mmol, 1.0 eq) in DCM (500.0 mL) was added TEA (79.8 g, 788.7 mmol, 3.0 eq) and acetyl chloride (30.9 g, 394.4 mmol, 1.5 eq). The mixture was stirred at 20° C. for 0.5 hr. The reaction mixture was quenched by addition water 100 mL at 20° C., and then adjusted pH to 5-6 by 4 N HCl, then extracted with DCM (100 mL×2). The combined organic layers were washed with brine (200 mL×2), dried over $Na_2SO_4$, filtered and concentrated under reduced pressure to give 4-formyl-2-methoxyphenyl acetate (53.0 g, crude) as a light brown solid. $^1$H NMR (DMSO-$d_6$, 400 MHz) δ 9.97 (s, 1H), 7.61 (d, J=1.3 Hz, 1H), 7.58 (dd, J=1.8, 7.9 Hz, 1H), 7.36 (d, J=7.9 Hz, 1H), 3.87 (s, 3H), 2.30 (s, 3H).

To a solution of 4-formyl-2-methoxyphenyl acetate (30.0 g, 154.5 mmol, 1.0 eq) in DCM (300.0 mL) was added fuming nitric acid (154.5 mmol, 1.0 eq) at −30° C. The mixture was stirred at 20° C. for 15 hrs. The reaction mixture was quenched by addition water 100 mL at 0° C., and then diluted with DCM 50 mL and extracted with DCM (50 mL×3). The combined organic layers were washed with brine (100 mL×2), dried over $Na_2SO_4$, filtered and concentrated under reduced pressure to give a residue. The residue was purified by column chromatography (SiO$_2$, Petroleum ether/Ethyl acetate=30/1 to 10:1) to give 4-formyl-2-methoxy-3-nitrophenyl acetate (23.0 g, 96.2 mmol, 62.2% yield) as a white solid. $^1$H NMR (DMSO-d$_6$, 400 MHz) δ 9.91 (s, 1H), 7.96 (d, J=8.5 Hz, 1H), 7.76 (d, J=8.5 Hz, 1H), 3.87 (s, 3H), 2.41 (s, 3H).

To a solution of FeSO$_4$.7H$_2$O (145.3 g, 522.6 mmol, 5.0 eq) in H$_2$O (500.0 mL) was added NH$_3$.H$_2$O (109.91 g, 3.14 mol, 120.78 mL, 30.00 eq), followed by 4-formyl-2-methoxy-3-nitrophenyl acetate (25.0 g, 104.5 mmol, 1.0 eq), and then the mixture was stirred at 100° C. for 2 hrs under N$_2$ atmosphere. LCMS showed the reaction was completed. The mixture was filtered, then washed with warm water (500 mL), the filtrate was adjusted pH to 4-5 by H$_2$SO$_4$, then extracted with EtOAc (100 mL×3), the combined organic layers was washed with brine (200 mL×1), dried over Na$_2$SO$_4$, filtered, concentrated to give a residue. The residue was purified by column chromatography (SiO$_2$, Petroleum ether/Ethyl acetate=10/1 to 2:1) to give 2-amino-4-hydroxy-3-methoxybenzaldehyde (7.0 g, 41.8 mmol, 40.1% yield) as a white solid. $^1$H NMR (DMSO-d$_6$, 400 MHz) δ 10.16 (s, 1H), 9.73 (s, 1H), 9.59 (s, 1H), 7.15 (d, J=8.5 Hz, 1H), 6.80 (br. s., 1H), 6.23 (d, J=9.0 Hz, 1H), 3.66 (s, 3H).

To a solution of 2-amino-4-hydroxy-3-methoxybenzaldehyde (6.5 g, 38.9 mmol, 1.0 eq) in HBr (10.0 mL) was added H$_2$O (100.0 mL) and the mixture was cooled to 0° C., a cold solution of NaNO$_2$ (2.7 g, 38.9 mmol, 2.1 mL, 1.0 eq) in H$_2$O (100.0 mL) was dropwise added during 10 mins, then CuBr (11.2 g, 77.8 mmol, 2.4 mL, 2.0 eq) was added to the mixture, after addition, the mixture was stirred at 70° C. for 1 hr. The reaction mixture was quenched by addition water 10 mL at 25° C., and then diluted with MTBE 20 mL and extracted with MTBE (30 mL×3). The combined organic layers were washed with brine (50 mL×2), dried over Na$_2$SO$_4$, filtered and concentrated under reduced pressure to give 2-bromo-4-hydroxy-3-methoxybenzaldehyde (7.0 g, 30.3 mmol, 77.9% yield) as a brown solid. $^1$H NMR (DMSO-d$_6$, 400 MHz) δ 11.06 (s, 1H), 10.05 (s, 1H), 7.54 (d, J=8.8 Hz, 1H), 7.01 (d, J=8.4 Hz, 1H), 3.77 (s, 3H).

A mixture of 2-bromo-4-hydroxy-3-methoxybenzaldehyde (7.0 g, 30.3 mmol, 1.0 eq), BnBr (5.2 g, 30.3 mmol, 3.6 mL, 1.0 eq), K$_2$CO$_3$ (8.4 g, 60.6 mmol, 2.0 eq) and KI (502.9 mg, 3.0 mmol, 0.1 eq) in DMF (100.0 mL) was degassed and purged with N$_2$ for 3 times, and then the mixture was stirred at 25° C. for 4 hrs under N$_2$ atmosphere. TLC showed the reaction was completed. The reaction mixture was quenched by addition water 200 mL at 0° C., and then diluted with EtOAc 20 mL and extracted with EtOAc (50 mL×3). The combined organic layers were washed with brine (100 mL×2), dried over Na$_2$SO$_4$, filtered and concentrated under reduced pressure to give a residue. The residue was purified by column chromatography (SiO$_2$, Petroleum ether/Ethyl acetate=30/1 to 10:1) to give 4-(benzyloxy)-2-bromo-3-methoxybenzaldehyde (8.0 g, 24.9 mmol, 82.2% yield) was obtained as an off-white solid. $^1$H NMR (DMSO-d$_6$, 400 MHz) δ 10.11 (s, 1H), 7.66 (d, J=8.5 Hz, 1H), 7.52-7.47 (m, 2H), 7.43 (t, J=7.3 Hz, 2H), 7.40-7.34 (m, 2H), 5.30 (s, 2H), 3.80 (s, 3H).

A mixture of 4-(benzyloxy)-2-bromo-3-methoxybenzaldehyde (800.0 mg, 2.5 mmol, 1.0 eq), Pin$_2$B$_2$(3.8 g, 14.9 mmol, 6.0 eq), KOAc (488.9 mg, 4.9 mmol, 2.0 eq) and Pd(dppf)Cl$_2$.CH$_2$Cl$_2$ (101.7 mg, 124.5 umol, 0.05 eq) in dioxane (30.0 mL) was degassed and purged with N$_2$ for 3 times, and then the mixture was stirred at 70° C. for 18 hrs under N$_2$ atmosphere. The reaction solution was filtered and concentrated to give a residue. The residue was purified by column chromatography (SiO$_2$, Petroleum ether/Ethyl acetate=20/1 to 5:1) to afford 4-(benzyloxy)-3-methoxy-2-(4,4,5,5-tetramethyl-1,3,2-dioxaborolan-2-yl)benzaldehyde (1 g, crude) as a yellow solid. $^1$H NMR (DMSO-d$_6$, 400 MHz) δ 9.80 (s, 1H), 7.51 (d, J=8.4 Hz, 1H), 7.45-7.32 (m, 5H), 7.04 (d, J=7.9 Hz, 1H), 5.20 (s, 2H), 3.90 (s, 3H), 1.47 (s, 12H).

To a solution of 4-(benzyloxy)-3-methoxy-2-(4,4,5,5-tetramethyl-1,3,2-dioxaborolan-2-yl)benzaldehyde (1.7 g, 4.6 mmol, 1.0 eq) in THF (20.0 mL) was added NaBH$_4$ (209.7 mg, 5.5 mmol, 1.2 eq) and MeOH (500.0 uL). The mixture was stirred at 25° C. for 10 mins. Water was added to the mixture, and then adjusted pH to 3-4, THF was removed under reduced pressure, the solid was precipitated, filtered, the solid was washed with water for three times, then washed with petroleum ether for three times to afford 6-(benzyloxy)-7-methoxybenzo[c][1,2]oxaborol-1 (3H)-ol (700.0 mg, 2.6 mmol, 56.1% yield) as a brown solid. $^1$H NMR (DMSO-d$_6$, 400 MHz) δ 9.03 (s, 1H), 7.46-7.29 (m, 5H), 7.19 (d, J=8.0 Hz, 1H), 6.94 (d, J=8.0 Hz, 1H), 5.08 (s, 2H), 4.88 (s, 2H), 3.93 (s, 3H)

To a solution of 6-(benzyloxy)-7-methoxybenzo[c][1,2] oxaborol-1(3H)-ol (700.0 mg, 2.6 mmol, 1.0 eq) in EtOAc (20.0 mL) was added Pd/C (10%, 1 g) under N$_2$ atmosphere. The suspension was degassed and purged with H$_2$ for 3 times. The mixture was stirred under H$_2$ (50 Psi) at 25° C. for 2 hrs. The reaction solution was filtered and the filtrate was concentrated to give 7-methoxybenzo[c][1,2]oxaborole-1,6(3H)-diol (420.0 mg, 2.3 mmol, 90.1% yield) as a white solid. $^1$H NMR (DMSO-d$_6$, 400 MHz) δ 8.97 (s, 1H), 8.68 (s, 1H), 6.95-6.91 (m, 1H), 6.83 (d, J=8.0 Hz, 1H), 4.85 (s, 2H), 3.90 (s, 3H).

A mixture of 7-methoxybenzo[c][1,2]oxaborole-1,6(3H)-diol (150.0 mg, 833.5 umol, 1.0 eq), pleuromutilintosylate (887.9 mg, 1.7 mmol, 2.0 eq), Na$_2$CO$_3$ (132.5 mg, 1.2 mmol, 1.5 eq), KI (69.2 mg, 416.7 umol, 0.5 eq) in DMSO (20.0 mL) was degassed and purged with N$_2$ for 3 times, and then the mixture was stirred at 30° C. for 24 hrs under N$_2$ atmosphere. Water (100 mL) was added to the mixture, then adjusted pH to 4-5, the solid was precipitated, filtered, and washed with water for three times. The solid was purified by prep-HPLC (column: Luna C18 100×30 mm, 5 m; liquid phase: [A-TFA/H$_2$O=0.075% v/v; B-ACN] B %: 35%-75%, 12 min]). MeCN was removed under reduced pressure. The residue was dried under freeze-drying to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-7-methoxy-1,3-dihydrobenzo[c][1,2]oxaborol-6-yl)oxy)acetate (200.0 mg, 370.1 umol, 44.4% yield) as a white solid. $^1$H NMR (DMSO-d$_6$, 400 MHz) δ 9.20-8.94 (m, 1H), 7.03 (d, J=8.4 Hz, 1H), 6.91 (d, J=8.4 Hz, 1H), 6.12 (dd, J=11.5, 17.6 Hz, 1H), 5.61 (d, J=8.4 Hz, 1H), 5.10-5.00 (m, 2H), 4.89 (s, 2H), 4.74-4.60 (m, 2H), 3.93 (s, 3H), 3.42 (d, J=6.2 Hz, 1H), 2.41 (br. s., 1H), 2.24-1.99 (m, 4H), 1.71-1.20 (m, 11H), 1.12-0.94 (m, 4H), 0.82 (d, J=7.1 Hz, 3H), 0.63 (d, J=6.6 Hz, 3H). MS (ESI): mass calcd. for C$_{30}$H$_{41}$BO$_8$ 540.3, m/z found 539.3 [M−1]$^-$. HPLC: 100% (220 nm), 100% (254 nm).

15. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-5-methoxy-1,3-dihydrobenzo[c][1,2]oxaborol-6-yl)oxy)acetate

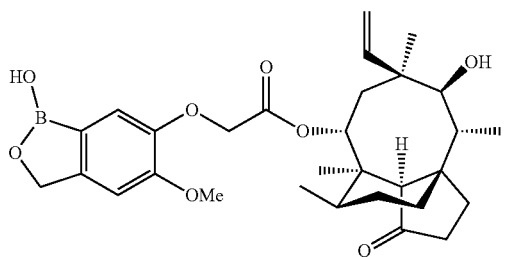

Ac$_2$O (24.1 g, 236.6 mmol, 22.1 mL, 1.2 eq) was added to a solution of 4-hydroxy-3-methoxy-benzaldehyde (30.0 g, 197.1 mmol, 1.0 eq) and TEA (39.9 g, 394.3 mmol, 54.6 mL, 2.0 eq) in DCM (100.00 mL) at 20° C. The mixture was stirred at 20° C. for 10 hours. TLC showed the reaction was completed. The reaction was quenched by addition of water (300 mL), and adjusted pH<5 with 2N HCl, extracted with DCM (100 mL×2). The combined organic phase was dried over Na$_2$SO$_4$ and concentrated in vacuo to give (4-formyl-2-methoxy-phenyl) acetate (36.0 g, 185.3 mmol, 94.0% yield) as colorless oil. $^1$H NMR (CDCl$_3$, 400 MHz) δ 9.95 (s, 1H), 7.50-7.47 (m, 2H), 7.23 (d, J=8.0 Hz, 1H), 3.92 (s, 3H), 2.35 (s, 3H).

To the suspension of (4-formyl-2-methoxy-phenyl) acetate (35.0 g, 180.2 mmol, 1.0 eq) and KBr (72.2 g, 607.4 mmol, 26.2 mL, 3.3 eq) in H$_2$O (600.0 mL) was added Br$_2$ (31.9 g, 200.0 mmol, 10.3 mL, 1.1 eq) dropwise. The reaction mixture was stirred for 10 hours at 20° C. The mixture was filtered, washed with water and dried. The residue was then added in petroleum ether (300 mL) and DCM (30 mL) and stirred for 12 hours. The mixture was filtered and washed with petroleum ether and dried to give (5-bromo-4-formyl-2-methoxy-phenyl) acetate (35.0 g, 128.1 mmol, 71.1% yield) as yellow solid. $^1$H NMR (CDCl$_3$, 400 MHz) δ 10.23 (s, 1H), 7.52 (s, 1H), 7.36 (s, 1H) 3.89 (s, 3H), 2.34 (s, 3H).

(5-bromo-4-formyl-2-methoxy-phenyl) acetate (10.0 g, 36.6 mmol, 1.0 eq), Pd(dppf)Cl$_2$ (803.8 mg, 1.10 mmol, 0.03 eq), KOAc (5.3 g, 54.9 mmol, 1.5 eq) and Pin$_2$B$_2$(27.9 g, 109.8 mmol, 3.0 eq) in dioxane (150.0 mL) were stirred at 70° C. under N$_2$ atmosphere for 12 hours. The mixture was filtered and concentrated in vacuo. The crude product was purified by flash column chromatography (petroleum ether/EtOAc=3/1) to give [4-formyl-2-methoxy-5-(4,4,5,5-tetramethyl-1,3,2-dioxaborolan-2-yl)phenyl]acetate (7.6 g, 23.7 mmol, 64.8% yield) as a yellow solid. $^1$H NMR (CDCl$_3$, 400 MHz) δ 10.68 (s, 1H), 7.63 (s, 1H), 7.62 (s, 1H) 3.92 (s, 3H), 2.33 (s, 3H), 1.37 (s, 12H).

MeOH (5.00 mL) was added to a solution of [4-formyl-2-methoxy-5-(4,4,5,5-tetramethyl-1,3,2-dioxaborolan-2-yl) phenyl]acetate (7.6 g, 23.7 mmol, 1.0 eq) and NaBH$_4$ (1.3 g, 35.6 mmol, 1.5 eq) in THF (100.0 mL) at 20° C. The mixture was stirred for 12 hours. The reaction was quenched by addition of water 50 mL and adjusted to pH<4 with 2N HCl aq. solution. The mixture was extracted with EtOAc (50 mL×3). The combined organic phase was dried over Na$_2$SO$_4$ and concentrated in vacuo to give (1-hydroxy-5-methoxy-3H-2,1-benzoxaborol-6-yl) acetate (4.5 g, crude) as yellow oil. $^1$H NMR (CDCl$_3$, 400 MHz) δ 7.32 (s, 1H), 7.16 (s, 1H), 4.94 (s, 2H), 3.79 (s, 3H), 2.26 (s, 3H).

NaOH (1.3 g, 33.7 mmol, 1.5 eq) was added to a solution of (1-hydroxy-5-methoxy-3H-2,1-benzoxaborol-6-yl) acetate (5.0 g, 22.5 mmol, 1.00 eq) in MeOH (15.0 mL) and H$_2$O (30.0 mL). The mixture was stirred at 20° C. for 3 hours. HPLC showed the reaction was completely. The reaction was quenched by addition of water (50 mL) and treated with 2 N HCl till pH<3. The mixture was extracted with EtOAc (50 mL×3), the combined organic phase was dried over Na$_2$SO$_4$ and concentrated in vacuo to give 1-hydroxy-5-methoxy-3H-2,1-benzoxaborol-6-ol (1.2 g, 6.67 mmol, 29.6% yield) as yellow solid. $^1$H NMR (CDCl$_3$, 400 MHz) δ 9.77 (s, 1H), 7.07 (s, 1H), 7.05 (s, 1H), 4.62 (s, 2H), 3.76 (s, 3H).

K$_2$CO$_3$ (306.8 mg, 2.2 mmol, 2.0 eq) was added to a solution of 1-hydroxy-5-methoxy-3H-2,1-benzoxaborol-6-ol (200.0 mg, 1.11 mmol, 1.0 eq) and [(12R,13R,14R,15S,16R,19S,20R,21S)-15-hydroxy-12,13,19,20-tetramethyl-17-oxo-19-vinyl-14-tricyclotetradecanyl]2-iodoacetate (542.1 mg, 1.11 mmol, 1.0 eq) in DMSO (10.0 mL). The mixture was stirred at 50° C. for 3 hours. The reaction was quenched by addition of water (50 mL) and treated with 2N HCl till pH<4. White solid was filtered to give crude product. The crude product was purified by prep-HPLC (column: Luna C18 100×30×5 μm; mobile phase: [water (0.1% TFA)-ACN]; B %: 40%-70%, 10 min) to give [(21R,22R,23R,24S,25R,28S,29R,30S)-24-hydroxy-21,22,28,29-tetramethyl-26-oxo-28-vinyl-23-tricyclotetradecanyl]-2-[(1-hydroxy-5-methoxy-3H-2,1-benzoxaborol-6-yl)oxy] acetate (86.0 mg, 159.1 umol, 14.3% yield) as white solid. $^1$H NMR (DMSO-d$_6$ 400 MHz) δ 7.11 (s, 1H), 7.02 (s, 1H), 6.09 (dd, J=11.2, 17.6 Hz, 1H), 5.58 (d, J=8.4 Hz, 1H), 5.02 (dd, J=17.6, 30.0 Hz, 2H), 4.87 (s, 2H), 4.65 (m, 2H), 3.79 (s, 3H), 3.40 (d, J=5.6 Hz, 1H), 2.40 (s, 1H), 2.19-2.02 (m, 4H), 1.67-1.60 (m, 2H), 1.35-1.29 (m, 8H), 1.03-1.00 (m, 4H), 0.81 (d, J=6.8 Hz, 3H), 0.61 (d, J=6.8 Hz, 3H). MS (ESI): mass calcd. for C$_{30}$H$_{41}$BO$_8$ 540.29, m/z found 539.1 [M−H]$^-$. HPLC: 99.8% (220 nm), 99.6% (254 nm).

16. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-cyano-1-hydroxy-1,3-dihydrobenzo[c][1,2]oxaborol-6-yl)oxy)acetate

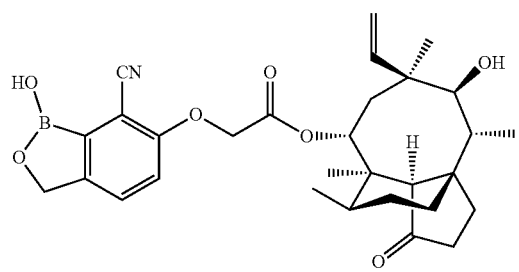

To a solution of 2-bromo-4-fluoro-1-methylbenzene (38.5 g, 203.7 mmol, 1.0 eq) in THF (1.0 L) was added LDA (2 M, 122.2 mL, 1.2 eq) at −78° C., the mixture was stirred at −78° C. for 1.5 hours, then ethyl formate (45.3 g, 611.1 mmol, 49.2 mL, 3.0 eq) was added to the mixture at −78° C. The mixture was stirred at −78° C. for 5 min. TLC showed the reaction was completed. The reaction mixture was quenched by addition water (500 mL) at −70° C., and then diluted with EtOAc 100 mL and extracted with EtOAc (500 mL×2). The combined organic layers were washed with brine (1000 mL×1), dried over $Na_2SO_4$, filtered and concentrated under reduced pressure. The residue was purified by column chromatograph ($SiO_2$, petroleum ether/ethyl acetate=I/O to 10/1) to give 2-bromo-6-fluoro-3-methylbenzaldehyde (34.0 g, 156.7 mmol 76.9% yield) was obtained as brown oil. $^1$H NMR ($CDCl_3$, 400 MHz) δ 10.40 (s, 1H), 7.43 (dd, J=5.6, 8.4 Hz, 1H), 7.05 (t, J=9.2 Hz, 1H), 2.56-2.37 (m, 3H).

To a solution of 2-bromo-6-fluoro-3-methylbenzaldehyde (29.0 g, 133.6 mmol, 1.0 eq) in MeOH (500.0 mL) was added NaOMe (28.9 g, 534.5 mmol, 4.0 eq). The mixture was stirred at 70° C. for 5 hours. TLC showed a new spot was formed. The reaction mixture was quenched by addition water (500 mL) at 25° C., and then diluted with EtOAc 100 mL and extracted with EtOAc (500 mL×2). The combined organic layers were washed with brine (500 mL×1), dried over $Na_2SO_4$, filtered and concentrated under reduced pressure to give 2-bromo-6-methoxy-3-methylbenzaldehyde (36.00 g crude) as a white solid. $^1$H NMR ($CDCl_3$, 400 MHz) δ 10.41 (s, 1H), 7.34 (d, J=8.4 Hz, 1H), 6.87 (d, J=8.4 Hz, 1H), 3.87 (s, 3H), 2.38 (s, 3H).

To a solution of 2-bromo-6-methoxy-3-methylbenzaldehyde (36.0 g, 157.2 mmol, 1.0 eq) in DCM (500.0 mL) was added $BBr_3$ (78.7 g, 314.3 mmol, 30.3 mL, 2.0 eq). The mixture was stirred at −78° C. for 0.5 hour. The reaction mixture was quenched by addition water (100 mL) at 25° C., and then diluted with DCM 200 mL and extracted with DCM (200 mL×2). The combined organic layers were washed with brine (500 mL×1), dried over $Na_2SO_4$, filtered and concentrated under reduced pressure. The residue was purified by column chromatography ($SiO_2$, petroleum ether/ethyl acetate=100/1 to 1/1) to give 2-bromo-6-hydroxy-3-methylbenzaldehyde (27.0 g, 125.6 mmol, 79.89% yield) as a white solid. $^1$H NMR ($CDCl_3$, 400 MHz) δ 12.00 (s, 1H), 10.43 (s, 1H), 7.36 (d, J=8.8 Hz, 1H), 6.87 (d, J=8.4 Hz, 1H), 2.39 (s, 3H).

To a solution of 2-bromo-6-hydroxy-3-methylbenzaldehyde (16.0 g, 74.4 mmol, 1.0 eq) in DCM (200.0 mL) was added MOMCl (9.0 g, 111.6 mmol, 8.5 mL, 1.5 eq) and DIEA (19.2 g, 148.8 mmol, 26.0 mL, 2.0 eq). The mixture was stirred at 0° C. for 15 hours. TLC showed the reaction was completed. The reaction mixture was quenched by addition water (500 mL) at 25° C., and then diluted with DCM 200 mL and extracted with DCM (200 mL×2). The combined organic layers were washed with brine (500 mL×2), dried over $Na_2SO_4$, filtered and concentrated under reduced pressure. The residue was purified by column chromatography ($SiO_2$, petroleum ether/ethyl acetate=I/O to 5/1). To give 2-bromo-6-(methoxymethoxy)-3-methylbenzaldehyde (8.0 g, 30.9 mmol, 41.5% yield) as a yellow solid. $^1$H NMR ($CDCl_3$, 400 MHz) δ 10.42 (s, 1H), 7.33 (d, J=8.4 Hz, 1H), 7.10 (d, J=8.8 Hz, 1H), 5.23 (s, 2H), 3.50 (s, 3H), 2.40 (s, 3H).

To a solution of 2-bromo-6-(methoxymethoxy)-3-methylbenzaldehyde (23.5 g, 90.7 mmol, 1.0 eq) in THF (200.0 mL) and $H_2O$ (50.0 mL) was added KOAc (17.8 g, 181.4 mmol, 2.0 eq) and $NH_2OH·HCl$ (9.5 g, 136.1 mmol, 1.5 eq). The mixture was stirred at 25° C. for 0.5 hour. TLC showed the reaction was completed. The reaction mixture was quenched by addition water (200 mL) at 0° C., and then diluted with EtOAc 50 mL and extracted with EtOAc (100 mL×2). The combined organic layers were washed with brine (300 mL×1), dried over $Na_2SO_4$, filtered and concentrated under reduced pressure to (E)-2-bromo-6-(methoxymethoxy)-3-methylbenzaldehyde oxime (25.0 g, crude) as a yellow solid. $^1$H NMR (DMSO-$d_6$, 400 MHz) δ 11.36 (s, 1H), 8.07 (s, 1H), 7.28 (d, J=8.8 Hz, 1H), 7.07 (d, J=8.4 Hz, 1H), 5.13 (s, 2H), 3.32 (s, 3H), 2.28 (s, 3H)

To a solution of (E)-2-bromo-6-(methoxymethoxy)-3-methylbenzaldehyde oxime (25.0 g, 91.2 mmol, 1.0 eq) in THF (300.0 mL) was added TEA (27.7 g, 273.6 mmol, 37.9 mL, 3.0 eq) and TFAA (38.3 g, 182.4 mmol, 25.4 mL, 2.0 eq). The mixture was stirred at 25° C. for 1 hour. TLC showed the reaction was completed. The reaction mixture was quenched by addition water (100 mL) at 0° C., and then diluted with EtOAc 50 mL and extracted with EtOAc (100 mL×2). The combined organic layers were washed with $NaHCO_3$ (100 mL×1), then brine (200 mL×1), dried over $Na_2SO_4$, filtered and concentrated under reduced pressure to give 2-bromo-6-(methoxymethoxy)-3-methylbenzonitrile (23.00 g, crude) as a yellow solid. $^1$H NMR ($CDCl_3$, 400 MHz) δ 11.36 (s, 1H), 8.07 (s, 1H), 7.28 (d, J=8.8 Hz, 1H), 7.07 (d, J=8.4 Hz, 1H), 5.21-5.09 (m, 2H), 3.32 (s, 3H), 2.28 (s, 3H).

To a solution of 2-bromo-6-(methoxymethoxy)-3-methylbenzonitrile (2.3 g, 9.0 mmol, 1.0 eq) in $CCl_4$ (150.0 mL) was added NBS (2.4 g, 13.5 mmol, 1.5 eq) and BPO (217.5 mg, 898.0 umol, 0.1 eq). The mixture was stirred at 80° C. for 15 hours. TLC showed the reaction was completed. The reaction mixture was quenched by addition water (100 mL) at 25° C., and then diluted with DCM (100 mL) and extracted with DCM (100 mL×2). The combined organic layers were washed with brine (200 mL×1), dried over $Na_2SO_4$, filtered and concentrated under reduced pressure to give 2-bromo-3-(bromomethyl)-6-(methoxymethoxy) benzonitrile (3.0 g, crude) as a brown solid. $^1$H NMR ($CDCl_3$, 400 MHz) δ 7.59 (d, J=8.8 Hz, 1H), 7.21 (d, J=8.8 Hz, 1H), 5.31 (s, 2H), 4.58 (s, 2H), 3.53 (s, 3H).

To a solution of 2-bromo-3-(bromomethyl)-6-(methoxymethoxy)benzonitrile (3.0 g, 9.0 mmol, 1.0 eq) in DMF (30.0 mL) was added KOAc (2.6 g, 26.9 mmol, 3.0 eq). The mixture was stirred at 25° C. for 0.5 hour. TLC showed a new spot was formed. The reaction mixture was quenched by addition water (30 ml) at 25° C., and then diluted with EtOAc 10 mL and extracted with EtOAc (10 mL×2). The combined organic layers were washed with brine (20 mL×2), dried over $Na_2SO_4$, filtered and concentrated under reduced pressure to give a residue. The residue was purified by column chromatography ($SiO_2$, petroleum ether/ethyl acetate=100/1 to 10/1) to give 2-bromo-3-cyano-4-(methoxymethoxy)benzyl acetate (2.0 g, 6.4 mmol, 71.0% yield) as a white solid. $^1$H NMR ($CDCl_3$, 400 MHz) δ 7.56 (d, J=8.4 Hz, 1H), 7.22 (d, J=9.2 Hz, 1H), 5.31 (s, 2H), 5.16 (s, 2H), 3.53 (s, 3H), 2.13 (s, 3H).

A mixture of 2-bromo-3-cyano-4-(methoxymethoxy)benzyl acetate (1.3 g, 4.1 mmol, 1.0 eq), Pd $(PPh_3)_2Cl_2$ (87.2 mg, 124.2 umol, 0.03 eq), KOAc (609.2 mg, 6.2 mmol, 1.5 eq) and Pin$_2$B$_2$ (3.2 g, 12.4 mmol, 3.0 eq) in dioxane (100.0 mL) was degassed and purged with N$_2$ for 3 times, and then the mixture was stirred at 70° C. for 15 hours under N$_2$ atmosphere. HPLC and LCMS showed the reaction was completed. The reaction mixture was quenched by addition water (50 mL) at 25° C., and then diluted with EtOAc 10 mL and extracted with EtOAc (50 mL×2). The combined organic layers were washed with brine (50 mL×1), dried over Na$_2$SO$_4$, filtered and concentrated under reduced pressure to give 3-cyano-4-(methoxymethoxy)-2-(4,4,5,5-tetramethyl-1,3,2-dioxaborolan-2-yl)benzyl acetate (1.5 g crude) as a black solid. $^1$H NMR (CDCl$_3$, 400 MHz) δ 7.50 (d, J=8.4 Hz, 1H), 7.22 (d, J=8.4 Hz, 1H), 5.29 (s, 2H), 5.15 (s, 2H), 3.79 (s, 3H), 3.52 (s, 3H), 1.42 (s, 12H).

To a solution of 3-cyano-4-(methoxymethoxy)-2-(4,4,5,5-tetramethyl-1,3,2-dioxaborolan-2-yl) benzyl acetate (1.3 g, 3.6 mmol, 1.0 eq) in MeOH (50.0 mL) and H$_2$O (100.0 mL) was added NaOH (287.9 mg, 7.2 mmol, 2.0 eq). The mixture was stirred at 25° C. for 12 hours. HPLC and LCMS showed the reaction was completely. The reaction mixture was quenched by addition water (100 mL), then the mixture was adjusted pH about 6 at 25° C., and then diluted with EtOAc 100 mL and extracted with EtOAc (100 mL×2). The combined organic layers were washed with brine (200 mL×2), dried over Na$_2$SO$_4$, filtered and concentrated under reduced pressure. The residue was purified by prep-HPLC (column: Luna C8 100×30×5 μm; mobile phase: [water (0.1% TFA)-ACN]; B %: 15%-40%, 12 min) to give 1-hydroxy-6-(methoxymethoxy)-1,3-dihydrobenzo [c][1,2]oxaborole-7-carbonitrile (120.0 mg, 548.0 umol, 15.2% yield) as a white solid. $^1$H NMR (CDCl$_3$, 400 MHz) δ 7.51 (d, J=8.4 Hz, 1H), 7.40 (d, J=8.8 Hz, 1H), 5.32 (s, 2H), 5.07 (s, 2H), 3.55 (s, 3H).

To a solution of 1-hydroxy-6-(methoxymethoxy)-1,3-dihydrobenzo[c][1,2]oxaborole-7-carbonitrile (80.0 mg, 365.3 umol, 1.0 eq) in DCM (20.0 mL) was added CF$_3$COOH (124.95 mg, 1.1 mmol, 81.1 uL, 3.0 eq). The mixture was stirred at 25° C. for 12 hours. HPLC showed the reaction was completed. The reaction was concentrated to give 1,6-dihydroxy-1,3-dihydrobenzo[c][1,2]oxaborole-7-carbonitrile (80.0 mg, crude) as a yellow solid, which was used directly for next step.

To a solution of 1,6-dihydroxy-1,3-dihydrobenzo[c][1,2]oxaborole-7-carbonitrile (90.0 mg, 514.4 umol, 1.0 eq) and [(12R,13R,14R,15S,16R,19S,20R,21 S)-15-hydroxy-12,13,19,20-tetramethyl-17-oxo-19-vinyl-14-tricyclotetradecanyl] 2-iodoacetate (276.4 mg, 565.9 umol, 1.1 eq) in DMSO (150 mL) was added K$_2$CO$_3$ (106.7 mg, 771.6 umol, 1.5 eq). The mixture was stirred at 40° C. for 15 hours. HPLC showed the reaction was completed. The reaction mixture was quenched by addition of ice (20 g) and water (50 mL), and was adjusted to pH=7. The solid was filtered, washed by water for 3 times and concentrated under reduced pressure. The residue was purified by prep-HPLC ([water (0.1% TFA)-ACN]; B %: 37%-67%, 12 min) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((7-cyano-1-hydroxy-1,3-dihydrobenzo[c][1,2]oxaborol-6-yl)oxy)acetate (70.0 mg, 130.7 umol, 25.4% yield) as a white solid. $^1$H NMR (DMSO-d$_6$, 400 MHz) δ 7.65-7.56 (m, 1H), 7.31-7.22 (m, 1H), 6.10 (dd, J=11.2, 17.7 Hz, 1H), 5.59 (d, J=8.0 Hz, 1H), 5.12-4.92 (m, 6H), 3.41 (d, J=6.0 Hz, 1H), 2.41 (br. s., 1H), 2.25-1.98 (m, 4H), 1.71-1.19 (m, 11H), 1.10-0.93 (m, 4H), 0.81 (d, J=6.8 Hz, 3H), 0.65 (d, J=6.8 Hz, 3H). MS (ESI): mass calcd for C$_{30}$H$_{38}$BNO$_7$ 535.44, m/z found 552.1 [M+H2O−H]$^−$. HPLC: 99.13% (220 nm), 100% (254 nm).

17. tert-butyl 4-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-4-yl)piperidine-1-carboxylate 18. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-4-(piperidin-4-yl)-1,3-dihydrobenzo[c][1,2]oxaborol-6-yl)oxy)acetate

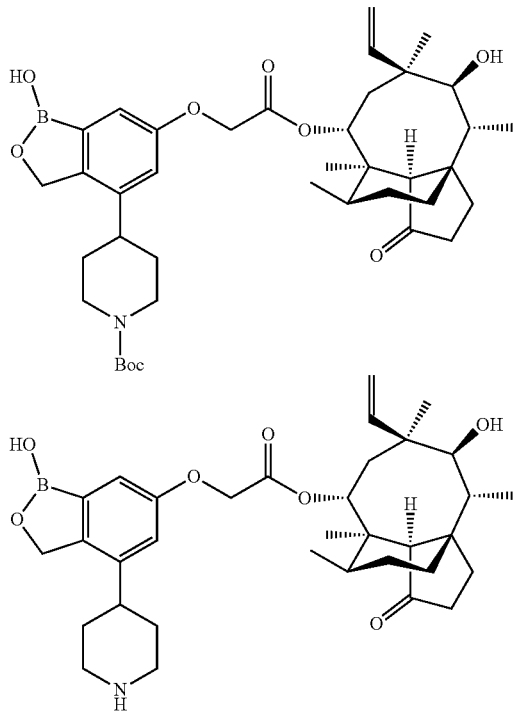

A solution of 3,5-dimethoxyaniline (4.74 g, 30 mmol) in water (50 mL) was cooled in ice-salt bath, and a thermal probe inserted to monitor internal temperature. To this suspension was slowly added 98% sulphuric acid (8.55 g, 82.8 mmol). A solution of NaNO$_2$ (2.45 g, 35.1 mmol) in 10 mL water was added slowly via syringe over a period of 15 minutes. The deep red solution was stirred at −5 to −3° C. for 30 minutes, then 25 mL of Et$_2$O was added. A solution of KI (15.3 g, 90.9 mmol) in 15 mL water was added via syringe over 30 minutes at such a rate that kept internal temperature around 1-2° C. Following complete addition, the reaction mixture was stirred for a further 3 hour at 0° C. The crude was then poured into a reparatory funnel, washed with saturated Na$_2$S$_2$O$_3$ solution (100 mL), and the aqueous washing extracted with EA (3×200 mL). The organics were pooled, washed successively with saturated Na$_2$S$_2$O$_3$ solution (100 mL) and brine (100 mL), dried over Na$_2$SO$_4$, and concentrated under reduced pressure. The residue obtained was purified by silica gel column chromatography (eluent: PE/EA=10:1) to give 1-iodo-3,5-dimethoxybenzene (4.00 g, yield 50.5%) as a yellow solid. $^1$H NMR (400 MHz, DMSO-d$_6$): δ 6.88 (s, 2H), 6.50 (s, 1H), 3.73 (s, 6H).

To a stirred solution of 1-iodo-3,5-dimethoxybenzene (17.4 g, 66.0 mmol) in DMF (112 mL) was carefully added dropwise POCl$_3$ (27.2 g, 176 mmol) over 30 min 0° C. The mixture obtained was heated to 100° C. for 24 h, then poured onto ice and left overnight. The precipitate was filtered and washed with water (4×500 mL) and the aqueous solution was extracted with DCM (4×300 mL). The combined organic layers were dried over Na$_2$SO$_4$, concentrated in vacuo. The crude residue was purified by column chromatography (eluent: PE/EA=10:1 to 3:1) to give 2-iodo-4,6-dimethoxybenzaldehyde (7.00 g, yield 36.4%) as a yellow solid. $^1$H NMR (400 MHz, CDCl$_3$): δ 10.14 (s, 1H), 7.13 (s, 1H), 6.48 (s, 1H), 3.89 (s, 1H), 3.87 (s, 1H).

To a solution of 2-iodo-4,6-dimethoxybenzaldehyde (7.00 g, 24.0 mmol) in DCM (40 mL) was added dropwise a 1 M solution of BBr$_3$ in DCM (96 mL) over 15 min at 25° C. under N$_2$. The orange solution was stirred at rt for 4 h, quenched with water (300 mL), and extracted with DCM (3×300 mL). The combined extracts were washed with brine (200 mL), dried with anhydrous Na$_2$SO$_4$ and concentrated in vacuo to give the residue which was purified by column chromatography (eluent: PE/EA=10:1 to 1:1) to give 2,4-dihydroxy-6-iodobenzaldehyde (5.25 g, yield 82.9%) as a yellow solid. $^1$H NMR (400 MHz, CDCl$_3$): δ 12.49 (s, 1H), 9.86 (s, 1H), 7.02 (s, 1H), 6.38 (s, 1H), 3.89-3.85 (m, 1H).

A stirring mixture of 2,4-dihydroxy-6-iodobenzaldehyde (5.25 g, 19.1 mmol), NaHCO$_3$ (1.84 g, 21.8 mmol) and KI (641 mg, 3.82 mmol) in MeCN (100 mL) was slowly warmed to 60° C. At this time, BnBr (3.98 g, 23.06 mmol) was added and the mixture was warmed to 80° C. After refluxing overnight, KHCO$_3$ (965 mg, 9.54 mmol) was added and the mixture was stirred for additional 5 hours. The mixture was then cooled to room temperature and concentrated by rotary evaporation. The residue was quenched with 10% aq. HCl (10 mL) and extracted with EA (3×300 mL). The combined organic extracts were washed with brine (100 mL), dried with anhydrous Na$_2$SO$_4$, filtered, and concentrated in vacuo to give the residue which was purified by column chromatography (eluent: PE/EA=10:1 to 8:1) to give 4-(benzyloxy)-2-hydroxy-6-iodobenzaldehyde (5.60 g, yield 92.8%) as a yellow solid. $^1$H NMR (400 MHz, DMSO-d$_6$): δ 12.22 (s, 1H), 9.83 (s, 1H), 7.46-7.34 (m, 5H), 7.23 (s, 1H), 6.64 (s, 1H), 5.22 (s, 2H).

To a solution of 4-(benzyloxy)-2-hydroxy-6-iodobenzaldehyde (4.26 g, 11.8 mmol) in dioxane (120 mL) were added successively Pd(PPh$_3$)Cl$_2$ (664 mg, 0.994 mmol), tert-butyl 4-(4,4,5,5-tetramethyl-1,3,2-dioxaborolan-2-yl)-5,6-dihydropyridine-1(2H)-carboxylate (4.60 g, 14.2 mmol), and Na$_2$CO$_3$ (3.79 g, 35.4 mmol) at RT. After stirring overnight at 110° C., Solvent was evaporated and the resulting oil was diluted with water (300 mL). The mixture was extracted with EA (3×300 mL). The combined organic extracts were washed with brine (300 mL), dried with anhydrous Na$_2$SO$_4$, filtered, and concentrated in vacuo to give the residue which was purified by column chromatography (eluent: PE/EA=6:1) to give tert-butyl 4-(5-(benzyloxy)-2-formyl-3-hydroxyphenyl)-3,6-dihydropyridine-1 (2H)-carboxylate (4.51 g, yield 93.4%) as a yellow solid. $^1$H NMR (400 MHz, DMSO-d$_6$): δ 12.15 (s, 1H), 9.85 (s, 1H), 7.47-7.35 (m, 5H), 6.52 (s, 2H), 5.69 (s, 1H), 5.20 (s, 2H), 3.98 (s, 2H), 3.57-3.53 (m, 2H), 2.37 (s, 2H), 1.43 (s, 9H), 1.40 (s, 2H).

To a mixture of tert-butyl 4-(5-(benzyloxy)-2-formyl-3-hydroxyphenyl)-3,6-dihydropyridine-1(2H)-carboxylate (4.69 g, 11.2 mmol), TEA (2.30 g, 22.5 mmol) and DMAP (2.10 g, 16.9 mmol) in DCM (60 mL) was added dropwise Tf$_2$O (4.85 g, 16.9 mmol) at 0° C. under nitrogen atmosphere. The reaction mixture was stirred overnight at room temperature and diluted with ice water (50 g) and separated. The aqueous layer was extracted with DCM (3×50 mL). The combined organic layer was washed sequentially with water (50 mL) and brine, dried over Na$_2$SO$_4$, filtered, and concentrated in vacuo to give the residue which was purified by column chromatography (eluent: PE/EA=5:1–3:1) to give tert-butyl 4-(5-(benzyloxy)-2-formyl-3-(((trifluoromethyl)sulfonyl)oxy)phenyl)-3,6-dihydropyridine-1(2H)-carboxylate (6.08 g, yield 59.1%) as a yellow solid. $^1$H NMR (400 MHz, DMSO-d$_6$): δ 9.86 (s, 1H), 7.49-7.37 (m, 5H), 7.25 (s, 1H), 7.07 (s, 1H), 5.68 (s, 1H), 5.29 (s, 2H), 4.02 (s, 2H), 3.60-3.57 (m, 2H), 2.46 (s, 2H), 1.44 (s, 9H).

A mixture of tert-butyl 4-(5-(benzyloxy)-2-formyl-3-(((trifluoromethyl)sulfonyl)oxy)phenyl)-3,6-dihydropyridine-1(2H)-carboxylate (3.42 g, 6.19 mmol), Bis(pinacolato)diboron (3.21 g, 12.4 mmol), Pd(dppf)Cl$_2$.CH$_2$Cl$_2$ (1.03 g, 1.24 mmol), KOAc (2.76 g, 27.8 mmol) in 1,4-dioxane (100 mL) was degassed with N$_2$ for 10 minutes. The reaction mixture was stirred at 70-80° C. for 16 h. TLC (EtOAc/petroleum ether=1:1) indicated the reaction was completed. The reaction mixture was poured into water (400 mL) and extracted with EtOAc (3×200 mL). The combined organic phases were dried over anhydrous Na$_2$SO$_4$, and concentrated in vacuo to give the residue which was purified by prep-HPLC to give tert-butyl 4-(5-(benzyloxy)-2-formyl-3-(4,4,5,5-tetramethyl-1,3,2-dioxaborolan-2-yl)phenyl)-3,6-dihydropyridine-1(2H)-carboxylate (750 mg, yield 23.3%) as a white solid. $^1$H NMR (400 MHz, DMSO-d$_6$): δ 9.88 (s, 1H), 7.50-7.35 (m, 5H), 7.02 (s, 1H), 6.96 (s, 1H), 5.67 (s, 1H), 5.22 (s, 2H), 4.00 (s, 2H), 3.59-3.58 (m, 2H), 2.44 (s, 2H), 1.44 (s, 9H), 1.32 (s, 12H).

To a solution of tert-butyl 4-(5-(benzyloxy)-2-formyl-3-(4,4,5,5-tetramethyl-1,3,2-dioxaborolan-2-yl)phenyl)-3,6-dihydropyridine-1 (2H)-carboxylate (750 mg) in EtOH (25 mL) was added NaBH$_4$ (204 mg, 5.20 mmol) in small portions at 0° C. under nitrogen atmosphere. The reaction mixture was stirred at rt for 4 h. To the reaction mixture was added dropwise 2 N HCl/water (30 mL) at 0° C. The reaction mixture was stirred overnight at rt and evaporated. The resulting oil was diluted with water (100 mL). The mixture was extracted with EA (3×500 mL). The combined organic extracts were washed with brine (100 mL), dried with anhydrous Na$_2$SO$_4$, filtered, and concentrated in vacuo to give the residue which was purified by column chromatography (eluent: PE/EA=5:1) to give tert-butyl 4-(6-(benzyloxy)-1-hydroxy-1,3-dihydrobenzo[c][1,2]oxaborol-4-yl)-3,6-dihydropyridine-1(2H)-carboxylate (396 mg, yield 72.4%) as a yellow solid. $^1$H NMR (400 MHz, DMSO-d$_6$): δ 9.16 (s, 1H), 7.47-7.33 (m, 5H), 7.25 (s, 1H), 7.04 (s, 1H), 5.87 (s, 1H), 5.14 (s, 2H), 5.00 (s, 2H), 4.12 (s, 2H), 3.52-3.50 (m, 2H), 2.40 (s, 2H), 1.43 (s, 9H).

To a solution of tert-butyl 4-(6-(benzyloxy)-1-hydroxy-1,3-dihydrobenzo[c][1,2]oxaborol-4-yl)-3,6-dihydropyridine-1(2H)-carboxylate (290 mg, 0.689 mmol) in MeOH (20 mL)) at rt under H$_2$ was added 10% Pd/C (100 mg). The reaction mixture was stirred at rt overnight. The mixture was filtered and concentrated under reduced pressure. The residue obtained was purified by prep-TLC (PE/EA=2/1) to get tert-butyl 4-(1,6-dihydroxy-1,3-dihydrobenzo[c][1,2]oxaborol-4-yl)piperidine-1-carboxylate (150 mg, yield 65.5%) as a white solid. $^1$H NMR (400 MHz, DMSO-d$_6$): δ 9.22 (s, 1H), 9.01 (s, 1H), 6.95 (s, 1H), 6.70 (s, 1H), 4.94 (s, 1H), 4.07-4.03 (m, 2H), 2.83-2.74 (m, 2H), 2.59-2.56 (m, 1H), 1.67 (d, J=12.4 Hz, 2H), 1.42 (s, 9H).

The mixture of tert-butyl 4-(1,6-dihydroxy-1,3-dihydrobenzo[c][1,2]oxaborol-4-yl)piperidine-1-carboxylate (100 mg, 0.294 mmol), Iodo-pleuromutilin (220 mg, 0.441 mmol) and $K_2CO_3$ (103 mg, 0.735 mmol) in DMF (4 mL) was stirred at rt overnight, filtered and concentrated under reduced pressure. The residue obtained was purified by prep-HPLC to give tert-butyl 4-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-4-yl)piperidine-1-carboxylate (130 mg, yield 65.5%) as a white solid. $^1$H NMR (400 MHz, DMSO-$d_6$): δ 9.16 (s, 1H), 7.15 (s, 1H), 6.85 (s, 1H), 6.16-6.06 (m, 1H), 5.59 (d, J=11.6 Hz, 2H), 5.10-4.98 (m, 4H), 4.73 (s, 2H), 4.52 (d, J=8.0 Hz, 1H), 4.09-4.04 (m, 2H), 3.42 (s, 1H), 2.78-2.42 (m, 4H), 2.20-1.98 (m, 4H), 1.78-1.25 (m, 22H), 1.11-0.95 (m, 5H), 0.78 (d, J=11.6 Hz, 3H), 0.66 (d, J=11.6 Hz, 3H).

To the solution of tert-butyl 4-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-4-yl)piperidine-1-carboxylate (580 mg, 0.830 mmol) in EA (15 mL) was added dropwise 2 N HCl/EA (15 mL) at 0° C. The reaction mixture was stirred for 3 h at rt and filtered. The white solid obtained was washed with EA (3×50 mL) and dried in vacuo to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-4-(piperidin-4-yl)-1,3-dihydrobenzo[c][1,2]oxaborol-6-yl)oxy)acetate (470 mg, 94.7%) as a white solid. $^1$H NMR (400 MHz, DMSO-$d_6$): δ 9.09 (s, 1H), 8.76 (s, 1H), 8.53 (s, 1H), 7.08 (d, J=2.0 Hz, 2H), 6.84 (d, J=2.0 Hz, 2H), 6.13-6.06 (m, 1H), 5.59 (d, J=8.4 Hz, 1H), 5.10-4.98 (m, 4H), 4.76-4.54 (m, 3H), 3.44-3.41 (m, 1H), 3.02-2.75 (m, 4H), 2.41 (s, 1H), 2.20-2.03 (m, 4H), 1.86 (s, 4H), 1.68-1.22 (m, 11H), 1.03-0.97 (m, 5H), 0.82 (d, J=6.8 Hz, 3H), 0.65 (d, J=1.6 Hz, 3H).

19. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3-methyl-1,3-dihydrobenzo[c][1,2]oxaborol-6-yl)oxy)acetate

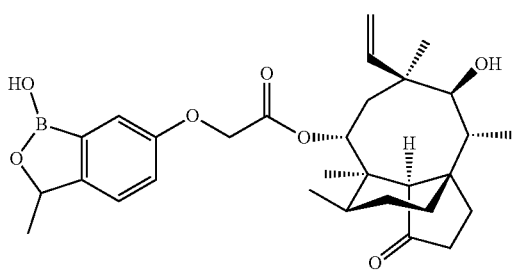

2-bromo-4-fluorobenzaldehyde (3 g, 14.7 mmol), benzyl alcohol (1.6 g, 14.7 mmol) and cesium carbonate (7.2 g, 22.1 mmol) in DMF (15 mL) were heated to 50-60° C. overnight. TLC shown 2-bromo-4-fluorobenzaldehyde consumed. Water (30 mL) was added, the aqueous layer was extracted with EtOAc (20 mL) twice. The combined organic layers were washed with brine, dried over $Na_2SO_4$, and concentrated to give crude product, which was purified by flash chromatography (EtOAc/petroleum ether, 1:10) to give 4-(benzyloxy)-2-bromobenzaldehyde (2.3 g, yield 80.9%).

$^1$H NMR (CDCl$_3$, 400 MHz) δ 10.23 (s, 1H), 7.90 (d, J=8.8 Hz, 1H), 7.47-7.30 (m, 5H), 7.24 (d, J=2.4 Hz, 1H), 7.02 (dd, J=8.8, 2.4 Hz, 1H), 5.14 (s, 2H).

Methyl magnesium bromide solution (4.7 mL, 15.7 mmol, 3M in THF) was added to a cooled solution of 4-(benzyloxy)-2-bromobenzaldehyde (2.4 g, 8.2 mmol) in THF (50 mL) at −5° C. The mixture was stirred at room temperature for 2 hrs. Water (50 mL) was added, the aqueous layer was extracted with EtOAc (50 mL) twice. The combined organic layers were washed with brine, dried over $Na_2SO_4$, and concentrated to give crude product, which was purified by flash chromatography (EtOAc/petroleum ether, 1:5) to give 1-(4-(benzyloxy)-2-bromophenyl)ethanol (1.8 g, yield 72.1%). $^1$H NMR (CDCl$_3$, 400 MHz) δ 7.49 (d, J=8.8 Hz, 1H), 7.47-7.31 (m, 5H), 7.17 (d, J=2.8 Hz, 1H), 6.97 (dd, J=8.6, 2.8 Hz, 1H), 5.21 (q, J=6.4 Hz, 1H), 5.05 (s, 2H), 1.48 (d, J=6.4 Hz, 3H).

A mixture of 1-(4-(benzyloxy)-2-bromophenyl) ethanol (1.8 g, 5.8 mmol), Pd(dppf)Cl$_2$ (0.21 g), potassium acetate (1.7 g, 17.5 mmol) and 4,4,4',4',5,5,5',5'-octamethyl-2,2'-bi(1,3,2-dioxaborolane) (2.2 g, 8.8 mmol) in dioxane (15 mL) was bubbled with nitrogen gas for 10 mins then stirred at 80° C. overnight under nitrogen atmosphere. After the reaction was completed, the mixture was filtered through celite and the filtrate was concentrated. The residue was purified by flash chromatography (EtOAc/petroleum ether, 1:20-1:2) to give 6-(benzyloxy)-3-methylbenzo[c][1,2]oxaborol-1(3H)-ol (0.5 g, yield 30%) as white solid. $^1$H NMR (DMSO-$d_6$, 400 MHz) δ 9.05 (s, 1H), 7.48-7.29 (m, 7H), 7.01-6.94 (m, 1H), 5.16-5.12 (m, 3H), 1.36 (d, J=8.4 Hz, 3H).

6-(benzyloxy)-3-methylbenzo[c][1,2]oxaborol-1(3H)-ol (0.8 g, 3.1 mmol) was dissolved in EtOAc (80 mL). To this solution under nitrogen was added Pd/C (0.4 g). The reaction mixture was vacuumed and backfilled hydrogen for 3 times, then hydrogenated at room temperature, 50 psi for 4 hrs. After filtration and rotary evaporation, the residue was purified by Pre-HPLC to give 3-methylbenzo[c][1,2]oxaborole-1,6(3H)-diol (0.2 g, 38% yield) as white solid. $^1$H NMR (DMSO-$d_6$, 400 MHz) δ 9.28 (s, 1H), 8.95 (br. s., 1H), 7.16 (d, J=8.4 Hz, 1H), 7.05 (d, J=2.4 Hz, 1H), 6.86 (dd, J=8.4, 2.4 Hz, 1H), 5.10 (q, J=6.4 Hz, 1H), 1.34 (d, J=6.4 Hz, 3H). MS (ESI): mass calcd. for $C_8H_9BO_3$ 164.1, m/z found 163.1 [M−1]$^-$. HPLC: 99.8% (220 nm), 100% (254 nm).

A mixture of Tos-pleuromutilin (0.32 g, 0.6 mmol), 3-methylbenzo[c][1,2]oxaborole-1,6(3H)-diol (0.1 g, 0.6 mmol) and $K_2CO_3$ (0.25 g, 1.8 mmol) in 20 mL DMF was heated at 50° C. overnight. Main peak on LCMS was desired product. Water (50 mL) was added and the mixture was adjust to pH=4 with 2N aqueous HCl. White solid precipitated and the mixture was filtered, the crude product was purified by prep-HPLC (column: Luna C18 100×30 mm, 5 μm; liquid phase: [A-TFA/H$_2$O=0.1% v/v; B-ACN] B %: 40%-70%, 20 min]) to give desired (3aR,4R,5R,7S,8S,9R,9aS,12R)-8-hydroxy-4,7,9,12-tetramethyl-3-oxo-7-vinyl-decahydro-4,9a-propanocyclopenta[8]annulen-5-yl 2-((1-hydroxy-3-methyl-1,3-dihydrobenzo[c][1,2]oxaborol-6-yl)oxy)acetate (171 mg, yield 53%) as white solid. $^1$H NMR (DMSO-d6, 400 MHz) δ 9.00 (s, 1H), 7.28 (d, J=9.2 Hz, 1H), 7.15 (d, J=2.4 Hz, 1H), 7.02 (d, J=8.0 Hz, 1H), 6.09 (dd, J=17.6, 11.4 Hz, 1H), 5.59 (d, J=8.0 Hz, 1H), 5.15-4.98 (m, 3H), 4.72-4.62 (m, 2H), 4.51 (d, J=6.0 Hz, 1H), 3.40 (m, 1H), 2.40 (s, 1H), 2.26-1.98 (m, 4H), 1.67-1.26 (m, 14H), 1.07-1.01 (m, 3H), 0.81 (d, J=6.8 Hz, 3H), 0.63 (d, J=6.8 Hz, 3H). MS (ESI): mass calcd. for $C_{30}H_{41}BO_7$ 524.3, m/z found 523.2 [M−1]$^-$. HPLC: 93.3% (220 nm), 100% (254 nm).

20. (3aR,4R,5R,7S,8S,9R,9aS,12R)-8-hydroxy-4,7,
9,12-tetramethyl-3-oxo-7-vinyldecahydro-4,9a-pro-
panocyclopenta[8]annulen-5-yl 2-((1-hydroxy-3,3-
dimethyl-1,3-dihydrobenzo[c][1,2]oxaborol-6-yl)
oxy)acetate

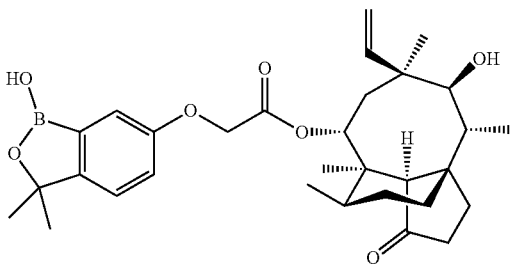

1-(2-bromo-4-hydroxyphenyl)ethanone (3.5 g, 16.3 mmol), benzyl bromide (3.3 g, 16.3 mmol) and potassium carbonate (3.5 g, 24.4 mmol) in DMF (15 mL) were stirred at room temperature overnight. Water (50 mL) was added, the aqueous layer was extracted with EtOAc three times. The combined organic layers were dried over $Na_2SO_4$, and concentrated. Crude product was purified by flash chromatography to give 1-(4-(benzyloxy)-2-bromophenyl)ethanone (4.3 g, yield 86%). $^1$H NMR: (DMSO-$d_6$, 400 MHz) δ 7.59 (d, J=8.5 Hz, 1H), 7.46-7.34 (m, 5H), 7.26 (d, J=2.4 Hz, 1H), 6.95 (dd, J=8.5, 2.4 Hz, 1H), 5.11 (s, 2H), 2.63 (s, 3H).

Methyl magnesium bromide solution (5 mL, 15 mmol, 3M in THF) was added to a cooled solution of 1-(4-(benzyloxy)-2-bromophenyl)ethanone (2.3 g, 7.5 mmol) in THF (50 mL) at −5° C. The mixture was stirred at room temperature for 2 hrs. Water (50 mL) was added, the aqueous layer was extracted with EtOAc (50 mL) twice, the crude product was purified by flash chromatography to give 2-(4-(benzyloxy)-2-bromophenyl)propan-2-ol (2 g, 83% yield). $^1$H NMR: (CDCl3, 400 MHz) δ 7.56 (d, J=9.0 Hz, 1H), 7.43-7.32 (m, 5H), 7.25 (d, J=2.8 Hz, 1H), 6.90 (dd, J=8.8, 2.8 Hz, 1H), 5.05 (s, 1H), 1.73 (s, 6H).

2-(4-(benzyloxy)-2-bromophenyl)propan-2-ol (1.5 g, 4.6 mmol), Pd(dppf)Cl$_2$ (0.17 g), potassium acetate (1.46 g, 14.9 mmol) and 4,4,4',4',5,5,5',5'-octamethyl-2,2'-bi(1,3,2-dioxaborolane) (1.8 g, 7.0 mmol) in dioxane (15 mL) was bubbled with nitrogen gas for 10 mins then stirred at 80° C. overnight under nitrogen atmosphere. After the reaction was completed, the mixture was filtered through celite and the filtrate was concentrated. The residue was purified by flash chromatography to give 6-(benzyloxy)-3,3-dimethylbenzo[c][1,2]oxaborol-1(3H)-ol (0.3 g, yield 24%).

6-(benzyloxy)-3,3-dimethylbenzo[c][1,2]oxaborol-1(3H)-ol (0.5 g, 1.8 mmol) was dissolved in EtOAc (80 ml). To this solution under nitrogen was added Pd/C (0.2 g). The reaction mixture was vacuumed and backfilled hydrogen for 3 times, then hydrogenated at room temperature, 50 psi for 4 hrs. After filtration and rotary evaporation, the residue was purified by Pre-HPLC to give 3,3-dimethylbenzo[c][1,2]oxaborole-1,6(3H)-diol (0.2 g, 60% yield). $^1$H NMR: (DMSO-$d_6$, 400 MHz) δ 9.26 (s, 1H), 8.88 (br. s., 1H), 7.16 (d, J=8.0 Hz, 1H), 6.99 (d, J=2.4 Hz, 1H), 6.83 (dd, J=8.0, 2.4 Hz, 1H), 1.38 (s, 6H). MS (ESI): mass calcd. for $C_9H_{11}BO_3$ 178.1, m/z found 177.1 [M−1]$^-$. HPLC: 99.2% (220 nm), 93.2% (254 nm).

(3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (0.12 g, 0.23 mmol), 3,3-dimethylbenzo[c][1,2]oxaborole-1,6(3H)-diol (40 mg, 0.23 mmol) and $K_2CO_3$ (0.1 g, 0.68 mmol) in 10 mL DMF was heated at 50° C. overnight. Main peak on LCMS was desired product. Water was added and the mixture was adjust to pH<4 with 2N aqueous HCl. White solid precipitated and the mixture was filtered, the crude product was purified by prep-HPLC (column: Luna C18 100×30 mm, 5 μm; liquid phase: [A-TFA/H$_2$O=0.075% v/v; B-ACN] B %: 30%-70%, 20 min]) to give desired (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3,3-dimethyl-1,3-dihydrobenzo[c][1,2]oxaborol-6-yl)oxy)acetate (66 mg, yield 54%) as white solid. $^1$H NMR (DMSO-$d_6$, 400 MHz) δ 8.92 (s, 1H), 7.29 (d, J=8.4 Hz, 1H), 7.11 (d, J=2.4 Hz, 1H), 7.00 (dd, J=8.4, 2.4 Hz, 1H), 6.09 (dd, J=17.6, 11.2 Hz, 1H), 5.59 (d, J=8.4 Hz, 1H), 5.08-4.95 (m, 2H), 4.75-4.61 (m, 2H), 4.51 (d, J=6.0 Hz, 1H), 3.45-3.38 (m, 1H), 2.40 (s, 1H), 2.25-1.98 (m, 5H), 1.73-1.55 (m, 3H), 1.52-1.15 (m, 12H), 1.08-0.98 (m, 4H), 0.81 (d, J=7.0 Hz, 3H), 0.62 (d, J=6.8 Hz, 3H). MS (ESI): mass calcd. for $C_{31}H_{43}BO7_3$ 538.3, m/z found 537.2 [M−1]$^-$. HPLC: 99.3% (220 nm), 100% (254 nm).

21. (3aR,4R,5R,7S,8S,9R,9aS,12R)-8-hydroxy-4,7,
9,12-tetramethyl-3-oxo-7-vinyldecahydro-4,9a-pro-
panocyclopenta[8]annulen-5-yl 2-((3-(aminom-
ethyl)-1-hydroxy-1,3-dihydrobenzo[c][1,2]oxaborol-
6-yl)oxy)acetate hydrochloride

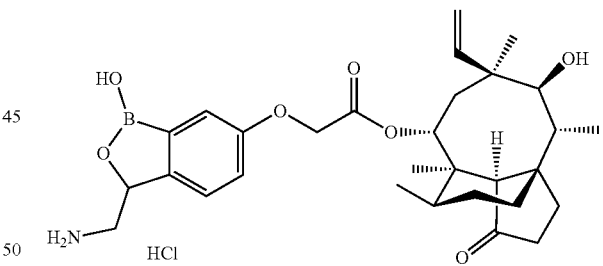

Nitromethane (2.7 g, 44.36 mmol) was added to a solution of 4-(benzyloxy)-2-(4,4,5,5-tetramethyl-1,3,2-dioxaborolan-2-yl)benzaldehyde (10.0 g, 29.6 mmol) and NaOH (1.2 g, 31.1 mmol) in H$_2$O (50.0 mL) at 25° C. The mixture was stirred at 25° C. for 1 hour. LCMS showed major as desired, water (50 mL) was added to the mixture and neutralized by 2N HCl. The mixture was treated with EtOAc (50 mL×3) and purified by flash silica gel chromatography to give 6-(benzyloxy)-3-(nitromethyl)benzo[c][1,2]oxaborol-1(3H)-ol (4.2 g, crude). $^1$H NMR (CDCl$_3$, 400 MHz) δ 8.17 (s, 1H), 7.83 (d, J=8.4 Hz, 2H), 7.36 (d, J=8.4 Hz, 2H), 6.23 (dd, J=11.4, 17.6 Hz, 1H), 5.71 (d, J=7.8 Hz, 1H), 5.30-5.14 (m, 2H), 5.03 (d, J=6.6 Hz, 1H), 4.49 (s, 2H), 3.08 (d, J=13.2 Hz, 1H).

6-(benzyloxy)-3-(nitromethyl)benzo[c][1,2]oxaborol-1 (3H)-ol (4.2 g, 14.0 mmol) and Fe (3.9 g, 70.2 mmol) in HCl (10.0 mL) and MeOH (50.0 mL) were heated to reflux for 3 hours. The mixture was cooled to 25° C., water (50 mL) was added to the mixture, and filtered and dried to give 3-(aminomethyl)-6-(benzyloxy)benzo[c][1,2]oxaborol-1(3H)-ol (2.0 g, 52.9% yield). $^1$H NMR (DMSO-$d_6$, 400 MHz) δ 9.50 (s, 1H), 8.14 (br. s., 3H), 7.50-7.37 (m, 6H), 7.34 (d, J=7.0 Hz, 1H), 7.18 (dd, J=2.4, 8.4 Hz, 1H), 5.28 (d, J=7.0 Hz, 1H), 5.13 (s, 2H), 3.46 (d, J=14.2 Hz, 1H), 2.79-2.69 (m, 1H).

3-(aminomethyl)-6-(benzyloxy)benzo[c][1,2]oxaborol-1 (3H)-ol (2.0 g, 7.4 mmol), TEA (2.3 g, 22.3 mmol) and Boc$_2$O (2.4 g, 11.2 mmol) in DCM (30.0 mL) were stirred at 25° C. for 2 hours. The solvent was evaporated. The crude product was purified by prep-HPLC to give tert-butyl ((6-(benzyloxy)-1-hydroxy-1,3-dihydrobenzo [c][1,2]oxaborol-3-yl)methyl)carbamate (600.0 mg, 21.9% yield).

To a solution of tert-butyl ((6-(benzyloxy)-1-hydroxy-1, 3-dihydrobenzo[c][1,2]oxaborol-3-yl)methyl)carbamate (1.0 g, 2.7 mmol) in EtOAc (100.0 mL) was added Pd/C (500.0 mg) under N$_2$. The suspension was degassed under vacuum and purged with H$_2$ several times. The mixture was stirred under H$_2$ (40 psi) at 25° C. for 2 hours. The reaction mixture was filtered and the filter was concentrated to give tert-butyl ((1,6-dihydroxy-1,3-dihydrobenzo[c][1,2]oxaborol-3-yl) methyl)carbamate (620.0 mg, 57.4% yield) as yellow solid. $^1$H NMR (DMSO-$d_6$, 400 MHz) δ 9.34 (s, 1H), 9.07 (s, 1H), 7.17 (d, J=8.4 Hz, 1H), 7.07 (d, J=2.2 Hz, 1H), 6.91 (br. s., 1H), 6.85 (dd, J=2.4, 8.2 Hz, 1H), 5.00 (dd, J=4.4, 7.1 Hz, 1H), 2.96 (dd, J=6.8, 14.3 Hz, 2H), 1.38-1.34 (s, 9H.).

To a solution of tert-butyl ((1,6-dihydroxy-1,3-dihydrobenzo[c][1,2]oxaborol-3-yl) methyl)carbamate (250.0 mg, 895.7 umol), pleuromutilintosylate (477.2 mg, 895.7 umol) and K$_2$CO$_3$ (371.4 mg, 2.7 mmol) in CH$_3$CN (10.0 mL) was stirred at 70° C. for 12 hours. Water (10 mL) was added to the mixture and filtered to give the product (3aR, 4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(((tert-butoxycarbonyl)amino)methyl)-1-hydroxy-1,3-dihydrobenzo[c][1,2]oxaborol-6-yl)oxy) acetate (205.0 mg, 35.8% yield) as yellow solid, which was purified by pre-HPLC. $^1$H NMR (CDCl$_3$, 400 MHz) δ 7.28 (br. s., 1H), 7.14-7.07 (m, 2H), 6.48 (dd, J=11.0, 16.8 Hz, 1H), 5.86 (d, J=8.4 Hz, 1H), 5.38-5.19 (m, 3H), 4.86 (br. s., 1H), 4.61-4.55 (m, 2H), 3.37 (d, J=6.2 Hz, 1H), 2.43-2.05 (m, 7H), 1.93-1.09 (m, 20H), 0.97-0.72 (m, 10H).

HCl/EtOAc (4 M, 4.0 mL) was added to a solution of (3aR,4R,5R,7S,8S,9R,9aS,12R)-8-hydroxy-4,7,9,12-tetramethyl-3-oxo-7-vinyldecahydro-4,9a-propanocyclopenta [8]annulen-5-yl 2-((3-(((tert-butoxycarbonyl)amino) methyl)-1-hydroxy-1,3-dihydrobenzo[c][1,2]oxaborol-6-yl) oxy)acetate (200.0 mg, 312.7 umol) in DCM (50.0 mL) at 25° C. for 2 hours. The solvent was concentrated and filtered to give (3aR,4R,5R,7S,8S,9R,9aS,12R)-8-hydroxy-4,7,9, 12-tetramethyl-3-oxo-7-vinyldecahydro-4,9a-propanocyclopenta[8]annulen-5-yl 2-((3-(aminomethyl)-1-hydroxy-1, 3-dihydrobenzo[c][1,2]oxaborol-6-yl)oxy)acetate (96.0 mg, 52.8% yield) as white solid. $^1$H NMR (DMSO-$d_6$, 400 MHz) δ 9.47 (br. s., 1H), 8.13 (br. s., 3H), 7.44 (d, J=8.4 Hz, 1H), 7.28 (d, J=2.2 Hz, 1H), 7.09 (td, J=2.4, 8.5 Hz, 1H), 6.10 (dd, J=11.2, 17.9 Hz, 1H), 5.60 (d, J=8.4 Hz, 1H), 5.28 (dd, J=2.6, 9.3 Hz, 1H), 5.12-4.96 (m, 2H), 4.80-4.64 (m, 2H), 4.62-4.48 (m, 1H), 3.42 (d, J=5.7 Hz, 2H), 2.78-2.63 (m, 1H), 2.42 (br. s., 1H), 2.26-2.00 (m, 4H), 1.73-1.18 (m, 7H), 1.05 (s, 2H), 0.89-0.78 (m, 5H), 0.63 (d, J=7.2 Hz, 3H). MS (ESI): mass calcd. for C$_{30}$H$_{42}$BNO$_7$ 539.31, m/z found 540.1[M+H]$^+$. HPLC: 99.2% (220 nm), 100.0% (254 nm).

22. (3aR,4R,5R,7S,8S,9R,9aS,12R)-8-hydroxy-4,7, 9,12-tetramethyl-3-oxo-7-vinyldecahydro-4,9a-propanocyclopenta[8]annulen-5-yl 2-((3-(acetamidomethyl)-1-hydroxy-1,3-dihydrobenzo[c][1,2]oxaborol-6-yl)oxy)acetate

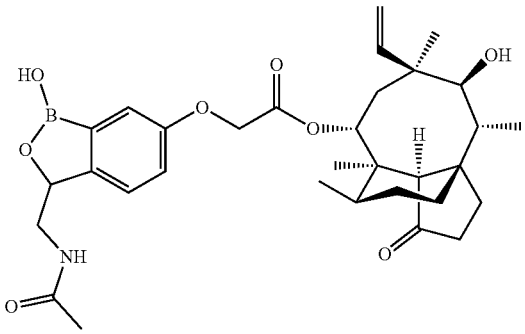

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-1-hydroxy-1,3-dihydrobenzo[c][1,2]oxaborol-6-yl)oxy) acetate hydrochloride (30.0 mg, 52.1 umol, 1.0 eq) and Et$_3$N (15.8 mg, 156.3 umol, 3.0 eq) in DCM (10 mL) was added acetyl chloride (4.1 mg, 52.1 umol, 1.0 eq). The mixture was stirred at 25° C. for 6 hours. HPLC indicated reactant was consumed completely. The reaction mixture was quenched by addition water 30 mL at 0° C., and then extracted with DCM 90 mL (30 mL×3). The combined organic layers were washed with brine 150 mL (50 mL×3), dried over Na$_2$SO$_4$, filtered and concentrated under reduced pressure to give (3aR,4R,5R,7S,8S,9R,9aS,12R)-8-hydroxy-4,7,9,12-tetramethyl-3-oxo-7-vinyldecahydro-4,9a-propanocyclopenta [8]annulen-5-yl2-((3-(acetamidomethyl)-1-hydroxy-1,3-dihydrobenzo[c][1,2]oxaborol-6-yl)oxy)acetate (30.0 mg, 51.6 umol, 99.0% yield) as a white solid. $^1$H NMR (DMSO-$d_6$, 400 MHz) δ 9.18 (s, 1H), 8.10 (brs, 1H), 7.30 (d, J=8.4 Hz, 1H), 7.19 (s, 1H), 7.03 (dd, J=8.4, 2.4 Hz, 1H), 6.09 (dd, J=17.6, 11.2 Hz, 1H), 5.59 (d, J=8.4 Hz, 1H), 5.03-5.11 (m, 2H), 5.00 (d, J=10.8 Hz, 1H), 4.64-4.77 (m, 2H), 4.55 (d, J=5.6 Hz, 1H), 3.51 (d, J=13.6 Hz, 1H), 3.41 (brs, 1H), 2.96-3.11 (m, 1H), 2.42 (s, 1H), 2.14-2.25 (m, 1H), 2.00-2.12 (m, 4H), 1.81 (s, 3H), 1.57-1.72 (m, 2H), 1.34 (s, 3H), 1.22-1.28 (m, 3H), 1.04-0.92 (m, 4H), 0.81 (d, J=6.8 Hz, 3H), 0.63 (d, J=6.8 Hz, 3H). MS (ESI): mass calcd. for C$_{32}$H$_{44}$BNO$_8$ 581.5, m/z found 582.3[M+H]$^+$. HPLC: 96.0% (220 nm), 92.8% (254 nm).

23. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3-(methylsulfonamidomethyl)-1,3-dihydrobenzo[c][1,2]oxaborol-6-yl)oxy)acetate

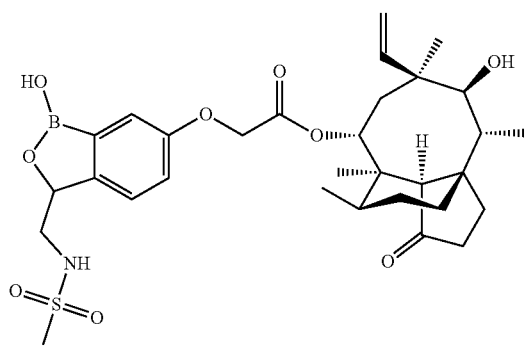

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-1-hydroxy-1,3-dihydrobenzo[c][1,2]oxaborol-6-yl)oxy)acetate hydrochloride (30.0 mg, 52.1 umol, 1.0 eq) and TEA (15.8 mg, 156.3 umol, 3.0 eq) in DCM (10 mL) was added MsCl (6.0 mg, 52.1 umol, 1.0 eq). The mixture was stirred at 15° C. for 4 hours. HPLC indicated (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-1-hydroxy-1,3-dihydrobenzo[c][1,2]oxaborol-6-yl)oxy)acetate hydrochloride was consumed completely. The reaction mixture was quenched by addition H$_2$O 20 mL at 0° C., and then adjusted PH=5 (aq. HCl, 2m) and extracted with DCM 60 mL (20 mL×3). The combined organic layers were washed with brine 30 mL, dried over Na$_2$SO$_4$, filtered and concentrated under reduced pressure to give a residue. The residue was purified by prep-HPLC (column: Luna C18 150×25 mm, 5 μm; liquid phase: [A-TFA/H$_2$O=0.075% v/v; B-ACN] B %: 33%-53%, 12 min]). (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-3-(methylsulfonamidomethyl)-1,3-dihydrobenzo[c][1,2]oxaborol-6-yl)oxy)acetate (10.00 mg, 16.2 umol, 31.1% yield) was obtained as a light purple solid. $^1$H NMR (DMSO-d$_6$, 400 MHz) δ 7.37 (d, J=8.4 Hz, 1H), 7.23-7.15 (m, 2H), 7.05 (dd, J=8.4, 2.8 Hz, 1H), 6.10 (dd, J=17.6, 11.2 Hz, 1H), 5.60 (d, J=8.0 Hz, 1H), 5.13-5.10 (m, 1H), 5.04-5.09 (m, 1H), 5.00 (d, J=10.8 Hz, 1H), 4.78-4.64 (m, 2H), 3.04 (dt, J=13.6, 6.8 Hz, 1H), 2.87 (s, 3H), 2.41 (brs, 1H), 2.24-2.14 (m, 1H), 2.12-2.02 (m, 3H), 1.70-1.30 (m, 13H), 1.07-0.96 (m, 4H), 0.82 (d, J=7.2 Hz, 3H), 0.64 (d, J=7.2 Hz, 3H). MS (ESI): mass calcd. for C$_{31}$H$_{44}$BNO$_9$S 617.6, m/z found 635.3[M+NH$_3$+H]$^+$. HPLC: 100% (220 nm), 100% (254 nm).

24. tert-Butyl 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetate 25. 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetic acid

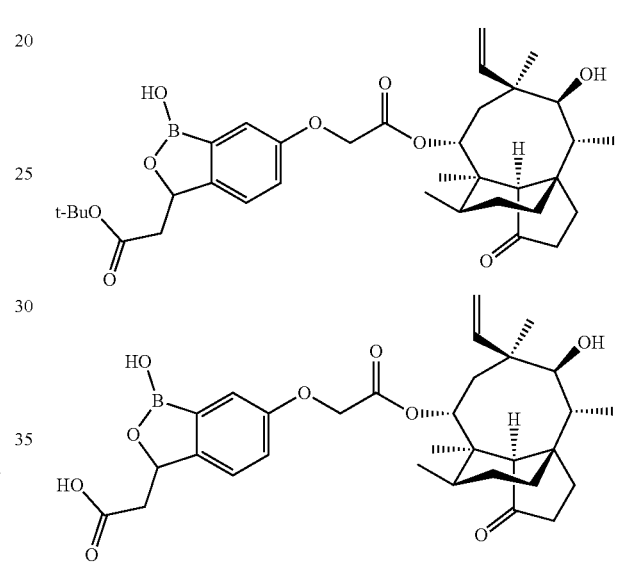

A solution of 4-(benzyloxy)-2-hydroxybenzaldehyde (42.0 g, 184.0 mmol, 1.0 eq.), pyridine (36.4 g, 460.0 mmol, 2.5 eq.) and DMAP (449.6 mg, 3.7 mmol, 0.02 eq.) in DCM (1.0 L) was added Tf$_2$O (77.9 g, 276.0 mmol, 1.5 eq.). The mixture was stirred at 25° C. for 2 hours. TLC indicated 4-(benzyloxy)-2-hydroxybenzaldehyde was consumed completely. The reaction mixture was quenched by addition H$_2$O 500 mL at 25° C., and then the organic layer were washed with 0.5 M HCl (aq, 500 mL) and brine 500 mL, dried over Na$_2$SO$_4$, filtered and concentrated under reduced pressure to give a residue. The residue was purified by column chromatography (SiO$_2$, Petroleum ether/Ethyl acetate=50/1 to 10:1). 5-(benzyloxy)-2-formylphenyl trifluoromethanesulfonate (50.0 g, 138.8 mmol, 75.4% yield) was obtained as a colorless oil.

To a solution of 5-(benzyloxy)-2-formylphenyl trifluoromethanesulfonate (80.0 g, 222.0 mmol, 1.0 eq.) in dioxane (200.0 mL) was added KOAc (65.4 g, 666.1 mmol, 3.0 eq.), Pd (dppf) Cl$_2$ (3.2 g, 4.4 mmol, 0.02 eq.) and Pin$_2$B$_2$(62.0 g, 244.2 mmol, 3.0 eq.). The mixture was stirred at 80° C. for 12 hours. TLC indicated 5-(benzyloxy)-2-formylphenyl trifluoro methanesulfonate was consumed completely. The reaction mixture was filtered and concentrated under reduced pressure to give a residue. The residue was purified by column chromatography (SiO$_2$, Petroleum ether/Ethyl acetate=20/1 to 5:1). 4-(benzyloxy)-2-(4,4,5,5-tetramethyl-1,3,2-dioxaborolan-2-yl)benzaldehyde (56.0 g, 165.6 mmol, 74.6% yield) was obtained as a white solid.

To a solution of zinc powder (26.1 g, 399.9 mmol, 1.0 eq.) in THF (2.0 L) was added TMSCl (4.0 g, 37.3 mmol, 0.1 eq.), the mixture was stirred at 15° C. for 0.5 hour, and then tert-butyl 2-bromoacetate (78.0 g, 399.9 mmol, 1.0 eq.) was added. The mixture was stirred at 15° C. for another 15 hours. (2-(tert-butoxy)-2-oxoethyl)zinc(II) bromide (104.1 g, 399.7 mmol, 99.9% yield) was obtained as a solution in THF (0.2 M). To a solution of 4-(benzyloxy)-2-(4,4,5,5-tetramethyl-1,3,2-dioxaborolan-2-yl)benzaldehyde (2.0 g, 5.9 mmol, 1.0 eq.) in THF (20.0 mL) was added bromo-(2-tert-butoxy-2-oxo-ethyl) zinc (0.2 M, 206.85 mL, 7.00 eq.). The mixture was stirred at 15° C. for 4 hours. HPLC indicated 4-(benzyloxy)-2-(4,4,5,5-tetramethyl-1,3,2-dioxaborolan-2-yl)benzaldehyde was consumed completely and a new peak was formed, LCMS indicated it was desired product. The reaction mixture was quenched by addition H$_2$O 200 mL at 0° C., and then extracted with EtOAc 1200 mL (400 mL×3). The combined organic layers were washed with brine 200 mL, dried over Na$_2$SO$_4$, filtered and concentrated under reduced pressure to give a residue. The crude product tert-butyl 2-(6-(benzyloxy)-1-hydroxy-1,3-dihydrobenzo[c][1,2]oxaborol-3-yl)acetate (2.0 g, 5.6 mmol, 95.5% yield) was used into the next step without further purification. MS: m/z=399.1 [M−55]

To a solution of tert-butyl 2-(6-(benzyloxy)-1-hydroxy-1,3-dihydrobenzo[c][1,2]oxaborol-3-yl)acetate (500.0 mg, 1.4 mmol, 1.0 eq.) in EtOAC (50.0 mL) was added Pd/C (500.0 mg), the mixture was then stirred at 15° C. for 3 hours under H$_2$ atmosphere (pressure 40 psi). HPLC indicated tert-butyl 2-(6-(benzyloxy)-1-hydroxy-1,3-dihydrobenzo[c][1,2]oxaborol-3-yl)acetate was consumed completely and a new peak was formed. The reaction mixture was filtered and concentrated under reduced pressure to give a residue. The crude product tert-butyl 2-(1,6-dihydroxy-1,3-dihydrobenzo[c][1,2]oxaborol-3-yl)acetate (350.0 mg, 1.3 mmol, 94.0% yield) was used into the next step without further purification. MS: m/z=209.1 [M−55]$^-$ To a solution of tert-butyl 2-(1,6-dihydroxy-1,3-dihydrobenzo[c][1,2]oxaborol-3-yl)acetate (359.1 mg, 1.3 mmol, 1.0 eq.) and (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-(tosyloxy)acetate (724.4 mg, 1.3 mmol, 1.0 eq.) in DMF (10.0 mL) were added K$_2$CO$_3$ (563.9 mg, 4.1 mmol, 3.0 eq.) and KI (22.6 mg, 136.0 umol, 0.1 eq.). The mixture was stirred at 50° C. for 15 hours. HPLC indicated tert-butyl 2-(1,6-dihydroxy-1,3-dihydrobenzo[c][1,2]oxaborol-3-yl)acetate was consumed completely and a new peak was formed. The reaction mixture was quenched by addition H$_2$O 20 mL at 0° C., and then adjusted to pH=7, solid was dissolved, filtered (filter cake) to give a residue. The residue was purified by prep-HPLC (column: Phenomenex luna C18 250×50 mm, 10 μm; liquid phase: [A-TFA/H$_2$O=0.075% v/v; B-ACN] B %: 45%-75%, 20 min]). tert-butyl 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetate (320.0 mg, 506.5 umol, 37.2% yield, 100.0% purity) was obtained as a white solid. $^1$H NMR (DMSO-d$_6$, 400 MHz) δ 9.14 (s, 1H), 7.16 (s, 1H), 7.33 (d, J=8.4 Hz, 1H), 7.03 (d, J=8.4 Hz, 1H), 6.10 (dd, J=17.6, 11.2 Hz, 1H), 5.59 (d, J=8.0 Hz, 1H), 5.04-5.10 (m, 1H), 5.36 (dd, J=8.0, 4.0 Hz, 1H), 5.00 (d, J=11.2 Hz, 1H), 4.64-4.77 (m, 2H), 4.52 (d, J=6.0 Hz, 1H), 4.52 (d, J=6.0 Hz, 1H), 3.38-3.46 (m, 1H), 2.87 (dd, J=15.2, 3.2 Hz, 1H), 2.41 (br. s., 1H), 2.34 (dd, J=15.2, 8.0 Hz, 1H), 2.13-2.25 (m, 1H), 2.01-2.12 (m, 4H), 1.58-1.70 (m, 2H), 1.35-1.39 (m, 7H), 1.32-1.34 (m, 4H), 1.29 (d, J=15.2 Hz, 3H), 0.93-1.12 (m, 5H), 0.82 (d, J=6.4 Hz, 3H), 0.63 (d, J=6.4 Hz, 3H) MS (ESI): mass calcd. for C$_{35}$H$_{49}$BO$_9$ 624.57, m/z found 563.4[M−H]$^-$. HPLC: 100.0% (220 nm), 87.5% (254 nm).

To a solution of tert-butyl 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetate (100.0 mg, 160.1 umol, 1.0 eq.) in DCM (15.0 mL) was added CF$_3$COOH (182.5 mg, 1.6 mmol, 10.0 eq.). The mixture was stirred at 15° C. for 48 hours. HPLC indicated tert-butyl 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetate was consumed completely. The reaction mixture was quenched by addition H$_2$O 40 mL at 0° C., and then diluted with DCM 20 mL and extracted with DCM 60 mL (30 mL×2). The combined organic layers were washed with H$_2$O 40 mL (20 mL×2), dried over Na$_2$SO$_4$, filtered and concentrated under reduced pressure to give a residue. The residue was purified by prep-HPLC (column: Luna C8 100×30 mm, 5 μm; liquid phase: [A-TFA/H$_2$O=0.075% v/v; B-ACN] B %: 35%-65%, 12 min]). 2-(1-hydroxy-6-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-1,3-dihydrobenzo[c][1,2]oxaborol-3-yl)acetic acid (51.0 mg, 89.7 umol, 56.0% yield, 100.0% purity) was obtained as a white solid. $^1$H NMR (DMSO-d$_6$, 400 MHz) δ 7.35 (d, J=8.4 Hz, 1H), 7.15 (s, 1H), 7.04 (d, J=8.0 Hz, 1H), 6.10 (dd, J=11.2, 18.0 Hz, 1H), 5.60 (d, J=8.0 Hz, 1H), 5.38 (dd, J=3.6, 8.8 Hz, 1H), 5.11-4.97 (m, 2H), 4.79-4.62 (m, 2H), 2.89 (dd, J=3.6, 15.6 Hz, 1H), 2.41 (br. s., 1H), 2.27 (dd, J=8.8, 15.6 Hz, 1H), 2.2-2.13 (m, 1H), 2.12-2.02 (m, 3H), 1.72-1.57 (m, 2H), 1.52-1.43 (m, 1H), 1.42-1.20 (m, 8H), 1.04 (s, 3H), 1.02-0.95 (m, 1H), 0.82 (d, J=6.4 Hz, 3H), 0.63 (d, J=6.4 Hz, 3H) MS (ESI): mass calcd. for C$_{31}$H$_{41}$BO$_9$ 568.46, m/z found 567.3[M−H]$^-$. HPLC: 100.0% (220 nm), 87.5% (254 nm).

26. (3aR,4R,5R,7S,8S,9R,9aS,12R)-8-hydroxy-4,7, 9,12-tetramethyl-3-oxo-7-vinyldecahydro-4,9a-propanocyclopenta[8]annulen-5-yl 2-((1-hydroxy-3-(2-methoxy-2-oxoethyl)-1,3-dihydrobenzo[c][1,2] oxaborol-6-yl)oxy)acetate

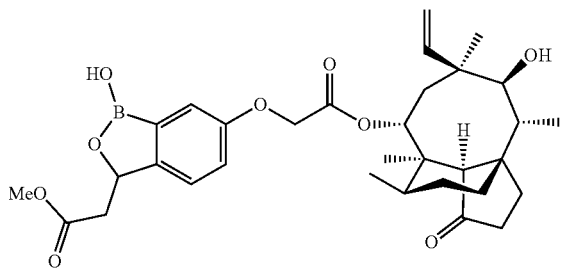

A solution of tert-butyl 2-(6-(benzyloxy)-1-hydroxy-1,3-dihydrobenzo[c][1,2]oxaborol-3-yl)acetate (700.0 mg, 1.9 mmol, 1.0 eq.) in CH₃OH (50.0 mL) was added H₂SO₄ (58.1 mg, 592.8 umol, 0.3 eq.). The mixture was stirred at 50° C. for 28 hours. HPLC and LCMS indicated tert-butyl 2-(6-(benzyloxy)-1-hydroxy-1,3-dihydrobenzo[c][1,2]oxaborol-3-yl)acetate was consumed and a main peak was formed, LCMS indicated it was desired product. The reaction mixture was quenched by added saturated NaHCO₃ (aq, 30 mL) and removed the excessive MeOH, then the mixture was extracted with EtOAc 90 mL (30 mL×3). The combined organic layers were washed with brine 40 mL, dried over Na₂SO₄, filtered and concentrated under reduced pressure to give a residue. The residue was purified by column chromatography (SiO₂, Petroleum ether/Ethyl acetate=10/1 to 3:1). methyl 2-(6-(benzyloxy)-1-hydroxy-1,3-dihydrobenzo[c][1,2]oxaborol-3-yl)acetate (500.0 mg, 1.6 mmol, 80.9% yield) was obtained as a light colorless oil. MS: m/z=311.1 [M−1]⁻

A solution of methyl 2-(6-(benzyloxy)-1-hydroxy-1,3-dihydrobenzo[c][1,2]oxaborol-3-yl)acetate (500.0 mg, 1.6 mmol, 1.0 eq) in EtOAc (50.0 mL) was added Pc/C (200.0 mg). The mixture was stirred at 25° C. for 3 hrs under H₂ (50 psi) atmosphere. HPLC indicated methyl 2-(6-(benzyloxy)-1-hydroxy-1,3-dihydrobenzo[c][1,2]oxaborol-3-yl)acetate was consumed completely. The reaction mixture was filtered and concentrated under reduced pressure to give a residue. The crude product methyl 2-(1,6-dihydroxy-1,3-dihydrobenzo[c][1,2]oxaborol-3-yl)acetate (200.0 mg, light yellow oil, 630.6 umol, 39.4% yield, 70% purity) was used into the next step without further purification. MS: m/z=221.1 [M−1]⁻

To a solution of methyl 2-(1,6-dihydroxy-1,3-dihydrobenzo[c][1,2]oxaborol-3-yl)acetate (108.0 mg, 340.5 umol, 1.0 eq.) and (20R,21R,22S,23R,26S,27R)-22-hydroxy-19,20,26,27-tetramethyl-24-oxo-26-vinyl-21-tricyclotetradecanyl] 2-(p-tolyl-sulfo nyloxy)acetate (181.4 mg, 340.5 umol, 1.0 eq.) in DMF (8.0 mL) was added K₂CO₃ (141.2 mg, 1.0 mmol, 3.0 eq.) and KI (5.6 mg, 34.0 umol, 0.1 eq.). The mixture was stirred at 50° C. for 14 hours. HPLC indicated methyl 2-(1,6-dihydroxy-1,3-dihydrobenzo [c][1,2]oxaborol-3-yl)acetate was consumed completely. The reaction mixture was quenched by addition H₂O 50 mL at 0° C., and then adjusted pH=7 (aq HCl, 2M), light yellow solid was dissolved out, filtered and concentrated under reduced pressure to give a residue. The residue was purified by prep-HPLC (column: Luna C18 100×30 mm, 5 μm; liquid phase: [A-TFA/H₂O=0.075% v/v; B-ACN] B %: 40%-70%, 12 min]). (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3-(2-methoxy-2-oxoethyl)-1,3-dihydrobenzo [c][1,2]oxaborol-6-yl)oxy)acetate (95.8 mg, 162.8 umol, 47.8% yield, 99.0% purity) was obtained as a light yellow solid (combined with ET3173-148-P1). ¹H NMR (DMSO-d₆, 400 MHz) δ 7.32 (d, J=8.4 Hz, 1H), 7.14 (d, J=2.2 Hz, 1H), 7.02 (dd, J=2.0, 8.4 Hz, 1H), 6.06 (dd, J=11.2, 18.0 Hz, 1H), 5.58 (d, J=8.4 Hz, 1H), 5.39 (dd, J=3.6, 9.2 Hz, 1H), 5.08-4.95 (m, 2H), 4.75-4.62 (m, 2H), 3.61 (s, 3H), 3.38 (d, J=5.6 Hz, 1H), 2.99 (dd, J=4.0, 15.6 Hz, 1H), 2.40-2.29 (m, 2H), 2.23-2.12 (m, 1H), 2.11-1.96 (m, 3H), 1.69-1.53 (m, 2H), 1.49-1.41 (m, 1H), 1.39-1.29 (m, 6H), 1.29-1.19 (m, 4H), 1.06-0.93 (m, 4H), 0.80 (d, J=6.4 Hz, 3H), 0.62 (d, J=6.4 Hz, 3H) MS (ESI): mass calcd. for C₃₅H₄₉BO₉ 582.30, m/z found 581.3 [M−H]⁻. HPLC: 99.0% (220 nm), 88.8% (254 nm).

27. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-((dimethylamino)methyl)-1-hydroxy-1,3-dihydrobenzo[c][1,2]oxaborol-6-yl)oxy)acetate

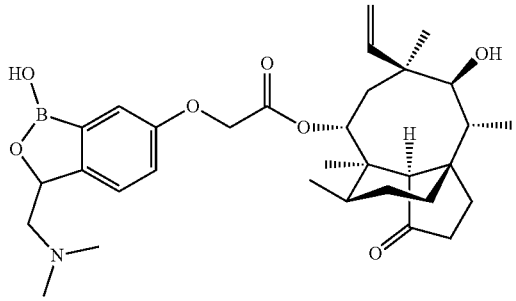

To a solution of 4-(benzyloxy)-2-(4,4,5,5-tetramethyl-1,3,2-dioxaborolan-2-yl)benzaldehyde (10.0 g, 29.5 mmol, 1.0 eq.) in MeOH (50.0 mL) and H₂O (50.0 mL) were added NaOH (2.3 g, 59.1 mmol, 2.0 eq.) and nitromethane (5.4 g, 88.7 mmol, 3.0 eq.). The mixture was stirred at 15° C. for 12 hours. HPLC indicated 4-(benzyloxy)-2-(4,4,5,5-tetramethyl-1,3,2-dioxaborolan-2-yl)benzaldehyde was consumed completely LCMS indicated it was desired product. The reaction mixture was quenched by addition H₂O 30 mL at 0° C., and then adjusted pH=5 (aq. HCl, 2M) at 0° C. The mixture was removed MeOH under reduced pressure, and then extracted with EtOAC 300 mL (100 mL×3). Dried over Na₂SO₄, filtered and concentrated under reduced pressure to give a residue. The crude product 6-(benzyloxy)-3-(nitromethyl)benzo[c][1,2]oxaborol-1 (3H)-ol (9.3 g, black-brown oil, crude, HPLC indicated major was desired product) was used into the next step without further purification. MS: m/z=298.1 [M−1]⁻.

To a solution of 6-(benzyloxy)-3-(nitromethyl)benzo[c][1,2]oxaborol-1(3H)-ol (10.0 g, 33.4 mmol, 1.0 eq.) in AcOH (100.0 mL) was added Zn (4.3 g, 66.8 mmol, 2.0 eq.). The mixture was stirred at 15° C. for 26 hours. HPLC indicated 6-(benzyloxy)-3-(nitromethyl)benzo[c][1,2]oxaborol-1 (3H)-ol was consumed completely and a new peak was formed. The reaction mixture was filtered and concentrated under reduced pressure to give a residue. The crude product 3-(aminomethyl)-6-(benzyloxy)benzo[c][1,2]oxaborol-1(3H)-ol (15.0 g, blackbrown oil, crude) was used into the next step without further purification. MS: m/z=268.2 [M+1]⁺.

A solution of 3-(aminomethyl)-6-(benzyloxy)benzo[c][1,2]oxaborol-1(3H)-ol (4.0 g, 7.8 mmol, 1.0 eq.) in CH₃CN (80.0 mL) was added NaBH₃CN (734.8 mg, 11.6 mmol, 1.5 eq.) and HCHO (780.7 mg, 30% in H$_2$O, 7.8 mmol, 1.0 eq.). The mixture was stirred at 15° C. for 14 hours. HPLC indicated 3-(aminomethyl)-6-(benzyloxy)benzo[c][1,2]oxaborol-1 (3H)-ol was consumed completely. The reaction mixture was concentrated under reduced pressure to remove CH$_3$CN. The residue was dissolved in water and trace CH$_3$CN. The residue was purified prep-HPLC (column: Phenomenex luna C18 250×50 mm, 10 μm; liquid phase: [A-TFA/H$_2$O=0.075% v/v; B-ACN] B %: 15%-45%, 20 min]). 6-(benzyloxy)-3-((dimethyl amino)methyl)benzo[c][1,2]oxaborol-1 (3H)-ol (900.0 mg, 3.0 mmol, 38.8% yield) was obtained as a black-brown oil. MS: m/z=298.2 [M+1].

A solution of 6-(benzyloxy)-3-((dimethylamino)methyl)benzo[c][1,2]oxaborol-1(3H)-ol (500.0 mg, 1.6 mmol, 1.0 eq) in EtOAc (50.0 mL) was added Pd/C (500.0 mg). The mixture was stirred at 15° C. for 18 hours under H$_2$ atmosphere (50 psi). HPLC indicated 6-(benzyloxy)-3-((dimethylamino)methyl)benzo[c][1,2]oxaborol-1 (3H)-ol was consumed completely. The reaction mixture was filtered and concentrated under reduced pressure to give a residue. 3-((dimethylamino)methyl)benzo[c][1,2]oxaborole-1,6 (3H)-diol (350.0 mg, crude) was obtained as black-blown oil. MS: m/z=208.2 [M+1]$^+$.

A solution of 3-((dimethylamino)methyl)benzo[c][1,2]oxaborole-1,6(3H)-diol (110.0 mg, 531.3 umol, 1.0 eq) and [(19R,20R,21R,22S,23R,26S,27R,28S)-22-hydroxy-19,20, 26,27-tetramethyl-24-oxo-26-vinyl-21-tricyclotetradecanyl] 2-(p-tolylsulfonyloxy)acetate (283.0 mg, 531.3 umol, 1.0 eq) in DMF (5.0 mL) was added K$_2$CO$_3$ (220.3 mg, 1.5 mmol, 3.0 eq) and KI (8.8 mg, 53.1 umol, 0.1 eq). The mixture was stirred at 50° C. for 36 hours. HPLC indicated [(19R,20R,21R,22S,23R,26S,27R,28S)-22-hydroxy-19,20, 26,27-tetramethyl-24-oxo-26-vinyl-21-tricyclotetradecanyl] 2-(p-tolylsulfonyloxy)acetate was consumed completely and one new peak formed. The reaction mixture was quenched by adjusted pH=7 (2M aq. HCl), filtered to give a residue (solvent in DMF). The residue was purified by prep-HPLC (column: Luna C18 100×30 mm, 5 μm; liquid phase: [A-TFA/H$_2$O=0.075% v/v; B-ACN] B %: 28%-58%, 12 min]). Concentrated under reduced pressure to remove CH$_3$CN and then two drops of aq. HCl (2M) was added, freeze-drying to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-((dimethyl amino) methyl)-1-hydroxy-1,3-dihydrobenzo[c][1,2]oxaborol-6-yl) oxy)acetate (11.0 mg, 18.9 umol, 3.5% yield, 99.0% purity) as a white solid. $^1$H NMR (DMSO-d$_6$, 400 MHz) δ 7.37 (d, J=8.4 Hz, 1H), 7.25 (d, J=2.0 Hz, 1H), 7.08 (d, J=8.8 Hz, 1H), 6.07 (dd, J=11.2, 18.0 Hz, 1H), 5.62-5.44 (m, 2H), 5.10-4.93 (m, 2H), 4.77-4.64 (m, 2H), 3.69 (d, J=12.0 Hz, 1H), 3.38 (d, J=5.6 Hz, 1H), 3.02-2.94 (m, 1H), 2.91 (s, 3H), 2.85 (s, 3H), 2.66 (d, J=6.2 Hz, 2H), 2.38-2.28 (m, 2H), 2.23-2.12 (m, 1H), 2.11-1.97 (m, 4H), 1.68-1.53 (m, 2H), 1.40-1.18 (m, 7H), 1.07-0.95 (m, 4H), 0.79 (d, J=7.2 Hz, 3H), 0.60 (d, J=7.2 Hz, 3H) MS (ESI): mass calcd. for C$_{32}$H$_{47}$BClNO$_7$ 567.34, m/z found 568.4 [M+H]$^+$. HPLC: 99.0% (220 nm), 88.8% (254 nm).

28. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(((tert-butoxycarbonyl)amino)methyl)-7-fluoro-1-hydroxy-1,3-dihydrobenzo[c][1,2]oxaborol-6-yl)oxy)acetate

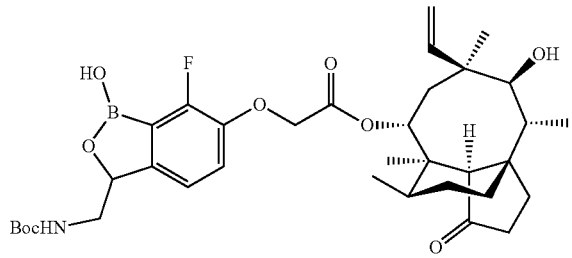

NaOH (842.4 mg, 21.1 mmol, 1.5 eq) was added to a solution of 4-(benzyloxy)-3-fluoro-2-(4,4,5,5-tetramethyl-1,3,2-dioxaborolan-2-yl)benzaldehyde (5.0 g, 14.0 mmol, 1.0 eq) and nitromethane (2.6 g, 42.1 mmol, 3.0 eq) in H$_2$O (25 mL) and MeOH (15 mL) at 25° C. and the mixture was stirred for 12 hours, TLC showed major as desired, water was added to the mixture and adjusted pH<4, the aqueous layer was treated with EtOAc, the crude product was purified by flash chromatography (PE/EA=50/1, 10/1) to give 6-(benzyloxy)-7-fluoro-3-(nitromethyl)benzo[c][1,2]oxaborol-1(3H)-ol (3.4 g, 10.7 mmol, 76.37% yield). $^1$H NMR (DMSO-d$_6$, 400 MHz) δ 9.57 (brs, 1H), 7.49-7.31 (m, 6H), 7.30-7.26 (m, 1H), 5.73 (dd, J=2.4, 8.4 Hz, 1H), 5.29 (dd, J=3.2, 13.6 Hz, 1H), 5.20 (s, 1H), 4.62 (dd, J=9.6, 13.6 Hz, 1H).

HCl (10.2 g, 102.1 mmol, 9.5 eq) was added to a solution of 6-(benzyloxy)-7-fluoro-3-(nitromethyl)benzo[c][1,2]oxaborol-1(3H)-ol (3.4 g, 10.7 mmol, 1.0 eq) and iron powder (3.0 g, 53.6 mmol, 5.0 eq) in MeOH (50 mL) and the mixture was heated to reflux for 4 hours. The mixture was cooled to room temperature. Water was added to the mixture, and filtered. The aqueous layer was treated with EtOAc to give crude 3-(aminomethyl)-6-(benzyloxy)-7-fluorobenzo[c][1,2]oxaborol-1(3H)-ol hydrochloride (3.1 g, crude).

Boc$_2$O (3.1 g, 14.3 mmol, 1.5 eq) was added to a solution of 3-(aminomethyl)-6-(benzyloxy)-7-fluorobenzo[c][1,2]oxaborol-1(3H)-ol hydrochloride (3.1 g, 9.5 mmol, 1.0 eq) and TEA (2.9 g, 28.7 mmol, 3.0 eq) in DCM (100 mL) at 25° C. The mixture was stirred at 25° C. for 2 hours, Water was added to the mixture and adjusted pH<5, the aqueous layer was treated with DCM to give crude tert-butyl ((6-(benzyloxy)-7-fluoro-1-hydroxy-1,3-dihydrobenzo[c][1,2]oxaborol-3-yl)methyl)carbamate (2.5 g, 6.4 mmol, 67.4% yield) as yellow solid.

To a solution of tert-butyl ((6-(benzyloxy)-7-fluoro-1-hydroxy-1,3-dihydrobenzo[c][1,2]oxaborol-3-yl)methyl) carbamate (1.0 g, 2.5 mmol, 1.0 eq) in EtOAc (100 mL) was added Pd/C (500.0 mg, 2.5 mmol, 1.0 eq) under N$_2$. The suspension was degassed under vacuum and purged with H$_2$ several times. The mixture was stirred under H$_2$ (40 psi) at 15° C. for 2 hours. The reaction mixture was filtered and the filtrate was concentrated to give crude tert-butyl ((7-fluoro-1,6-dihydroxy-1,3-dihydrobenzo[c][1,2]oxaborol-3-yl) methyl)carbamate (610.0 mg, 2.0 mmol, 79.6% yield) as yellow solid.

To a solution of tert-butyl ((7-fluoro-1,6-dihydroxy-1,3-dihydrobenzo[c][1,2]oxaborol-3-yl)methyl)carbamate (300.0 mg, 1.0 mmol, 1.0 eq) and Tos-pleuromutilin (537.9 mg, 1.0 mmol, 1.0 eq) in DMF (15 mL) was added Na₂CO₃ (321.1 mg, 3.0 mmol, 3.0 eq) and the mixture was stirred at 40° C. for 10 hours. HPLC showed major as desired, and water was added to the mixture and filtered to give the crude product, which was purified by Pre-HPLC (Instrument: Shimadzu LC-8A preparative-HPLC System Mobile phase: A: 0.01M NH₄HCO₃ in H₂O; B: ACN Column: Dasio C18 250×50 mm, 10 m, Wavelength: 220&254 nm Gradient: a gradient of B % from 30% to 60% in 22 min with hold at initial for 3 min) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-7-fluoro-1-hydroxy-1,3-dihydrobenzo[c][1,2]oxaborol-6-yl)oxy)acetate (100.0 mg, 152.1 umol, 15.1% yield) as yellow solid. ¹H NMR (DMSO-d₆, 400 MHz) δ 9.28 (brs, 1H), 7.22-7.14 (m, 1H), 7.07 (d, J=8.0 Hz, 1H), 6.96 (brs, 1H), 6.11 (dd, J=11.2, 18.0 Hz, 1H), 5.59 (d, J=8.0 Hz, 1H), 5.11-4.98 (m, 3H), 4.83-4.77 (m, 2H), 4.53 (d, J=5.6 Hz, 1H), 3.41 (m, 1H), 3.07 (d, J=7.6 Hz, 2H), 2.41 (s, 1H), 2.03-2.09 (m, 5H), 1.70-1.44 (m, 2H), 1.63-1.15 (m, 16H), 1.04 (d, J=5.6 Hz, 3H), 0.81 (d, J=7.2 Hz, 3H), 0.62 (d, J=7.2 Hz, 3H). MS (ESI): mass calcd. for $C_{35}H_{49}BFNO_9$ 657.6, m/z found 656.3 (M−H)⁻. HPLC: 93.3% (220 nm), 100.0% (254 nm).

29. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(aminomethyl)-7-fluoro-1-hydroxy-1,3-dihydrobenzo[c][1,2]oxaborol-6-yl)oxy)acetate Hydrochloride

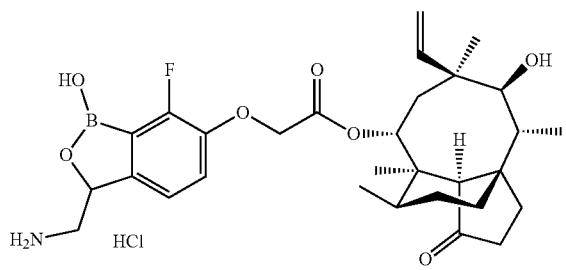

HCl/EtOAc (4 M, 3.00 mL) was added to a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-7-fluoro-1-hydroxy-1,3-dihydrobenzo[c][1,2]oxaborol-6-yl)oxy)acetate (100.0 mg, 152.1 umol, 1.0 eq) in DCM (20 mL), the mixture was stirred at 25° C. for 2 hours, Petroleum ether was added to the mixture and white solid precipitated, the mixture was filtered and the cake was dried to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-7-fluoro-1-hydroxy-1,3-dihydrobenzo[c][1,2]oxaborol-6-yl)oxy)acetate (61.0 mg, 102.7 umol, 67.5% yield) as white solid. ¹H NMR (DMSO-d₆, 400 MHz) δ 9.51 (brs., 1H), 8.14 (brs, 3H), 7.27-7.22 (m, 2H), 6.11 (dd, J=10.8, 18.0 Hz, 1H), 5.60 (d, J=7.6 Hz, 1H), 5.30 (d, J=8.8 Hz, 1H), 5.06 (d, J=18.0 Hz, 1H), 5.03 (d, J=10.8 Hz, 1H), 4.86-4.82 (m, 2H), 2.84-2.82 (m, 2H), 2.41 (s, 1H), 2.18-2.05 (m, 4H), 1.64-1.20 (m, 9H), 1.09-0.94 (m, 4H), 0.83-0.79 (d, J=6.8 Hz, 3H), 0.63 (d, J=6.8 Hz, 3H). MS (ESI): mass calcd. for $C_{30}H_{42}BClFNO_7$ 593.3, m/z found 558.0 (M+H)⁺. HPLC: 99.0% (220 nm), 96.3% (254 nm).

30. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(((tert-butoxycarbonyl)amino)methyl)-7-chloro-1-hydroxy-1,3-dihydrobenzo[c][1,2]oxaborol-6-yl)oxy)acetate 31. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(aminomethyl)-7-chloro-1-hydroxy-1,3-dihydrobenzo[c][1,2]oxaborol-6-yl)oxy)acetate Hydrochloride

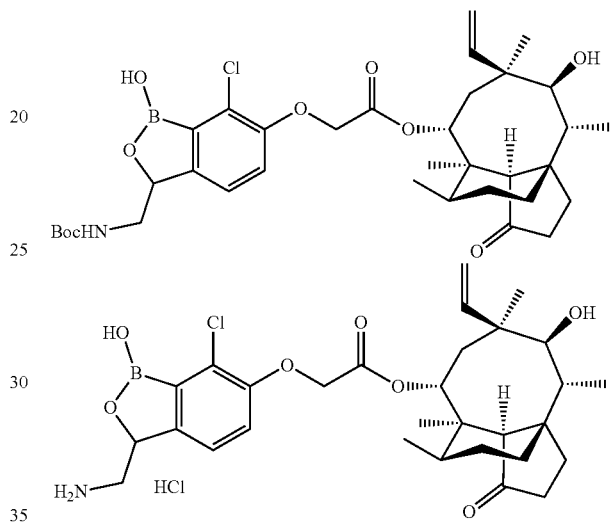

To a solution of tert-butyl (1,6-dihydroxy-1,3-dihydrobenzo[c][1,2]oxaborol-3-yl) methyl carbamate (135 mg, 0.48 mmol) in DMF (3 mL) was added NCS (78 mg, 0.58 mmol). The mixture was stirred at 50° C. overnight. The obtained mixture was filtered and purified by prep-HPLC to give tert-butyl (7-chloro-1,6-dihydroxy-1,3-dihydrobenzo[c][1,2]oxaborol-3-yl)methylcarbamate (70 mg, yield 50%) as a white solid. ¹H NMR (400 MHz, DMSO-d₆) δ 8.97 (s, 1H), 7.11 (d, J=6.4 Hz, 1H), 7.05 (d, J=6.4 Hz, 1H), 6.94-6.90 (m, 1H), 5.03-5.01 (m, 1H), 3.08-3.03 (m, 1H), 1.35 (s, 9H). MS (ESI): mass calcd. for $C_{13}H_{17}BClNO_3$ 313.09, m/z found 336.0 [M+Na]⁺.

To a solution of tert-butyl (7-chloro-1,6-dihydroxy-1,3-dihydrobenzo[c][1,2]oxaborol-3-yl)methylcarbamate (100 mg, 0.32 mmol), Tos-Pleu (204 mg, 0.38 mmol) and K₂CO₃ (88 mg, 0.64 mmol) in acetonitrile (5 mL) was added KI (10 mg, 0.064 mmol). The mixture was stirred at 80° C. overnight. After cooled to room temperature, the mixture was filtered and the solvent was removed under reduced pressure. The residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(((tert-butoxycarbonyl)amino)methyl)-7-chloro-1-hydroxy-1,3-dihydrobenzo[c][1,2]oxaborol-6-yl)oxy)acetate (100 mg, yield 47%) as a white solid. ¹H NMR (400 MHz, DMSO-d₆) δ 9.13 (b, 1H), 7.22 (d, J=8.4 Hz, 1H), 7.20-7.13 (m, 1H), 6.99 (t, J=5.6 Hz, 1H), 6.11-6.07 (m, 1H), 5.59 (d, J=7.6 Hz, 1H), 5.11-4.83 (m, 5H), 3.41-3.08 (m, 3H), 2.42 (s, 1H), 2.23-2.02 (m, 4H), 1.67-1.04 (m, 23H), 0.82 (d, J=6.8 Hz, 3H), 0.63 (d, J=6.8 Hz, 3H). HPLC purity: 100% (220 nm); MS (ESI): mass calcd. for $C_{35}H_{49}BClNO_9$ 673.32, m/z found 696.2 [M+Na]$^+$.

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((3-(((tert-butoxycarbonyl)amino)methyl)-7-chloro-1-hydroxy-1,3-dihydrobenzo[c][1,2]oxaborol-6-yl)oxy)acetate (60 mg, 0.09 mmol) in THF (3 mL) was added HCl/1,4-dioxane (4 M, 0.5 mL). The mixture was stirred at room temperature overnight. The solvent was removed under reduced pressure and the residue was purified by prep-HPLC under basic condition to give target as free amine. To a solution of free amine in MeCN (2 mL) was added HCl (2 mL, 0.5 M). The mixture was freeze-dried to give product as HCl salt (34 mg, yield 67%) as a white solid. $^1$H NMR (400 MHz, DMSO-d$_6$) δ 9.31 (s, 1H), 8.13 (s, 3H), 7.40 (d, J=8.4 Hz, 1H), 7.18 (t, J=8.4 Hz, 1H), 6.15-6.08 (m, 1H), 5.60 (d, J=7.2 Hz, 1H), 5.29 (d, J=8.0 Hz, 1H), 5.14-4.57 (m, 5H), 3.47-3.38 (m, 3H), 2.87 (b, 1H), 2.42 (s, 1H), 2.23-2.02 (m, 4H), 1.67-1.05 (m, 14H), 0.82 (d, J=6.8 Hz, 3H), 0.63 (d, J=6.8 Hz, 3H). HPLC purity: 100% (220 nm); MS (ESI): mass calcd. for $C_{30}H_{41}BClNO_7$ 573.27, m/z found 574.2 [M+H]$^+$.

32. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-5-yl)oxy)acetate

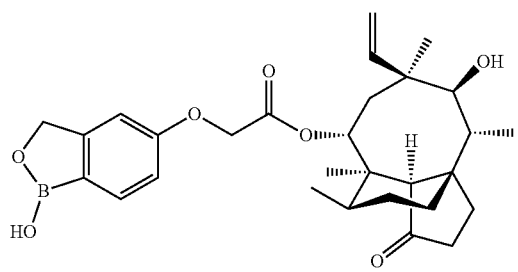

Sodium hydride (60% in oil, 190 mg, 4.76 mmol) was added to a solution of benzo[c][1,2]oxaborole-1,5(3H)-diol (269 mg, 1.79 mmol) in 5 mL of DMF. After the suspension was stirred at 50° C. for two hours, a solution of Tos-pleuromutilin (634 mg, 1.19 mmol) in 5 mL DMF was added. The mixture was stirred at room temperature overnight. The crude was purified by prep HPLC (column: SunFire C18 OBD 100×30 mm, 5 μm) eluted with gradient water/acetonitrile (0.1% TFA) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-5-yl)oxy)acetate as white flakes. $^1$H NMR (400 MHz, DMSO-d$_6$) δ 9.05 (s, 1H), 7.54 (d, J=7.2 Hz, 1H), 6.82 (m, 2H), 6.03 (dd, J=17.6, 11.2 Hz, 1H), 5.54 (d, J=8.4 Hz, 1H), 5.00 (m, 2H), 4.81 (s, 2H), 4.70 (m, 2H), 4.51 (d, J=6 Hz, 1H), 3.36 (m, 1H), 2.35 (s, 1H), 2.11-1.97 (m, 4H), 1.68-1.17 (m, 10H), 0.92 (m, 4H), 0.74 (d, J=7.2 Hz, 3H), 0.56 (d, J=7.2 Hz, 3H). HPLC: 100% (220 nm), 100% (254 nm).

33. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-5-yl)oxy)acetate

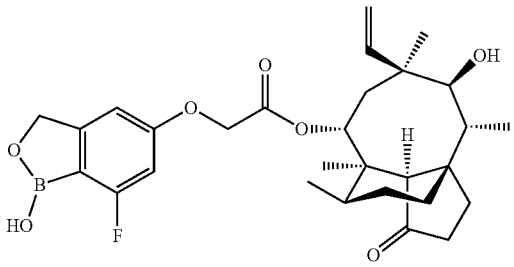

Sodium hydride (60% in oil, 190 mg, 4.76 mmol) was added to a solution of 7-fluorobenzo[c][1,2]oxaborole-1,5(3H)-diol (301 mg, 1.79 mmol) in 5 mL of DMF. After the suspension was stirred at 50° C. for two hours, a solution of Tos-pleuromutilin (634 mg, 1.19 mmol) in 5 mL DMF was added. The mixture was stirred at room temperature overnight. The crude was purified by prep HPLC (column: SunFire C18 OBD 100×30 mm, 5 μm) eluted with gradient water/acetonitrile (0.1% TFA) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-5-yl)oxy)acetate as white flakes. $^1$H NMR (400 MHz, DMSO-d$_6$) δ 9.20 (s, 1H), 6.73 (s, 1H), 6.60 (d, J=10 Hz, 1H), 6.03 (dd, J=18.0, 11.2 Hz, 1H), 5.54 (d, J=8.4 Hz, 1H), 4.97 (m, 2H), 4.84 (s, 2H), 4.75 (m, 2H), 4.51 (d, J=6 Hz, 1H), 3.36 (m, 1H), 2.35 (s, 1H), 2.13-1.96 (m, 4H), 1.61-1.17 (m, 10H), 0.98-0.91 (m, 4H), 0.75 (d, J=7.2 Hz, 3H), 0.57 (d, J=6.8 Hz, 3H). MS (ESI): mass calcd. For $C_{29}H_{38}BO_7F$ 528.42, m/z found 586.0 [M+59–H]$^-$. HPLC: 100% (220 nm), 100% (254 nm).

34. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((6-fluoro-1-hydroxy-1,3-dihydrobenzo[c][1,2]oxaborol-5-yl)oxy)acetate

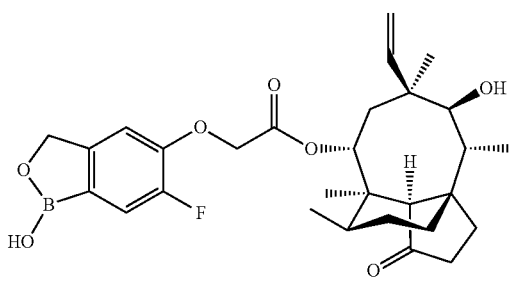

Sodium hydride (60% in oil, 190 mg, 4.76 mmol) was added to a solution of 6-fluorobenzo[c][1,2]oxaborole-1,5

(3H)-diol (300 mg, 1.79 mmol) in 5 mL of DMF. After the suspension was stirred at 50° C. for two hours, a solution of Tos-pleuromutilin (634 mg, 1.19 mmol) in 5 mL DMF was added. The mixture was stirred at room temperature overnight. The crude was purified by prep HPLC (column: SunFire C18 OBD 100×30 mm, 5 μm) eluted with gradient water/acetonitrile (0.1% TFA) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((6-fluoro-1-hydroxy-1,3-dihydrobenzo[c][1,2]oxaborol-5-yl)oxy)acetate as white flakes. $^1$H NMR (400 MHz, DMSO-d$_6$) δ 9.28 (s, 1H), 7.39 (d, J=10.4 Hz, 1H), 7.02 (d, J=7.2 Hz, 1H), 6.03 (dd, J=18.0, 11.2 Hz, 1H), 5.53 (d, J=8.0 Hz, 1H), 4.96 (m, 2H), 4.81 (d, 2H), 4.78 (s, 2H), 4.50 (d, J=6 Hz, 1H), 3.36 (m, 1H), 2.35 (s, 1H), 2.08-1.96 (m, 4H), 1.60-1.19 (m, 10H), 0.98-0.93 (m, 4H), 0.74 (d, J=6.8 Hz, 3H), 0.56 (d, J=7.2 Hz, 3H). MS (ESI): mass calcd. For $C_{29}H_{38}BO_7F$ 528.42, m/z found 527.2 [M−H]$^−$. HPLC: 100% (220 nm), 100% (254 nm).

35. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate 36. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate 37. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((5-fluoro-1-hydroxy-1,3-dihydrobenzo[c][1,2]oxaborol-6-yl)oxy)acetate

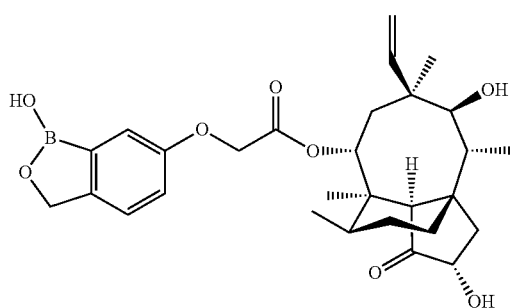

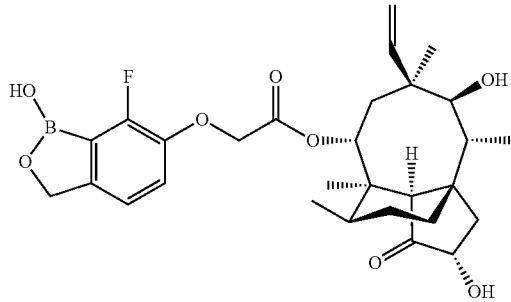

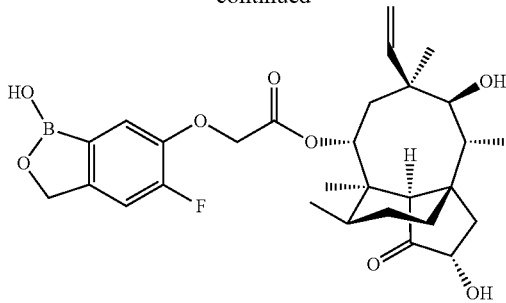

A mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-hydroxyacetate (30.0 g, 79.8 mmol, 1.0 eq) and NaOH (50% w/w, 12.0 g, 303.0 mmol, 3.8 eq) in ethanol (100.0 mL)/water (60.0 mL) was stirred at 50° C. for 3 hours. The mixture was concentrated. The crystalline product was isolated by filtration, washed with water (100 mL) and heptanes (100 mL), and then dried under vacuum to provide (25.0 g, 98.0% yield) of (3aR,4R,5R,7S,8S,9R,9aS,12R)-5,8-dihydroxy-4,7,9,12-tetramethyl-7-vinyloctahydro-4,9a-propanocyclopenta[8]annulen-3(3aH)-one. $^1$H NMR (CDCl3, 400 MHz) δ 6.15 (dd, J=11.2, 17.6 Hz, 1H), 5.44-5.23 (m, 2H), 4.42-4.29 (m, 1H), 3.41 (t, J=6.4 Hz, 1H), 2.33-2.11 (m, 3H), 2.05 (s, 1H), 1.98-1.86 (m, 1H), 1.80-1.38 (m, 7H), 1.36 (s, 2H), 1.31 (d, J=5.6 Hz, 1H), 1.15 (s, 3H), 0.96 (d, J=7.2 Hz, 3H), 0.92 (d, J=7.2 Hz, 3H).

(3aR,4R,5R,7S,8S,9R,9aS,12R)-5,8-dihydroxy-4,7,9,12-tetramethyl-7-vinyloctahydro-4,9a-propanocyclopenta[8]annulen-3(3aH)-one (21.0 g, 65.6 mmol, 1.0 eq) and sodium methylate (5.0 g, 92.6 mmol) in ethyl formate (150.0 mL) and toluene (100.0 mL) were stirred at 25° C. for 12 hours. Ice was added and the mixture was adjusted pH<4 with 2 N HCl, the aqueous layer was treated with EtOAc (100 mL), the crude product was purified by flash chromatography to give (3aR,4R,5R,7S,8S,9R,9aS,12R,E)-5-hydroxy-2-(hydroxymethylene)-4,7,9,12-tetramethyl-3-oxo-7-vinyldecahydro-4,9a-propanocyclopenta[8]annulen-8-yl formate (6.0 g, 24.0% yield). $^1$H NMR (CDCl3, 400 MHz) δ 8.18 (d, J=0.8 Hz, 1H), 6.99 (s, 1H), 6.10 (dd, J=11.4, 17.6 Hz, 1H), 5.45 (dd, J=1.0, 17.6 Hz, 1H), 5.29 (s, 1H), 5.04 (d, J=6.8 Hz, 1H), 4.33 (d, J=7.8 Hz, 1H), 2.56-2.43 (m, 2H), 2.26 (t, J=7.2 Hz, 1H), 2.08-1.95 (m, 1H), 1.87-1.58 (m, 3H), 1.49-1.33 (m, 5H), 1.02 (s, 3H), 1.00 (d, J=7.2 Hz, 3H), 0.81 (d, J=7.2 Hz, 3H).

Tosyl azide (4.7 g, 24.0 mmol) was added to a cooled solution of (3aR,4R,5R,7S,8S,9R,9aS,12R,E)-5-hydroxy-2-(hydroxymethylene)-4,7,9,12-tetramethyl-3-oxo-7-vinyldecahydro-4,9a-propanocyclopenta[8]annulen-8-yl formate (6.0 g, 16.0 mmol) and TEA (7.2 g, 71.0 mmol) in anhydrous DCM (50.0 mL) at −15° C., the mixture was stirred at room temperature for 3 hours. Major as desired, and the crude product was purified by flash chromatography to give (3aR,4R,5R,7S,8S,9R,9aS,12R)-2-diazo-5-hydroxy-3a,4,7,9,12-pentamethyl-3-oxo-7-vinyldecahydro-4,9a-propanocyclopenta[8]annulen-8-yl formate (3.5 g, 55.0% yield). $^1$H NMR (CDCl3, 400 MHz) δ 8.19 (s, 1H), 6.09 (dd, J=11.2, 17.8 Hz, 1H), 5.46 (dd, J=1.2, 17.8 Hz, 1H), 5.34-5.28 (m, 1H), 5.02 (d, J=6.6 Hz, 1H), 4.30 (t, J=6.4 Hz, 1H), 3.08 (d, J=13.2 Hz, 1H), 2.46 (d, J=2.2 Hz, 1H), 2.28 (t, J=6.8 Hz, 1H), 2.20 (d, J=12.8 Hz, 1H), 1.98 (dd, J=7.6, 16.1 Hz, 1H), 1.84-1.67 (m, 3H), 1.63-1.37 (m, 6H), 1.32 (d, J=5.6 Hz, 1H), 1.03 (s, 3H), 0.99 (d, J=7.2 Hz, 3H), 0.84 (d, J=7.2 Hz, 3H).

Dichloroacetic acid (2.0 mL) was added to a cooled solution of (3aR,4R,5R,7S,8S,9R,9aS,12R)-2-diazo-5-hydroxy-3a,4,7,9,12-pentamethyl-3-oxo-7-vinyldecahydro-4,9a-propanocyclopenta[8]annulen-8-yl formate (1.0 g, 2.5 mmol) in anhydrous DCM (30.0 mL) at −15° C., the mixture was stirred at 25° C. for 12 hours. The solvent was evaporated, the crude product was purified by prep-HPLC to give (2S,3aR,4R,5R,7S,8S,9R,9aS,12R)-8-(formyloxy)-5-hydroxy-4,7,9,12-tetramethyl-3-oxo-7-vinyldecahydro-4,9a-propanocyclopenta[8]annulen-2-yl 2,2-dichloroacetate (0.6 g, 48.0% yield). $^1$H NMR (CDCl3, 400 MHz) δ 8.16 (s, 1H), 6.09 (dd, J=11.2, 17.8 Hz, 1H), 6.00 (s, 1H), 5.45 (d, J=17.8 Hz, 1H), 5.32 (d, J=11.2 Hz, 1H), 5.09 (t, J=9.0 Hz, 1H), 4.91 (d, J=6.8 Hz, 1H), 4.30 (d, J=7.2 Hz, 1H), 2.39 (d, J=2.8 Hz, 1H), 2.27 (t, J=6.8 Hz, 1H), 2.12 (dd, J=8.8, 13.4 Hz, 1H), 2.05-1.86 (m, 3H), 1.78 (d, J=16.0 Hz, 1H), 1.56-1.37 (m, 4H), 1.04 (s, 3H), 1.00 (d, J=6.4 Hz, 3H), 0.85 (d, J=7.2 Hz, 3H).

Chloroacetyl chloride (0.9 g, 7.6 mmol) was added to a solution of (2S,3aR,4R,5R,7S,8S,9R,9aS,12R)-8-(formyloxy)-5-hydroxy-4,7,9,12-tetramethyl-3-oxo-7-vinyldecahydro-4,9a-propanocyclopenta[8]annulen-2-yl 2,2-dichloroacetate (1.2 g, 2.5 mmol) and pyridine (1.2 g, 15.0 mmol) in DCM (30.0 mL) at 0° C. The mixture was stirred at 25° C. for 2 hours, water (30 mL) was added, and the aqueous layer was treated with DCM (30 mL×3). The crude product was purified by prep-HPLC to give (2S,3aR,4R,5R,7S,8S,9R,9aS,12R)-5-(2-chloroacetoxy)-8-(formyloxy)-4,7,9,12-tetramethyl-3-oxo-7-vinyldecahydro-4,9a-propanocyclopenta[8]annulen-2-yl 2,2-dichloroacetate (0.8 g, 54.0% yield). $^1$H NMR (CDCl3, 400 MHz) δ 8.15 (s, 1H), 6.31 (dd, J=11.2, 17.4 Hz, 1H), 6.00 (s, 1H), 5.72 (d, J=8.0 Hz, 1H), 5.36-5.19 (m, 2H), 5.10 (t, J=8.8 Hz, 1H), 4.96 (d, J=6.5 Hz, 1H), 3.99 (d, J=1.8 Hz, 2H), 2.52-2.45 (m, 2H), 2.26-2.09 (m, 4H), 2.01-1.89 (m, 1H), 1.63-1.38 (m, 8H), 1.12-1.04 (m, 3H), 0.87 (d, J=6.8 Hz, 3H), 0.76 (d, J=6.8 Hz, 3H).

(2S,3aR,4R,5R,7S,8S,9R,9aS,12R)-5-(2-chloroacetoxy)-8-(formyloxy)-4,7,9,12-tetramethyl-3-oxo-7-vinyldecahydro-4,9a-propanocyclopenta[8]annulen-2-yl 2,2-dichloroacetate (0.3 g, 0.5 mmol), benzo[c][1,2]oxaborole-1,6(3H)-diol (81.0 mg, 0.5 mmol) and potassium carbonate (225.0 mg, 1.6 mmol) with cata. amount sodium iodide in DMF (15.0 mL) were stirred at 50° C. for 12 hours. Water (15 mL) was added, the mixture was filtered and dried to give crude (2S,3aR,4R,5R,7S,8S,9R,9aS,12R)-8-(formyloxy)-5-(2-((1-hydroxy-1,3-dihydrobenzo[c][1,2]oxaborol-6-yl)oxy)acetoxy)-4,7,9,12-tetramethyl-3-oxo-7-vinyldecahydro-4,9a-propanocyclopenta[8]annulen-2-yl 2,2-dichloroacetate (0.3 g, crude) and used directly.

Sodium hydroxide (30.0 mg, 0.8 mmol) was added to (2S,3aR,4R,5R,7S,8S,9R,9aS,12R)-8-(formyloxy)-5-(2-((1-hydroxy-1,3-dihydrobenzo[c][1,2]oxaborol-6-yl)oxy)acetoxy)-4,7,9,12-tetramethyl-3-oxo-7-vinyldecahydro-4,9a-propanocyclopenta[8]annulen-2-yl 2,2-dichloroacetate (0.3 g, 0.4 mmol) in EtOH (10.0 mL) and water (10.0 mL). The mixture was stirred at 25° C. for 15 mins, the mixture was adjusted pH<4 with 2N HCl. Solvent was evaporated, the crude product was purified by prep-HPLC to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate (35.0 mg, 17.5% yield). $^1$H NMR (DMSO-d6, 400 MHz) δ 9.09 (br. s., 1H), 7.30 (d, J=8.4 Hz, 1H), 7.19 (s, 1H), 7.04 (dd, J=2.4, 8.4 Hz, 1H), 6.09 (dd, J=11.0, 17.6 Hz, 1H), 5.59 (d, J=7.6 Hz, 1H), 5.12-4.97 (m, 2H), 4.91 (s, 2H), 4.78-4.65 (m, 3H), 3.75 (t, J=8.4 Hz, 1H), 3.32 (d, J=5.8 Hz, 1H), 2.35 (br. s., 1H), 2.12-1.96 (m, 2H), 1.87-1.71 (m, 2H), 1.46-1.27 (m, 7H), 1.22 (br. s., 1H), 1.05 (s, 3H), 0.83 (d, J=6.8 Hz, 3H), 0.64 (d, J=5.8 Hz, 3H). MS (ESI): mass calcd. for $C_{29}H_{39}BO_8$ 526.27, m/z found 525.2 [M−H]$^-$. HPLC: 99.7% (220 nm), 73.1% (254 nm).

(2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate was synthesized similarly by using 7-fluorobenzo[c][1,2]oxaborole-1,6(3H)-diol. $^1$H NMR (DMSO-d6, 400 MHz) δ 7.18 (br. s., 1H), 7.09 (br. s., 1H), 6.09 (dd, J=11.2, 17.8 Hz, 1H), 5.58 (d, J=8.8 Hz, 1H), 5.10-4.97 (m, 2H), 4.91 (br. s., 1H), 4.78 (br. s., 2H), 3.74 (t, J=8.4 Hz, 1H), 3.42 (q, J=7.2 Hz, 1H), 3.30 (d, J=6.2 Hz, 1H), 2.33 (br. s., 1H), 2.12-1.96 (m, 3H), 1.87-1.69 (m, 2H), 1.48-1.17 (m, 7H), 1.10-1.00 (m, 4H), 0.82 (d, J=7.2 Hz, 2H), 0.63 (br. s., 2H). MS (ESI): mass calcd. for $C_{29}H_{38}BFO_8$ 544.26, m/z found 543.3[M−H]$^-$. HPLC: 99.8% (220 nm), 81.1% (254 nm).

(2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((5-fluoro-1-hydroxy-1,3-dihydrobenzo[c][1,2]oxaborol-6-yl)oxy)acetate was synthesized similarly by using 5-fluorobenzo[c][1,2]oxaborole-1,6(3H)-diol. $^1$H NMR (DMSO-d6, 400 MHz) δ 9.11 (s, 1H), 7.38-7.27 (m, 2H), 6.07 (dd, J=11.4, 17.6 Hz, 1H), 5.64-5.51 (m, 2H), 5.12-4.96 (m, 2H), 4.90 (br. s., 2H), 4.87-4.74 (m, 2H), 4.65 (d, J=5.8 Hz, 1H), 3.75 (d, J=7.2 Hz, 1H), 2.35 (br. s., 1H), 2.13-1.93 (m, 2H), 1.87-1.67 (m, 2H), 1.46-1.16 (m, 8H), 1.04 (br. s., 4H), 0.82 (d, J=6.4 Hz, 3H), 0.63 (br. s., 3H). MS (ESI): mass calcd. for $C_{29}H_{39}O_8$ 544.3, m/z found 543.3[M−H]$^-$. HPLC: 98.9% (220 nm), 100.0% (254 nm).

38. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate 39. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate 40. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((5-fluoro-1-hydroxy-1,3-dihydrobenzo[c][1,2]oxaborol-6-yl)oxy)acetate

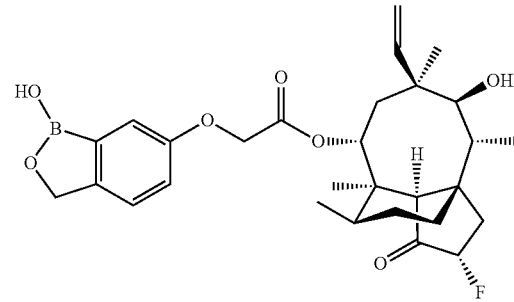

-continued

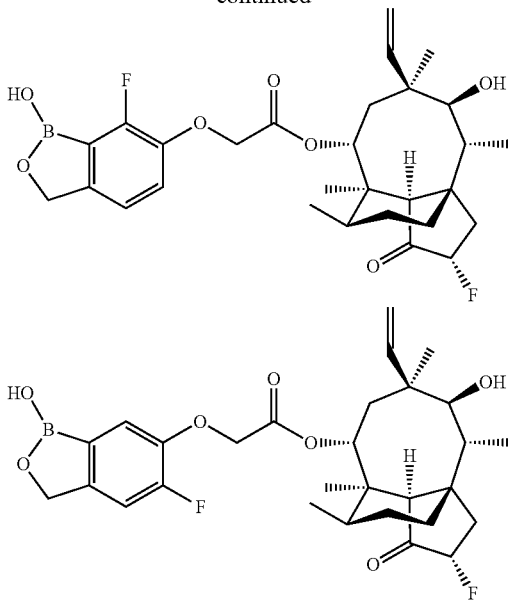

Hydrogen fluoride pyridine complex (35.0 mL) was added to a cooled solution of (3aR,4R,5R,7S,8S,9R,9aS,12R)-2-diazo-5-hydroxy-3a,4,7,9,12-pentamethyl-3-oxo-7-vinyldecahydro-4,9a-propanocyclopenta[8]annulen-8-yl formate (11.0 g, 28.3 mmol) in anhydrous THF (100.0 ml) at −15° C. The mixture was stirred at 25° C. for 12 hours. Water (100 mL) was added, the aqueous layer was treated with EtOAc (150 mL), the crude product was purified by flash chromatography to give (2S,3aR,4R,5R,7S,8S,9R,9aS,12R)-2-fluoro-5-hydroxy-4,7,9,12-tetramethyl-3-oxo-7-vinyldecahydro-4,9a-propanocyclopenta[8]annulen-8-yl formate (4.0 g, 38.7% yield). $^1$H NMR (CDCl3, 400 MHz) δ 8.18 (d, J=1.2 Hz, 1H), 6.10 (ddd, J=1.2, 11.2, 17.8 Hz, 1H), 5.45 (dd, J=1.2, 17.8 Hz, 1H), 5.35-5.27 (m, 1H), 4.92 (d, J=6.6 Hz, 1H), 4.79-4.70 (m, 1H), 4.64-4.57 (m, 1H), 4.29 (d, J=3.2 Hz, 1H), 2.39 (d, J=3.2 Hz, 1H), 2.33-2.18 (m, 1H), 2.14-1.85 (m, 4H), 1.77 (d, J=16.2 Hz, 1H), 1.63-1.23 (m, 8H), 1.04 (s, 2H), 1.01-0.97 (m, 2H), 0.85 (d, J=7.2 Hz, 3H).

2-(tosyloxy)acetic acid (2.6 g, 11.3 mmol), PFPOH (2.5 g, 13.5 mmol), DCC (2.8 g, 13.5 mmol) and cata amount DMAP in anhydrous THF (50.0 mL) were stirred at 25° C. for 15 hours. The mixture was filtered, the crude product was purified by flash chromatography to give perfluorophenyl 2-(tosyloxy) acetate (2.1 g, 47.0% yield). $^1$H NMR (CDCl3, 400 MHz) δ 7.87 (d, J=8.4 Hz, 2H), 7.39 (d, J=8.0 Hz, 2H), 4.97 (s, 2H), 2.48 (s, 3H). (2S,3aR,4R,5R,7S,8S,9R,9aS,12R)-2-fluoro-5-hydroxy-4,7,9,12-tetramethyl-3-oxo-7-vinyldecahydro-4,9a-propanocyclopenta[8]annulen-8-yl formate (4.0 g, 10.9 mmol), perfluorophenyl 2-(tosyloxy) acetate (10.8 g, 27.0 mmol) and DMAP (1.3 g, 10.9 mmol) in anhydrous THF (100.0 mL) were stirred at 25° C. for 12 hours. The solvent was evaporated, the crude product was purified by Pre-HPLC to give (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy)acetate (2.7 g, yield 43%). 1H NMR (CDCl3, 400 MHz) δ 8.16 (s, 1H), 7.83 (d, J=8.0 Hz, 2H), 7.37 (d, J=8.0 Hz, 2H), 6.23 (dd, J=17.6, 11.2 Hz, 1H), 5.68 (d, J=8.4 Hz, 1H), 5.14-5.37 (m, 1H), 4.93 (d, J=6.4 Hz, 1H), 4.75 (t, J=8.0 Hz, 1H), 4.62 (t, J=8.0 Hz, 1H), 4.50 (s, 2H), 2.38-2.51 (m, 5H), 1.85-2.17 (m, 5H), 1.66 (s, 2H), 1.30-1.57 (m, 7H), 1.05 (s, 3H), 0.85 (d, J=6.8 Hz, 4H).

(2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy)acetate (1.5 g, 2.6 mmol), benzo[c][1,2]oxaborole-1,6(3H)-diol (3890 mg, 2.6 mmol) and potassium carbonate (1.1 g, 7.7 mmol) with cata. Amount sodium iodide in DMF (30.0 mL) was stirred at 50° C. for 1 hour. Water (50 mL) was added, the mixture was filtered and dried to give crude (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate (1.6 g, crude) and used directly. Potassium carbonate (794.0 mg, 5.8 mmol) was added to (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy) acetate (1.6 g, crude, 2.9 mmol) in MeOH (50.0 mL) and THF (50.0 mL). The mixture was stirred at 50° C. for 2 hours, the mixture was adjusted pH<4 with 2N HCl. Solvent was evaporated, the crude product was purified by prep-HPLC to give (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)oxy)acetate (230.0 mg, 15.0% yield). 1H NMR (DMSO-d6, 400 MHz) δ 7.30 (d, J=8.4 Hz, 1H), 7.20 (s, 1H), 7.05 (d, J=8.0 Hz, 1H), 6.14-6.03 (m, 1H), 5.57 (d, J=8.4 Hz, 1H), 5.11-4.97 (m, 3H), 4.91 (s, 2H), 4.85 (t, J=9.0 Hz, 1H), 4.79-4.65 (m, 2H), 3.34 (br. s., 1H), 2.61 (br. s., 1H), 2.26-1.97 (m, 4H), 1.81 (d, J=15.2 Hz, 1H), 1.67-1.17 (m, 7H), 1.05 (s, 3H), 0.84 (d, J=6.4 Hz, 3H), 0.64 (d, J=6.4 Hz, 3H). MS (ESI): mass calcd. for $C_{29}H_{38}BFO_7$ 528.27, m/z found 526.9[M−H]$^-$. HPLC: 93.5% (220 nm), 71.9% (254 nm).

(2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate was synthesized similarly as above by using 7-fluorobenzo[c][1,2]oxaborole-1,6(3H)-diol. $^1$H NMR (DMSO-d6, 400 MHz) δ 7.25-7.18 (m, 1H), 7.10 (d, J=7.8 Hz, 1H), 6.09 (dd, J=11.4, 18.1 Hz, 1H), 5.57 (d, J=7.8 Hz, 1H), 5.10-4.98 (m, 2H), 4.92 (s, 2H), 4.88 (br. s., 1H), 4.83 (d, J=4.8 Hz, 2H), 3.34 (br. s., 1H), 2.61 (br. s., 1H), 2.27-1.93 (m, 3H), 1.80 (d, J=13.3 Hz, 1H), 1.70-1.18 (m, 10H), 1.05 (br. s., 3H), 0.84 (d, J=6.8 Hz, 3H), 0.63 (d, J=6.0 Hz, 3H). MS (ESI): mass calcd. for $C_{29}H_{37}BF_2O_7$ 546.26, m/z found 563.3[M+H$_2$O−H]$^-$. HPLC: 97.8% (220 nm), 100.0% (254 nm).

(2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((5-fluoro-1-hydroxy-1,3-dihydrobenzo[c][1,2]oxaborol-6-yl)oxy)acetate was synthesized similarly as above by using 5-fluorobenzo[c][1,2]oxaborole-1,6(3H)-diol. $^1$H NMR (DMSO-d6, 400 MHz) δ 7.36-7.28 (m, 2H), 6.06 (dd, J=12.0, 17.4 Hz, 1H), 5.56 (d, J=8.2 Hz, 1H), 5.10-4.96 (m, 3H), 4.90 (s, 2H), 4.85 (br. s., 1H), 4.82 (d, J=5.6 Hz, 2H), 3.34 (s, 1H), 2.61 (br. s., 1H), 2.22-1.92 (m, 3H), 1.80 (d, J=14.6 Hz, 1H), 1.67-1.17 (m, 9H), 1.04 (s, 3H), 0.84 (d, J=6.4 Hz, 2H), 0.63 (d, J=6.4 Hz, 3H). MS (ESI): mass calcd. for $C_{29}H_{37}BF_2O_7$ 546.26, m/z found 545.3[M−H]⁻. HPLC: 96.4% (220 nm), 91.5% (254 nm).

41. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-1-hydroxy-1,3-dihydrobenzo[c][1,2]oxaborol-6-yl)oxy)acetate

42. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy)acetate

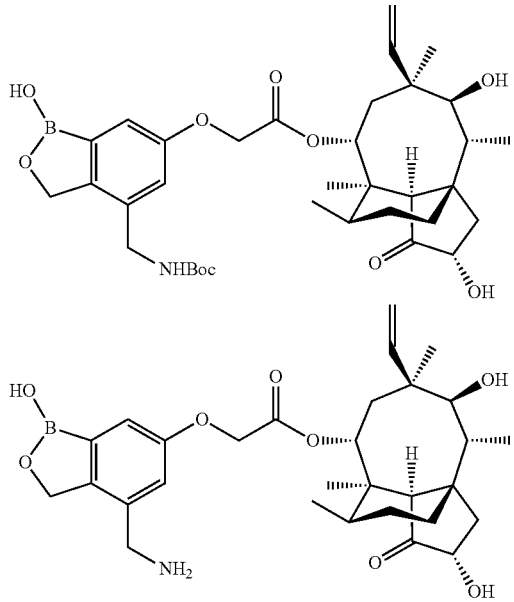

To a solution of tert-butyl (1,6-dihydroxy-1,3-dihydrobenzo[c][1,2]oxaborol-4-yl)methylcarbamate (28 mg, 0.1 mmol) and $K_2CO_3$ (27 mg, 0.2 mmol) in MeCN (5 mL) was added (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-iodoacetate (50 mg, 0.1 mmol). The reaction mixture was heated to reflux overnight. After removed the solvent, the residue was purified by prep-HPLC to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-1-hydroxy-1,3-dihydrobenzo [c][1,2]oxaborol-6-yl)oxy)acetate (13 mg, yield 20%) as a white solid. $^1$H NMR (400 MHz, DMSO-$d_6$) δ 9.08 (s, 1H), 7.37 (t, J=5.2 Hz, 1H), 7.06 (s, 1H), 6.90 (s, 1H), 6.17-6.03 (m, 1H), 5.58 (d, J=7.6 Hz, 2H), 5.15-4.99 (m, 2H), 4.93 (s, 2H), 4.74-4.60 (m, 3H), 4.05 (d, J=5.6 Hz, 2H), 3.76 (s, 1H), 2.36-1.75 (m, 6H), 1.43-0.63 (m, 28H). HPLC purity: 100% (214 nm); MS (ESI): mass calcd. for $C_{35}H_{50}BNO_{10}$ 655.35, m/z found 556.2 [M−99]⁺.

To a solution of (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((4-(((tert-butoxycarbonyl)amino)methyl)-1-hydroxy-1,3-dihydrobenzo [c][1,2]oxaborol-6-yl)oxy)acetate (8 mg, 0.012 mmol) in MeOH (3 mL) was added HCl/1,4-dioxane (4 N, 0.5 mL). The reaction mixture was stirred at r.t for 3 h. The solvent was removed and the residue was purified by prep-HPLC to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy)acetate (1.2 mg, yield 18%) as a white solid. $^1$H NMR (400 MHz, DMSO-$d_6$) δ 9.03 (s, 1H), 7.06 (d, J=2.4 Hz, 1H), 7.03 (d, J=2.4 Hz, 1H), 6.13-6.04 (m, 1H), 5.60-5.55 (m, 2H), 5.10-4.99 (m, 2H), 4.95 (s, 2H), 4.75-4.64 (m, 3H), 3.77-3.72 (m, 1H), 3.64 (s, 2H), 2.41-1.95 (m, 5H), 1.39-0.64 (m, 22H). HPLC purity: 100% (220 nm); MS (ESI): mass calcd. for $C_{30}H_{42}BNO_8$ 555.30, m/z found 556.2 [M+H]⁺.

43. (3aR,4R,5R,7S,9R,9aS,12R)-4,7,9,12-tetramethyl-3,8-dioxo-7-vinyldecahydro-4,9a-propanocyclopenta[8]annulen-5-yl (1-hydroxy-1,3-dihydrobenzo[c][1,2]oxaborol-6-yl)carbamate

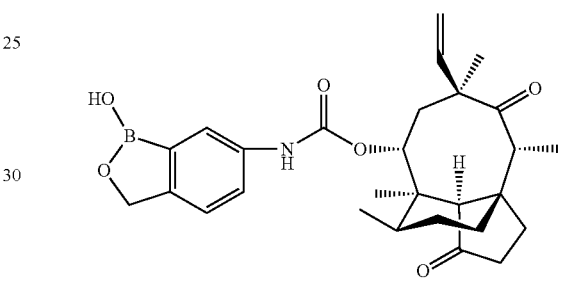

(3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-hydroxyacetate (40.0 g, 106.0 mmol) was dissolved in methanol (150 mL) and trimethyl orthoformate (50.0 g, 475.0 mmol) at 20° C. Concentrated sulphuric acid (19.8 g, 206.0 mmol) was added over 10 min at <30° C. The mixture was heated to 30° C. and stirred for 16 hrs. A solution of NaOH (32.0 g, 0.8 mol) in water (35 mL) was added to the methanol mixture, and the contents were heated to 60-70° C. for 2 h. The mixture was cooled to 40° C., and methanol was removed by vacuum. The reaction mixture was extracted with ethyl acetate for three times, the combined organic phases were washed by brine, dried over $Na_2SO_4$. The solvent was removed to give (3R,3aR,4R,5R,7S,9R,9aR,12R)-5-hydroxy-3-methoxy-4,7,9,12-tetramethyl-7-vinyloctahydro-4,9a-propanocyclopenta[8]annulen-8(9H)-one and (30.0 g, 84.5% yield) used for the next step directly. $^1$H NMR (DMSO-$d_6$, 400 MHz) δ 6.05 (dd, J=10.8 Hz, 1H), 5.29 (m, 2H), 4.66 (d, J=8.8 Hz, 1H), 3.48 (m, 1H), 3.22 (s, 3H), 2.92 (m, 1H), 2.45 (m, 1H), 2.18 (m, 1H), 1.99 (m, 3H), 1.85 (d, 1H), 1.71 (d, 1H), 1.58 (m, 2H), 1.46 (m, 1H), 1.32 (m, 1H), 1.18 (m, 7H), 1.09 (d, 3H), 0.95 (d, 3H).

Trichloromethylchloroformate (215.0 mL, 1.5 mmol) followed $Et_3N$ (495.0 mL, 3.6 mmol) was added to an-ice-cooled solution of (3R,3aR,4R,5R,7S,9R,9aR,12R)-5-hydroxy-3-methoxy-4,7,9,12-tetramethyl-7-vinyloctahydro-4,9a-propanocyclopenta[8]annulen-8(9H)-one (1.0 g, 3.0 mmol) in THF (10 mL). The mixture was stirred at r.t for 2 hrs and then treated with further quantities of Trichloromethylchloroformate (215.0 mL, 1.5 mmol) and $Et_3N$ (495.0 mL, 3.6 mmol). After a further 2 hrs, the mixture was diluted with EtOAc and washed by brine. The organic phase was dried by Na$_2$SO$_4$, concentrated to give (3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl carbonochloridate without further purification. (1.2 g, 100.0%).

To a solution of 6-aminobenzo[c][1,2]oxaborol-1(3H)-ol (200.0 mg, 1.4 mmol) in DCM (15 mL) were added Et$_3$N (137.0 mg, 1.4 mmol) and (3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl carbonochloridate (1.2 g, 3.0 mmol). The reaction mixture was stirred at r.t overnight, After TLC showed the staring materials were consumed completely, and the mixture was extracted with EtOAc, washed with brine, dried over anhydrous Na$_2$SO$_4$, and concentrated in vacuo give the crude compound which was used for the next step directly. (crude 1.3 g)

The mixture of (3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl(1-hydroxy-1,3-dihydrobenzo[c][1,2]oxaborol-6-yl)carbamate (crude 1.3 g) was added the solution of ZnCl$_2$ in conc.HCl. The mixture was stirred at r.t for 0.5 hr. Then the mixture was added water and extracted with EtOAc. The crude product was purified by pre-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydrobenzo[c][1,2]oxaborol-6-yl)carbamate. (61.0 mg). $^1$H NMR (DMSO-d$_6$, 400 MHz) δ 9.38 (s, 1H), 7.89 (s, 1H), 7.43 (d, J=7.6 Hz, 1H), 7.27 (d, J=8.0 Hz, 1H), 6.26 (m, 1H), 5.58 (s, 1H), 5.13 (m, 2H), 4.89 (s, 2H), 2.38 (m, 1H), 2.05 (m, 4H), 1.06-1.50 (m, 13H), 1.07 (m, 4H), 0.82 (d, 3H), 0.69 (d, 3H).

44. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-fluoro-1-hydroxy-1,3-dihydrobenzo[c][1,2]oxaborol-6-yl)carbamate

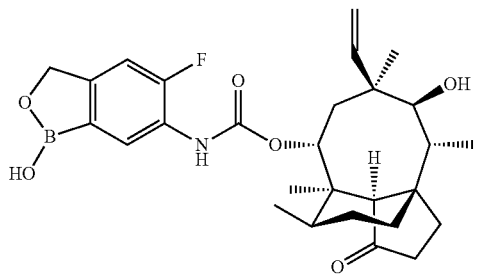

To a solution of 6-amino-5-fluorobenzo[c][1,2]oxaborol-1(3H)-ol (200 mg, 1.2 mmol) in THF (15 mL) were added pyridine (1.2 g, 18 mmol) and (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl carbonochloridate (1.4 g, 3.5 mmol). The reaction mixture was stirred at room temperature overnight. After TLC showed the staring materials were consumed completely, and the mixture was extracted with EtOAc, washed with brine, dried over anhydrous Na$_2$SO$_4$, and concentrated in vacuum give the crude product which was purified by prep-HPLC (column: Luna C18 100×30 mm, 5 μm; liquid phase: [A-TFA/H$_2$O=0.075% v/v; B-ACN] B %: 40%-70%, 15 min]) to give (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl (5-fluoro-1-hydroxy-1,3-dihydrobenzo[c][1,2]oxaborol-6-yl)carbamate (400 mg, 64.2% yield) as white solid. $^1$H NMR (DMSO-d$_6$, 400 MHz) δ 9.25 (s, 2H), 7.99 (s, 1H), 7.32 (d, J=10.4 Hz, 1H), 6.74 (dd, J=10.8, 17.6 Hz, 1H), 5.64 (d, J=9.6 Hz, 1H), 5.29 (d, J=10.8 Hz, 1H), 4.98 (m, 3H), 3.40 (s, 1H), 3.12 (s, 3H), 2.88 (m, 1H), 2.34 (m, 1H), 2.04 (s, 3H), 1.90 (m, 1H), 1.72 (m, 1H), 1.67 (d, 2H), 1.43 (m, 2H), 1.25-1.07 (m, 9H), 0.87-0.75 (m, 5H). MS (ESI): mass calcd. for C$_{29}$H$_{39}$BNO$_6$ 527.2, m/z found 526.2 [M−H]$^-$. HPLC: 99.6% (220 nm), 100% (254 nm).

(3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl (5-fluoro-1-hydroxy-1,3-dihydrobenzo[c][1,2]oxaborol-6-yl)carbamate (300.0 mg, 0.6 mmol) was added to the solution of ZnCl$_2$ in conc.HCl (10 mL, 50% wt). The mixture was stirred at room temperature for 0.5 h. Then the mixture was diluted with water (50 mL) and extracted with EtOAc (50 mL) three times. The crude product was purified by prep-HPLC (column: Luna C18 100×30 mm, 5 μm; liquid phase: [A-TFA/H$_2$O=0.075% v/v; B-ACN] B %: 35%-60%, 20 min]) to give the (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-fluoro-1-hydroxy-1,3-dihydrobenzo[c][1,2]oxaborol-6-yl)carbamate (82.0 mg, 28.2% yield). $^1$H NMR (DMSO-d$_6$, 400 MHz) δ 9.22 (s, 1H), 9.06 (s, 1H), 7.90 (s, 1H), 7.26 (d, J=10.8 Hz, 1H), 6.25 (dd, J=10.8, 17.6 Hz, 1H), 5.52 (d, J=8.0 Hz, 1H), 5.11 (d, J=18.0 Hz, 1H), 5.04 (d, J=10.8 Hz, 1H), 4.91 (s, 2H), 4.46 (d, J=6.0 Hz, 1H), 3.40 (m, 1H), 2.37 (s, 1H), 2.13-2.06 (m, 4H), 1.70-1.25 (m, 10H), 1.06 (m, 4H), 0.80 (d, J=7.2 Hz, 3H), 0.71 (d, J=7.2 Hz, 3H). MS (ESI): mass calcd. for C$_{28}$H$_{37}$BFNO$_6$ 513.2, m/z found 512.2 [M−H]$^-$. HPLC: 96.4% (220 nm), 100% (254 nm).

45. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydrobenzo[c][1,2]oxaborol-6-yl)glycinate

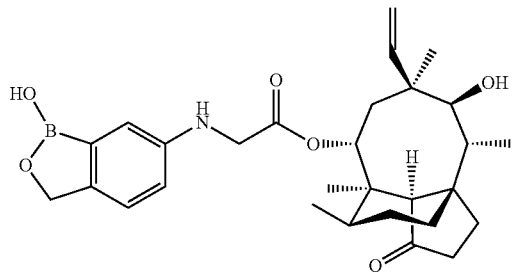

To a solution of 6-aminobenzo[c][1,2]oxaborol-1(3H)-ol (299.4 mg, 2.0 mmol, 1.0 eq.) and Iodo-pleoromutilin (981.7 mg, 2.0 mmol, 1.0 eq.) in DMF (40.0 mL) was added K$_2$CO$_3$ (833.4 mg, 6.0 mmol, 3.0 eq.). The mixture was stirred at 40° C. for 16 hours. HPLC indicated 6-aminobenzo[c][1,2]

oxaborol-1(3H)-ol was consumed completely two new peaks formed. The reaction mixture was quenched by addition H₂O 100 mL, and then adjusted pH~6, solid was dissolved out, filtered to give a residue. The residue was purified by prep-HPLC (column: Phenomenex luna (2) C18 250×50 mm, 10 μm; liquid phase: [A-TFA/H₂O=0.075% v/v; B-ACN] B %: 20 min]), removed CH₃CN, and then a drop of 2 N HCl was added, freeze-dried to give the product. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl) amino)acetate hydrochloride (138.0 mg, 252.8 umol, 12.6% yield) was obtained as a yellow solid (detected by ¹H NMR). ¹H NMR (DMSO-d₆, 400 MHz) δ 7.09 (d, J=8.4 Hz, 1H), 6.83 (br. s., 1H), 6.72 (d, J=8.4 Hz, 1H), 6.12-5.96 (m, 1H), 5.53 (d, J=8.0 Hz, 1H), 5.07-4.90 (m, 2H), 4.87-4.77 (m, 1H), 3.78 (d, J=5.2 Hz, 2H), 3.37 (d, J=5.2 Hz, 1H), 2.33 (br. s., 1H), 2.22-2.12 (m, 1H), 2.10-1.91 (m, 3H), 1.70-1.52 (m, 3H), 1.43 (br. s., 2H), 1.37-1.15 (m, 8H), 1.06-0.89 (m, 5H), 0.79 (d, J=6.4 Hz, 3H), 0.61 (d, J=6.4 Hz, 3H). MS (ESI): mass calcd. for C₂₉H₄₁BClNO₆ 545.27, m/z found 508.3[M−H]⁻. HPLC: 100.0% (220 nm), 100.0% (254 nm).

46. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-fluoro-1-hydroxy-1,3-dihydrobenzo[c][1,2]oxaborol-6-yl)glycinate

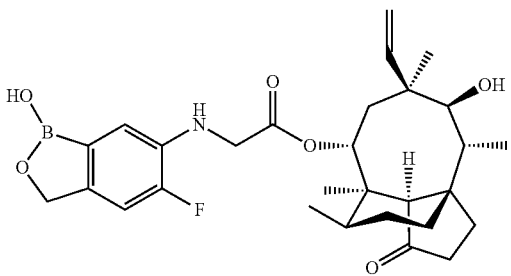

To a solution of (3aR,4S,5 S,7S,8S,9R,9aS,12R)-8-hydroxy-5-(3-iodo-2-oxopropyl)-4,7,9,12-tetramethyl-7-vinyloctahydro-4,9a-propanocyclopenta[8]annulen-3(3aH)-one (50.0 mg, 0.1 mmol) in NMP (5 mL) were added K₂CO₃ (73.6 mg, 0.2 mmol) and 6-amino-5-fluorobenzo[c][1,2]oxaborol-1(3H)-ol (16.7 mg, 0.1 mmol). The reaction mixture was irradiated under microwave at 100° C. for 2 hrs, extracted with EtOAc (10 mL×3). The combined organic phases were dried over anhydrous Na₂SO₄, and concentrated in vacuum give the crude compound which was purified by prep-HPLC to obtained (3aR,4R,5R,7S,8S,9R,9aS,12R)-8-hydroxy-4,7,9,12-tetramethyl-3-oxo-7-vinyl-decahydro-4,9a-propanocyclopenta[8]annulen-5-yl2-((5-fluoro-1-hydroxy-1,3-di-hydrobenzo[c][1,2]oxaborol-6-yl) amino)acetate (25.0 mg, 47.4%) as a yellow solid. ¹H NMR (DMSO-d₆, 400 MHz) δ 8.88 (s, 1H), 7.11-7.09 (d, J=8.0 Hz, 1H), 6.88-6.86 (d, J=8.0 Hz, 1H), 6.09-6.04 (m, 1H), 5.75 (s, 1H), 5.54-5.42 (d, J=8.0 Hz, 1H), 5.05-5.01 (m, 1H), 4.95-4.93 (m, 1H), 4.83 (s, 2H), 3.86-3.83 (m, 2H), 2.37-2.17 (m, 1H), 2.14-2.08 (m, 2H), 2.06-2.01 (m, 3H), 1.66-1.62 (m, 3H), 1.59-1.32 (m, 5H), 1.24-1.21 (m, 4H), 1.00 (s, 3H), 0.81-0.79 (d, J=8.0 Hz, 3H), 0.62-0.61 (d, J=4.0 Hz, 3H).

47. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-(aminomethyl)-1-hydroxy-1,3-dihydrobenzo[c][1,2]oxaborol-6-yl) glycinate

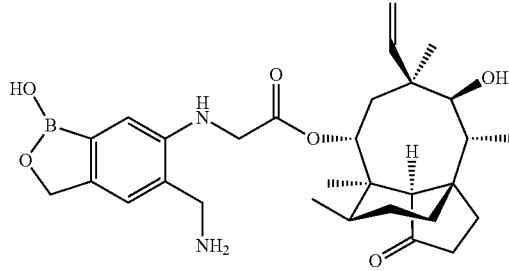

A mixture of 4-bromo-3-methylbenzonitrile (15.0 g, 76.9 mmol, 1 eq), NBS (16.3 g, 92.3 mmol, 1.2 eq) and AIBN (0.95 g, 3.8 mmol, 5%) in CCl₄ (220 ml) was stirred at 78° C. for overnight. The mixture was filtered, then the clear solution was washed by brine, dried with Na₂SO₄ and concentrated in vacuum to give 4-bromo-3-(bromomethyl)benzonitrile (16.0 g) as a brown solid.

A mixture of 4-bromo-3-(bromomethyl)benzonitrile (crude product, 15.0 g, 54.6 mmol, 1 eq), and KOAc (15.9 g, 163.5 mmol, 3.0 eq) in DMF (135 mL) was stirred at 80° C. for 2 h. The mixture was filtered and then the clear solution was washed by brine, dried with Na₂SO₄, concentrated in vacuum to give 2-bromo-5-cyanobenzyl acetate (15.6 g) as a brown solid.

A mixture of 2-bromo-5-cyanobenzyl acetate (crude product, 13.5 g, 54.6 mmol, 1.0 eq), NaOH (2.55 g, 63.9 mmol, 1.2 eq) in methanol (150 ml) and water (50 mL) was stirred at room temperature for 2 h. The water (150 ml) was added to mixture. Then the mixture was extracted with EA (3×60 mL) and the organic phase was washed by brine, dried with Na₂SO₄, concentrated in vacuum to give 4-bromo-3-(hydroxymethyl)benzonitrile (14.0 g) as brown solid.

A solution of 4-bromo-3-(hydroxymethyl)benzonitrile (crude product, 13.5 g, 63.0 mmol, 1.0 eq), DIEA (24.6 g, 190.8 mmol, 3.0 eq) and (chloromethoxy)ethane (7.2 g, 76.2 mmol, 1.2 eq) in DCM (90 ml) was stirred at 40° C. for overnight. After completion, the reaction was washed with brine, dried over Na₂SO4, filtered and concentrated in vacuum. The residue was purified by column chromatography (petroleum ether:ethyl acetate=10:1) to give 4-bromo-3-((ethoxymethoxy)methyl)benzonitrile (6.7 g, 32.4% yield over four steps) as colorless liquid.

A solution of 4-bromo-3-((ethoxymethoxy)methyl)benzonitrile (5.1 g, 18.9 mmol, 1.0 eq) and trimethyl borate (2.9 g, 28.4 mmol, 1.5 eq) in THF (75 ml) was stirred at −78° C. and N₂ for 30 min. The n-BuLi (2.5 M in hexane, 9.1 ml, 22.6 mmol, 1.2 eq) added to the solution slowly at −78° C. and N₂, and the solution was warmed to room temperature. After 2 h, 6 HCl (7 ml) was added to the solution. The solution was extracted with ethyl acetate (3×20 mL) and the organic phase was washed by brine, dried with Na₂SO₄, concentrated in vacuum to give light brown liquid. Methanol (2 ml) was added to the liquid and the white solid precipitated. Filtration to give 1-methyl-1,3-dihydrobenzo[c][1,2] oxaborole-5-carbonitrile as a white solid (1.8 g, 62% yield).

1-methyl-1,3-dihydrobenzo[c][1,2]oxaborole-5-carbonitrile (210 mg, 1.32 mmol, 1.0 eq) was added to $HNO_3$ (fuming, 1 ml) and $H_2SO_4$ (98%, 6 ml) at −45° C. The mixture was stirred for 2 h at −45° C., and warmed to room temperature. The mixture was poured into ice water (5 ml), and warmed to room temperature to give yellow solution. The solution was dried with $Na_2SO_4$ and $NaHCO_3$ and concentrated in vacuum to give 1-hydroxy-6-nitro-1,3-dihydrobenzo[c][1,2]oxaborole-5-carbonitrile (290 mg, light yellow solid).

A solution of 1-methyl-6-nitro-1,3-dihydrobenzo[c][1,2] oxaborole-5-carbonitrile (crude product, 260 mg, 1.27 mmol, 1.0 eq) and borane (THF solution, 1.0 M, 6.35 ml, 6.35 mmol, 5.0 eq) in THF (20 ml) was stirred at 70° C. and $N_2$ for 5 h. After completion, the reaction was quenched with methanol (10 ml), washed with brine, dried over $Na_2SO_4$, filtered and concentrated in vacuum give 5-(aminomethyl)-6-nitrobenzo[c][1,2]oxaborol-1(3H)-ol (280 mg) as yellow solid.

A solution of of 5-(aminomethyl)-6-nitrobenzo[c][1,2] oxaborol-1(3H)-ol (crude product, 280 mg, 1.35 mmol, 1.0 eq), $NaHCO_3$ (435 mg, 5.4 mmol, 4.0 eq) and $BOC_2O$ (440 mg, 2.01 mmol, 1.5 eq) in water (20 mL) and THF (50 mL) was stirred at room temperature for 2 h. After completion, the reaction was washed with brine, dried over $Na_2SO_4$, filtered and concentrated in vacuum. The residue was purified by column chromatography (petroleum ether, 1000 ml, then methanol 200 mL) to give tert-butyl ((1-hydroxy-6-nitro-1,3-dihydrobenzo [c][1,2]oxaborol-5-yl)methyl)carbamate (320 mg) as a yellow solid.

A mixture of tert-butyl (1-hydroxy-6-nitro-1,3-dihydrobenzo[c][1,2]oxaborol-5-yl)methylcarbamate (crude product, 280 mg, 0.91 mmol, 1.0 eq) and Pd/C (28 mg, 10%) in ethyl acetate (10 ml) was stirred at room temperature for 2 h. Then the mixture was filtered, concentrated in vacuum to give tert-butyl ((6-amino-1-hydroxy-1,3-dihydrobenzo[c][1,2]oxaborol-5-yl)methyl)carbamate (201 mg) as yellow liquid.

A mixture of tert-butyl (6-amino-1-hydroxy-1,3-dihydrobenzo[c][1,2]oxaborol-5-yl)methylcarbamate (crude product, 201 mg, 0.72 mmol, 1.0 eq) and (1 S,2R,3 S,4S,6R,7R,8R,14R)-4-ethenyl-3-hydroxy-2,4,7,14-tetramethyl-9-oxotricyclo[5.4.3.01,8]tetradecan-6-yl 2-iodoacetate (423.0 mg, 0.86 mmol) in DMF (15 ml) was stirred at 80° C. for overnight. Then the mixture was concentrated in vacuum to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-((((11-methyl)(11-oxidanyl)boranyl)amino)methyl)-1-hydroxy-1,3-dihydrobenzo[c][1,2]oxaborol-6-yl)glycinate (420 mg) as brown liquid.

A mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (5-((((11-methyl)(11-oxidanyl)boranyl)amino)methyl)-1-hydroxy-1,3-dihydrobenzo[c][1,2]oxaborol-6-yl)glycinate (crude product, 420 mg, 0.66 mmol, 1.0 eq) in TFA (1 mL) and DCM (3 mL) was stirred at room temperature for 1 h. Then the mixture was concentrated in vacuum to give the brown crude product and purified by prep-HPLC to provide (3aR,4R,5R,7S,8S,9R,9aS,12R)-8-hydroxy-4,7,9,12-tetramethyl-3-oxo-7-vinyl-decahydro-4,9a-propanocyclopenta[8]annulen-5-yl (5-(aminomethyl)-1-hydroxy-1,3-dihydrobenzo[c][1,2] oxaborol-6-yl)glycinate (50 mg, 6.9% yield from over 5 steps) as a white solid. $^1H$ NMR (400 MHz, DMSO-$d_6$): δ 8.98 (s, 1H), 7.22 (s, 1H), 6.82 (s, 1H), 6.00-6.08 (dd, 1H), 5.56 (s, 1H), 5.53-5.57 (d, 1H), 4.88-5.02 (m, 3H), 4.43-4.54 (m, 1H), 3.85-4.04 (m, 2H), 3.04 (s, 1H), 2.07-2.50 (m, 7H), 1.31-1.66 (m, 13H), 1.05-1.24 (m, 4H), 0.50-0.60 (m, 3H), 0.22-0.37 (m, 3H). HPLC purity: 100% (214 nm), 100% (254 nm); MS (ESI): mass calcd. for $C_{30}H_{43}BN_2O_6$ 538.32, m/z found 539.3 $[M+H]^+$.

48. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-(((tert-butoxycarbonyl)amino)methyl)-1-hydroxy-1,3-dihydrobenzo [c][1,2]oxaborol-6-yl)glycinate 49. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-(aminomethyl)-1-hydroxy-1,3-dihydrobenzo[c][1,2]oxaborol-6-yl)glycinate

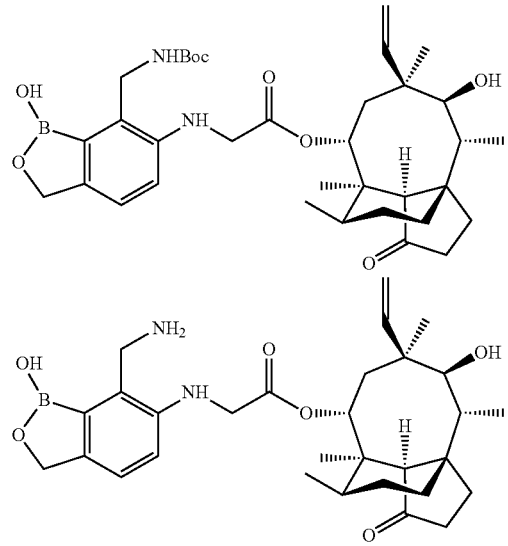

To the solution of (2,4-dibromophenyl)methanol (10.0 g, 37.6 mmol) was added TBSCl (6.8 g, 45.1 mmol), imidazole (5.1 g, 75.2 mmol). The mixture was stirred at 40° C. overnight. After the reaction completed, the mixture was washed by water and DCM was removed under vacuo. The residue was purified by column chromatography on silica gel by elution with petroleum ether:ethyl acetate=50:1 to give tert-butyl(2,4-dibromobenzyloxy)dimethylsilane (14 g, yield 98%) as a light yellow liquid. $^1H$ NMR (400 MHz, $CDCl_3$) δ 7.68 (d, 1H), 7.47 (m, 2H), 4.69 (s, 2H), 0.94 (s, 9H), 0.15 (s, 6H).

To the solution of tert-butyl(2,4-dibromobenzyloxy)dimethylsilane (10.0 g, 26.3 mmol) in dry THF (200 mL) was added LDA (2M, 26.3 mL) dropwise at −78° C. The mixture was stirred at this temperature for 1 hour and DMF (10 mL) was added in one portion. The mixture was stirred at −78° C. for 1 hour and warmed to RT for additional 2 hours. After the reaction completed, the mixture was washed by water, extracted by ethyl acetate (200 mL×3). The organic layers were combined, dried over $Na_2SO_4$ and concentrated to dryness, The residue was purified by column chromatography on silica gel by elution with petroleum ether:ethyl acetate=30:1 to 2,6-dibromo-3-((tert-butyldimethylsilyloxy)

methyl)benzaldehyde (9.5 g, yield 89%). $^1$H NMR (400 MHz, CDCl$_3$) δ 10.29 (s, 1H), 7.67 (m, 2H), 4.75 (s, 2H), 0.99 (s, 9H), 0.17 (s, 6H).

To the solution of 2,6-dibromo-3-((tert-butyldimethylsilyloxy)methyl)benzaldehyde (7.0 g, 17.1 mmol) was added NH$_2$OH.HCl (1.3 g, 18.9 mmol), NaOH (0.76 g, 18.9 mmol). The mixture was stirred at RT for 1 hour. The solid was filtrated as the product (6.8 g, 94% yield), which was dried by oil pump and used in the next step directly.

To the suspension of LAH (1.22 g, 32.2 mmol) in dry THF (50 mL) was added concentrated H$_2$SO$_4$ (1.58 g, 16.1 mmol) dropwise at 0° C. After the addition, the mixture was stirred at 0° C. for 1 hour. The (E)-2,6-dibromo-3-((tert-butyldimethylsilyloxy)methyl)benzaldehyde oxime (6.8 g, 16.1 mmol) was added to the mixture, and it was stirred at RT for 2 hours. After the reaction completed, the mixture was quenched by alcohol and the solid was removed by filtration. The filtrate was concentrated to afford the (2,6-dibromo-3-((tert-butyldimethylsilyloxy)methyl)phenyl)methanamine (6.0 g, 91% yield) as a colorless oil. MS (ESI): mass calcd. for C$_{14}$H$_{23}$Br$_2$NOSi 408.99, m/z found 408.1 [M+H]$^+$.

To the solution of (2,6-dibromo-3-((tert-butyldimethylsilyloxy)methyl)phenyl)methanamine (6.0 g, 14.7 mmol) in DCM (50 mL) was added Boc$_2$O (3.5 g, 16.1 mmol). The mixture was stirred at RT overnight. After the reaction completed, the mixture was concentrated to dryness and the residue was purified by column chromatography on silica gel by elution with petroleum ether:ethyl acetate=20:1 to afford tert-butyl 2,6-dibromo-3-((tert-butyldimethylsilyloxy)methyl)benzylcarbamate (7.0 g, yield 93%) as a white solid. MS (ESI): mass calcd. for C$_{19}$H$_{31}$Br$_2$NO$_3$Si 509.04, m/z found 532.1 [M+Na]$^+$.

To the solution of tert-butyl 2-bromo-3-((tert-butyldimethylsilyloxy)methyl)-6-(diphenylmethyleneamino)benzylcarbamate (3.3 g, 6.5 mmol) in 30 mL toluene was added Pd$_2$(dba)$_3$ (0.60 g, 0.65 mmol), Xantphos (0.75 g, 1.3 mmol), Cs$_2$CO$_3$ (6.3 g, 19.5 mmol), diphenylmethanimine (2.35 g, 13 mmol). The mixture was refluxed at 120° C. overnight. After the reaction completed, the mixture was purified by column chromatography on silica gel by elution with petroleum ether:ethyl acetate=20:1 to afford tert-butyl 2-bromo-3-((tert-butyldimethylsilyloxy)methyl)-6-(diphenylmethyleneamino)benzylcarbamate (3.0 g, yield 75%) as a deep yellow oil. MS (ESI): mass calcd. for C$_{32}$H$_{41}$BrN$_2$O$_3$Si 610.20, m/z found 611.0 [M+H]$^+$.

To the solution of tert-butyl 2-bromo-3-((tert-butyldimethylsilyloxy)methyl)-6-(diphenylmethyleneamino)benzylcarbamate (2.4 g, 3.9 mmol) and 4,4,4',4',5,5,5',5'-octamethyl-2,2'-bi(1,3,2-dioxaborolane) (2.0 g, 7.8 mmol) in dioxane (30 mL) was added Pd(OAc)$_2$ (87 mg, 0.39 mmol), PCy$_3$ (218 mg, 0.78 mmol). The reaction mixture was stirred at 100° C. overnight under N$_2$. After the reaction completed, the solvent was removed under vacuo, the residue was purified by column chromatography on silica gel by elution with petroleum ether:ethyl acetate=20:1 to afford tert-butyl 3-((tert-butyldimethylsilyloxy)methyl)-6-(diphenylmethyleneamino)-2-(4,4,5,5-tetramethyl-1,3,2-dioxaborolan-2-yl)benzylcarbamate (970 mg, 38.5% yield) as a yellow oil. MS (ESI): mass calcd. for C$_{38}$H$_{53}$BrN$_2$O$_5$Si 656.38, m/z found 657.4 [M+H]$^+$.

To the solution of tert-butyl 3-((tert-butyldimethylsilyloxy)methyl)-6-(diphenylmethyleneamino)-2-(4,4,5,5-tetramethyl-1,3,2-dioxaborolan-2-yl)benzylcarbamate (970 mg, 1.5 mmol) in THF (20 mL) was added HCl (0.1 mL, 12 M) to keep the PH of the mixture was 1. The reaction mixture was stirred at r.t. for 2 hours. The solid was filtrated and dried by oil pump as the product (300 mg, 63% yield). MS (ESI): mass calcd. for C$_{13}$H$_{19}$BN$_2$O$_4$ 278.14, m/z found 301.0 [M+Na]$^+$.

To the solution of tert-butyl (6-amino-1-hydroxy-1,3-dihydrobenzo[c][1,2]oxaborol-7-yl)methylcarbamate (105 mg, 0.38 mmol) in DMF (10 mL) was added Iodo-pleuromutilin (221 mg, 0.45 mmol) and DIPEA (245 mg, 1.9 mmol). The reaction mixture was stirred at 80° C. under N$_2$ overnight. The solvent was removed under vacuo and the residue was purified by prep-TLC (petroleum ether: ethyl acetate=2:1) to afford the target product as brown oil ((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-(((tert-butoxycarbonyl)amino)methyl)-1-hydroxy-1,3-dihydrobenzo [c][1,2]oxaborol-6-yl)glycinate, 80 mg, 33%). $^1$H NMR (500 MHz, DMSO-d$_6$) δ 8.92 (s, 1H), 7.05 (d, J=8.0 Hz, 1H), 6.56 (d, J=7.5 Hz, 1H), 6.08 (m, 1H), 5.55 (d, J=8.0 Hz, 1H), 4.93-5.08 (m, 2H), 4.83 (s, 1H), 4.33-4.50 (m, 3H), 3.89 (m, 1H), 3.40 (m, 1H), 2.40 (m, 1H), 2.01-2.22 (m, 3H), 1.47-1.78 (m, 4H), 1.36 (s, 9H), 1.22-1.27 (m, 4H), 1.00 (m, 4H), 0.75 (m, 3H), 0.64 (m, 3H). HPLC purity: 100% (214 nm), 100% (254 nm); MS (ESI): mass calcd. for C$_{35}$H$_{51}$BN$_2$O$_8$ 638.37, m/z found 639.4 [M+H]$^+$.

To the solution of above compound (82 mg, 0.13 mmol) in DCM (5 mL) was added TFA (1.5 mL). The mixture was stirred at r.t. for 2 hours. The solvent was removed under vacuo and the residue was purified by prep-HPLC (NH$_4$HCO$_3$ as buffer) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-(aminomethyl)-1-hydroxy-1,3-dihydrobenzo[c][1,2]oxaborol-6-yl)glycinate as white solid (30 mg, 43%). $^1$H NMR (500 MHz, added one drop of con. HCl, DMSO-d$_6$) δ 8.2 (s, 3H), 7.19 (d, J=8.0 Hz, 1H), 6.70 (d, J=8.5 Hz, 1H), 6.08 (m, 1H), 5.55 (d, J=8.5 Hz, 2H), 4.89 (s, 4H), 4.21 (m, 2H), 3.91 (m, 2H), 3.41 (m, 1H), 2.41 (s, 1H), 2.00-2.22 (m, 4H), 1.58-1.66 (m, 2H), 1.48 (m, 1H), 1.24-1.39 (m, 7H), 0.97-1.03 (m, 4H), 0.80 (d, J=7.5 Hz, 3H), 0.64 (d, J=7.0 Hz, 3H). HPLC purity: 100% (214 nm), 100% (254 nm); MS (ESI): mass calcd. for C$_{30}$H$_{43}$BN$_2$O$_6$ 538.32, m/z found 539.4 [M+H]$^+$.

50. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (4-(aminomethyl)-1-hydroxy-1,3-dihydrobenzo[c][1,2]oxaborol-6-yl)glycinate

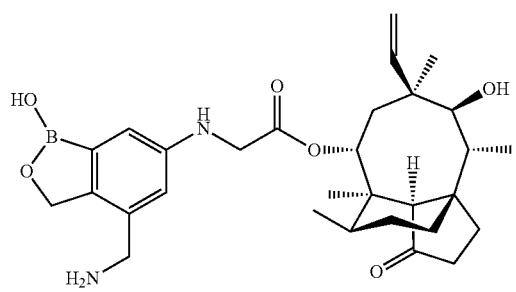

To a CHCl$_3$ solution (120 mL) of 1-methyl-4-nitrobenzene (30.0 g, 218.8 mmol), iron powder (3.6 g, 64.5 mmol) was added with mechanically stirring. Then bromine (124.8 g, 40 mL, 780.9 mmol) was added slowly while raising temperature to 40° C. After addition of the bromine, the mixture was heated to reflux for 48 h. After cooling, the solution was washed with a saturated Na$_2$SO$_3$ solution, saturated Na$_2$CO$_3$ solution, brine, and dried over anhydrous Na$_2$SO$_4$. After the solvent was removed, the residue was purified by column chromatography to give the desired product, giving 60 g (yield, 93%) of 1,3-dibromo-2-methyl-5-nitrobenzene as yellow crystals.

To a solution of 1,3-dibromo-2-methyl-5-nitrobenzene (60 g, 0.204 mol) in pyridine:DMF (1:2) (550 mL) was added CuCN (21.7 g, 0.245 mol). The reaction mixture was heated to 140° C. overnight. After cooled to room temperature, ethyl acetate (500 mL) and ammonia water (400 mL) were added. The mixture was washed with water (300 mL×3). The solvent was removed and the residue was purified by silica gel column chromatography using petroleum ether:ethyl acetate=100:1 to give 3-bromo-2-methyl-5-nitrobenzonitrile (15 g, yield: 30.6%) as a white solid.

To a solution of 3-bromo-2-methyl-5-nitrobenzonitrile (9.3 g, 38.6 mmol), 4,4,4',4',5,5,5,5'-octamethyl-2,2,-bi(1,3,2-dioxaborolane) (11.78 g, 46.3 mmol) and KOAc (7.75 g, 77.2 mmol) in 1,4-dioxane (200 ml) was added Pd(dppf)Cl$_2$ (3.5 g, 4.63 mmol) then the reaction mixture was stirred at 90° C. under N$_2$ atmosphere overnight. The reaction mixture was filtered through Celite and washed with EtOAc (200 mL). The filtrate was concentrated and the crude product was purified by silica gel column to give 2-methyl-5-nitro-3-(4,4,5,5-tetramethyl-1,3,2-dioxaborolan-2-yl)benzonitrile (9.64 g, 86% yield).

The mixture of 2-methyl-5-nitro-3-(4,4,5,5-tetramethyl-1,3,2-dioxaborolan-2-yl)benzonitrile (1 g, 3.5 mmol), NBS (740 mg, 4.2 mmol) and AIBN (60 mg, 0.35 mmol) in CCl4 (50 ml) was refluxed overnight. The mixture was filtered and the filtrate was concentrated to give 2-(bromomethyl)-5-nitro-3-(4,4,5,5-tetramethyl-1,3,2-dioxaborolan-2-yl)benzonitrile (820 mg, 64.5% yield) as a white solid.

The mixture of 2-methyl-5-nitro-3-(4,4,5,5-tetramethyl-1,3,2-dioxaborolan-2-yl)benzonitrile (1 g, 2.7 mmol) and NaOAc (1.07 g, 10.9 mmol) in DMF (15 mL) was stirred at 110° C. overnight, and then diluted with water and extracted with ethyl acetate. The organic layer was washed with brine, dried over Na$_2$SO$_4$ and concentrated under vacuum. The product (2-(acetoxymethyl)-3-cyano-5-nitrophenyl)boronic acid (600 mg, 83% yield) was directly used without further purification.

A solution of 2-(acetoxymethyl)-3-cyano-5-nitrophenylboronic acid (crude product, 100 mg, 0.38 mmol) and borane (THF solution, 1.0 M, 3 ml, 3 mmol) in THF (20 ml) was stirred at 70° C. and N2 for 5 h. After completion, the reaction was quenched with methanol (10 ml), washed with brine, dried over Na$_2$SO$_4$, filtered and concentrated in vacuum. The crude product 4-(aminomethyl)-6-nitrobenzo[c][1,2]oxaborol-1(3H)-ol was directly used in next step.

To a solution of 4-(aminomethyl)-6-nitrobenzo[c][1,2]oxaborol-1 (3H)-ol (2.46 g, 0.0118 mol) and Boc2O (3.09 g, 0.0142 mol) in THF (300 ml) was added Et$_3$N (2.38 g, 0.0236 mol) at 0° C. Then the mixture was stirred at r.t for 3 h, the reaction mixtures was concentrated under vacuum, and purified by prep-HPLC to give 800 mg desired product.

A mixture of tert-butyl (1-hydroxy-6-nitro-1,3-dihydrobenzo[c][1,2]oxaborol-4-yl)methylcarbamate (110 mg, 0.36 mmol, 1.0 eq) and Pd/C (28 mg, 10%) in MeOH (10 ml) was stirred at room temperature for 2 h. Then the mixture was filtrated, concentrated in vacuum to give the desired product (89 mg) as yellow liquid.

A mixture of tert-butyl (6-amino-1-hydroxy-1,3-dihydrobenzo[c][1,2]oxaborol-4-yl)methylcarbamate (89 mg, 0.36 mmol, 1.0 eq) and SM-1 [(1 S,2R,3 S,4S,6R,7R,8R, 14R)-4-ethenyl-3-hydroxy-2,4,7,14-tetramethyl-9-oxotricyclo[5.4.3.01,8]tetradecan-6-yl 2-iodoacetate] (187 mg, 0.38 mmol) in DMF (15 ml) was stirred at 80° C. for overnight. Then the mixture was concentrated in vacuum to give the crude product as brown liquid.

A mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (4-(((tert-butoxycarbonyl)amino)methyl)-1-hydroxy-1,3-dihydrobenzo [c][1,2] oxaborol-6-yl)glycinate (crude product, 420 mg, 0.66 mmol, 1.0 eq) in TFA (1 ml) and DCM (3 ml) was stirred at room temperature for 1 h. Then the mixture was concentrated in vacuum to give the brown crude product and purified by prep-HPLC to provide (3aR,4R,5R,7S,8S,9R,9aS,12R)-8-hydroxy-4,7,9,12-tetramethyl-3-oxo-7-vinyldecahydro-4, 9a-propanocyclopenta[8]annulen-5-yl (4-(aminomethyl)-1-hydroxy-1,3-dihydrobenzo[c][1,2]oxaborol-6-yl)glycinate ((3aR,4R,5R,7S,8S,9R,9aS,12R)-8-hydroxy-4,7,9,12-tetramethyl-3-oxo-7-vinyldecahydro-4,9a-propanocyclopenta [8]annulen-5-yl (4-(aminomethyl)-1-hydroxy-1,3-dihydrobenzo[c][1,2]oxaborol-6-yl)glycinate, 100 mg, yield 28%) as a white solid. $^1$H NMR (400 MHz, DMSO-d$_6$): δ 8.84 (s, 1H), 6.71 (m, 2H), 6.09 (m, 1H), 5.92 (m, 1H), 5.54 (m, 1H), 4.89-5.07 (m, 4H), 4.52 (d, 1H), 3.78 (m, 2H), 3.58 (s, 4H), 3.41 (m, 1H), 2.41 (m, 1H), 2.02-2.09 (m, 5H), 1.34-1.67 (m, 7H), 1.24-1.28 (m, 4H), 1.01 (s, 4H). HPLC purity: 98.4% (214 nm), 100% (254 nm); MS (ESI): mass calcd. for C$_{30}$H$_{43}$BN$_2$O$_6$ 538.32, m/z found 539.2 [M+H]$^+$.

51. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-3,3-dimethyl-1,3-dihydrobenzo[c][1,2]oxaborol-6-yl) glycinate

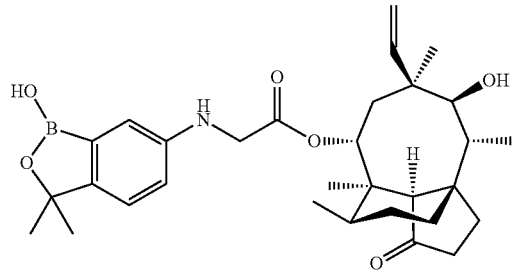

To a solution of 6-amino-3,3-dimethyl-3H-benzo[c][1,2] oxaborol-1-ol (177 mg, 1 mmol) in DMF (3 mL) were added K$_2$CO$_3$ (276 mg, 2 mmol) and Iodo-pleuromutilin (500 mg, 1 mmol). The reaction mixture was irradiated under microwave at 60° C. for 1 h. It was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta [8]annulen-5-yl (1-hydroxy-3,3-dimethyl-1,3-dihydrobenzo [c][1,2]oxaborol-6-yl)glycinate (600 mg, 29% yield) as yellow solid. $^1$H NMR (400 MHz, DMSO-d$_6$) δ 8.72 (s, 1H), 7.06 (d, J=8.4 Hz, 1H), 6.75-6.65 (m, 2H), 6.11-6.03 (m, 2H), 5.55 (d, J=8.4 Hz, 1H), 5.04-4.93 (m, 2H), 4.50 (d, J=6 Hz, 1H), 3.83-3.75 (m, 2H), 3.40 (t, J=7.8 Hz, 1H), 2.39 (s, 1H), 1.48-1.21 (m, 21H), 0.80 (d, J=6.8 Hz, 3H), 0.63 (d, J=8.8 Hz, 3H). MS (ESI): mass calcd. For C$_{31}$H$_{44}$BNO$_6$ 537.33, m/z found 538.4 [M+H]$^+$. HPLC: 98.8% (220 nm), 99.5% (254 nm).

52. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (3-(aminomethyl)-1-hydroxy-1,3-dihydrobenzo[c][1,2]oxaborol-6-yl)glycinate

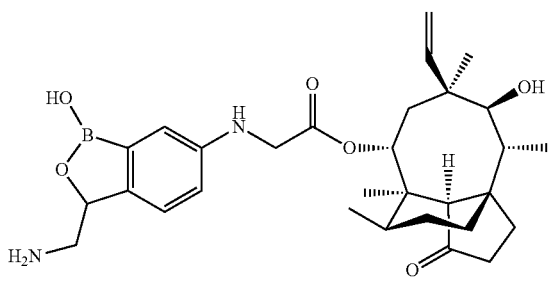

To a solution of Iodo-pleuromutilin (1.4 g, 2.9 mmol, 1.0 eq.) and 6-amino-3-(nitromethyl)benzo[c][1,2]oxaborol-1(3H)-ol (600.0 mg, 2.9 mmol, 1.0 eq.) in DMSO (10.00 mL) was added $Ag_2SO_4$ (2.70 g, 8.65 mmol, 3.00 eq.). The mixture was stirred at 25° C. for 26 hours. HPLC indicated pleur-Iodide was consumed completely. The reaction mixture was quenched by addition $H_2O$ 150 mL, and filtered to give crude product, then diluted with DCM 100 mL and wished with brine 100 mL, dried over $Na_2SO_4$, filtered and concentrated under reduced pressure to give a residue. Combined with ET3173-294,295-P1, we obtained 1.6 g desired product (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3-(nitromethyl)-1,3-dihydrobenzo [c][1,2]oxaborol-6-yl) amino) acetate (83%, purity), detected by HPLC.

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((1-hydroxy-3-(nitromethyl)-1,3-dihydrobenzo[c][1,2]oxaborol-6-yl)amino) acetate (1.0 g, 1.8 mmol, 1.0 eq.) in AcOH (20.0 mL) was added Zn (920.2 mg, 14.1 mmol, 8.0 eq.). The mixture was stirred at 25° C. for 4 hours. HPLC indicated (3aR,4R,5R,7S,8S,9R,9aS,12R)-8-hydroxy-4,7,9,12-tetramethyl-3-oxo-7-vinyldeca hydro-4,9a-propanocyclopenta[8]annulen-5-yl2-((1-hydroxy-3-(nitrome-thyl)-1,3-dihydrobenzo[c][1,2]oxaborol-6-yl)amino) acetate was consumed completely and a new peak was formed. The reaction mixture was filtered and concentrated under reduced pressure to give a residue. The residue was purified by prep-HPLC (column: Luna C18 100×30 mm, 5 μm; liquid phase: [A-TFA/$H_2O$=0.075% v/v; B-ACN]B %: 13%-53%, 12 min]). The reaction mixture was concentrated under reduced pressure to remove $CH_3CN$, a drop of 1N HCl was added, then freeze-drying. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((3-(aminomethyl)-1-hydroxy-1,3-dihydrobenzo[c][1,2]oxaborol-6-yl)amino)acetate (159.00 mg, 295.28 umol, 16.78% yield) was obtained as a yellow solid. (combined with ET3173-306-P1)$^1$H NMR (DMSO-$d_6$, 400 MHz) δ 8.12 (br. s., 2H), 7.20 (d, J=7.9 Hz, 1H), 6.91 (br. s., 1H), 6.73 (dd, J=1.6, 8.4 Hz, 1H), 6.08 (dd, J=11.2, 17.6 Hz, 1H), 5.55 (d, J=8.0 Hz, 1H), 5.19 (d, J=7.6 Hz, 1H), 5.04 (d, J=19.2 Hz, 1H), 4.95 (d, J=11.2 Hz, 1H), 3.80 (d, J=13.2 Hz, 2H), 3.41 (d, J=5.6 Hz, 2H), 2.39 (br. s., 1H), 2.22-2.14 (m, 1H), 2.12-1.98 (m, 3H), 1.69-1.57 (m, 2H), 1.54-1.39 (m, 2H), 1.38-1.32 (m, 5H), 1.31-1.18 (m, 3H), 1.08-0.94 (m, 4H), 0.81 (d, J=6.4 Hz, 3H), 0.64 (d, J=6.4 Hz, 3H). MS (ESI): mass calcd. For $C_{30}H_{44}BClN_2O_6$ 574.9, m/z found 539.5[M+H]+. HPLC: 98.9% (220 nm), 100.0% (254 nm).

53. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1H-spiro[benzo[c][1,2]oxaborole-3,4'-piperidin]-6-yl)glycinate

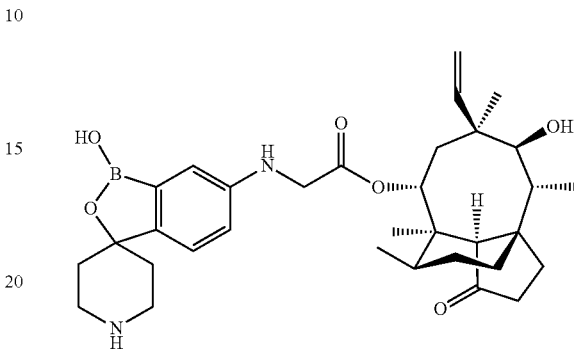

To a stirred solution of 1-bromo-2-iodobenzene (25.6 g, 0.0753 mol, 1 eq) in 90 mL of THF was added 1N i-PrMgCl (113 mL, 1.5 eq) under $N_2$ at −15~20° C. After stirred for 2 hrs, tert-butyl 4-oxopiperidine-1-carboxylate (15 g, 0.0903 mol, 1.2 eq) in 75 mL of THF was added and the reaction was stirred overnight. The reaction was quenched with saturated $NH_4Cl$ and the organic layer was separated. The aqueous phase was extracted with ethyl acetate (250 mL×2). The organic layers were combined, washed with water, brine, dried over anhydrous $Na_2SO_4$, filtered and concentrated. The crude product was chromatographed on silica gel (25% ethyl acetate/petroleum ether) to give the tert-butyl 4-(2-bromophenyl)-4-hydroxypiperidine-1-carboxylate (9.2 g, 40.3%) as a white solid.

To a solution of tert-butyl 4-(2-bromophenyl)-4-hydroxypiperidine-1-carboxylate (10 g, 0.0281 mol) in 120 mL of THF was added n-BuLi (2.5 M, 23.6 mL, 2.1 eq) under $N_2$ at −78° C. The reaction was stirred for 2 hrs and trimethyl borate (5.8 g, 0.0561 mol, 2 eq) was added. The temperature was warm to RT gradually and the reaction was stirred overnight. 1N HCl was added to adjust pH-4, the organic layer was separated and the aqueous phase was extracted with ethyl acetate for two times. The organic layers were combined, washed with brine, died over anhydrous $Na_2SO_4$, filtered and concentrated. The crude product was chromatographed on silica gel (25% ethyl acetate/petroleum ether) to give tert-butyl 1-hydroxy-1H-spiro[2,1-benzoxaborole-3,4'-piperidine]-1'-carboxylate (5.3 g, 62.3%) as a white solid.

tert-butyl 1-hydroxy-1H-spiro[2,1-benzoxaborole-3,4'-piperidine]-1'-carboxylate (4.0 g, 13.2 mmol, 1.0 eq) was added to $HNO_3$ (fuming, 0.7 mL) at −45° C. The mixture was stirred for 2 h at −45° C., and warmed to room temperature. The mixture was poured into ice water (5 mL), and the yellow crude product precipitated. After filtration, crude product 6-nitro-1H-spiro[2,1-benzoxaborole-3,4'-piperidine]-1-ol was obtained (2.1 g) as a light yellow solid.

A solution of of 6-nitro-1H-spiro[2,1-benzoxaborole-3,4'-piperidine]-1-ol (crude product, 2.0 g, 8.06 mmol, 1.0 eq), $NaHCO_3$ (2.44 g, 29.04 mmol, 3.6 eq) and $BOC_2O$ (2.11 g, 9.68 mmol, 1.2 eq) in water (15 mL) and THF (15 mL) was stirred at room temperature for 2 h. After completion, the reaction was washed with brine, dried over $Na_2SO_4$, filtered and concentrated in vacuum. The residue was purified by column chromatography (petroleum ether, 1000 mL, then methanol 200 mL) to give the crude product (1.02 g) as a yellow solid.

A mixture of tert-butyl 1-hydroxy-6-nitro-1H-spiro[2,1-benzoxaborole-3,4'-piperidine]-1'-carboxylat (crude product, 1.0 g, 3.14 mmol, 1.0 eq) and Pd/C (100 mg, 10%) in ethyl acetate (10 mL) was stirred at room temperature for 2 h. Then the mixture was filtrated, concentrated in vacuum to give the crude product (250 mg) as yellow liquid.

A mixture of tert-butyl 6-amino-1-hydroxy-1H-spiro[2,1-benzoxaborole-3,4'-piperidine]-1'-carboxylate (crude product, 240 mg, 0.65 mmol, 1.0 eq) and Iodo-pleuromutilin (722 mg, 1.2 mmol) in DMF (15 mL) was stirred at 80° C. for overnight. Then the mixture was concentrated in vacuum to give the crude product (350 mg) as brown liquid.

A mixture of above compound (350 mg, 1.1 mmol, 1.0 eq) in TFA (1 mL) and DCM (3 mL) was stirred at room temperature for 1 h. Then the mixture was concentrated in vacuum to give the brown crude product and purified by prep-HPLC to provide product ((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1H-spiro[benzo[c][1,2]oxaborole-3,4'-piperidin]-6-yl) glycinate, 26 mg, 1.7% yield) as a white solid. $^1$H NMR (400 MHz, DMSO-$d_6$): δ 9.12 (s, 1H), 8.21-8.50 (m, 1H), 8.38-8.46 (m, 1H), 6.97-6.99 (d, 1H, J=8.0 Hz), 6.83 (s, 1H), 6.71-6.73 (m, 1H), 6.03-6.10 (m, 2H), 5.45-5.56 (d, J=8.4 Hz, 1H), 4.92-5.04 (m, 2H), 4.50 (s, 1H), 3.77-3.81 (m, 3H), 3.08-3.11 (m, 3H), 2.39 (s, 2H), 2.11-2.39 (m, 7H), 1.49-1.63 (m, 2H), 1.34-1.45 (m, 3H), 1.21-1.30 (m, 5H), 1.02 (s, 4H), 0.79-0.81 (m, 3H), 0.61-0.63 (m, 3H). HPLC purity: 100% (214 nm), 100% (254 nm); MS (ESI): mass calcd. for $C_{33}H_{47}BN_2O_6$ 578.35, m/z found 579.1 [M+H]$^+$.

54. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-fluoro-1-hydroxy-1,3-dihydrobenzo[c][1,2]oxaborol-6-yl)glycinate 55. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(((7-fluoro-1-hydroxy-1,3-dihydrobenzo[c][1,2]oxaborol-6-yl)carbamoyl)oxy)acetate

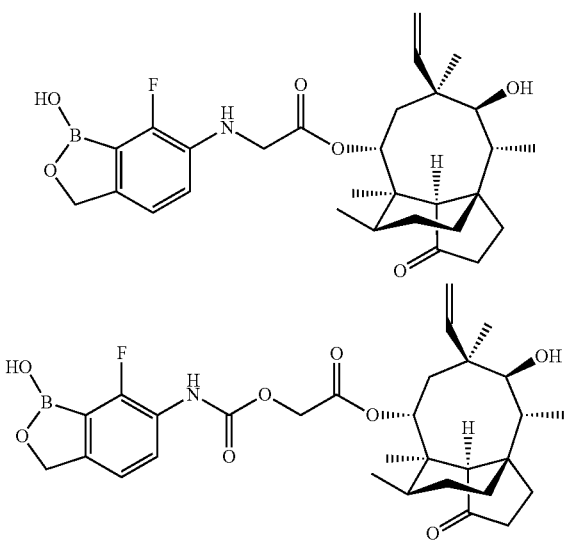

To a solution of 3,4-difluorobenzoic acid (8.0 g, 50.6 mmol, 1.00 eq.) in THF (400 mL) was added n-BuLi (2.5 M, 50.6 mL, 2.50 eq.), The mixture was stirred at −78° C. for 2.5 hrs, then I$_2$ (32.1 g, 126.5 mmol, 2.50 eq.) in THF 100 mL was added, the mixture was stirred for another 0.5 hr. TLC indicated the 3,4-difluorobenzoic acid was consumed completely, a new spot was formed. The reaction mixture was quenched by addition of saturation Na$_2$S$_2$O$_3$, and the mixture was extracted with EtOAc 1500 mL (500 mL×3), the combined organic layers were wished with brine 800 mL, drying over Na$_2$SO$_4$, filtered and concentrated under reduced pressure to give a residue. 3,4-Difluoro-2-iodobenzoic acid (11.0 g, 38.7 mmol, 76.5% yield) was obtained as a yellow solid. $^1$H NMR (CDCl$_3$, 400 MHz) δ 7.91 (ddd, J=2.0, 5.2, 8.8 Hz, 1H), 7.32-7.23 (m, 1H)

To a solution of 3,4-difluoro-2-iodobenzoic acid (13.0 g, 45.8 mmol, 1.00 eq) in EtOH (100.0 mL) was added con.H$_2$SO$_4$ (18.4 g) 10 mL. The mixture was stirred at 90° C. for 16 hrs. TLC indicated 3,4-difluoro-2-iodobenzoic acid was consumed completely, a new spot was formed. The reaction mixture was concentrated under reduced pressure to remove EtOH. The residue was diluted with H$_2$O 100 mL and extracted with DCM 300 mL (100 mL×3). The combined organic layers were washed with brine 200 mL, dried over Na$_2$SO$_4$, filtered and concentrated under reduced pressure to give a residue. The residue was purified by column chromatography (SiO$_2$, Petroleum ether/Ethyl acetate=5:1). Ethyl 3,4-difluoro-2-iodobenzoate (14.0 g, 44.9 mmol, 98.0% yield) was obtained as a yellow oil. $^1$H NMR (CDCl$_3$, 400 MHz) δ7.67 (ddd, J=2.0, 5.0, 8.4 Hz, 1H), 7.25-7.18 (m, 1H), 4.41 (q, J=7.0 Hz, 2H), 1.42 (t, J=7.0 Hz, 3H).

To a solution of ethyl 3,4-difluoro-2-iodobenzoate (14.5 g, 46.5 mmol, 1.0 eq.) and phenylmethanamine (7.5 g, 69.7 mmol, 1.5 eq.) in DMSO (150.0 mL) was added Et$_3$N (14.1 g, 139.4 mmol, 3.0 eq.). The mixture was stirred at 100° C. for 16 hrs. TLC indicated ethyl 3,4-difluoro-2-iodobenzoate was consumed completely and a new pot was formed. The reaction mixture was quenched by addition H$_2$O 100 mL at 0° C., and then diluted with EtOAc 150 mL and extracted with EtOAc 600 mL (200 mL×3). The combined organic layers were washed with brine 240 mL (80 mL×3), dried over Na$_2$SO$_4$, filtered and concentrated under reduced pressure to give a residue. The residue was purified by column chromatography (SiO$_2$, Petroleum ether/Ethyl acetate=50/1 to 10:1). ethyl 4-(benzylamino)-3-fluoro-2-iodobenzoate (12.0 g, 30.1 mmol, 64.7% yield) was obtained as a yellow solid. $^1$H NMR (CDCl$_3$, 400 MHz) δ 7.67 (d, J=8.4 Hz, 1H), 7.41-7.29 (m, 5H), 6.58 (t, J=8.4 Hz, 1H), 4.82 (br. s., 1H), 4.44 (d, J=5.6 Hz, 2H), 4.34 (q, J=7.0 Hz, 1H), 1.38 (t, J=7.0 Hz, 1H).

To a solution of ethyl 4-(benzylamino)-3-fluoro-2-iodobenzoate (4.5 g, 11.3 mmol, 1.0 eq.) and Pin$_2$B$_2$(28.6 g, 112.7 mmol, 10.0 eq.) in dioxane (150.0 mL) was added KOAc (3.3 g, 33.8 mmol, 3.0 eq.) and Pd (PPh$_3$)$_2$Cl$_2$ (791.22 mg, 1.13 mmol, 0.1 eq.). The mixture was stirred at 120° C. for 16 hrs. HPLC indicated ethyl 4-(benzylamino)-3-fluoro-2-iodobenzoate was consumed completely, main new formed peak as desired (Rf=4.2). The reaction mixture was filtered and concentrated under reduced pressure to give a residue. The residue was purified by column chromatography (SiO$_2$, Petroleum ether/Ethyl acetate=50/1). ethyl 4-(benzylamino)-3-fluoro-2-(4,4,5,5-tetramethyl-1,3,2-dioxaborolan-2-yl)benzoate (6.0 g, crude) was obtained as a white solid. $^1$H NMR (CDCl$_3$, 400 MHz) δ 7.62 (d, J=8.0 Hz, 1H), 7.38-7.28 (m, 5H), 6.57 (t, J=8.4 Hz, 1H), 4.75 (br. s., 1H), 4.42 (d, J=5.6 Hz, 2H), 4.32 (q, J=7.4 Hz, 2H), 1.44 (s, 12H).

To a solution of ethyl 4-(benzylamino)-3-fluoro-2-(4,4,5,5-tetramethyl-1,3,2-dioxaborolan-2-yl)benzoate (5.0 g, 12.5 mmol, 1.0 eq.) in THF (20.0 mL) was added NaBH$_4$ (710.6 mg, 18.8 mmol, 1.5 eq.) and CH$_3$OH (2.5 mmol, 0.2 eq.) at 0° C. The mixture was stirred at 25° C. for 16 hours. HPLC indicated ethyl 4-(benzylamino)-3-fluoro-2-(4,4,5,5-tetramethyl-1,3,2-dioxaborolan-2-yl) benzoate was consumed completely. The reaction mixture was quenched by addition H$_2$O (30 mL) dropwise, and then adjusted pH=6 and extracted with EtOAc 300 mL (100 mL×3). The combined organic layers were washed with brine 100 mL, dried over Na$_2$SO$_4$, filtered and concentrated under reduced pressure to give a residue. 6-(benzylamino)-7-fluorobenzo[c][1,2]oxaborol-1(3H)-ol (1.50 g, 5.83 mmol, 46.57% yield) was obtained as a black solid. $^1$H NMR (CDCl$_3$, 400 MHz) δ 7.42-7.28 (m, 5H), 6.98-6.91 (m, 1H), 6.88-6.82 (m, 1H), 5.11 (s, 1H), 5.02 (s, 2H), 4.45-4.34 (m, 3H).

To a solution of 6-(benzylamino)-7-fluorobenzo[c][1,2] oxaborol-1 (3H)-ol (100.0 mg, 389.0 umol, 1.0 eq.) in EtOAc (50.0 mL) was added Pd/C (100.0 mg). The mixture was stirred at 25° C. for 4 hrs under H$_2$ atmosphere (50 psi). The reaction mixture filtered and concentrated under reduced pressure to give a residue. 6-amino-7-fluorobenzo[c][1,2]oxaborol-1(3H)-ol (50.0 mg, 299.5 umol, 77.0% yield) was obtained as a yellow solid. $^1$H NMR (CDCl$_3$, 400 MHz) δ 7.00-6.90 (m, 2H), 5.07-5.00 (m, 2H), 4.83 (br. s., 1H), 3.73 (br. s., 2H).

To a solution of 6-amino-7-fluorobenzo[c][1,2]oxaborol-1(3H)-ol (710.0 mg, 4.3 mmol, 1.0 eq.) and Iodo-pleuromutilin (2.1 g, 4.3 mmol, 1.0 eq.) in DMSO (20.0 mL) was added Na$_2$CO$_3$ (901.50 mg, 8.50 mmol, 2.00 eq.). The mixture was stirred at 30° C. for 16 hrs. HPLC indicated 6-amino-7-fluorobenzo[c][1,2]oxaborol-1(3H)-ol was consumed completely. The reaction mixture was quenched by addition H$_2$O 200 mL, and then adjusted pH=6 (aq. 2N HCl). Filtered and concentrated under reduced pressure to give a residue. The residue was purified by prep-HPLC (column: Phenomenex luna (2) C18 250×50 mm, 10 μm; liquid phase: [A-TFA/H$_2$O=0.075% v/v; B-ACN] B %: 30%-60%, 20 min]). (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo [c][1,2]oxaborol-6-yl) amino) acetate (160.0 mg, 303.4 umol, 7.1% yield) was obtained as a white solid. $^1$H NMR (DMSO-d$_6$, 400 MHz) δ 9.10 (s, 1H), 6.94 (d, J=7.9 Hz, 1H), 6.73 (t, J=8.2 Hz, 1H), 6.09 (dd, J=11.0, 17.6 Hz, 1H), 5.63 (br. s., 1H), 5.55 (d, J=7.9 Hz, 1H), 5.08-4.96 (m, 2H), 4.86 (s, 2H), 4.49 (d, J=6.2 Hz, 1H), 3.91-3.81 (m, 2H), 3.38 (s, 1H), 2.38 (br. s., 1H), 2.23-2.12 (m, 1H), 2.11-1.97 (m, 3H), 1.69-1.56 (m, 2H), 1.52-1.42 (m, 2H), 1.32 (s, 3H), 1.29-1.16 (m, 3H), 1.05-0.96 (m, 3H), 0.80 (d, J=7.1 Hz, 3H), 0.63 (d, J=6.6 Hz, 3H). MS (ESI): mass calcd. For C$_{29}$H$_{39}$BFNO$_6$ 527.4, m/z found 526.3[M−H]$^−$. HPLC: 96.7% (220 nm), 100.00% (254 nm).

At the same time, (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(((7-fluoro-1-hydroxy-1,3-dihydro benzo[c][1,2]oxaborol-6-yl)carbamoyl)oxy)acetate (170.0 mg, 280.4 umol, 6.2% yield) was obtained as a white solid. $^1$H NMR (DMSO-d$_6$, 400 MHz) δ 9.55 (br. s., 1H), 9.28 (s, 1H), 7.65 (t, J=7.3 Hz, 1H), 7.29-7.12 (m, 1H), 6.14 (dd, J=11.2, 18.0 Hz, 1H), 5.61 (d, J=8.0 Hz, 1H), 5.14-5.03 (m, 2H), 4.97 (s, 2H), 4.60 (d, J=2.2 Hz, 2H), 4.52 (d, J=6.2 Hz, 1H), 3.43 (t, J=6.0 Hz, 1H), 2.44 (s, 1H), 2.25-2.14 (m, 1H), 2.14-2.00 (m, 3H), 1.74-1.57 (m, 2H), 1.53-1.20 (m, 8H), 1.13-0.95 (m, 4H), 0.83 (d, J=7.1 Hz, 3H), 0.65 (d, J=6.6 Hz, 3H). MS (ESI): mass calcd. For C$_{30}$H$_{39}$BFNO$_8$ 571.3, m/z found 570.3[M−H]$^−$. HPLC: 99.4% (220 nm), 100% (254 nm).

56. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-1,3-dihydrobenzo[c][1,2]oxaborol-6-yl)methyl) carbamate

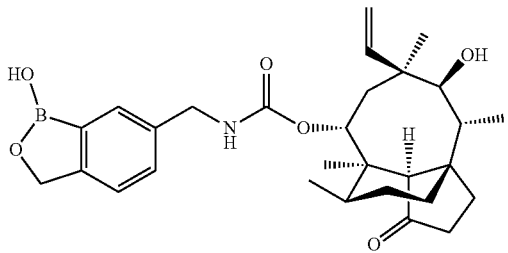

To a suspension of 6-(aminomethyl)benzo[c][1,2]oxaborol-1 (3H)-ol hydrochloride salt (200 mg, 1.0 mmol) and K$_2$CO$_3$ (414 mg, 3.0 mmol) in DCM (20 mL) was added (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl carbonochloridate (794 mg, 2.0 mmol) at 0° C. The mixture was stirred at room temperature overnight. Then filtered, washed with DCM and concentrated to give the crude. The residue was purified by prep-HPLC (column: Luna C18 100×30 mm, 5 μm; liquid phase: [A-TFA/H$_2$O=0.075% v/v; B-ACN] B %: 40%-65%, 20 min]) to give the desired product (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl ((1-hydroxy-1,3-dihydrobenzo[c][1,2]oxaborol-6-yl)methyl)carbamate (225 mg, yield 43.1%) as white solid. $^1$H NMR (DMSO-d$_6$, 400 MHz) δ 7.70 (t, J=5.8 Hz, 1H), 7.61 (s, 1H), 7.38-7.33 (m, 2H), 6.74 (dd, J=10.8, 17.6 Hz, 1H), 5.53 (d, J=9.6 Hz, 1H), 5.24 (d, J=10.4 Hz, 1H), 4.96-4.90 (m, 3H), 4.32-4.16 (m, 2H), 3.13-3.10 (m, 3H), 2.85 (d, J=6.4 Hz, 1H), 2.36-2.33 (m, 1H), 2.07-1.61 (m, 5H), 1.41-1.38 (m, 2H), 1.18-1.01 (m, 1H), 0.90 (d, J=6.4 Hz, 3H), 0.78 (d, J=6.8 Hz, 3H). MS (ESI): mass calcd. for C$_{30}$H$_{42}$BNO$_6$ 523.3, m/z found 522.2 [M−H]$^−$. HPLC: 99.0% (220 nm), 100% (254 nm).

A solution of (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl ((1-hydroxy-1,3-dihydrobenzo[c][1,2]oxaborol-6-yl)methyl)carbamate (170 mg, 0.33 mmol) in 1,4-dioxane (10 mL) cooled to 10° C. and treated with a half-saturated solution of zinc chloride in concd HCl (2 mL, 1 g ZnCl$_2$) keeping the temperature <15° C. The mixture was stirred at room temperature overnight. Then added water and extracted with EtOAc. The combined organic layer was washed with brine, dried over Na$_2$SO$_4$ and concentrated. The residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-1,3-dihydrobenzo[c][1,2]oxaborol-6-yl)methyl)carbamate (51 mg, yield 31%) as white solid. $^1$H NMR (DMSO-d$_6$, 400 MHz) δ 7.58 (s, 1H), 7.50 (t, J=6.0 Hz, 1H), 7.35-7.30 (m, 3H), 6.28-6.25 (dd, J=10.8, 17.6 Hz, 1H), 5.44 (d, J=7.6 Hz, 1H), 5.09-4.94 (m, 4H), 4.18 (d, J=5.6 Hz, 2H), 2.34 (s, 1H), 2.17-2.02 (m, 5H), 1.65-1.63 (m, 2H), 1.48-1.47 (m, 2H), 1.30 (s, 3H), 1.35-1.09 (m, 4H), 1.05 (s, 3H), 0.80 (d, J=6.8 Hz, 3H), 0.65 (d, J=5.6 Hz, 3H). MS (ESI): mass calcd. for $C_{29}H_{40}BNO_6$ 509.2, m/z found 508.3 [M–H]⁻. HPLC: 99.3% (220 nm), 100% (254 nm).

57. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((7-fluoro-1-hydroxy-1,3-dihydrobenzo[c][1,2]oxaborol-6-yl)methyl)carbamate

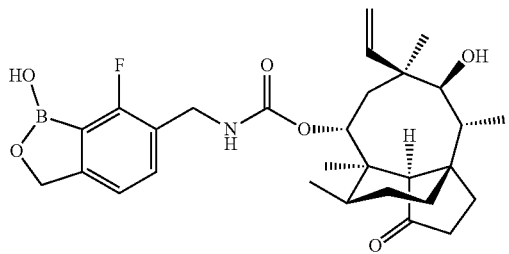

To a solution of TMP (20.4 g, 144.3 mmol, 1.3 eq.) in THF (150 mL) at –78° C. was slowly added n-BuLi (2.5 M, 57.7 mL, 1.3 eq.). The reaction vessel was transferred to a 0° C. ice bath for 1 hour and then recooled to –78° C. 2-fluoro-4-methyl-benzonitrile (15.0 g, 111.0 mmol, 1.0 eq.) as a solution in THF (20 mL) was then slowly added. The reaction mixture was stirred at –78° C. for 2 hours, and then a solution of $I_2$ (42.3 g, 166.5 mmol, 1.5 eq.) in THF (10 mL) was slowly added and then the reaction mixture was allowed to warm to room temperature. 100 mL sodium thiosulfate aqueous solution was added to the mixture, yellow solution turn to colorless. The mixture was eluted with EtOAc 50 mL and separated via a separatory funnel. The aqueous phase was treated with EtOAc (50 mL×3). The combined organic phase was washed with brine (100 mL×1), dried over $Na_2SO_4$ and concentrated under reduced pressure to give 2-fluoro-3-iodo-4-methylbenzonitrile (16.0 g, crude) as a yellow solid. ¹H NMR (CDCl₃, 400 MHz) δ 7.49 (dd, J=6.4, 7.8 Hz, 1H), 7.16 (d, J=7.8 Hz, 1H), 2.57 (s, 3H).

2-fluoro-3-iodo-4-methyl-benzonitrile (17.0 g, 65.1 mmol, 1.0 eq.), NBS (17.4 g, 97.7 mmol, 1.5 eq.) and AIBN (1.1 g, 6.5 mmol, 0.1 eq.) in CCl₄ (150 mL) were stirred at 80-90° C. for 24 hours. The mixture was filtered and concentrated to give crude product. The crude product was purified by flash column chromatography (petroleum ether/EtOAc=10/1) to give 4-(bromomethyl)-2-fluoro-3-iodobenzonitrile (4.5 g, 13.2 mmol, 20.3% yield) as a white solid. ¹H NMR (CDCl₃, 400 MHz) δ 7.60 (m, 1H), 7.39 (d, J=9.2 Hz, 1H), 4.62 (s, 2H).

4-(bromomethyl)-2-fluoro-3-iodo-benzonitrile (4.5 g, 13.2 mmol, 1.0 eq.) and KOAc (3.9 g, 39.7 mmol, 3.0 eq.) in DMF (25 mL) were stirred at 15° C. for 1 hour. $H_2O$ (50 mL) was added to the mixture. White solid was precipitated and filtered to give crude product, which was purified by flash chromatography (petroleum ether/EtOAc=1/1) to give 4-cyano-3-fluoro-2-iodobenzyl acetate (3.5 g, 11.0 mmol, 82.9% yield) as a white solid. ¹H NMR (CDCl₃, 400 MHz) δ 7.62 (dd, J=6.2, 7.6 Hz, 1H), 7.29 (dd, J=0.8, 7.6 Hz, 1H), 5.17 (s, 2H), 2.20 (s, 3H).

4-cyano-3-fluoro-2-iodobenzyl acetate (2.0 g, 6.3 mmol, 1.0 eq.), Pd(dppf)Cl₂ (367.0 mg, 501.6 umol, 0.08 eq.), KOAc (1.9 g, 18.8 mmol, 3.0 eq.) and Pin₂B₂(15.9 g, 62.7 mmol, 10.0 eq. in 1,4-dioxane (100 mL) were heated to 120° C. for 24 hours under nitrogen atmosphere. Two major peaks were detected. The mixture was filtered via celite, the solvent was concentrated in vacuo to give crude residue. The residue was purified by flash chromatography (petroleum ether/EtOAc=10/1 to 2/1) to give product. Then the mixture was further purified by prep-HPLC ((column: Phenomenex luna (2) C18 250×50 mm, 10 μm; liquid phase: [A-TFA/H₂O=0.075% v/v; B-ACN] B %: 30%-60%, 30 min])). The organic solvent was evaporated, and the aqueous phase was treated with DCM (100 mL×3). The combined organic phase was dried over Na₂SO₄ and concentrated in vacuo to give 4-cyano-3-fluoro-2-(4,4,5,5-tetramethyl-1,3,2-dioxaborolan-2-yl)benzyl acetate (600.0 mg, crude) as a yellow solid.

NaOH (150.4 mg, 3.8 mmol, 2.0 eq.) was added to a solution of 4-cyano-3-fluoro-2-(4,4,5,5-tetramethyl-1,3,2-dioxaborolan-2-yl)benzyl acetate (600.0 mg, 1.9 mmol, 1.0 eq.) in MeOH (10 mL) and H₂O (20 mL). The mixture was stirred at 15° C. for 3 hours. HPLC and LCMS showed major as desired. The mixture was adjusted to pH<4 with 2N HCl aqueous solution, and treated with DCM (50 mL×3). The combined organic phase was dried over Na₂SO₄ and concentrated in vacuo to give crude 7-fluoro-1-hydroxy-1,3-dihydrobenzo[c][1,2]oxaborole-6-carbonitrile (300.0 mg, crude) as a white solid. ¹H NMR (DMSO-d₆, 400 MHz) δ 9.61 (s, 1H), 7.99 (dd, J=6.2, 8.0 Hz, 1H), 7.46 (d, J=7.2 Hz, 1H), 5.09 (s, 2H).

7-fluoro-1-hydroxy-1,3-dihydrobenzo[c][1,2]oxaborole-6-carbonitrile (300.0 mg, 1.7 mmol, 1.0 eq.) and Raney nickel (728.2 mg, 8.5 mmol, 5.0 eq.) were stirred in EtOH (50 mL) under 10 Psi hydrogen atmosphere for 2 hours. The mixture was filtered via a celite. The filtrate was concentrated to give 6-(aminomethyl)-7-fluorobenzo[c][1,2]oxaborol-1(3H)-ol (250.0 mg, crude) as a white solid.

(3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl carbonochloridate (219.4 mg, 552.6 umol, 1.0 eq.) was added to a solution of 6-(aminomethyl)-7-fluorobenzo[c][1,2]oxaborol-1(3H)-ol (100.0 mg, 552.6 umol, 1.0 eq.) and TEA (167.8 mg, 1.7 mmol, 3.0 eq.) in DCM (20 mL) at 15° C. The mixture was stirred at this temperature for 2 hours. HPLC and LCMS showed major as desired. The reaction was quenched by addition of water (30 mL). The mixture was treated with DCM (30 mL×3). The combined organic phase was dried over Na₂SO₄ and concentrated in vacuo to give (3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl(7-fluoro-1-hydroxy-1,3-dihydrobenzo[c][1,2]oxaborol-6-yl)methyl)carbamate (270.0 mg, crude) as white foam.

(3R,3aR,4R,5R,7S,9R,9aR,12R)-3-methoxy-4,7,9,12-tetramethyl-8-oxo-7-vinyldecahydro-4,9a-propanocyclopenta[8]annulen-5-yl((7-fluoro-1-hydroxy-1,3-dihydrobenzo[c][1,2]oxaborol-6-yl)methyl)carbamate (200.0 mg, 369.4 umol, 1.0 eq.) in ZnCl₂ saturated in HCl solution (14.6 g, 106.8 mmol, 289.0 eq.) and THF (5 mL) were stirred at 15° C. for 0.5 hour. 30 mL water was added to quench the reaction. The mixture was treated with DCM (30 mL×3). The combined organic phase was dried over Na₂SO₄ and concentrated in vacuo. The crude product was purified by prep-HPLC (column: Luna C18 100×30 mm, 5 μm; liquid phase: [A-TFA/H₂O=0.075% v/v; B-ACN] B %: 43%-63%, 12 min]). The solvent was concentrated to about 20 mL solution left and dried over lyophilizer to give (3R,3aR,4R,5R,7S,9R,9aR,12R)-3-methoxy-4,7,9,12-tetramethyl-8-oxo-7-vinyldecahydro-4,9a-propanocyclopenta[8]annulen-5-ylcarbonochloridate (59.0 mg, 111.9 umol, 30.3% yield, 100% purity) as a white solid. ¹H NMR (DMSO-d₆, 400 MHz) δ 9.23 (s, 1H), 7.50 (t, J=6.0 Hz, 1H), 7.38 (t, J=7.2

Hz, 1H), 7.14 (d, J=8.0 Hz, 1H), 6.20 (dd, J=11.2, 18.0 Hz, 1H), 5.41 (d, J=8.8 Hz, 1H), 5.09-4.86 (m, 4H), 4.25-4.10 (m, 2H), 3.38 (d, J=5.6 Hz, 1H), 2.29 (s., 1H), 2.22-1.95 (m, 4H), 1.69-1.14 (m, 10H), 1.06-0.88 (m, 4H), 0.78 (d, J=6.6 Hz, 3H), 0.62 (d, J=5.2 Hz, 3H). MS (ESI): mass calcd. for $C_{29}H_{39}BFNO_6$ 527.29, m/z found 526.3 [M−H]−. HPLC: 100% (220 nm), 100% (254 nm).

58. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydrobenzo[c][1,2]oxaborole-6-carbonyl)carbamate

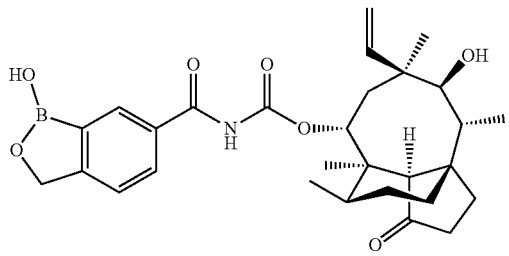

To a solution of (3R,3aS,4R,5R,7S,9R,9aR,12R)-5-hydroxy-3-methoxy-4,7,9,12-tetramethyl-7-vinyloctahydro-4,9a-propanocyclopenta[8]annulen-8(9H)-one (2.0 g, 6.0 mmol) and sodium cyanate (1.2 g, 18.0 mmol) in anhydrous toluene (20 mL) was added trifluroacetic acid (1 mL) slowly. The mixture was stirred for 16 hrs at ambient temperature after which no STM was detected by HPLC analysis. Water (50 mL) was added to the mixture with stirring and organic layer was separated. The aqueous layer was discarded and the toluene layer was concentrated under reduced pressure to a final volume of ~5 mL. Heptane (25 mL) was added and the mixture was stirred at 65° C. for 30 min. The mixture was cooled to 0° C. and stirred for 1 hr. The resulted slurry was filtered and washed with cold heptane, then dried under vacuum to give (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl carbamate (2.0 g, yield: 90.9%). $^1$H NMR (CDCl$_3$, 400 MHz) δ 6.72 (dd, J=17.6, 10.8 Hz, 1H), 5.66 (d, J=10.0 Hz, 1H), 5.29 (d, J=10.8 Hz, 1H), 5.02 (d, J=17.6 Hz, 1H), 4.60 (s, 2H), 3.47 (ddd, J=11.2, 8.0, 5.4 Hz, 1H), 3.23 (s, 3H), 2.95 (q, J=6.4 Hz, 1H), 2.44 (dd, J=15.2, 10.0 Hz, 1H), 2.27-2.15 (m, 1H), 2.07-1.93 (m, 2H), 1.79-1.54 (m, 4H), 1.50-1.40 (m, 1H), 1.36-1.24 (m, 3H), 1.23-1.18 (m, 6H), 0.99 (d, J=6.4 Hz, 3H), 0.88 (d, J=6.4 Hz, 3H).

A solution of (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl carbamate (1.6 g, 4.2 mmol) in dry THF (30 mL) under a nitrogen atmosphere was cooled to −5 to 0° C., to the solution was added sodium tert-butoxide (1.4 g, 12.6 mmol) over ~10 min, maintaining the process temperature below 5° C. The reaction mixture was stirred at 0° C. for 1 hr. At the same time, the mixture of 1-hydroxy-1,3-dihydrobenzo[c][1,2]oxaborole-6-carboxylic acid (754 mg, 4.2 mmol) and CDI (1.4 g, 8.4 mmol) in THF (20 mL) was refluxed for 1 hr, then added to the above solution dropwise and the mixture was stirred overnight. Water was added, the mixture was extracted with EtOAc, washed with brine, dried and concentrated. The crude product was purified by prep-HPLC to give (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl (1-hydroxy-1,3-dihydrobenzo[c][1,2]oxaborole-6-carbonyl) carbamate 1-hydroxy-1,3-dihydrobenzo[c][1,2]oxaborole-6-carboxylate (0.4 g, ~65% purity).

To a mixture of (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl (1-hydroxy-1,3-dihydrobenzo[c][1,2]oxaborole-6-carbonyl)carbamate 1-hydroxy-1,3-dihydrobenzo[c][1,2]oxaborole-6-carboxylate (0.3 g, 0.56 mmol) in dioxane (10 mL) was added saturated zinc chloride hydrochloric acid solution (10 mL) dropwise and the mixture was stirred at r.t for 30 min. Water was added to quench the reaction. The mixture was extracted with EtOAc, washed with brine, concentrated. The residue was purified by prep-HPLC (column: Luna C18 100×30 mm, 5 μm; liquid phase: [A-TFA/H$_2$O=0.075% v/v; B-ACN] B %: 25%-60%, 20 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydrobenzo[c][1,2]oxaborole-6-carbonyl)carbamate (133 mg, yield: 45.5%) as white solid. $^1$H NMR (DMSO-d$_6$, 400 MHz) δ 10.80 (s, 1H), 9.35 (br.s., 1H), 8.19 (s, 1H), 7.91 (dd, J=8.0, 1.6 Hz, 1H), 7.52 (d, J=8.0 Hz, 1H), 6.27 (dd, J=17.6, 10.8 Hz, 1H), 5.59 (d, J=8.0 Hz, 1H), 5.19-5.08 (m, 2H), 5.06 (s, 2H), 3.46 (d, J=5.6 Hz, 1H), 2.40 (s, 1H), 2.29-2.02 (m, 4H), 1.75-1.49 (m, 4H), 1.45 (s, 3H), 1.43-1.22 (m, 4H), 1.11 (s, 3H), 0.85 (d, J=6.4 Hz, 3H), 0.72 (d, J=6.4 Hz, 3H). MS (ESI): mass calcd. for $C_{29}H_{38}BNO_7$ 523.3, m/z found 522.2 [M−H]−. HPLC: 100% (220 nm), 100% (254 nm).

59. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-1,3-dihydrobenzo[c][1,2]oxaborol-6-yl)methyl)glycinate

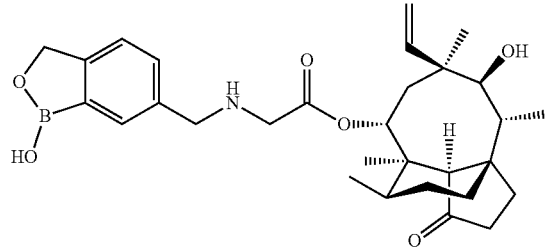

Tos-pleuromutilin (106 mg, 0.2 mmol), 6-(aminomethyl)benzo[c][1,2]oxaborol-1(3H)-ol (65 mg, 0.4 mmol) and K$_2$CO$_3$ (166 mg, 1.2 mmol) in 1 mL ACN was heated at 50° C. overnight. Main peak on LCMS is desired product. The crude was purified by prep HPLC (column: SunFire C18 OBD 100×30 mm, 5 μm) eluted with gradient water/acetonitrile (0.1% TFA) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-1,3-dihydrobenzo[c][1,2]oxaborol-6-yl)methyl)glycinate (40 mg, yield 39%). $^1$H NMR (400 MHz, DMSO-d$_6$) δ 0.60 (d, J=7.2 Hz, 3H), 0.78 (d, J=6.8 Hz, 3H), 0.97 (br. s, 1H), 1.02 (d, 3H), 1.24 (d, 3H), 1.25 (s, 1H), 1.4, (m, 3H), 1.61-1.9 (m, 3H), 2.02 (m, 2H), 2.07 (m, 2H), 2.4 (s, 2H), 3.8 (m, 2H), 4.1 (m, 2H), 4.4 (br, s, 1H), 5.0-5.1 (m, 4H), 5.59 (d, J=8.4 Hz, 1H), 6.06 (dd, J=17.8, 11.2 Hz, 1H), 7.5 (m, 2H), 7.75 (s, 1H), 9.3 (br, s, 1H), 9.5 (br, s, 1H). MS (ESI): mass calcd. For $C_{30}H_{42}BNO_6$ 523.31, m/z found 524.3 [M+H]+. HPLC: 99.0% (220 nm).

60. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-3,3-dimethyl-1,3-dihydrobenzo[c][1,2]oxaborol-6-yl)methyl)glycinate

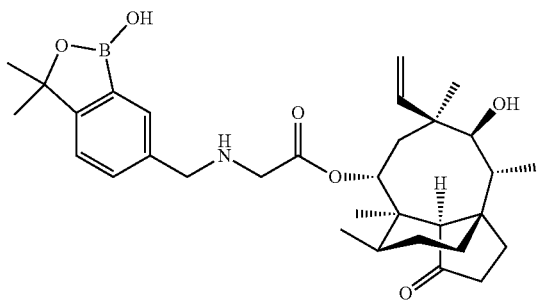

To a solution of Tos-Pleu (112 mg, 0.211 mmol), KI (6 mg, 0.035 mmol) and K$_2$CO$_3$ (48 mg, 0.352 mmol) in MeCN (3 mL) was added 6-(aminomethyl)-3,3-dimethyl-benzo[c][1,2]oxaborol-1(3H)-ol (40 mg, 0.176 mmol). The reaction mixture was heated to reflux overnight. After removed the solvent, the residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((1-hydroxy-3,3-dimethyl-1,3-dihydrobenzo[c][1,2]oxaborol-6-yl)methyl)glycinate (42 mg, yield 43%) as a white solid. $^1$H NMR (400 MHz, DMSO-d$_6$) δ 8.96 (s, 1H), 7.57 (s, 1H), 7.38-7.32 (m, 2H), 6.24-6.17 (m, 1H), 5.62 (d, J=8.0 Hz, 1H), 5.12-5.06 (m, 2H), 4.53 (d, J=6.0 Hz, 1H), 3.71-3.68 (m, 2H), 3.43-3.17 (m, 3H), 2.42 (s, 2H), 2.16-2.08 (m, 4H), 1.70-1.03 (m, 21H), 0.83 (d, J=6.8 Hz, 3H), 0.62 (d, J=6.8 Hz, 3H). HPLC purity: 100% (214 nm), 100% (254 nm); MS (ESI): mass calcd. for C$_{32}$H$_{46}$BNO$_6$ 551.34, m/z found 552.2 [M+H]$^+$.

61. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)thio)acetate 62. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((R)-(1-hydroxy-1,3-dihydrobenzo[c][1,2]oxaborol-6-yl)sulfinyl)acetate 63. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((S)-(1-hydroxy-1,3-dihydrobenzo[c][1,2]oxaborol-6-yl)sulfinyl)acetate 64. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)sulfonyl)acetate

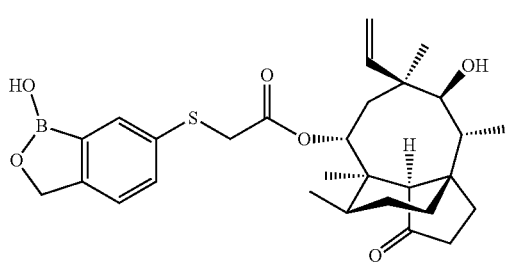

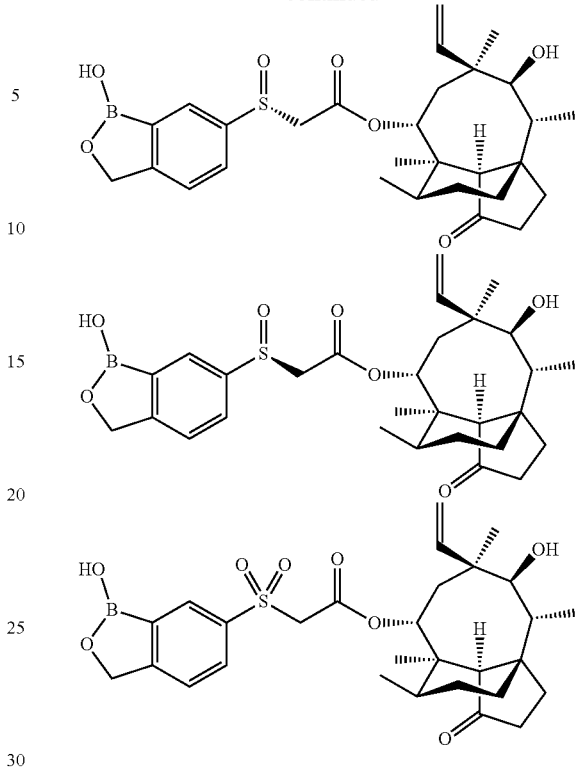

To a mixture of 2-bromo-4-fluorobenzaldehyde (30.0 g, 147.8 mmol, 1.0 eq) and K$_2$CO$_3$ (32.7 g, 236.5 mmol, 1.6 eq) in DMF (350 mL) was added 2-methylpropane-2-thiol (20.0 g, 221.7 mmol, 1.5 eq) at 15° C. under N$_2$. The mixture was stirred at 60° C. for 40 hrs. The reaction mixture was poured into cold water (450 mL) and yellow solid precipitated. The solid was filtered and washed with water twice, concentrated in vacuum to afford 2-bromo-4-(tert-butylthio)benzaldehyde (28.5 g, 104.3 mmol, 70.6% yield) as a yellow solid. $^1$H NMR: (CDCl$_3$, 400 MHz) δ 10.35 (d, J=0.8 Hz, 1H), 7.87-7.81 (m, 2H), 7.56 (dd, J=0.8, 8.0 Hz, 1H), 1.37 (s, 9H).

To a mixture of 2-bromo-4-(tert-butylthio)benzaldehyde (38.5 g, 140.9 mmol, 1.0 eq) and BPD (178.9 g, 704.6 mmol, 5.0 eq) in dioxane (500 mL) was added KOAc (41.5 g, 422.8 mmol, 3.0 eq), Pd(dppf)Cl$_2$.CH$_2$Cl$_2$ (11.5 g, 14.1 mmol, 0.1 eq) at 20° C. under N$_2$. The mixture was stirred at 80° C. for 16 hrs. To the reaction mixture was added activated carbon (500 mg), then filtered through celite and concentrated in vacuum. The residue was purified by column chromatography (SiO$_2$, Petroleum ether/Ethyl acetate=50/1 to 24:1) to afford 4-(tert-butylthio)-2-(4,4,5,5-tetramethyl-1,3,2-dioxaborolan-2-yl)benzaldehyde (46.00 g, crude) as a yellow solid. $^1$H NMR (CDCl$_3$, 400 MHz) δ 10.53 (s, 1H), 7.98 (d, J=2.0 Hz, 1H), 7.89 (d, J=8.0 Hz, 1H), 7.70 (dd, J=2.0, 8.0 Hz, 1H), 1.39 (s, 12H), 1.33 (s, 9H)

To a mixture of 4-(tert-butylthio)-2-(4,4,5,5-tetramethyl-1,3,2-dioxaborolan-2-yl)benzaldehyde (4.6 g, 14.4 mmol, 1.0 eq) in DCM (300 mL) was added NaBH$_4$ (815.1 mg, 21.5 mmol, 1.5 eq) at 0° C. under N$_2$. The mixture was stirred at 0° C. for 2 hrs under N$_2$. The reaction mixture was poured into water (100 mL) and acidified with aqueous HCl to pH=6. The aqueous phase was extracted with ethyl acetate (30 mL×3). The combined organic phase was washed with saturated brine (80 mL×2), dried with anhydrous Na$_2$SO$_4$, filtered and concentrated in vacuum. The residue was purified by prep-HPLC (column: Phenomenex luna(2) C18 250×50 mm, 10 m; liquid phase: [A-TFA/H$_2$O=0.075% v/v; B-ACN] B %: 30%-60%, 20 min) to give 6-(tert-butylthio)benzo[c][1,2]oxaborol-1(3H)-ol (3.1 g, 14.0 mmol, 97.2% yield) as a white solid. $^1$H NMR (DMSO-d$_6$, 400 MHz) δ 9.26 (s, 1H), 7.87 (d, J=2.0 Hz, 1H), 7.58 (dd, J=2.0, 8.0 Hz, 1H), 7.43 (d, J=8.0 Hz, 1H), 5.02 (s, 2H), 1.23 (s, 9H).

To a mixture of AlCl$_3$ (5.7 g, 42.7 mmol, 5.0 eq) in toluene (300.0 mL) was added a solution of 6-(tert-butylthio)benzo[c][1,2]oxaborol-1(3H)-ol (1.9 g, 8.6 mmol, 1.0 eq) in DCM (50.0 mL) dropwise at −5° C. under N$_2$. The mixture was stirred at −5° C. for 4.5 hrs. The reaction mixture was poured into water (450 mL) and acidified with 4 M HCl to pH=2 at 0° C. The aqueous phase was extracted with ethyl acetate (200 mL×3). The combined organic phase was washed with saturated brine (300 mL×2), dried with anhydrous Na$_2$SO$_4$, filtered and concentrated in vacuum to give a residue. The residue was purified by prep-HPLC (column: Daiso 250×50 mm, 10 um; liquid phase: [A-TFA/H$_2$O=0.075% v/v; B-ACN] B %: 25%-55%, 20 min]) to give 6-mercaptobenzo[c][1,2]oxaborol-1(3H)-ol (0.3 g, 21.1%) as a white solid. $^1$H NMR (DMSO-d$_6$, 400 MHz) δ 9.20 (s, 1H), 7.62 (s, 1H), 7.39 (dd, J=1.2, 8.0 Hz, 1H), 7.29 (d, J=8.0 Hz, 1H), 5.38 (br. s., 1H), 4.92 (s, 2H).

A mixture of 6-mercaptobenzo[c][1,2]oxaborol-1(3H)-ol (150.0 mg, 903.6 umol, 1.0 eq), Tos-pleuromutilin (529.4 mg, 993.9 umol, 1.1 eq), K$_2$CO$_3$ (312.2 mg, 2.2 mmol, 2.5 eq), KI (7.5 mg, 45.2 umol, 0.05 eq) in DMSO (20 mL) was degassed and purged with N$_2$ for 3 times, and then the mixture was stirred at 40° C. for 4 hrs under N$_2$ atmosphere. The mixture was poured into ice-water (50 mL), and then adjusted pH to 4-5, the solid was precipitated, filtered, and the solid was washed with water for three times to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)thio)acetate (450.0 mg, 854.7 umol, 94.6% yield) as a white solid. $^1$H NMR (DMSO-d$_6$, 400 MHz) δ 9.18 (s, 1H), 7.72 (s, 1H), 7.49 (dd, J=1.2, 8.0 Hz, 1H), 7.35 (d, J=8.0 Hz, 1H), 6.03-5.94 (m, 1H), 5.47 (d, J=8.8 Hz, 1H), 4.94 (s, 2H), 4.90 (d, J=4.4 Hz, 1H), 4.47 (d, J=6.0 Hz, 1H), 3.79 (q, J=16.0 Hz, 2H), 3.37 (s, 1H), 2.37-2.31 (m, 1H), 2.22-1.87 (m, 4H), 1.68-1.55 (m, 2H), 1.50-1.14 (m, 7H), 1.08-0.93 (m, 6H), 0.79 (d, J=6.4 Hz, 3H), 0.55 (d, J=6.4 Hz, 3H). MS (ESI): mass calcd. for C$_{29}$H$_{39}$BO$_6$S 526.26, m/z found 549.3 [M+Na]$^+$. HPLC: 96.5% (220 nm), 96.8% (254 nm).

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)thio)acetate (200.0 mg, 379.9 umol, 1.0 eq) in MeOH (10.0 mL) and H$_2$O (2.0 mL) was added NaIO$_4$ (243.8 mg, 1.1 mmol, 3.0 eq). The mixture was stirred at 40° C. for 15 hrs. The reaction mixture was quenched by addition water 20 mL at 0° C., and then diluted with EtOAc 10 mL and extracted with EtOAc (10 mL×3). The combined organic layers were washed with brine (50 mL), dried over Na$_2$SO$_4$, filtered and concentrated under reduced pressure to give a residue. The residue was purified by prep-HPLC (column: Luna C18 100×30 mm, 5 m; liquid phase: [A-TFA/H$_2$O=0.075% v/v; B-ACN] B %: 40%-50%, 12 min]), MeCN was removed under reduced pressure, the residue was dried under freeze-drying to afford two isomers, randomly assigned as (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((R)-(1-hydroxy-1,3-dihydrobenzo[c][1,2]oxaborol-6-yl)sulfinyl)acetate (80.0 mg, 147.5 umol, 38.8% yield) as a white solid. $^1$H NMR (DMSO-d$_6$, 400 MHz) δ 9.33 (s, 1H), 8.10 (s, 1H), 7.83 (dd, J=1.2, 8.0 Hz, 1H), 7.60 (d, J=8.0 Hz, 1H), 6.03 (dd, J=11.6, 17.6 Hz, 1H), 5.47 (d, J=8.0 Hz, 1H), 5.08-4.97 (m, 4H), 4.05-3.92 (q, J=14.4 Hz, 2H), 2.34 (s, 1H), 2.23-1.86 (m, 5H), 1.69-1.12 (m, 10H), 1.09-0.93 (m, 5H), 0.80 (d, J=6.4 Hz, 3H), 0.53 (d, J=6.4 Hz, 3H). MS (ESI): mass calcd. for C$_{29}$H$_{39}$BO$_7$S 542.25, m/z found 541.2 [M−1]$^-$. HPLC: Rt=2.89 min, 100% (220 nm), 100% (254 nm).

and (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((S)-(1-hydroxy-1,3-dihydrobenzo[c][1,2]oxaborol-6-yl)sulfinyl)acetate (76.0 mg, 140.1 umol, 36.9% yield) as a white solid. $^1$H NMR (DMSO-d$_6$, 400 MHz) δ 9.39 (br. s., 1H), 8.0 (s, 1H), 7.81 (dd, J=1.2, 8.0 Hz, 1H), 7.60 (d, J=8.0 Hz, 1H), 6.03 (dd, J=11.2, 18.0 Hz, 1H), 5.54 (d, J=8.4 Hz, 1H), 5.09-4.98 (m, 4H), 4.11 (d, J=14.4 Hz, 1H), 3.79 (d, J=14.4 Hz, 1H), 2.39 (s, 1H), 2.24-1.96 (m, 5H), 1.70-1.13 (m, 10H), 1.01 (m, 5H), 0.81 (d, J=6.4 Hz, 3H), 0.65 (d, J=6.41 Hz, 3H). MS (ESI): mass calcd. for C$_{29}$H$_{39}$BO$_7$S 542.25, m/z found 541.2 [M−1]$^-$. HPLC: Rt=2.94 min, 100% (220 nm), 100% (254 nm).

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)thio)acetate (400.0 mg, 759.8 umol, 1.0 eq) in MeOH (20.0 mL) was added NaIO$_4$ (812.5 mg, 3.8 mmol, 5.0 eq). The mixture was stirred at 60° C. for 72 hrs. The reaction mixture was quenched by addition water 30 mL at 25° C., and then diluted with EtOAc 10 mL and extracted with EtOAc (20 mL×3). The combined organic layers were washed with brine (100 mL×1), dried over Na$_2$SO$_4$, filtered and concentrated under reduced pressure to give a residue. The residue was purified by prep-HPLC (column: Luna C18 100×30 mm, 5 μm; liquid phase: [A-TFA/H$_2$O=0.075% v/v; B-ACN] B %: 33%-63%, 12 min]), MeCN was removed under reduced pressure, the residue was dried under freeze-drying to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydrobenzo[c][1,2]oxaborol-6-yl)sulfonyl)acetate (95.0 mg, 170.1 umol, 22.4% yield) as a white solid. $^1$H NMR (400 MHz, DMSO-d$_6$) δ 9.47 (s, 1H), 8.26 (s, 1H), 8.00 (d, J=8.4 Hz, 1H), 7.64 (d, J=8.0 Hz, 1H), 5.97-5.86 (m, 1H), 5.38 (d, J=8.4 Hz, 1H), 5.04 (s, 2H), 4.93 (s, 1H), 4.90 (d, J=4.4 Hz, 1H), 4.69 (d, J=15.2 Hz, 1H), 4.50 (d, J=15.2 Hz, 1H), 3.31 (d, J=6.0 Hz, 1H), 2.27 (s, 1H), 2.16-1.75 (m, 5H), 1.61-1.14 (m, 6H), 1.12 (s, 3H), 0.92 (m, 5H), 0.74 (d, J=6.4 Hz, 3H), 0.45 (d, J=7.2 Hz, 3H). MS (ESI): mass calcd. for C$_{29}$H$_{39}$BO$_8$S 558.25, m/z found 557.3 [M−1]$^-$. HPLC: 99.8% (220 nm), 83.3% (254 nm).

65. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)thio)acetate 66. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((S)-(7-fluoro-1-hydroxy-1,3-dihydrobenzo[c][1,2]oxaborol-6-yl)sulfinyl)acetate 67. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((R)-(7-fluoro-1-hydroxy-1,3-dihydrobenzo[c][1,2]oxaborol-6-yl)sulfinyl)acetate

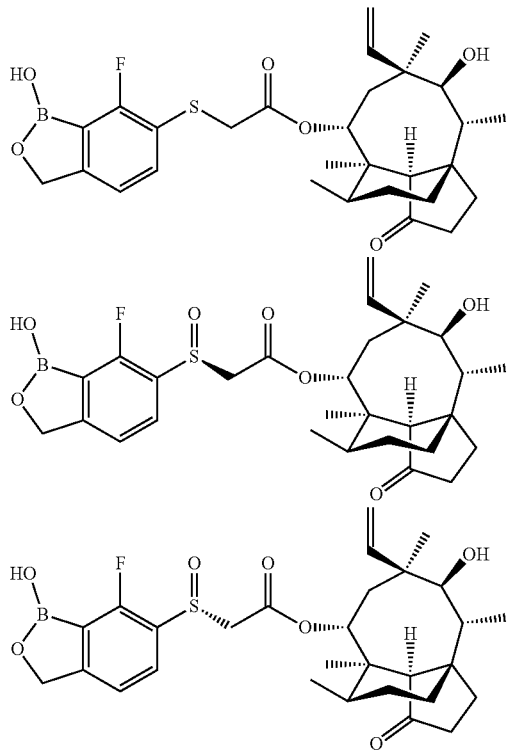

To a solution of 3,4-difluoro-2-iodobenzaldehyde (10.0 g, 37.3 mmol, 1.0 eq) in DMSO (100.00 mL) was added $Na_2S$ (4.1 g, 52.2 mmol, 1.4 eq) at 25° C. The mixture was stirred at 25° C. for 2 hours. To the mixture was added $H_2O$ (100 mL) and solid precipitated. After filtration, the filtrate was used directly in the next step.

To a mixture of 3-fluoro-2-iodo-4-mercaptobenzaldehyde (10.5 g, 37.2 mmol, 1.0 eq) and Tos-pleuromutilin (19.8 g, 37.2 mmol, 1.0 eq) in THF (20 mL) was added $Na_2CO_3$ (11.8 g, 111.6 mmol, 3.0 eq) in one portion at 25° C. The mixture was stirred at 25° C. for 2 hours. The mixture was added $H_2O$ (100 mL). The aqueous phase was extracted with ethyl acetate (100 mL×3). The combined organic phase was washed with brine (20 mL×2), dried with anhydrous $Na_2SO_4$, filtered and concentrated in vacuum. The residue was purified by silica gel chromatography (petroleum ether/ethyl acetate=20/1, 10/1, 5/1, 1/1) to afford product (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-fluoro-4-formyl-3-iodophenyl)thio)acetate (3.0 g, 4.7 mmol, 25.3% yield) as a light yellow solid. $^1$H NMR (DMSO-$d_6$, 400 MHz) δ 10.02 (s, 1H), 7.61 (d, J=8.0 Hz, 1H), 7.38 (t, J=7.6 Hz, 1H), 6.36 (dd, J=11.2, 17.2 Hz, 1H), 5.75 (d, J=8.4 Hz, 1H), 5.27 (d, J=11.6 Hz, 1H), 5.15 (d, J=17.2 Hz, 1H), 4.13 (d, J=7.6 Hz, 1H), 3.75-3.63 (m, 2H), 3.37-3.29 (m, 1H), 2.37-1.98 (m, 4H), 1.81-1.32 (m, 9H), 1.21-1.07 (m, 6H), 0.87 (d, J=6.8 Hz, 3H), 0.70 (d, J=6.8 Hz, 3H).

To a mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-fluoro-4-formyl-3-iodophenyl) thio)acetate (1.5 g, 2.3 mmol, 1.0 eq) and 4,4,4',4',5,5,5',5'-octamethyl-2,2'-bi(1,3,2-dioxaborolane) (5.9 g, 23.3 mmol, 10.0 eq) in anhydrous dioxane (15 mL) was added KOAc (503.1 mg, 5.1 mmol, 2.2 eq) and $Pd(PPh_3)_2Cl_2$ (81.9 mg, 116.7 umol, 0.05 eq) in one portion at 25° C. under $N_2$. The mixture was heated to 110° C. and stirred for 20 hours. The mixture was cooled to 25° C., then filtered and concentrated in vacuum to give crude product, which was purified by silica gel chromatography (petroleum ether/ethyl acetate=10/1, 3/1) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-fluoro-4-formyl-3-(4,4,5,5-tetramethyl-1,3,2-dioxaborolan-2-yl) phenyl)thio)acetate (240.0 mg, 373.5 umol, 48.0% yield) as yellow solid.

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-fluoro-4-formyl-3-(4,4,5,5-tetramethyl-1,3,2-dioxaborolan-2-yl)phenyl)thio)acetate (900.0 mg, 1.4 mmol, 1.0 eq) in DCM (50 mL) was added sodium; triacetoxyboranuide (593.4 mg, 2.8 mmol, 2.0 eq) at 25° C. The mixture was stirred at 25° C. for 12 hours. HPLC and LCMS showed the reaction was complete. $H_2O$ (30 mL) was added the mixture. The aqueous layer was extracted with DCM (30 mL×3). The combined organic layers were washed with brine (20 mL) and dried over $Na_2SO_4$. After filtration via filter paper, the organic layer was concentrated under reduced pressure to provide crude product, which was purified by prep-HPLC (column: Waters X bridge 150×25 5u; liquid phase: [A-10 mM $NH_4HCO_3$ in $H_2O$; B-ACN] B %: 20%-50%, 12 min]). After prep-HPLC purification, the eluent was concentrated to remove organic solvent. The residual aqueous solution was lyophilized to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)thio)acetate (260.0 mg, 477.5 umol, 34.1% yield, 100% purity) as a white solid. $^1$H NMR (DMSO-$d_6$, 400 MHz) δ 9.34 (s, 1H), 7.61 (t, J=7.2 Hz, 1H), 7.22 (d, J=8.0 Hz, 1H), 6.04-5.94 (m, 1H), 5.46 (d, J=8.0 Hz, 1H), 5.00-4.88 (m, 4H), 4.50 (d, J=6.0 Hz, 1H), 3.88-3.71 (m, 2H), 3.41-3.36 (m, 2H), 2.38-2.35 (m, 1H), 2.24-1.87 (m, 4H), 1.69-1.55 (m, 2H), 1.50-1.40 (m, 1H), 1.29 (s, 5H), 1.06-0.93 (m, 5H), 0.80 (d, J=6.8 Hz, 3H), 0.55 (d, J=6.8 Hz, 3H). MS (ESI): mass calcd. for $C_{29}H_{38}BFO_6S$ 544.25, m/z found 543.2 [M−H]$^-$. HPLC: 100% (220 nm), 100% (254 nm).

To a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-di hydrobenzo[c][1,2]oxaborol-6-yl)thio)acetate (160.0 mg, 293.8 umol, 1.0 eq) in MeOH (5 mL) was added sodium; periodate (628.5 mg, 2.9 mmol, 162.8 uL, 10.0 eq), then added H₂O (5 mL) at 25° C. The mixture was heated to 50° C. and stirred for 12 hours. The mixture was cooled to 25° C. The mixture was extracted with ethyl acetate (10 mL×3). The combined organic phase was washed with brine (10 mL×2), dried with anhydrous Na₂SO₄, filtered and concentrated in vacuum. The residue was purified by prep-HPLC (column: Luna C8 100×30 mm, 5 μm; liquid phase: [A-TFA/H₂O=0.075% v/v; B-ACN] B %: 35%-45%, 12 min]). After prep-HPLC purification, the eluent was concentrated to remove organic solvent. The residual aqueous solution was lyophilized to give product (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((S)-(7-fluoro-1-hydroxy-1,3-dihydrobenzo[c][1,2]oxaborol-6-yl)sulfinyl)acetate (19.0 mg, 33.5 umol, 11.4% yield, 98.9% purity, sulfoxide chiral center was randomly assigned) as a white solid. ¹H NMR (DMSO-d₆, 400 MHz) δ 7.89 (t, J=6.8 Hz, 1H), 7.52 (d, J=8.0 Hz, 1H), 6.05 (dd, J=11.6, 17.6 Hz, 1H), 5.57 (d, J=8.0 Hz, 1H), 5.13-4.97 (m, 4H), 4.20 (d, J=14.4 Hz, 1H), 3.87 (d, J=14.4 Hz, 1H), 2.42 (br. s., 2H), 2.26-1.98 (m, 4H), 1.73-1.58 (m, 2H), 1.56-1.47 (m, 1H), 1.39 (s, 4H), 1.34-1.20 (m, 3H), 1.04 (s, 4H), 0.83 (d, J=6.4 Hz, 3H), 0.65 (d, J=6.8 Hz, 3H). MS (ESI): mass calcd. for C₂₉H₃₈BFO₇S 560.24, m/z found 559.3 [M–H]⁻. HPLC: 100% (220 nm), 100% (254 nm).

and (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((R)-(7-fluoro-1-hydroxy-1,3-dihydrobenzo[c][1,2]oxaborol-6-yl)sulfinyl)acetate (34.0 mg, 60.6 umol, 20.6% yield, 100% purity, sulfoxide chiral center was randomly assigned) as a white solid. ¹H NMR (DMSO-d₆, 400 MHz) δ 7.89 (t, J=7.2 Hz, 1H), 7.52 (d, J=7.4 Hz, 1H), 6.03 (dd, J=10.8, 18.4 Hz, 1H), 5.48 (d, J=8.4 Hz, 1H), 5.12-4.95 (m, 4H), 4.19-3.96 (m, 2H), 2.35 (d, J=9.2 Hz, 2H), 2.23-1.86 (m, 5H), 1.65 (d, J=16.0 Hz, 1H), 1.28 (s, 6H), 1.05-0.91 (m, 6H), 0.81 (d, J=6.8 Hz, 3H), 0.59 (d, J=6.8 Hz, 3H). MS (ESI): mass calcd. for C₂₉H₃₈BFO₇S 560.24, m/z found 559.2 [M–H]⁻. HPLC: 98.9% (220 nm), 100% (254 nm).

68. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-3,4-dihydro-1H-benzo[c][1,2]oxaborinin-7-yl)oxy)acetate

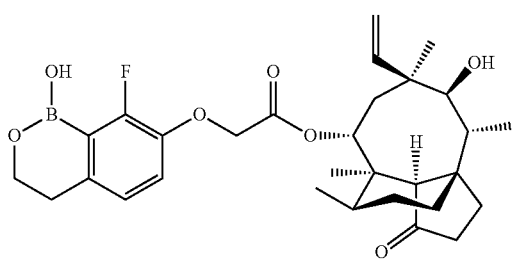

To a solution of 3,4-difluorobenzoic acid in THF (1 L) was added n-BuLi (2.5 M, 227.2 mL, 2.50 eq.). The mixture was stirred at −78° C. for 2.5 hr, then I₂ (144.1 g, 567.9 mmol, 2.5 eq.) (in 500 mL THF) was added drop-wise, The mixture was stirred at −78° C. for 0.5 hr. TLC indicated 3,4-difluorobenzoic acid was consumed completely, one new spot formed. The reaction mixture was quenched by addition saturation Na₂S₂O₃ 500 mL, and then extracted with EtOAc 1500 mL (500 mL×3). The combined organic layers were washed with brine 600 mL, dried over Na₂SO₄, filtered and concentrated under reduced pressure to give a residue. 3,4-difluoro-2-iodobenzoic acid (45.0 g, 149.0 mmol, 65.6% yield) was obtained as a white solid.

To a mixture of 3,4-difluoro-2-iodobenzoic acid (100.0 g, 352.1 mmol, 1.0 eq.) in THF (1.0 L) was added BH₃·Me₂S (10 M, 105.6 mL, 3.0 eq.) dropwise at 0° C. under N₂. The mixture was stirred at 25° C. for 12 hours. TLC (Petroleum ether: Ethyl acetate=2:1) showed the reaction was completed. The mixture was cooled to 0° C. and quenched with MeOH (100 mL), H₂O (100 mL), adjusted pH~4 with HCl (aq., 4N), concentrated under reduced pressure. The residue was poured into brine (100 mL) and stirred for 5 min. The aqueous phase was extracted with ethyl acetate (200 mL×3). The combined organic phase was washed with brine (100 mL×2), dried with anhydrous Na₂SO₄, filtered and concentrated in vacuum to give the (3,4-difluoro-2-iodophenyl)methanol (92.0 g, 340.7 mmol, 96.8% yield) as a yellow solid.

To a solution of (3,4-difluoro-2-iodophenyl)methanol (10.0 g, 37.0 mmol, 1.0 eq.) and DMSO (5.8 g, 74.1 mmol, 5.8 mL, 2.0 eq.) in DCM (200.00 mL) was added (COCl)₂ (7.1 g, 55.6 mmol, 4.9 mL, 1.5 eq.) dropwise at −78° C. over a period of 30 min under N₂. The reaction mixture stirred at −78° C. for 0.5 hour. TLC (petroleum ether/ethyl acetate=3:1) showed the starting material was consumed completely. The reaction was quenched by TEA (11.24 g, 111.1 mmol, 15.4 mL, 3.0 eq.) slowly and then extracted with DCM (150 mL×3). The combined organic phase was washed with brine (50 mL×3), dried over anhydrous Na₂SO₄, filtered and concentrated in vacuo to give the 3,4-difluoro-2-iodobenzaldehyde (5.0 g, 18.7 mmol, 50.4% yield) as a white solid.

To a solution of 3,4-difluoro-2-iodobenzaldehyde (14.0 g, 52.2 mmol, 1.0 eq.) and phenylmethanol (5.6 g, 52.2 mmol, 5.4 mL, 1.0 eq.) in DMF (150.0 mL) was added Cs₂CO₃ (22.1 g, 67.9 mmol, 1.3 eq.). The mixture was stirred at 50° C. for 16 hours. HPLC indicated 3,4-difluoro-2-iodobenzaldehyde was consumed completely. The crude product 4-(benzyloxy)-3-fluoro-2-iodobenzaldehyde (crude) (dissolved in DMF) was used into the next step without further purification, about half of the all was de-Bn (3-fluoro-4-hydroxy-2-iodobenzaldehyde).

To a solution of 3-fluoro-4-hydroxy-2-iodobenzaldehyde (mixed in 4-(benzyloxy)-3-fluoro-2-iodobenzaldehyde) (12.0 g, 45.1 mmol, 1.0 eq.) and BnBr (11.5 g, 67.7 mmol, 8.0 mL, 1.5 eq.) in DMF (150.0 mL) was added Cs₂CO₃ (29.4 g, 90.2 mmol, 2.0 eq.). The mixture was stirred at 50° C. for 5 hours. HPLC indicated main as desired product. The reaction mixture was quenched by addition H₂O 500 mL, and adjusted pH=6, solid was dissolved out, filtered to give a desired. 4-(benzyloxy)-3-fluoro-2-iodobenzaldehyde (15.0 g, 42.2 mmol, 93.3% yield) was obtained as a light yellow solid. ¹H NMR (CDCl₃, 400 MHz) δ 9.98 (s, 1H), 7.69 (dd, J=1.6, 8.4 Hz, 1H), 7.44-7.33 (m, 5H), 7.07 (t, J=8.0 Hz, 1H), 5.25 (s, 2H)

To a solution of 4-(benzyloxy)-3-fluoro-2-iodobenzaldehyde (1.0 g, 2.8 mmol, 1.0 eq.) in THF (30.0 mL) was added NaBH₄ (106.2 mg, 2.8 mmol, 1.0 eq.). The mixture was stirred at 25° C. for 10 min. TLC indicated 4-(benzyloxy)-3-fluoro-2-iodobenzaldehyde) was consumed completely and one new spot formed. The reaction mixture was quenched by addition H₂O 50 mL, and then adjusted pH=6 and extracted with ETOAc 150 mL (50 mL×3). The combined organic layers were washed with brine 100 mL, filtered and concentrated under reduced pressure to give a residue. (4-(benzyloxy)-3-fluoro-2-iodophenyl) methanol (1.0 g, crude) was used into the next step without further purification. $^1$H NMR (CDCl$_3$, 400 MHz) δ 7.42-7.36 (m, 5H), 7.13 (d, J=8.4 Hz, 1H), 6.97 (t, J=8.4 Hz, 1H), 5.15 (s, 2H), 4.66 (s, 2H)

To a solution of (4-(benzyloxy)-3-fluoro-2-iodophenyl) methanol (900.0 mg, 2.5 mmol, 1.0 eq.) in DCM (30.0 mL) was added MsCl (862.6 mg, 7.5 mmol, 582.8 uL, 3.0 eq.) and Et$_3$N (457.8 mg, 4.5 mmol, 626.2 uL, 1.8 eq.). The mixture was stirred at 25° C. for 16 hours. TLC indicated (4-(benzyloxy)-3-fluoro-2-iodophenyl) methanol was consumed completely, and a new spot was formed. The reaction mixture was quenched by addition H$_2$O (50 mL), and then adjusted pH=7, extracted with EtOAc 150 mL (50 mL×3). The combined organic layers were washed with brine 100 mL, dried over Na$_2$SO$_4$, filtered and concentrated under reduced pressure to give a residue. The residue was purified by column chromatography (SiO$_2$, petroleum ether/ethyl acetate=20/1 to 10:1). 1-(Benzyloxy)-4-(chloromethyl)-2-fluoro-3-iodobenzene (900.0 mg, 2.4 mmol, 95.2% yield) was obtained as a white solid. $^1$H NMR (CDCl$_3$, 400 MHz) δ 7.45-7.29 (m, 5H), 7.2 (d, J=8.8 Hz, 1H), 7.01-6.89 (m, 1H), 5.15 (s, 2H), 4.68 (s, 2H)

To a solution of 1-(benzyloxy)-4-(chloromethyl)-2-fluoro-3-iodobenzene (200.0 mg, 531.0 umol, 1.0 eq.) in DMSO (2.0 mL) was added NaCN (78.0 mg, 1.6 mmol, 3.0 eq.). The mixture was stirred at 50° C. for 4 hours. TLC indicated (4-(benzyloxy)-3-fluoro-2-iodophenyl) methanol was consumed completely. The reaction mixture was quenched by addition H$_2$O 10 mL, and then extracted with EtOAc 60 mL (20 mL×3). The combined organic layers were washed with brine 40 mL, dried over Na$_2$SO$_4$, filtered and concentrated under reduced pressure to give a residue. 2-(4-(benzyloxy)-3-fluoro-2-iodophenyl)acetonitrile (190.0 mg, 517.5 umol, 97.4% yield) was obtained as a white solid. $^1$H NMR (CDCl$_3$, 400 MHz) δ 7.44-7.35 (m, 5H), 7.22 (d, J=8.8 Hz, 1H), 7.01 (t, J=8.8 Hz, 1H), 5.17 (s, 2H), 3.80 (s, 2H)

A solution of 2-(4-(benzyloxy)-3-fluoro-2-iodophenyl)acetonitrile (5.0 g, 13.6 mmol, 1.0 eq.) in HCl/CH$_3$OH (10 M, 400.1 mL, 293.7 eq.) was stirred at 70° C. for 48 hours. TLC indicated the reaction was completely. The reaction mixture was concentrated under reduced pressure to remove CH$_3$OH to give a crude product. methyl 2-(3-fluoro-4-hydroxy-2-iodophenyl) acetate (5.0 g, crude, yellow oil) was used into the next step without further purification.

To a solution of methyl 2-(3-fluoro-4-hydroxy-2-iodophenyl) acetate (4.20 g, 13.55 mmol, 1.00 eq.) in DMF (20.00 mL) was added Cs$_2$CO$_3$ (8.8 g, 27.1 mmol, 2.0 eq.) and bromomethylbenzene (2.8 g, 16.2 mmol, 1.9 mL, 1.2 eq.). The mixture was stirred at 50° C. for 2 hours. TLC indicated methyl 2-(3-fluoro-4-hydroxy-2-iodophenyl) acetate was consumed completely. The reaction mixture was quenched by addition H$_2$O 50 mL, and then extracted with EtOAc 600 mL (200 mL×3). The combined organic layers were washed with brine 300 mL, dried over Na$_2$SO$_4$, filtered and concentrated under reduced pressure to give a residue. The residue was purified by column chromatography (SiO$_2$, petroleum ether/ethyl acetate=50/1 to 10:1). methyl 2-(4-(benzyloxy)-3-fluoro-2-iodophenyl)acetate (1.0 g, 2.5 mmol, 18.5% yield) was obtained as a yellow solid. $^1$H NMR (CDCl$_3$, 400 MHz) δ 7.74-7.46 (m, 5H), 7.03-7.65 (m, 2H), 5.17 (s, 2H), 3.83 (s, 2H), 3.74 (s, 3H)

To a solution of methyl methyl 2-(4-(benzyloxy)-3-fluoro-2-iodophenyl)acetate (3.2 g, 8.0 mmol, 1.0 eq.), AcOK (61.3 mg, 624.7 umol, 2.5 eq.) and Pin$_2$B$_2$(20.3 g, 79.9 mmol, 10.0 eq.) in dioxane (20.0 mL) was added Pd (PPh3)$_2$Cl$_2$ (224.6 mg, 320.0 umol, 0.04 eq.). The mixture was stirred at 120° C. for 16 hours. HPLC indicated the methyl 2-(4-(benzyloxy)-3-fluoro-2-iodophenyl) acetate was consumed completely. The reaction mixture was filtered and concentrated under reduced pressure to give a residue. The residue was purified by column chromatography (SiO$_2$, petroleum ether/ethyl acetate=100/1 to 5:1). methyl 2-(4-(benzyloxy)-3-fluoro-2-(4,4,5,5-tetramethyl-1,3,2-dioxaborolan-2-yl)phenyl) acetate (2.7 g, 6.7 mmol, 84.3% yield) was obtained as a brown oil. $^1$H NMR (CDCl$_3$, 400 MHz) δ 7.45-7.31 (m, 5H), 6.95 (d, J=8.8 Hz, 1H), 6.87 (t, J=8.8 Hz, 1H), 5.12 (s, 2H), 3.79 (s, 2H), 3.67 (s, 3H), 1.36 (s, 12H)

To a solution of methyl 2-(4-(benzyloxy)-3-fluoro-2-(4,4,5,5-tetramethyl-1,3,2-dioxaborolan-2-yl)phenyl)acetate (1.0 g, 2.5 mmol, 1.0 eq.) in THF (10.0 mL) was added NaBH$_4$ (189.0 mg, 5.0 mmol, 2.0 eq.). The mixture was stirred at 0° C. for 20 min. TLC, HPLC and LCMS indicated the reaction was completely. The reaction mixture was quenched by addition H$_2$O 50 mL, and then adjusted pH=6 and extracted with DCM 150 mL (50 mL×3). Dried over Na$_2$SO$_4$, filtered and concentrated under reduced pressure to give a residue. The residue was purified by prep-HPLC (column: Phenomenex luna(2) C18 250×50 mm, 10 μm; liquid phase: [A-TFA/H$_2$O=0.075% v/v; B-ACN] B %: 25%-55%, 20 min]). 7-(benzyloxy)-8-fluoro-3,4-dihydro-1H-benzo[c][1,2]oxaborinin-1-ol (290.0 mg, 1.0 mmol, 42.6% yield) was obtained as a white solid. MS (ESI): mass calcd. for C$_{15}$H$_{14}$BFO$_3$ 272.08, m/z found 271.0 [M−H]$^-$. HPLC: 100.00% (220 nm), 100.00% (254 nm). $^1$H NMR (DMSO-d$_6$, 400 MHz) δ 8.44 (s, 1H), 7.47-7.29 (m, 5H), 7.24 (t, J=8.4 Hz, 1H), 6.95 (d, J=8.0 Hz, 1H), 5.2 (s, 2H), 4.00 (t, J=5.6 Hz, 2H), 2.78 (t, J=5.6 Hz, 2H)

To a solution of 7-(benzyloxy)-8-fluoro-3,4-dihydro-1H-benzo[c][1,2]oxaborinin-1-ol (200.0 mg, 735.1 umol, 1.0 eq) in EtOAc (40.0 mL) was added Pd/C (100.0 mg). The mixture was stirred at 25° C. for 4 hours under H$_2$ atmosphere (50 psi). TLC indicated 7-(benzyloxy)-8-fluoro-3,4-dihydro-1H-benzo[c][1,2]oxaborinin-1-ol was consumed completely. The reaction mixture was filtered and concentrated under reduced pressure to give a residue. 8-fluoro-3,4-dihydro-1H-benzo[c][1,2]oxaborinine-1,7-diol (100.0 mg, 549.6 umol, 74.7% yield) was obtained as a white solid. MS (ESI): mass calcd. for C$_{30}$H$_{40}$BFO$_7$ 182.06, m/z found 180.9 [M−H]$^-$. HPLC: 98.6% (220 nm), 100.0% (254 nm). 1H NMR (DMSO-d$_6$, 400 MHz) δ 9.42 (s, 1H), 8.34 (s, 1H), 6.95 (t, J=8.4 Hz, 1H), 6.83 (d, J=8.4 Hz, 1H), 3.98 (t, J=5.6 Hz, 1H), 2.74 (t, J=5.6 Hz, 1H)

To a solution of 8-fluoro-3,4-dihydro-1H-benzo[c][1,2] oxaborinine-1,7-diol (150.0 mg, 824.4 umol, 1.0 eq.) and Tos-pleuromutilin (402.6 mg, 824.3 umol, 1.0 eq.) in DMSO (20.0 mL) was added Na$_2$CO$_3$ (218.4 mg, 2.1 mmol, 2.5 eq.). The mixture was stirred at 25° C. for 16 hours. HPLC indicated the 8-fluoro-3,4-dihydro-1H-benzo[c][1,2]oxaborinine-1,7-diol was consumed completely, a new peak formed. The reaction was quenched by addition of H$_2$O 100 mL, and then adjusted pH=6, light yellow solid precipitated. The mixture was filtered and light yellow cake was washed cold water twice. The crude desired product was dissolved in THF (2 mL), then methyl tert-butyl ether 30 mL and Petroleum ether gradient 30 mL was added, light yellow solid precipitated, filtered and the filtrate was concentrated under reduced pressure to give desired product. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((8-fluoro-1-hydroxy-3,4-dihydro-1H-benzo[c][1,2] oxaborinin-7-yl)oxy)acetate (110.0 mg, 202.8 umol, 24.6% yield) was obtained as a light yellow solid. $^1$H NMR (DMSO-d$_6$, 400 MHz) δ. 8.41 (s, 1H) 7.20 (t, J=8.4 Hz, 1H), 6.91 (d, J=8.4 Hz, 1H), 6.08 (dd, J=11.2, 17.6 Hz, 1H), 5.58 (d, J=8.0 Hz, 1H), 5.08-4.97 (m, 3H), 4.82-4.65 (m, 2H), 3.98 (t, J=5.6 Hz, 2H), 3.42-3.37 (m, 1H), 2.76 (t, J=5.6 Hz, 2H), 2.38-2.32 (m, 1H), 2.23-1.98 (m, 4H), 1.72-1.19 (m, 8H), 1.08-0.94 (m, 5H), 0.80 (d, J=6.4 Hz, 3H), 0.61 (d, J=6.4 Hz, 3H). MS (ESI): mass calcd. for $C_{30}H_{40}BFO_7$ 542.29, m/z found 541.3 [M−H]⁻. HPLC: 95.7% (220 nm), 100.0% (254 nm).

69. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3,4-dihydro-1H-benzo[c][1,2]oxaborinin-7-yl)oxy)acetate

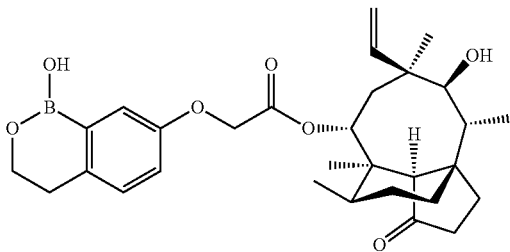

A mixture of Tos-pleuromutilin (294 mg, 0.55 mmol), 3,4-dihydro-1H-benzo[c][1,2]oxaborinine-1,7-diol (90.7 mg, 0.55 mmol) and $K_2CO_3$ (228 mg, 1.65 mmol) in 5 mL of DMF was stirred at 50° C. overnight. Water was added and the mixture was adjust pH<4 with 2N HCl. The solid was filtered and the crude product was purified by Pre-HPLC (column: SunFire C18 OBD 100×30 mm, 5 μm) eluted with gradient water/acetonitrile (0.1% TFA) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-3,4-dihydro-1H-benzo[c][1,2]oxaborinin-7-yl)oxy)acetate as a white solid (85 mg, yield 29.5%). ¹H NMR (DMSO-d₆, 400 MHz) δ 7.14 (s, 1H), 7.07 (d, J=8.4 Hz, 1H), 6.90 (d, J=8.4 Hz, 1H), 6.06 (dd, J=11.2, 17.6 Hz, 1H), 5.56 (d, J=8.0 Hz, 1H), 5.05-4.95 (m, 3H), 4.82-4.65 (m, 2H), 3.99 (t, J=5.6 Hz, 2H), 3.42-3.37 (m, 1H), 2.74 (t, J=5.6 Hz, 2H), 2.38-2.32 (m, 1H), 2.23-1.98 (m, 4H), 1.72-1.19 (m, 10H), 1.08-0.94 (m, 4H), 0.77 (d, J=6.4 Hz, 3H), 0.60 (d, J=6.4 Hz, 3H). MS (ESI): mass calcd. for $C_{30}H_{41}BO_7$ 524.29, m/z found 523.2[M−H]⁻. HPLC: 99.9% (220 nm), 99.9% (254 nm).

70. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate

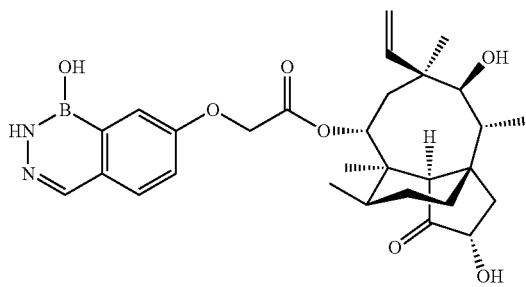

To a solution of 4-(benzyloxy)-2-(4,4,5,5-tetramethyl-1,3,2-dioxaborolan-2-yl)benzaldehyde (36.0 g, 106.5 mmol, 1.0 eq) in DCM (500 mL) was added trichloroborane (425 mL, 425.0 mmol, 4.0 eq) at 0° C. over a period of 30 mins under N₂. During which the temperature was maintained below 0° C. The reaction mixture was warmed to 25° C. over a period of 30 mins and stirred at room temperature for 2 hours. The solvent was concentrated at room temperature and to the residue was add 200 mL water, green solid precipitated and the mixture was filtered, the cake was dried to give (2-formyl-5-hydroxyphenyl)boronic acid (16.0 g, 96.4 mmol, 90.5% yield) as green solid. ¹H NMR (DMSO-d₆, 400 MHz) δ 9.85 (s, 1H), 7.74 (d, J=8.4 Hz, 1H), 6.93 (d, J=2.4 Hz, 1H), 6.87 (dd, J=2.4, 8.4 Hz, 1H).

A solution of (2-formyl-5-hydroxyphenyl)boronic acid (200.0 mg, 1.2 mmol, 1.0 eq) and tert-butyl N-aminocarbamate (159.3 mg, 1.2 mmol, 1.0 eq) in EtOH (5 mL) was stirred at 25° C. for 12 hours. The mixture was filtered to give tert-butyl 1,7-dihydroxybenzo[d][1,2,3]diazaborinine-2(1H)-carboxylate (200.0 mg, 763.6 umol, 63.1% yield) as white solid. ¹H NMR (DMSO-d₆, 400 MHz) δ 10.30 (s, 1H), 8.51 (s, 1H), 8.02 (s, 1H), 7.64 (d, J=8.4 Hz, 1H), 7.40 (d, J=2.4 Hz, 1H), 7.19 (dd, J=2.4, 8.4 Hz, 1H), 1.57 (s, 9H).

A solution (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-iodoacetate (300.0 mg, 594.8 umol, 1.0 eq), tert-butyl 1,7-dihydroxybenzo[d][1,2,3]diazaborinine-2(1H)-carboxylate (155.8 mg, 594.8 umol, 1.00 eq) and $K_2CO_3$ (246.6 mg, 1.7 mmol, 3.0 eq) in DMF (10 mL) was stirred at 50° C. for 2 hours. Water was added to the mixture and acidified with 2N HCl (aq), white solid was precipitated and filtered to give the crude product, which was purified by prep-TLC (petroleum ether/EtOAc=1/1) to give tert-butyl 7-(2-(((2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (92.0 mg, 144.0 umol, 24.2% yield) as yellow solid.

A solution of tert-butyl 7-(2-(((2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl)oxy)-2-oxoethoxy)-1-hydroxy benzo[d][1,2,3]diazaborinine-2(1H)-carboxylate (150.0 mg, 234.9 umol, 1.0 Eq) and 2N HCl (5 mL) in MeOH (15 mL) was stirred at 20° C. for 2 hours. The mixture was concentrated in reduced pressure. The aqueous phase was extracted with EtOAc (50 mL×3). The combined organic phase was washed with saturated brine (50 mL×2), dried with anhydrous $Na_2SO_4$, filtered and concentrated to afford crude product, which was purified by prep-HPLC (Instrument: Gilson 281 semi-preparative HPLC system. Column: Synergi Max-RP C12 100×30 4 u. Mobile phase: A: TFA/$H_2O$=0.075% v/v; B: ACN Gradient: B % 24-100, 14.6 min. Flow rate: 25 ml/min. Monitor wavelength: 220&254 nm) to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate (20.0 mg, 37.1 umol, 15.8% yield) as yellow solid. ¹H NMR (DMSO-d₆, 400 MHz) δ 9.86 (s, 1H), 7.96 (s, 1H), 7.70 (d, J=8.8 Hz, 1H), 7.67 (d, J=2.4 Hz, 1H), 7.31 (dd, J=2.4, 8.4 Hz, 1H), 6.09 (dd, J=11.2, 17.8 Hz, 1H), 5.60 (d, J=8.8 Hz, 1H), 5.12-4.96 (m, 2H), 4.89-4.76 (m, 2H), 3.32 (d, J=5.6 Hz, 1H), 2.35 (s, 1H), 2.10-1.69 (m, 5H), 1.49-1.17 (m, 9H), 1.11-0.97 (m, 3H), 0.83 (d, J=7.1 Hz, 3H), 0.65 (d, J=6.2 Hz, 3H). MS (ESI): mass calcd. for $C_{29}H_{39}BN_2O_7$ 538.3, m/z found 539.3 (M+H)⁺. HPLC: 94.3% in 220 nm; 98.4% in 254 nm.

71. tert-butyl 1-hydroxy-7-(2-(((3aR,4R,5R,7S,8S, 9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate 72. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate

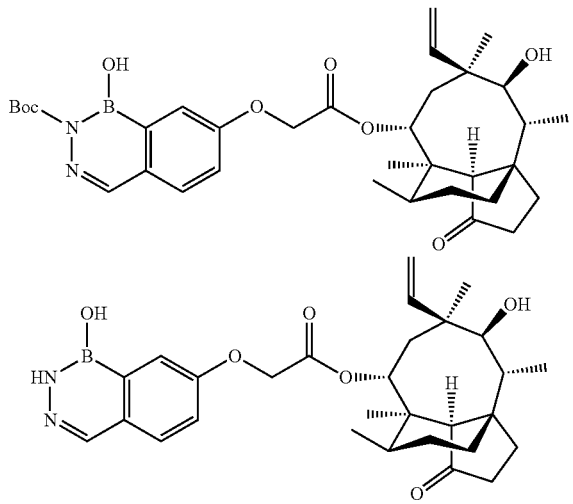

A solution of Tos-pleuromutilin (200.0 mg, 375.5 umol, 1.0 eq), tert-butyl 1,7-dihydroxybenzo[d][1,2,3]diazaborinine-2(1H)-carboxylate (98.4 mg, 375.5 umol, 1.0 eq) and K$_2$CO$_3$ (155.7 mg, 1.1 mmol, 3.0 eq) in DMF (10 mL) was stirred at 50° C. for 1.5 hours. Water was added to the mixture and acidified with 2N HCl (aq), white solid was precipitated and filtered to give the crude product which was purified by prep-HPLC (Instrument: Gilson 281 semi-preparative HPLC system Mobile phase: A: 10 mM NH$_4$HCO$_3$ in H2O; Gradient B: 55-100% CAN Column: Luna C18 100×30 mm, 5 μm. Flow rate: 25 ml/min, 18 mins. Monitor wavelength: 220&254 nm). tert-butyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate (56.0 mg, 89.9 umol, 23.9% yield) was obtained as yellow solid. $^1$H NMR (DMSO-d$_6$, 400 MHz) δ 8.57 (s, 1H), 8.10 (s, 1H), 7.75 (d, J=8.2 Hz, 1H), 7.47 (br. s., 1H), 7.38 (d, J=9.2 Hz, 1H), 6.09 (dd, J=11.0, 17.8 Hz, 1H), 5.60 (d, J=8.6 Hz, 1H), 5.11-4.96 (m, 2H), 4.89 (d, J=6.0 Hz, 1H), 4.53 (d, J=6.0 Hz, 1H), 2.41 (s, 1H), 2.26-1.96 (m, 4H), 1.65-1.58 (m, 11H), 1.53-1.21 (m, 8H), 1.13-0.97 (m, 5H), 0.81 (d, J=6.8 Hz, 3H), 0.66 (d, J=6.8 Hz, 3H). MS (ESI): mass calcd. for C$_{34}$H$_{47}$BN$_2$O$_8$ 622.3, m/z found 639.4 (M+H$_2$O—H)$^-$. HPLC: 96.4% in 220 nm; 96.5% in 254 nm.

To a mixture of tert-butyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate (400.0 mg, 642.5 mmol, 1.0 eq) in DCM (30 mL) was added a solution of hydrochloride in EtOA (5 mL, 4N) and the mixture was stirred for 2 hours. The mixture was filtered and washed with DCM to afford (3aR,4R,5R,7S,8S, 9R,9aS,12R)-8-hydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate (200.0 mg, 382.8 mmol, 59.6% yield) as yellow solid. $^1$H NMR (DMSO-d$_6$, 400 MHz) δ 9.90 (s, 1H), 7.96 (s, 1H), 7.75-7.64 (m, 2H), 7.31 (d, J=8.8 Hz, 1H), 6.09 (dd, J=11.2, 17.8 Hz, 1H), 5.60 (d, J=8.2 Hz, 1H), 5.13-4.95 (m, 2H), 4.89-4.74 (m, 2H), 3.41 (d, J=5.6 Hz, 1H), 2.41 (s, 1H), 2.25-1.97 (m, 4H), 1.71-1.18 (m, 10H), 1.07-0.93 (m, 4H), 0.81 (d, J=6.8 Hz, 3H), 0.64 (d, J=6.8 Hz, 3H). MS (ESI): mass calcd. for C$_{29}$H$_{39}$BN$_2$O$_6$ 522.3, m/z found 521.3 (M−H)$^-$. HPLC: 99.7% in 220 nm; 100% in 254 nm.

73. tert-butyl 7-(2-(((2S,3aR,4R,5R,7S,8S,9R,9aS, 12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate 74. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate

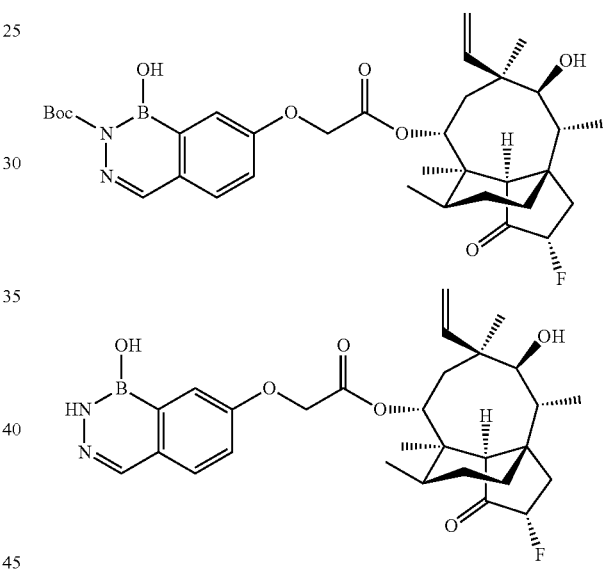

To a solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy)acetate (500.0 mg, 864.0 umol, 1.0 eq), tert-butyl 1,7-dihydroxybenzo[d][1,2,3]diazaborinine-2(1H)-carboxylate (226.43 mg, 864.02 umol, 1.0 eq) and K$_2$CO$_3$ (358.3 mg, 2.6 mmol, 3.0 eq) in DMF (20 mL) was stirred at 50° C. for 1.5 hours. Water was added to the mixture and acidified with 2N HCl (aq), white solid was precipitated and filtered to give the crude product tert-butyl 7-(2-(((2S,3aR, 4R,5R,7S,8S,9R,9aS,12R)-2-fluoro-8-(formyloxy)-4,7,9, 12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (400.0 mg, 598.3 umol, 69.3% yield) as yellow solid.

To a solution of tert-butyl 7-(2-(((2S,3aR,4R,5R,7S,8S, 9R,9aS,12R)-2-fluoro-8-(formyloxy)-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (400.0 mg, 598.3 umol, 1.0 eq) and K$_2$CO$_3$ (825.0 mg, 5.9 mmol, 3.0 eq) in MeOH (50 mL) was stirred at 25° C. for 2 hours. The mixture was filtered and the solvent was evaporated to give the crude product, which was further purified by prep-HPLC (Instrument: Gilson 281 semi-preparative HPLC system. Column: Luna C18 100×30 mm, 5 μm. Mobile phase: A: TFA/$H_2O$=0.075% v/v; B: ACN Gradient: B % 40-100, 16 min. Flow rate: 25 ml/min. Monitor wavelength: 220&254 nm) to give tert-butyl 7-(2-(((2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (66.0 mg, 103.0 umol, 17.2% yield) as white solid, $^1$H NMR (DMSO-$d_6$, 400 MHz) δ 8.57 (s, 1H), 8.11 (s, 1H), 7.76 (d, J=8.2 Hz, 1H), 7.48 (s, 1H), 7.39 (d, J=8.8 Hz, 1H), 6.08 (dd, J=10.8, 17.6 Hz, 1H), 5.59 (d, J=6.8 Hz, 1H), 5.13-4.83 (m, 5H), 4.68 (d, J=16.6 Hz, 1H), 2.28-1.94 (m, 3H), 1.69 (m, 2H), 1.59 (s, 10H), 1.51-1.21 (m, 7H), 1.15-1.00 (m, 4H), 0.95-0.78 (m, 3H), 0.69 (d, J=5.6 Hz, 3H). MS (ESI): mass calcd. for $C_{34}H_{46}BFN_2O_8$ 640.33, m/z found 656.8 (M+$H_2O$—H)$^-$. HPLC: 93.1% in 220 nm; 93.1% in 254 nm.

To a solution of tert-butyl 7-(2-(((2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (200.0 mg, 312.2 umol, 1.0 eq) in MeOH (25 mL) was added aqueous HCl (2N, 10 mL), the mixture was stirred at 25° C. for 2 hours. The mixture was concentrated under reduced pressure to remove methanol. The aqueous phase was extracted with EtOAc (20 mL×3). The combined organic phase was washed with saturated brine (20 mL×2), dried with anhydrous $Na_2SO_4$, filtered and concentrated in vacuum to afford crude product, which was purified by prep-HPLC (Instrument: Gilson 281 semi-preparative HPLC system. Column: Synergi Max-RP C12 100×30 4 u. Mobile phase: A: TFA/$H_2O$=0.075% v/v; B: ACN Gradient: B % 20-100, 14.6 min. Flow rate: 25 ml/min. Monitor wavelength: 220&254 nm) to give (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1,2-dihydrobenzo[d][1,2,3]diazaborinin-7-yl)oxy)acetate (12.0 mg, 22.2 umol, 7.1% yield) as white solid. $^1$H NMR (DMSO-$d_6$, 400 MHz) δ. 9.80 (s, 1H), 7.91 (s, 1H), 7.74-7.62 (m, 2H), 7.29 (d, J=8.0 Hz, 1H), 6.07 (dd, J=11.0, 17.8 Hz, 1H), 5.58 (d, J=8.8 Hz, 1H), 5.09 (dd, J=8.2, 17.6 Hz, 2H), 4.98 (d, J=10.0 Hz, 1H), 4.91-4.75 (m, 3H), 3.34 (s, 1H), 2.61 (s, 1H), 2.22-1.74 (m, 5H), 1.46-1.16 (m, 7H), 1.04 (s, 3H), 0.87-0.77 (m, 3H), 0.65 (d, J=6.0 Hz, 3H). MS (ESI): mass calcd. for $C_{29}H_{38}BFN_2O_6$ 540.3, m/z found 541.3 (M+H)$^+$. HPLC: 93.6% in 220 nm; 92.5% in 254 nm.

75. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl)oxy)acetate

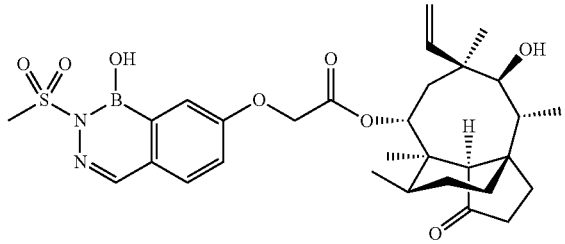

A stirred mixture of 4-(benzyloxy)-2-(4,4,5,5-tetramethyl-1,3,2-dioxaborolan-2-yl) benzaldehyde (2.0 g, 5.9 mmol) and methanesulfonohydrazide (0.06 g, 5.90 mmol) in EtOH (20 mL) was stirred at 90° C. for 20 hrs. The mixture was concentrated to give a crude product which was purified by silica gel chromatography (petroleum ether: EtOAc=100:1 to 3:1) to give 7-(benzyloxy)-2-(methylsulfonyl)benzo[d][1,2,3]diazaborinin-1 (2H)-ol (1.0 g, 51.0% yield) as a yellow solid. $^1$H NMR (CDCl$_3$, 400 MHz) δ 8.06 (s, 1H), 7.70 (d, J=2.4 Hz, 1H), 7.60 (d, J=8.4 Hz, 1H), 7.45-7.42 (m, 2H), 7.41-7.35 (m, 4H), 7.16 (s, 1H), 5.20 (s, 2H), 3.33 (s, 3H).

To a stirred suspension of 7-(benzyloxy)-2-(methylsulfonyl)benzo[d][1,2,3]diazaborinin-1(2H)-ol (4.0 g, 12.1 mmol) in EtOAc (50 mL) was added Pd/C (1.0 g) under $H_2$. The resulting mixture was stirred at r.t overnight. The mixture was concentrated to give 2-(methylsulfonyl)benzo[d][1,2,3]diazaborinine-1,7(2H)-diol (2.5 g, 86.0% yield) as a yellow solid.

A stirred mixture of 2-(methylsulfonyl)benzo[d][1,2,3]diazaborinine-1,7(2H)-diol (100.0 mg, 0.4 mmol) and Tospleuromutilin (222 mg, 0.4 mmol), $K_2CO_3$ (172.0 mg, 1.3 mmol) in DMF (5 mL) was stirred at 50° C. for 12 hrs. The mixture was diluted with water and extracted with EtOAc The combined organic layers were washed with brine, dried over anhydrous $Na_2SO_4$ and concentrated to give the crude product which was purified with prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl)oxy)acetate (68.0 mg, 26.9%). $^1$H NMR (DMSO-$d_6$, 400 MHz) δ 8.18 (s, 1H), 8.80-8.78 (m, 1H), 8.66 (s, 1H), 7.41-7.39 (m, 1H), 6.12-6.08 (m, 1H), 5.12-5.08 (m, 1H), 5.01-4.98 (m, 2H), 4.88-4.86 (m, 2H), 3.37 (s, 5H), 2.40 (s, 1H), 2.09-2.03 (m, 4H), 1.70-1.45 (m, 3H), 1.33-1.25 (m, 8H), 1.05-0.95 (m, 4H), 0.82-0.80 (m, 3H), 0.65-0.64 (m, 3H).

76. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((8-fluoro-1-hydroxy-2-(methylsulfonyl)-1,2-dihydrobenzo[d][1,2,3]diazaborinin-7-yl)oxy)acetate

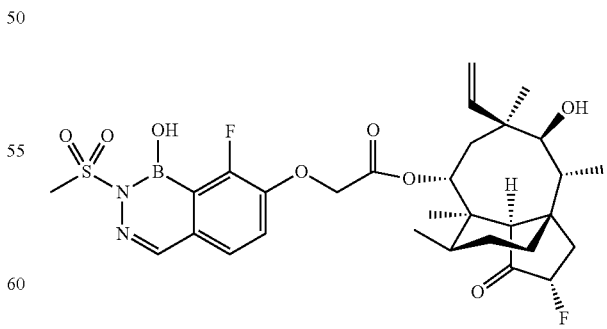

4-benzyloxy-3-fluoro-2-(4,4,5,5-tetramethyl-1,3,2-dioxaborolan-2-yl)benzaldehyde (8.0 g, 22.5 mmol, 1.0 eq) and NaIO$_4$ (24.0 g, 112.3 mmol, 5.0 eq) in THF (50 mL) and H$_2$O (50 mL) were stirred at 25° C. overnight, TLC shown major as desired, the mixture was filtered, the filtrate was treated with EtOAc. The organic layer was evaporated to give product (3-benzyloxy-2-fluoro-6-formyl-phenyl) boronic acid (6.0 g, crude) as white solid. $^1$HNMR (DMSO-$d_6$, 400 MHz) δ 9.80 (d, J=2.8 Hz, 1H), 8.27-8.09 (br. s., 2H), 7.80-7.66 (m, 1H), 7.53-7.21 (m, 6H), 5.30 (s, 2H).

To a solution of (3-benzyloxy-2-fluoro-6-formyl-phenyl) boronic acid and MsNH$_2$NH$_2$ (6.0 g, 21.9 mmol, 1.0 eq) in EtOH (50 mL) was stirred at 50° C. for 12 hours. The mixture was filtered to give 7-(benzyloxy)-8-fluoro-2-(methylsulfonyl)benzo[d][1,2,3]diazaborinin-1 (2H)-ol (4.0 g, 11.5 mmol, 52.5% yield) as yellow solid. $^1$H NMR (DMSO-$d_6$, 400 MHz) δ 7.90 (d, J=2.2 Hz, 1H), 7.62-7.28 (m, 6H), 5.27 (s, 2H), 3.24 (s, 3H).

To a solution of 7-(benzyloxy)-8-fluoro-2-(methylsulfonyl)benzo[d][1,2,3]diazaborinin-1 (2H)-ol (1.0 g, 2.9 mmol, 1.0 eq) in EtOAc (100 mL) was Pd/C (600.0 mg, 10%) under N$_2$. The suspension was degassed under vacuum and purged with H$_2$ several times. The mixture was stirred under H$_2$ (40 psi) at 20° C. for 2 hours. TLC (Petroleum ether: EtOAc=100:1 to 1) showed the starting material was consumed completely. The reaction mixture was filtered and the filtrate was concentrated to give 8-fluoro-2-(methylsulfonyl)benzo[d][1,2,3]diazaborinine-1,7(2H)-diol (700.0 mg, 2.7 mmol, 94.5% yield) as white solid. $^1$H NMR (DMSO-$d_6$, 400 MHz) δ 10.53 (s, 1H), 8.02 (s, 1H), 7.44 (d, J=7.8 Hz, 1H), 7.37-7.28 (m, 2H), 3.33 (s, 3H).

To a solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl2-(tosyloxy) acetate (600.0 mg, 1.0 mmol, 1.0 eq), 8-fluoro-2-(methylsulfonyl)benzo[d][1,2,3]diazaborinine-1,7(2H)-diol (267.5 mg, 1.0 mmol, 1.0 eq) and K$_2$CO$_3$ (429.9 mg, 3.1 mmol, 3.0 eq) in DMF (15 mL) was stirred at 50° C. for 2 hour. Water 50 mL was added to the mixture and acidified with 2N HCl (aq.), white solid was precipitated and filtered to give the crude product (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl2-((8-fluoro-1-hydroxy-2-(methylsulfonyl)-1,2-dihydrobenzo[d][1,2,3]diazaborinin-7-yl)oxy)acetate (550.0 mg, crude) as yellow solid.

To a solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl2-((8-fluoro-1-hydroxy-2-(methylsulfonyl)-1,2-dihydrobenzo[d][1,2,3]diazaborinin-7-yl)oxy)acetate (400.0 mg, 601.9 umol, 1.0 eq) and K$_2$CO$_3$ (414.0 mg, 3.0 mmol, 5.0 eq) in MeOH (50 mL) was stirred at 50° C. for 5 hours. Water 50 mL was added to the mixture and acidified with 2N HCl (aq.), white solid was precipitated and filtered to give the crude product, which was purified by prep-HPLC (Instrument: Gilson 281 semi-preparative HPLC system. Column: Luna C18 100×30 mm, 5 m. Mobile phase: A: 5 mM NH$_4$HCO$_3$ in H$_2$O; B: ACN Gradient: B % 15-100, 14.6 min. Flow rate: 20 ml/min. Monitor wavelength: 220&254 nm) to give (2S,3aR,4R,5R,7S,8S,9R,9aS,12R)-2-fluoro-8-hydroxy-4,7,9,12-tetramethyl-3-oxo-7-vinyldecahydro-4, 9a-propanocyclopenta[8]annulen-5-yl 2-((8-fluoro-1-hydroxy-2-(methylsulfonyl)-1,2-dihydrobenzo[d][1,2,3]diazaborinin-7-yl)oxy)acetate (40.0 mg, 62.8 umol, 10.4% yield) as white solid. $^1$H NMR (DMSO-$d_6$, 400 MHz) δ 7.84 (br. s., 1H), 7.35 (br. s., 2H), 6.10 (dd, J=11.2, 17.8 Hz, 1H), 5.58 (d, J=7.8 Hz, 1H), 5.13-4.99 (m, 2H), 4.99-4.82 (m, 2H), 4.69 (d, J=6.2 Hz, 1H), 3.20 (s, 3H), 2.61 (s, 1H), 2.28-1.96 (m, 4H), 1.87-1.49 (m, 3H), 1.44-1.18 (m, 6H), 1.07 (s, 3H), 0.84 (d, J=7.0 Hz, 3H), 0.66 (d, J=6.8 Hz, 3H). MS (ESI): mass calcd. for C$_{30}$H$_{39}$BF$_2$N$_2$O$_8$S 636.2, m/z found 637.2 (M+H)$^+$. HPLC: 98.4% in 220 nm; 100% in 254 nm.

77. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((8-fluoro-1-hydroxy-2-(methylsulfonyl)-1,2-dihydrobenzo[d][1,2,3]diazaborinin-7-yl)oxy)acetate

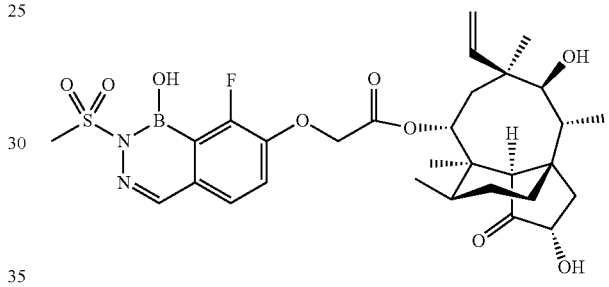

A solution of (2S,3aR,4R,5R,7S,8S,9R,9aS,12R)-2,8-dihydroxy-4,7,9,12-tetramethyl-3-oxo-7-vinyldecahydro-4, 9a-propanocyclopenta[8]annulen-5-yl 2-(tosyloxy)acetate (400.0 mg, 729.0 umol, 1.0 eq), 8-fluoro-2-(methylsulfonyl)benzo[d][1,2,3]diazaborinine-1,7(2H)-diol (188.1 mg, 729.0 umol, 1.0 eq) and K$_2$CO$_3$ (302.3 mg, 2.2 mmol, 3.0 eq) in DMF (15 mL) was stirred at 50° C. for 2 hours. Water 50 mL was added to the mixture and acidified with 2N HCl (aq.), white solid was precipitated and filtered to give the crude product, which was purified by prep-HPLC (Instrument: Gilson 281 semi-preparative HPLC system. Column: Luna C18 100×30 mm, 5 μm. Mobile phase: A: 5 mM NH$_4$HCO$_3$ in H$_2$O; B: ACN Gradient: B % 15-100, 14.6 min. Flow rate: 20 ml/min. Monitor wavelength: 220&254 nm) to give (2S,3aR,4R,5R,7S,8S,9R,9aS,12R)-2,8-dihydroxy-4,7,9, 12-tetramethyl-3-oxo-7-vinyldecahydro-4,9a-propanocyclopenta[8]annulen-5-yl2-((8-fluoro-1-hydroxy-2-(methylsulfonyl)-1,2-dihydrobenzo[d][1,2,3]diazaborinin-7-yl)oxy) acetate (30.0 mg, 47.3 umol, 6.5% yield) as white solid. $^1$H NMR (DMSO-$d_6$, 400 MHz) δ 7.75 (m, 1H), 7.28-7.21 (m, 2H), 6.11 (dd, J=11.2, 17.6 Hz, 1H), 5.60 (d, J=8.0 Hz, 1H), 5.54 (d, J=6.0 Hz, 1H), 5.12 (d, J=17.6 Hz, 1H), 5.00 (d, J=11.2 Hz, 1H), 4.88 (d, J=6.0 Hz, 2H), 4.65 (d, J=6.4 Hz, 1H), 3.81-3.70 (m, 1H), 3.16 (s, 3H), 2.36 (s, 1H), 2.14-1.95 (m, 2H), 1.82-1.72 (m, 2H), 1.41-1.16 (m, 9H), 1.07 (s, 3H), 0.83 (d, J=7.2 Hz, 3H), 0.66 (d, J=6.0 Hz, 3H). MS (ESI):

mass calcd. for $C_{30}H_{40}BFN_2O_9S$ 634.3, m/z found 657.3 $(M+Na)^+$. HPLC: 100% in 220 nm; 100% in 254 nm.

78. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl)oxy)acetate

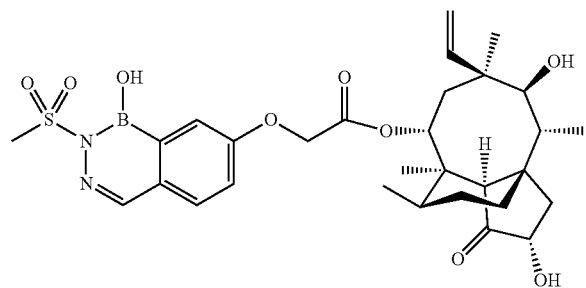

(2S,3aR,4R,5R,7S,8S,9R,9aS,12R)-5-(2-chloroacetoxy)-8-(formyloxy)-4,7,9,12-tetramethyl-3-oxo-7-vinyldecahydro-4,9a-propanocyclopenta[8]annulen-2-yl 2,2-dichloroacetate (500.0 mg, 906.0 umol, 1.0 eq) and KI (752.0 mg, 4.5 mmol, 5.0 eq) in $CH_3CN$ (50 mL) were stirred at 80° C. for 12 hours. The mixture was filtered, the organic layer was evaporated to give (2S,3aR,4R,5R,7S,8S,9R,9aS,12R)-5-(2-chloroacetoxy)-8-(formyloxy)-4,7,9,12-tetramethyl-3-oxo-7-vinyldecahydro-4,9a-propanocyclopenta[8]annulen-2-yl 2,2-dichloroacetate (520.0 mg, 808.3 umol, 89.2% yield). $^1H$ NMR ($CDCl_3$, 400 MHz) δ. 8.15 (s, 1H), 6.25 (dd, J=11.2, 17.6 Hz, 1H), 6.01 (s, 1H), 5.66 (d, J=7.8 Hz, 1H), 5.38-5.18 (m, 2H), 5.10 (t, J=9.0 Hz, 1H), 4.95 (d, J=6.4 Hz, 1H), 3.71-3.56 (m, 2H), 2.57-2.40 (m, 2H), 2.22-2.08 (m, 2H), 2.02-1.88 (m, 2H), 1.68-1.37 (m, 6H), 1.09 (s, 3H), 0.87 (d, J=7.0 Hz, 3H), 0.76 (d, J=6.8 Hz, 3H).

A solution of (2S,3aR,4R,5R,7S,8S,9R,9aS,12R)-8-(formyloxy)-5-(2-iodoacetoxy)-4,7,9,12-tetramethyl-3-oxo-7-vinyldecahydro-4,9a-propanocyclopenta[8]annulen-2-yl, 2-dichloroacetate (500.0 mg, 777.2 umol, 1.00 eq) and $K_2CO_3$ (322.3 mg, 2.3 mmol, 3.0 eq) in MeOH (50 mL) was stirred at room temperature for 12 hours. The mixture was filtered and the solvent was evaporated to give the crude product (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-iodoacetate (400.0 mg, crude) as yellow solid, and used directly.

A solution of (2S,3aR,4R,5R,7S,8S,9S,9aS,12R)-2-hydroxy-4,7,8,9,12-pentamethyl-3-oxo-7-vinyldecahydro-4,9a-propanocyclopenta[8]annulen-5-yl 2-(tosyloxy)acetate (110.0 mg, 200.4 umol, 1.0 eq), 2-methylbenzo[d][1,2,3]diazaborinine-1,7(2H)-diol (35.2 mg, 200.48 umol, 1.0 eq) and $K_2CO_3$ (83.1 mg, 601.4 umol, 3.0 eq) in DMF (5 mL) was stirred at 50° C. for 2 hours. Water was added and adjusted pH<4 with 2N aq. HCl white solid was precipitated and filtered to give the crude product, which was purified by prep-HPLC (Instrument: Gilson 281 semi-preparative HPLC system. Column: Luna C18 100×30 mm, 5 μm. Mobile phase: A: $TFA/H_2O$=0.075% v/v; B: ACN Gradient: B % 30-100, 14.6 min. Flow rate: 25 ml/min. Monitor wavelength: 220&254 nm) to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl)oxy)acetate (25.0 mg, 45.3 umol, 22.6% yield) as yellow solid, $^1H$ NMR (DMSO-$d_6$, 400 MHz) δ 8.19 (s, 1H), 7.80 (d, J=8.4 Hz, 1H), 7.66 (s, 1H), 7.40 (d, J=6.4 Hz, 1H), 6.09 (dd, J=11.2, 17.6 Hz, 1H), 5.60 (d, J=8.0 Hz, 1H), 5.11-4.81 (m, 4H), 3.75 (t, J=8.4 Hz, 1H), 3.48 (s, 3H), 3.31 (m, 1H), 2.35 (s, 1H), 2.07 (m, 2H), 1.87-1.70 (m, 2H), 1.51-1.18 (m, 7H), 1.10-0.99 (m, 4H), 0.83 (d, J=7.0 Hz, 3H), 0.64 (d, J=6.8 Hz, 3H). MS (ESI): mass calcd. for $C_{30}H_{41}BN_2O_9S$ 616.3, m/z found 632.8 $(M+H_2O-H)^-$. HPLC: 99.0% in 220 nm; 98.8% in 254 nm.

79. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl)oxy)acetate

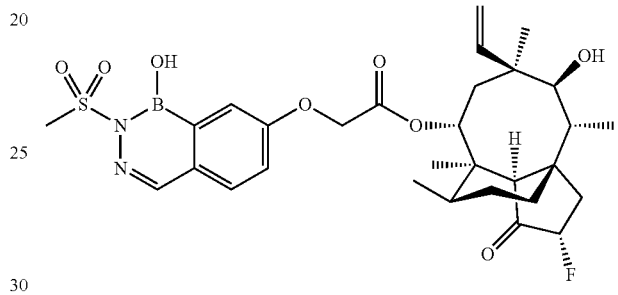

(2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy)acetate (350.0 mg, 605.0 umol), 2-(methylsulfonyl)benzo[d][1,2,3]diazaborinine-1,7(2H)-diol (145.0 mg, 605.0 umol) and potassium carbonate (250.0 mg, 1.8 mmol) in DMF (25.0 mL) were stirred at 50° C. for 2 hours, water was added, the mixture was filtered to give (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-2-(methylsulfonyl)-1,2-dihydrobenzo[d][1,2,3]diazaborinin-7-yl) oxy)acetate (300.0 mg, crude). Potassium carbonate (192.0 mg, 1.4 mmol) was added to (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-2-(methylsulfonyl)-1,2-dihy drobenzo[d][1,2,3]diazaborinin-7-yl)oxy)acetate (0.3 g, 464.0 umol) in MeOH (20.0 mL) and THF (20.0 mL). The mixture was stirred at 50° C. for 2 hours, the mixture was adjusted pH<4 with 2N HCl. Solvent was evaporated, the crude product was purified by prep-HPLC to give (2S,3aR,4R,5R,7S,8S,9R,9aS,12R)-2-fluoro-8-hydroxy-4,7,9,12-tetramethyl-3-oxo-7-vinyl decahydro-4,9a-propanocyclopenta[8]annulen-5-yl2-((1-hydroxy-2-(methylsulfonyl)-1,2-dihydrobenzo[d][1,2,3]diazaborinin-7-yl)oxy)acetate (46.0 mg, 12.0% yield). $^1H$ NMR (DMSO-d6, 400 MHz) δ 8.19 (s, 1H), 7.80 (d, J=8.4 Hz, 1H), 7.67 (s, 1H), 7.40 (d, J=8.8 Hz, 1H), 6.08 (dd, J=11.4, 18.1 Hz, 1H), 5.58 (d, J=9.0 Hz, 1H), 5.09 (d, J=17.6 Hz, 2H), 5.00 (d, J=11.8 Hz, 1H), 4.95 (br. s., 1H), 4.90 (d, J=10.4 Hz, 2H), 3.37 (s, 3H), 3.34 (br. s., 1H), 2.62 (br. s., 1H), 2.25-1.93 (m, 4H), 1.81 (d, J=14.8 Hz, 1H), 1.50-1.18 (m, 9H), 1.05 (s, 3H), 0.84 (d, J=7.2 Hz, 3H), 0.67 (d, J=6.0 Hz, 3H). MS (ESI): mass calcd. for $C_{30}H_{40}BFN_2O_8S$ 618.26, m/z found 635.3$[M+H_2O-H]^-$. HPLC: 95.0% (220 nm), 96.5% (254 nm).

80. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-2-(methylsulfonyl)-1,2-dihydrobenzo[d][1,2,3]diazaborinin-7-yl)oxy)acetate 81. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-1,2-dihydrobenzo[d][1,2,3]diazaborinin-7-yl)oxy)acetate

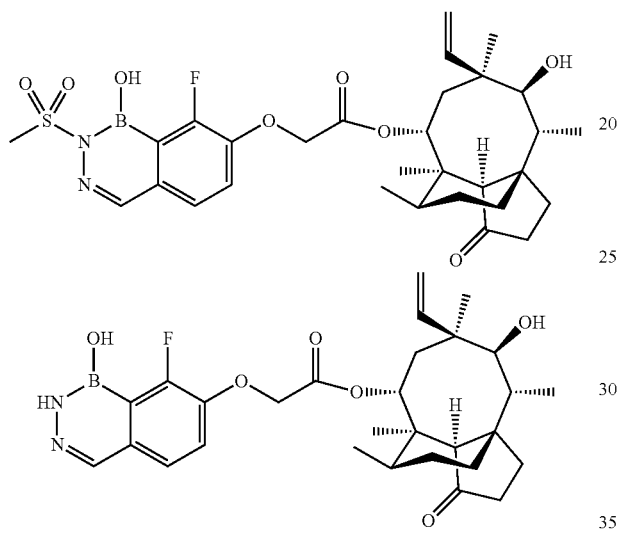

A solution of Tos-pleuromutilin (250.0 mg, 469.3 umol, 1.0 eq), 8-fluoro-2-(methylsulfonyl)benzo[d][1,2,3]diazaborinine-1,7(2H)-diol (121.1 mg, 469.3 umol, 1.0 eq) and $K_2CO_3$ (194.6 mg, 1.4 mmol, 3.0 eq) in DMF (15 mL) was stirred at 50° C. for 2 hours. Water 50 mL was added to the mixture and acidified with 2N HCl (aq.), white solid was precipitated and filtered to give the crude product, which was further purified by prep-HPLC (Instrument: Gilson 281 semi-preparative HPLC system. Column: Synergi Max-RP C12 100×30 4u. Mobile phase: A: $TFA/H_2O$=0.075% v/v; B: ACN Gradient: B % 35-100, 14.6 min. Flow rate: 25 ml/min. Monitor wavelength: 220&254 nm) to give two products:

(3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-2-(methylsulfonyl)-1,2-dihydrobenzo[d][1,2,3]diazaborinin-7-yl)oxy)acetate (16.0 mg, 25.9 umol, 5.5% yield) as yellow solid. $^1$H NMR (DMSO-$d_6$, 400 MHz) δ 7.90 (s, 1H), 7.50-7.28 (m, 2H), 6.13 (m, 1H), 5.61 (s, 1H), 5.19-4.84 (m, 3H), 4.54 (s, 1H), 3.24 (s, 3H), 2.41 (s, 1H), 2.07 (m, 4H), 1.73-1.19 (m, 11H), 1.06 (m, 4H), 0.82 (d., J=6.8 Hz, 3H), 0.65 (d, J=6.8 Hz, 3H). MS (ESI): mass calcd. for $C_{30}H_{40}BFN_2O_8S$ 618.3, m/z found 619.2 (M+H)$^+$. HPLC: 95.2% in 220 nm; 98.0% in 254 nm.

and (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-1,2-dihydrobenzo[d][1,2,3]diazaborinin-7-yl)oxy)acetate (26.0 mg, 52.2 umol, 11.1% yield) as white solid. $^1$H NMR (DMSO-$d_6$, 400 MHz) δ 9.64 (s, 1H), 7.93 (d, J=2.2 Hz, 1H), 7.55-7.40 (m, 2H), 6.10 (dd, J=11.2, 17.8 Hz, 1H), 5.60 (d, J=8.4 Hz, 1H), 5.11-4.97 (m, 2H), 4.94 (d, J=3.2 Hz, 1H), 3.41 (d, J=6.2 Hz, 1H), 2.40 (s, 1H), 2.27-1.97 (m, 4H), 1.73-1.20 (m, 11H), 1.04 (s, 4H), 0.81 (d, J=7.0 Hz, 3H), 0.64 (d, J=7.0 Hz, 3H). MS (ESI): mass calcd. for $C_{29}H_{38}BFN_2O_6$ 540.3, m/z found 541.3 (M+H)$^+$. HPLC: 96.7% in 220 nm; 97.9% in 254 nm.

82. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-2-methyl-1,2-dihydrobenzo[d][1,2,3]diazaborinin-7-yl)oxy)acetate

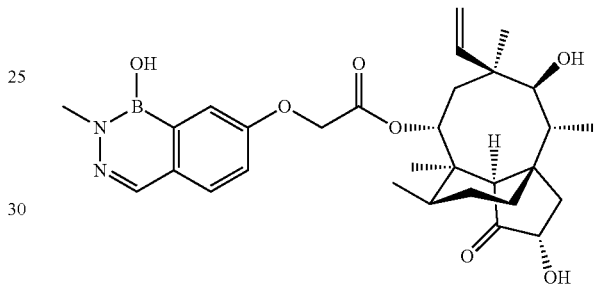

To a solution of (2S,3aR,4R,5R,7S,8S,9S,9aS,12R)-2-hydroxy-4,7,8,9,12-pentamethyl-3-oxo-7-vinyldecahydro-4,9a-propanocyclopenta[8]annulen-5-yl 2-(tosyloxy)acetate (110.0 mg, 200.4 umol, 1.0 eq), 2-methylbenzo[d][1,2,3]diazaborinine-1,7(2H)-diol (35.2 mg, 200.48 umol, 1.0 eq) and $K_2CO_3$ (83.1 mg, 601.4 umol, 3.0 eq) in DMF (5 mL) was stirred at 50° C. for 2 hours. Water (20 mL) was added and the solution was acidified to pH=4 with 2N aq. HCl acid, white solid was precipitated and the mixture was filtered to give the crude product, which was purified by prep-HPLC (Instrument: Gilson 281 semi-preparative HPLC system. Column: Luna C18 100×30 mm, 5 μm. Mobile phase: A: $TFA/H_2O$=0.075% v/v; B: ACN Gradient: B % 30-100, 14.6 min. Flow rate: 25 ml/min. Monitor wavelength: 220&254 nm) to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-2-methyl-1,2-dihydrobenzo[d][1,2,3]diazaborinin-7-yl)oxy)acetate (25.0 mg, 45.3 umol, 22.6% yield) as white solid, $^1$H NMR (DMSO-$d_6$, 400 MHz) δ 7.91 (s, 1H), 7.77 (d, J=2.4 Hz, 1H), 7.68 (d, J=8.4 Hz, 1H), 7.28 (dd, J=2.4, 8.8 Hz, 1H), 6.09 (dd, J=11.2, 17.6 Hz, 1H), 5.60 (d, J=8.0 Hz, 1H), 5.10 (d, J=17.6 Hz, 1H), 5.00 (d, J=11.2 Hz, 1H), 4.81 (t, J=15.2 Hz, 2H), 3.75 (t, J=8.4 Hz, 1H), 3.48 (s, 3H), 3.31 (d, J=5.6 Hz, 1H), 2.35 (s, 1H), 2.07-1.95 (m, 2H), 1.87-1.70 (m, 2H), 1.51-1.18 (m, 9H), 1.04 (s, 3H), 0.83 (d, J=7.0 Hz, 3H), 0.64 (d, J=6.2 Hz, 3H). MS (ESI): mass calcd. for $C_{30}H_{41}BN_2O_7$ 552.3, m/z found 553.3 (M+H)$^+$. HPLC: 98.9% in 220 nm; 97.7% in 254 nm.

181

83. (3aR,4R,5R,7S,8S,9aS,12R)-8-hydroxy-4,7,12-trimethyl-3-oxo-7-vinyldecahydro-4,9a-propanocyclopenta[8]annulen-5-yl 2-((1-hydroxy-2-methyl-1,2-dihydrobenzo[d][1,2,3]diazaborinin-7-yl)oxy)acetate

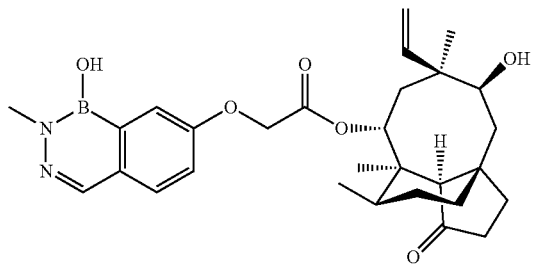

To a stirred solution of 4-(benzyloxy)-2-(4,4,5,5-tetramethyl-1,3,2-dioxaborolan-2-yl) benzaldehyde (6.0 g, 17.7 mmol) in EtOH (300 mL) was added the methylhydrazine hydrochloride (1.3 g, 17.7 mmol). The mixture was stirred at 50° C. for 12 hours. The mixture was cooled and the solid was filtered, washed by EtOH. 7-(benzyloxy)-2-methylbenzo[d][1,2,3]diazaborinin-1(2H)-ol was obtained without further purification (3.6 g, 69.0% yield). $^1$H NMR (DMSO-$d_6$, 400 MHz) δ 7.94 (s, 2H), 7.71 (d, J=8.0 Hz, 1H), 7.50 (d, J=8.0 Hz, 1H), 7.41-7.34 (m, 5H), 5.20 (s, 2H), 3.49 (s, 3H).

To a stirred solution of 7-(benzyloxy)-2-methylbenzo[d][1,2,3]diazaborinin-1(2H)-ol (2.6 g, 9.8 mmol) in EtOH (30 mL) was added Pd/C (1 g) and the mixture was stirred at 50 psi under hydrogen atmosphere for 12 hours. The mixture was filtered through celite and the filtrate was concentrated in vacuo to give 2-methylbenzo[d][1,2,3]diazaborinine-1,7(2H)-diol (1.1 g, 64.0% yield) as white solid without further purification. $^1$H NMR (DMSO-$d_6$, 400 MHz) δ 7.93 (s, 1H), 7.63 (d, J=8.0 Hz, 1H), 7.55 (s, 1H), 7.16 (m, 1H), 3.47 (s, 3H).

Tos-pleuromutilin (500.0 mg, 938.0 umol), 2-methylbenzo[d][1,2,3]diazaborinine-1,7(2H)-diol (165.0 mg, 938.0 umol) and potassium carbonate (389.0 mg, 2.8 mmol) in DMF with cata. amount potassium iodide were heated to 50° C. for 4 hours, water was added and adjusted pH<4 with 2N aq. HCl white solid was precipitated and filtered to give to give crude product which was purified by prep-HPLC (Instrument: Gilson 281 semi-preparative HPLC system. Column: Luna C18 100×30 mm, 5 μm. Mobile phase: A: TFA/H$_2$O=0.075% v/v; B: ACN Gradient: B % 35-100, 16 min. Flow rate: 20 ml/min. Monitor wavelength: 220&254 nm) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-2-methyl-1,2-dihydrobenzo[d][1,2,3]diazaborinin-7-yl)oxy)acetate (121.0 mg, 74.0%) as white solid. $^1$H NMR (DMSO-$d_6$, 400 MHz) δ 8.31 (s, 1H), 7.90 (s, 1H), 7.76 (br. s., 1H), 7.68 (d, J=8.8 Hz, 1H), 7.28 (d, J=7.3 Hz, 1H), 6.10 (dd, J=10.8, 17.2 Hz, 1H), 5.60 (d, J=7.8 Hz, 1H), 5.14-4.93 (m, 2H), 4.88-4.71 (m, 2H), 4.54 (d, J=5.8 Hz, 1H), 3.47 (s, 2H), 3.41 (br. s., 1H), 3.07 (s, 3H), 2.41 (br. s., 1H), 2.26-1.95 (m, 4H), 1.73-0.92 (m, 10H), 0.90-0.76 (m, 3H), 0.63 (d, J=6.0 Hz, 3H). MS (ESI): mass calcd. for $C_{30}H_{41}BN_2O_6$ 536.3, m/z found 535.3 (M−H)$^−$. HPLC: 90.7% in 220 nm; 93.3% in 254 nm.

182

84. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-2-methyl-1,2-dihydrobenzo[d][1,2,3]diazaborinin-7-yl)oxy)acetate

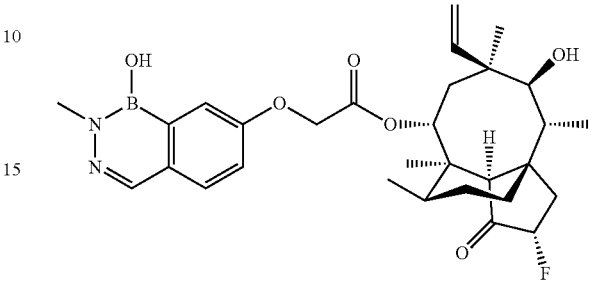

To a mixture of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy) acetate (157.0 mg, 271.3 umol, 1.0 eq) and 2-methylbenzo[d][1,2,3]diazaborinine-1,7(2H)-diol (50.1 mg, 284.87 umol, 1.1 eq) in DMF (5 mL) was added K$_2$CO$_3$ (75.0 mg, 542.6 umol, 2.0 eq) in one portion at r.t. under N$_2$. The mixture was stirred at 50-60° C. for 4.5 hours. The mixture was cooled to 25° C. and poured into ice-water. The mixture was acidified with HCl (aq) and filtered to give the crude (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-2-methyl-1,2-dihydrobenzo [d][1,2,3]diazaborinin-7-yl)oxy) acetate (100.0 mg, 120.1 umol, 44.3% yield, 70.0% purity) as white solid.

To a mixture of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-2-methyl-1,2-dihydrobenzo [d][1,2,3] diazaborinin-7-yl)oxy)acetate (100.0 mg, 120.1 umol, 1.0 eq) in MeOH (10 mL) was added K$_2$CO$_3$ (166.1 mg, 1.2 mmol, 10.0 eq) in one portion at room temperature under N$_2$. The mixture was stirred at 50° C. for 10 hours. The mixture was cooled to 25° C., and concentrated in reduced pressure. The residue was poured into ice-water and extracted with EtOAc (30 mL×3). Dried with anhydrous Na$_2$SO$_4$, filtered and concentrated in vacuum. The residue was purified by prep-HPLC (Instrument: Gilson 281 semi-preparative HPLC system. Column: Luna C18 100×30 mm, 5 μm. Mobile phase: A: TFA/H$_2$O=0.075% v/v; B: ACN Gradient: B % 30-100, 16 min. Flow rate: 20 ml/min. Monitor wavelength: 220&254 nm) to afford (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta [8]annulen-5-yl 2-((1-hydroxy-2-methyl-1,2-dihydrobenzo[d][1,2,3] diazaborinin-7-yl)oxy)acetate (15.0 mg, 27.1 umol, 22.5% yield) as light yellow solid. $^1$H NMR (DMSO-$d_6$, 400 MHz) δ 8.31 (s, 1H), 7.90 (s, 1H), 7.76 (s, 1H), 7.68 (d, J=8.2 Hz, 1H), 7.28 (d, J=8.0 Hz, 1H), 6.03-6.14 (m, 1H), 5.50-5.62 (m, 1H), 4.94-5.14 (m, 3H), 4.63-4.89 (m, 4H), 3.47 (s, 3H), 2.41 (s, 1H), 1.18-1.43 (m, 9H), 1.04 (br.s., 3H), 0.82 (d, J=7.0 Hz, 3H), 0.65 (m, 3H). MS (ESI): mass calcd. for $C_{30}H_{40}BFN_2O_6$ 554.3, m/z found 553.3 (M−H)$^−$. HPLC: 95.3% in 220 nm; 94.3% in 254 nm.

85. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((8-fluoro-1-hydroxy-2-methyl-1,2-dihydrobenzo[d][1,2,3]diazaborinin-7-yl)oxy)acetate

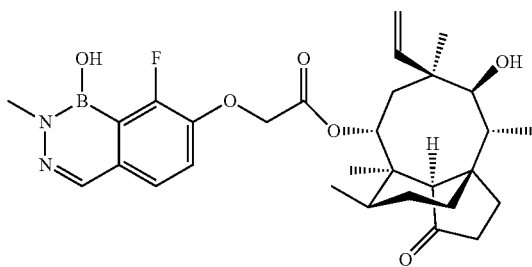

A solution of 4-(benzyloxy)-3-fluoro-2-(4,4,5,5-tetramethyl-1,3,2-dioxaborolan-2-yl)benzaldehyde (500.0 mg, 1.4 mmol) and methylhydrazine hydrochloride acid (140.0 mg, 1.7 mmol) in EtOH (10 mL) was stirred at 50° C. for 2 hours. After cooled to room temperature, the mixture was filtered to give 7-(benzyloxy)-8-fluoro-2-methylbenzo[d][1,2,3]diazaborinin-1(2H)-ol (340.0 mg, 85.5% yield) as white solid. $^1$H NMR (DMSO-d$_6$, 400 MHz) δ 7.92 (d, J=2.8 Hz, 1H), 7.70-7.63 (m, 1H), 7.55 (d, J=8.4 Hz, 1H), 7.51-7.46 (m, 2H), 7.44-7.32 (m, 3H), 5.29 (s, 2H), 3.48 (s, 3H).

To a solution of 7-(benzyloxy)-8-fluoro-2-methylbenzo[d][1,2,3]diazaborinin-1(2H)-ol (200.0 mg, 704.0 umol) in EtOAc (20 mL) was added Pd—C (10%, 2 g) under N$_2$. The suspension was degassed under vacuum and purged with H$_2$ several times. The mixture was stirred under H$_2$ (40 psi) at 20° C. for 2 hours. The reaction mixture was filtered and the filter was concentrated to give 8-fluoro-2-methylbenzo[d][1,2,3]diazaborinine-1,7(2H)-diol (29.0 mg, 21.2% yield) as white solid.

A solution of Tos-pleuromutilin (79.6 mg, 149.5 umol), 8-fluoro-2-methylbenzo[d][1,2,3]diazaborinine-1,7(2H)-diol (29.0 mg, 149.5 umol, 1.0 eq) and K$_2$CO$_3$ (61.9 mg, 448.5 umol) in DMF (5 mL) was stirred at 50° C. for 3 hours. Water was added to the mixture, and filtered to give crude product, which was purified by pre-HPLC (column: Waters Xbridge 150×25 mm, 5 μm; liquid phase: [A-10 mM NH$_4$HCO$_3$ in H$_2$O; B-ACN] B %: 1%-25%, 12 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((8-fluoro-1-hydroxy-2-methyl-1,2-dihydrobenzo[d][1,2,3]diazaborinin-7-yl)oxy)acetate (36.0 mg, 43.4% yield) as yellow solid. $^1$H NMR (DMSO-d$_6$, 400 MHz) δ 7.93 (d, J=2.4 Hz, 1H), 7.54-7.44 (m, 2H), 6.10 (dd, J=11.2, 17.6 Hz, 1H), 5.60 (d, J=8.4 Hz, 1H), 5.10-4.98 (m, 2H), 4.94 (d, J=3.6 Hz, 1H), 3.49 (s, 3H), 3.40 (d, J=6.4 Hz, 1H), 2.40 (brs, 1H), 2.24-1.97 (m, 5H), 1.72-1.19 (m, 10H), 1.04 (s, 4H), 0.81 (d, J=7.2 Hz, 3H), 0.63 (d, J=7.2 Hz, 3H). MS (ESI): mass calcd. for C$_{30}$H$_{40}$BFN$_2$O$_6$ 554.5, m/z found 555.3[M+H]$^+$. HPLC: 100.00% (220 nm), 100.00% (254 nm).

86. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate

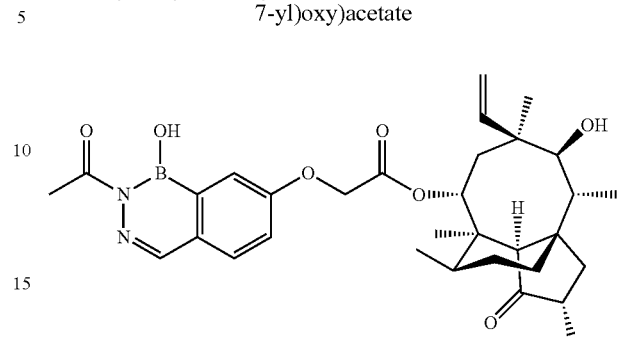

A solution of (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-(tosyloxy)acetate (300.0 mg, 594.8 umol, 1.0 eq), 1-(1,7-dihydroxybenzo[d][1,2,3]diazaborinin-2(1H)-yl)ethanone (121.3 mg, 594.8 umol, 1.0 eq) and K$_2$CO$_3$ (246.6 mg, 1.7 mmol, 3.0 eq) in DMF (10 mL) was stirred at 50° C. for 1.5 hours. Water (30 mL) was added to the mixture and acidified with 2N HCl (aq), white solid was precipitated and filtered to give the crude product, which was purified by prep-HPLC (Instrument: Gilson 281 semi-preparative HPLC system. Column: Durashell C18 150×25 mm, 5 m. Mobile phase: A: 5 mM NH$_4$HCO$_3$ in H$_2$O; B: ACN Gradient: B % 15-100, 14.6 min. Flow rate: 25 ml/min. Monitor wavelength: 220&254 nm) to give (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl2-((2-acetyl-1-hydroxy-1,2-dihydrobenzo[d][1,2,3]diazaborinin-7-yl)oxy)acetate (10.0 mg, 17.2 umol, 2.9% yield) as white solid. $^1$H NMR (DMSO-d$_6$, 400 MHz) δ 8.03 (s, 1H), 7.52 (d, J=8.0 Hz, 1H), 7.06-7.03 (m, 1H), 7.02-6.98 (m, 1H), 6.12-6.07 (m, 1H), 5.53 (d, J=5.6 Hz, 1H), 5.11-4.97 (m, 2H), 4.83-4.75 (m, 2H), 4.63 (m, 1H), 3.75 (br. s., 1H), 2.39-2.31 (m, 4H), 2.14-1.66 (m, 4H), 1.44-1.26 (m, 8H), 1.11-0.96 (m, 4H), 0.82 (d, J=6.6 Hz, 3H), 0.66-0.57 (m, 3H). MS (ESI): mass calcd. for C$_{31}$H$_{41}$BN$_2$O$_8$ 580.3, m/z found 596.9 (M+H$_2$O—H)$^-$. HPLC: 92.2% in 220 nm; 100% in 254 nm.

87. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate

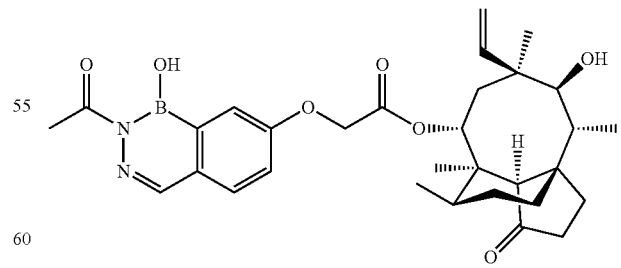

4-(benzyloxy)-2-(4,4,5,5-tetramethyl-1,3,2-dioxaborolan-2-yl)benzaldehyde (200.0 mg, 591.0 umol) and acetylhydrazine (44.0 mg, 591.0 umol) in anhydrous ethanol (20 mL) were stirred at 60-70° C. overnight, white solid was precipitated. The mixture was filtered to give 1-(7-(benzyloxy)-1-hydroxybenzo[d][1,2,3]diazaborinin-2(1H)-yl)ethanone (120.0 mg, 68.0%) as white solid. $^1$H NMR (DMSO-$d_6$, 400 MHz) δ 8.03 (s, 1H), 7.56 (d, J=8.4 Hz, 1H), 7.48-7.43 (m, 2H), 7.38 (t, J=7.2 Hz, 2H), 7.33 (d, J=7.0 Hz, 1H), 7.21 (d, J=2.4 Hz, 1H), 7.10 (dd, J=2.8, 8.4 Hz, 1H), 5.24-5.10 (m, 2H), 2.37 (s, 3H).

To a solution of 1-(7-(benzyloxy)-1-hydroxybenzo[d][1,2,3]diazaborinin-2(1H)-yl)ethanone (300.0 mg, 1.0 mmol, 1.0 eq) in DCM (10 mL) was added trichloroborane (2 mL, 2.0 mmol, 2.0 eq) at 0° C. over a period of 30 min under $N_2$. During which the temperature was maintained below 0° C. The reaction mixture was warmed to 25° C. over a period of 30 mins and stirred at room temperature for 2 hours. The solvent was evaporated, water (50 mL) was added to the mixture and solid precipitated, the mixture was filtered to give 1-(1,7-dihydroxybenzo[d][1,2,3]diazaborinin-2(1H)-yl)ethanone (200.0 mg, 980.4 umol, 96.1% yield) as yellow solid. $^1$H NMR (DMSO-$d_6$, 400 MHz) δ 10.58-9.62 (m, 1H), 7.94 (s, 1H), 7.42 (d, J=8.2 Hz, 1H), 6.98 (d, J=2.2 Hz, 1H), 6.83 (dd, J=2.2, 8.2 Hz, 1H), 2.34 (s, 3H).

Tos-pleuromutilin (400.0 mg, 750.0 umol), 1-(1,7-dihydroxybenzo[d][1,2,3]diazaborinin-2(1H)-yl)ethanone (153.0 mg, 750.0 umol) and potassium carbonate (311.0 mg, 2.3 mmol) in DMF (5 mL) with cata. amount of potassium iodide were heated to 50° C. for 1 hour, HPLC showed the reaction was completely, water was added and acidified with 2N HCl (aq), white solid was precipitated and filtered to give crude product which was purified by prep-HPLC (Instrument: Gilson 281 semi-preparative HPLC system. Column: Durashell C18 150×25 mm, 5 m. Mobile phase: A: 5 mM $NH_4HCO_3$ in $H_2O$; B: ACN Gradient: B % 25-100, 14.6 min. Flow rate: 25 ml/min. Monitor wavelength: 220&254 nm) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate (75.0 mg, yield 17.0%) as white solid. $^1$H NMR (DMSO-$d_6$, 400 MHz) δ 8.02 (s, 1H), 7.53 (d, J=8.4 Hz, 1H), 7.07-6.94 (m, 2H), 6.16-6.03 (m, 1H), 5.56 (t, J=8.0 Hz, 1H), 5.11-4.96 (m, 2H), 4.77 (t, J=10.0 Hz, 2H), 4.53 (d, J=5.8 Hz, 1H), 3.39 (d, J=5.2 Hz, 1H), 2.36 (d, J=1.4 Hz, 3H), 2.23-1.94 (m, 4H), 1.63 (br. s., 2H), 1.49-1.09 (m, 7H), 1.00 (d, J=17.8 Hz, 4H), 0.80 (d, J=3.6 Hz, 3H), 0.61 (dd, J=7.0, 12.0 Hz, 3H). MS (ESI): mass calcd. for $C_{31}H_{41}BN_2O_7$ 564.3, m/z found 581.3 (M+$H_2O$—H)$^-$. HPLC: 94.9% in 220 nm; 100% in 254 nm.

88. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate

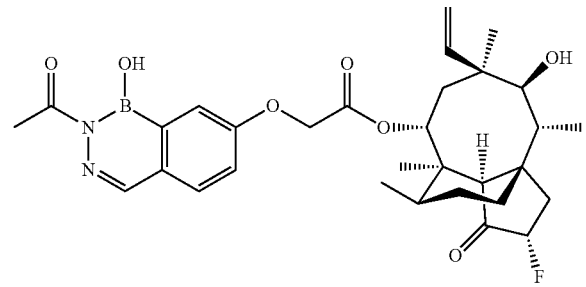

To a solution of (2S,3aR,4R,5R,7S,8S,9R,9aS,12R)-2-fluoro-8-(formyloxy)-4,7,9,12-tetramethyl-3-oxo-7-vinyl-decahydro-4,9a-propanocyclopenta[8]annulen-5-yl 2-(tosyloxy) acetate (800.0 mg, 1.3 mmol, 1.0 eq), 1-(1,7-dihydroxybenzo[d][1,2,3]diazaborinin-2(1H)-yl)ethanone (282.0 mg, 1.3 mmol, 1.0 eq) in DMF (20 mL) was added $K_2CO_3$ (572.2 mg, 4.1 mmol, 3.0 eq) and the mixture was stirred at 50° C. for 2 hours. Water was added to the mixture and acidified with 2N HCl (aq), white solid was precipitated and filtered to give the crude product (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate (700.0 mg, crude) as yellow solid.

A solution of (2S,3aR,4R,5R,7S,8S,9R,9aS,12R)-2-fluoro-8-(formyloxy)-4,7,9,12-tetramethyl-3-oxo-7-vinyl-decahydro-4,9a-propanocyclopenta[8]annulen-5-yl 2-((2-acetyl-1-hydroxy-1,2-dihydrobenzo[d][1,2,3]diazaborinin-7-yl)oxy)acetate (700.0 mg, 1.2 mmol, 1.0 eq) and $K_2CO_3$ (476.0 mg, 3.5 mmol) in MeOH (60 mL) was stirred at 50° C. for 2 hours. The mixture was filtered and evaporated to give the crude product which was purified by prep-HPLC (Instrument: Shimadzu LC-20AP preparative HPLC system. Column: Phenomenex Luna (2) C18 250×50 mm, 5 μm. Mobile phase: A: TFA/$H_2O$=0.075% v/v; B: ACN Gradient: B % 15-45, 23 min. Flow rate: 80 ml/min. Monitor wavelength: 220&254 nm) and then recrystallized from DCM/Petroleum ether (10:1) to give (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((2-acetyl-1-hydroxy-1,2-dihydrobenzo[d][1,2,3]diazaborinin-7-yl)oxy)acetate (22.0 mg, 33.6 umol, 2.9% yield, 89.0% purity) as white solid. $^1$H NMR (DMSO-$d_6$, 400 MHz) δ 8.02 (s, 1H), 7.53 (d, J=8.4 Hz, 1H), 7.07-6.96 (m, 2H), 6.10-6.02 (m, 1H), 5.54 (s, 1H), 5.12-4.97 (m, 3H), 4.87-4.64 (m, 4H), 3.30 (m, 1H), 2.36 (d, J=1.2 Hz, 3H), 2.25-1.96 (m, 4H), 1.43-1.22 (m, 7H), 1.12-0.98 (m, 4H), 0.86-0.80 (m, 3H), 0.62 (m, 3H). MS (ESI): mass calcd. for $C_{31}H_{40}BFN_2O_7$ 582.3, m/z found 599.3 (M+$H_2O$—H)$^-$. HPLC: 89.0% in 220 nm; 100% in 254 nm.

89. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-acetyl-8-fluoro-1-hydroxy-1,2-dihydrobenzo[d][1,2,3]diazaborinin-7-yl)oxy)acetate

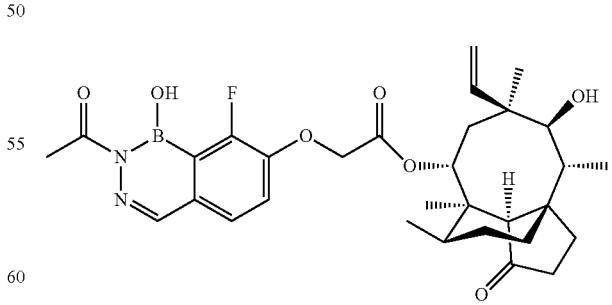

A solution of 4-(benzyloxy)-3-fluoro-2-(4,4,5,5-tetramethyl-1,3,2-dioxaborolan-2-yl) vbenzaldehyde (500.0 mg, 1.4 mmol) and acetohydrazide (104.0 mg, 1.4 mmol) EtOH (15 mL) was stirred at 50° C. for 12 hours. The mixture was added to product 1-(7-(benzyloxy)-8-fluoro-1-hydroxybenzo[d][1,2,3]diazaborinin-2(1H)-yl)ethanone (420.0 mg, crude) as white solid. $^1$H NMR (DMSO-$d_6$, 400 MHz) δ 8.04 (d, J=2.2 Hz, 1H), 7.49-7.30 (m, 7H), 5.26 (d, J=3.2 Hz, 1H), 2.42 (s, 3H).

BCl$_3$ (1 M, 6.1 mL) was added to a solution of 1-(7-(benzyloxy)-8-fluoro-1-hydroxybenzo[d][1,2,3]diazaborinin-2(1H)-yl)ethanone (474.0 mg, 1.5 mmol) in DCM (25 mL) at 0° C., the mixture was stirred at 0° C. for 2 hrs. The mixture was filtered to give 1-(8-fluoro-1,7-dihydroxybenzo[d][1,2,3]diazaborinin-2(1H)-yl)ethanone (300.0 mg, 88.9% yield). $^1$H NMR (DMSO-$d_6$, 400 MHz) δ 7.97 (d, J=2.4 Hz, 1H), 7.29 (d, J=8.4 Hz, 1H), 7.05 (t, J=8.4 Hz, 1H), 2.40 (s, 3H).

A solution of 1-(8-fluoro-1,7-dihydroxybenzo[d][1,2,3]diazaborinin-2(1H)-yl)ethanone (50.0 mg, 225.3 umol), pleuromutilitosylate (120.0 mg, 225.3 umol) and K$_2$CO$_3$ (93.4 mg, 675.8 umol) in DMF (10 mL) was stirred at 50° C. for 2 hours. Water was added to the mixture and filtered to give crude product, which was purified by pre-HPLC (column: Waters Xbridge 150×25 mm, 5 μm; liquid phase: [A-10 mM NH$_4$HCO$_3$ in H$_2$O; B-ACN] B %: 1%-25%, 12 min]) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-((2-acetyl-8-fluoro-1-hydroxy-1,2-dihydrobenzo[d][1,2,3]diazaborinin-7-yl)oxy)acetate (25.0 mg, 15.6% yield) as yellow solid. $^1$H NMR (DMSO-$d_6$, 400 MHz) δ 8.05 (s, 1H), 7.40 (d, J=8.4 Hz, 1H), 7.17-7.12 (m, 1H), 6.15-6.07 (m, 1H), 5.61 (d, J=7.6 Hz, 1H), 5.13-5.00 (d, J=3.6 Hz, 2H), 4.97-4.83 (m, 2H), 4.56-4.50 (m, 1H), 2.44-2.38 (m, 2H), 2.23-2.00 (m, 7H), 1.70-1.19 (m, 11H), 1.05 (d, J=3.2 Hz, 3H), 0.82 (d, J=6.8 Hz, 3H), 0.65 (dd, J=6.8, 17.6 Hz, 2H). MS (ESI): mass calcd. for C$_{31}$H$_{40}$BFN$_2$O$_7$ 582.5, m/z found 583.3 (M+H)$^+$. HPLC: 90.0% (220 nm), 90.4% (254 nm).

90. Methyl 7-(2-(((2S,3aR,4R,5R,7S,8S,9R,9aS, 12R)-2,8-dihydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate

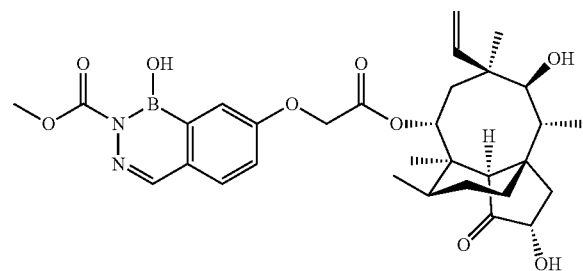

To a solution of (2-formyl-5-hydroxyphenyl)boronic acid (2.0 g, 12.1 mmol, 1.0 eq) and methyl hydrazinecarbamate (1.1 g, 12.0 mmol) in EtOH (20 mL) was stirred at 50° C. for 12 hours. The mixture was filtered to give methyl 1,7-dihydroxybenzo[d][1,2,3]diazaborinine-2(1H)-carboxylate (1.2 g, 5.5 mmol, 45.3% yield) as white solid. $^1$H NMR (DMSO-$d_6$, 400 MHz) δ 10.32 (s, 1H), 8.48 (s, 1H), 8.04 (s, 1H), 7.67 (d, J=8.4 Hz, 1H), 7.42 (d, J=2.4 Hz, 1H), 7.19 (dd, J=2.4, 8.4 Hz, 1H), 3.90 (s, 1H).

A solution (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-iodoacetate (300.0 mg, 594.8 umol, 1.0 eq), methyl 1,7-dihydroxybenzo[d][1,2,3]diazaborinine-2(1H)-carboxylate (130.8 mg, 594.8 umol, 1.00 eq) and K$_2$CO$_3$ (246.6 mg, 1.7 mmol, 3.0 eq) in DMF (15 mL) was stirred at 50° C. for 1 hour. Water was added to the mixture and acidified with 2N HCl (aq), white solid was precipitated and filtered to give the crude product, which was purified by prep-HPLC (Instrument: Gilson 281 semi-preparative HPLC system. Column: Luna C18 100×30 mm, 5 μm. Mobile phase: A: 5 mM NH$_4$HCO$_3$ in H$_2$O; B: ACN Gradient: B % 32-100, 14.6 min. Flow rate: 25 ml/min. Monitor wavelength: 220&254 nm) to give methyl 7-(2-(((2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (21.0 mg, 35.2 umol, 5.9% yield) as white solid, $^1$H NMR (DMSO-$d_6$, 400 MHz) δ 8.41 (s, 1H), 8.10 (s, 1H), 7.75 (d, 1H), 7.47 (s, 1H), 7.37 (d, 1H), 6.10 (dd, J=11.2, 17.8 Hz, 1H), 5.65-5.51 (m, 2H), 5.12-4.97 (m, 2H), 4.90 (d, J=8.0 Hz, 1H), 4.66 (d, J=6.4 Hz, 1H), 3.90 (s, 3H), 3.76 (m, 1H), 2.36 (s, 1H), 2.13-1.96 (m, 3H), 1.88-1.69 (m, 3H), 1.46-1.16 (m, 8H), 1.04 (m, 3H), 0.82 (d, J=6.8 Hz, 3H), 0.68 (m, 3H). MS (ESI): mass calcd. for C$_{31}$H$_{41}$BN$_2$O$_9$ 596.3, m/z found 594.8 (M−H)$^−$. HPLC: 93.8% in 220 nm; 94.0% in 254 nm.

91. Methyl 1-hydroxy-7-(2-(((3aR,4R,5R,7S,8S,9R, 9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate

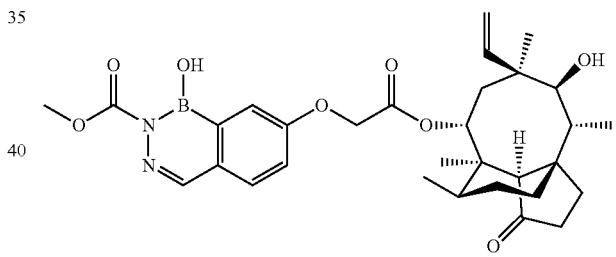

To a solution of Tos-pleuromutilin (400.0 mg, 750.9 umol, 1.0 eq) and methyl 1,7-dihydroxybenzo[d][1,2,3]diazaborinine-2(1H)-carboxylate (165.2 mg, 750.9 umol, 1.0 eq) in DMF (15 mL) was added K$_2$CO$_3$ (310 mg, 2.2 mmol, 3.0 eq) and the mixture was stirred at 50° C. for 2 hours. Water was added to the mixture and acidified with 2N HCl (aq), white solid was precipitated and filtered to give crude product which was purified by prep-HPLC (Instrument: Gilson 281 semi-preparative HPLC system. Column: Luna C18 100×30 mm, 5 μm. Mobile phase: A: TFA/H$_2$O=0.075% v/v; B: ACN Gradient: B % 45-100, 16 min. Flow rate: 25 ml/min. Monitor wavelength: 220&254 nm) to give methyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate (126.0 mg, 34.4% yield) as white solid, $^1$H NMR (DMSO-$d_6$, 400 MHz) δ 8.12 (s, 1H), 7.78 (d, J=8.4 Hz, 1H), 7.48 (s, 1H), 7.39 (dd, J=2.4, 8.4 Hz, 1H), 6.09 (dd, J=11.2, 17.6 Hz, 1H), 5.60 (d, J=7.8 Hz, 1H), 5.13-4.97 (m, 2H), 4.96-4.84 (m, 2H), 3.91 (s, 3H), 3.41 (d, J=5.8 Hz, 1H), 2.41 (s, 1H), 2.25-1.99 (m, 4H), 1.74-1.20 (m, 10H), 1.10-0.94 (m, 4H), 0.81 (d, J=6.8 Hz, 3H), 0.67 (d, J=6.8 Hz, 3H). MS (ESI): mass calcd. for C₃₁H₄₁BN₂O₈ 580.3, m/z found 597.4 (M+H₂O—H)⁻. HPLC: 97.2% in 220 nm; 96.1% in 254 nm.

92. Methyl 7-(2-(((2S,3aR,4R,5R,7S,8S,9R,9aS, 12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate

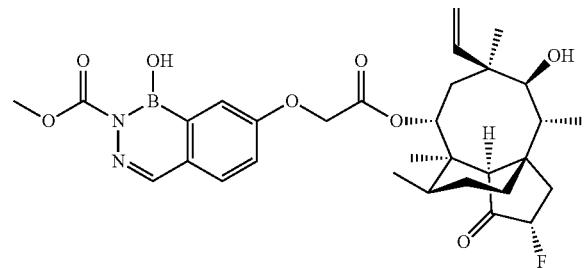

To a solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy) acetate (500.0 mg, 864.0 umol, 1.0 eq), methyl 1,7-dihydroxybenzo[d][1,2,3]diazaborinine-2(1H)-carboxylate (190.0 mg, 864.0 umol, 1.0 eq) in DMF (15 mL) was added K₂CO₃ (358.3 mg, 2.6 mmol, 3.0 eq), the mixture was stirred at 50° C. for 2 hours. Water was added to the mixture and acidified with 2N HCl (aq), white solid was precipitated and filtered to give the crude product methyl 7-(2-(((2S,3aR,4R, 5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl)oxy)-2-oxoethoxy)-1-hydroxybenzo[d][1, 2,3]diazaborinine-2(1H)-carboxylate (400.0 mg, crude) as yellow solid and used directly.

A solution of methyl 7-(2-(((2S,3aR,4R,5R,7S,8S,9R, 9aS,12R)-2-fluoro-8-(formyloxy)-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (500.0 mg, 798.1 umol, 1.0 eq) and K₂CO₃ (552.0 mg, 4.0 mmol, 5.0 eq) in MeOH (60 mL) was stirred at 50° C. for 5 hours. The mixture was filtered and the solvent was evaporated to give the crude product, which was purified by prep-HPLC (Instrument: Gilson 281 semi-preparative HPLC system. Column: Synergi Max-RP C12 100×30 4 u. Mobile phase: A: TFA/ H₂O=0.075% v/v; B: ACN Gradient: B % 35-100, 16 min. Flow rate: 25 ml/min. Monitor wavelength: 220&254 nm) to give methyl 7-(2-(((2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxybenzo[d][1,2,3]diazaborinine-2(1H)-carboxylate (38.0 mg, 63.5 umol, 7.9% yield) as yellow solid. ¹H NMR (DMSO-d₆, 400 MHz) δ. 8.12 (s, 1H), 7.78 (d, J=8.4 Hz, 1H), 7.48 (s, 1H), 7.39 (d, J=8.8 Hz, 1H), 6.07 (dd, J=11.0, 18.0 Hz, 1H), 5.58-4.96 (m, 2H), 4.92 (d, J=6.2 Hz, 2H), 3.91 (s, 3H), 3.34 (s, 1H), 2.61 (s, 1H), 2.27-1.93 (m, 4H), 1.47-1.18 (m, 9H), 1.10-1.00 (m, 4H), 0.89-0.78 (m, 3H), 0.68 (d, J=6.4 Hz, 3H). MS (ESI): mass calcd. for C₃₁H₄₀BFN₂O₈ 598.3, m/z found 599.1 (M+H)⁺. HPLC: 91.1% in 220 nm; 93.5% in 254 nm.

93. Methyl 8-fluoro-1-hydroxy-7-(2-(((3aR,4R,5R, 7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate

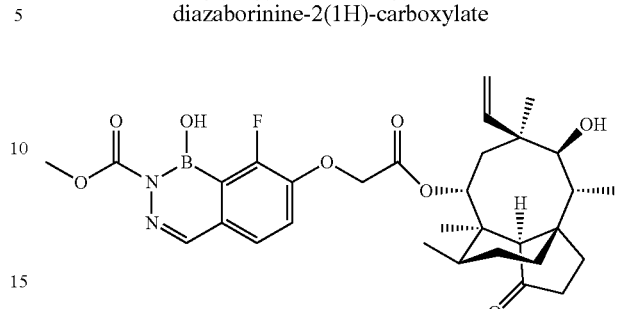

To a solution of (2-fluoro-6-formyl-3-hydroxyphenyl)boronic acid (250.0 mg, 1.4 mmol) and methyl N-aminocarbamate (122.2 mg, 1.4 mmol) in EtOH (5 mL) was stirred at 50° C. for 12 hours. The mixture was filtered to give the product methyl 8-fluoro-1,7-dihydroxybenzo[d][1,2,3]diazaborinine-2(1H)-carboxylate (180.0 mg, 55.6% yield) as white solid. ¹H NMR (DMSO-d₆, 400 MHz) δ 10.61 (s, 1H), 8.56 (brs, 1H), 8.01 (d, J=2.4 Hz, 1H), 7.48 (d, J=8.4 Hz, 1H), 7.40-7.34 (m, 1H), 3.90 (s, 3H).

To a solution of methyl 8-fluoro-1,7-dihydroxybenzo[d][1,2,3]diazaborinine-2(1H)-carboxylate (180.0 mg, 756.4 umol), pleuromutilitosylate (402.9 mg, 756.4 umol) and Cs₂CO₃ (739.3 mg, 2.3 mmol) in DMF (5 mL) was stirred at 25° C. for 12 hours. Water was added to the mixture and filtered to give the product methyl 8-fluoro-1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate (18.0 mg, 3.5% yield) as beige solid, which was purified by pre-HPLC (column: Waters Xbridge 150×25 mm, 5 µm; liquid phase: [A-10 mM NH₄HCO₃ in H₂O; B-ACN] B %: 1%-25%, 12 min]). ¹H NMR (DMSO-d₆, 400 MHz) δ 8.53 (brs, 1H), 7.86 (brs, 1H), 7.48-7.29 (m, 2H), 6.11 (dd, J=10.8, 17.6 Hz, 1H), 5.60 (d, J=8.0 Hz, 1H), 5.13-4.99 (m, 2H), 4.98-4.86 (m, 2H), 4.54 (d, J=6.4 Hz, 1H), 3.84 (s, 2H), 3.44-3.39 (m, 1H), 2.41 (brs, 1H), 2.29-2.00 (m, 3H), 1.73-1.19 (m, 10H), 1.11-0.94 (m, 4H), 0.81 (d, J=6.4 Hz, 3H), 0.70-0.60 (m, 3H). MS (ESI): mass calcd. for C₃₁H₄₀BFN₂O₈ 598.5, m/z found 599.3 (M+H)⁺. HPLC: 89.1% (220 nm), 100.0% (254 nm).

94. Methyl 1-hydroxy-7-(2-(((3aR,4R,5R,7S,8S,9R, 9aS,12R)-8-hydroxy-4,7,9,12-tetramethyl-3-oxo-7-vinyldecahydro-4,9a-propanocyclopenta[8]annulen-5-yl)oxy)-2-oxoethoxy)-8-methylbenzo[d][1,2,3]diazaborinine-2(1H)-carboxylate

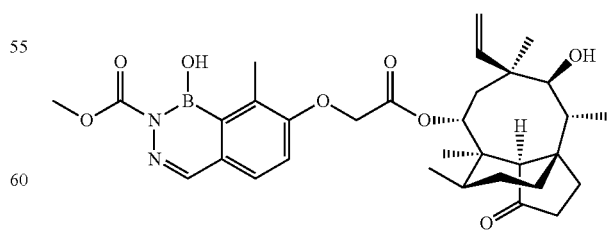

To a solution of 4-(benzyloxy)-3-methyl-2-(4,4,5,5-tetramethyl-1,3,2-dioxaborolan-2-yl)benzaldehyde (3.2 g, 9.1 mmol, 1.0 eq) in DCM (30 mL) was added BBr₃ (9.1 g, 36.3 mmol, 4.0 eq). The mixture was stirred at 0° C. for 1 hour. HPLC indicated STM was consumed completely. The reaction mixture was concentrated, H₂O (20 mL) was added and then filtered to give a residue. The residue was washed by H₂O and DCM. The crude product (6-formyl-3-hydroxy-2-methylphenyl)boronic acid (1.5 g, 8.1 mmol, 88.7% yield) was used into the next step without further purification. $^1$H NMR (DMSO-d$_6$, 400 MHz) δ 10.27 (s, 1H), 9.68 (s, 1H), 7.87 (s, 2H), 7.53 (d, J=8.0 Hz, 1H), 6.85 (d, J=8.0 Hz, 1H), 2.50 (s, 3H).

A solution of (6-formyl-3-hydroxy-2-methylphenyl)boronic acid (1.0 g, 5.7 mmol, 1.0 eq) and methyl N-aminocarbamate (515.5 mg, 5.7 mmol, 1.0 eq) in EtOH (10.0 mL) was stirred at 25° C. for 3 hours. HPLC indicated STM was consumed completely. The reaction mixture was concentrated to remove EtOH. The residue was diluted with MTBE (10 mL), the mixture was filtered to give a residue. The residue was washed by MTBE and PE (1:1) 10 mL. methyl 1,7-dihydroxy-8-methylbenzo[d][1,2,3]diazaborinine-2(1H)-carboxylate (1.1 g, 4.7 mmol, 82.2% yield) was obtained as a light gray solid. $^1$H NMR (DMSO-d$_6$, 400 MHz) δ10.16 (s, 1H), 9.14 (s, 1H), 7.95 (s, 1H), 7.48 (d, J=8.4 Hz, 1H), 7.24 (d, J=8.0 Hz, 1H), 3.91 (s, 3H), 2.55 (s, 3H). MS (ESI): mass calcd. for C$_{10}$H$_{11}$BN$_2$O$_4$ 234.0, m/z found 235.1 [M+H]⁺. HPLC: 99.9% (220 nm), 100.0% (254 nm).

To a solution of methyl 1,7-dihydroxy-8-methylbenzo[d][1,2,3]diazaborinine-2(1H)-carboxylate (100.0 mg, 427.3 umol, 1.0 eq) in DMF (10 mL) was added K$_2$CO$_3$ (177.2 mg, 1.3 mmol, 3.0 eq) and KI (7.1 mg, 42.7 umol, 0.1 eq). The mixture was stirred at 50° C. for 3 hours. HPLC indicated STM was consumed completely. The reaction mixture was quenched by addition H₂O (20 mL) at 0° C., and then adjusted pH=7 with HCl (2M, 4 mL), filtered to give a residue. The residue was dissolved by MTBE and PE, then concentrated until solid was dissolved out, filtered and concentrated the filtrate under reduced pressure to give a residue, repeat four times. methyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)-8-methylbenzo[d][1,2,3]diazaborinine-2(1H)-carboxylate (35.0 mg, 54.7 umol, 12.8% yield, 93% purity) was obtained as a white solid. $^1$H NMR (DMSO-d$_6$, 400 MHz) δ 9.15 (brs, 1H), 8.02 (brs, 1H), 7.59 (brs, 1H), 7.33 (brs, 1H), 6.11 (dd, J=17.6, 11.2 Hz, 1H), 5.61 (d, J=8.4 Hz, 1H), 5.09-4.98 (m, 2H), 4.90 (s, 1H), 4.52 (d, J=2.4 Hz, 2H), 3.90 (s, 3H), 3.41 (d, J=5.6 Hz, 1H), 2.33 (s, 3H), 2.20-2.05 (m, 4H), 1.72-1.55 (m, 2H), 1.54-1.36 (m, 2H), 1.34 (s, 3H), 1.31-1.15 (m, 3H), 1.03 (m, 4H), 0.82 (d, J=6.8 Hz, 3H), 0.65 (d, J=6.8 Hz, 3H). MS (ESI): mass calcd. for C$_{32}$H$_{43}$BN$_2$O$_8$, 594.5, m/z found 595.4 [M+H]⁺. HPLC: 93.0% (220 nm), 88.6% (254 nm).

95. Methyl 7-(2-(((2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxy-8-methylbenzo[d][1,2,3]diazaborinine-2(1H)-carboxylate

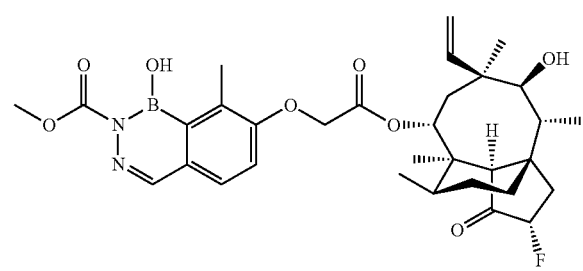

A mixture of methyl 1,7-dihydroxy-8-methyl-2,3,1-benzodiazaborinine-2-carboxylate (150.0 mg, 641.0 umol, 1.0 eq), (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl2-(tosyloxy)acetate (370.9 mg, 641.0 umol, 1.0 eq) and Na$_2$CO$_3$ (135.9 mg, 1.28 mmol, 2.0 eq) in DMF (15.0 mL) was degassed and purged with N$_2$ for 3 times, and then the mixture was stirred at 50° C. for 3 hour under N$_2$ atmosphere. The reaction mixture was quenched by addition H₂O 30 mL at 25° C., and then adjusted pH<4 with 2N HCl aqueous solution and filtered to give crude methyl 7-(2-(((2S,3aR,4R,5R,7S,8S,9R,9aS,12R)-2-fluoro-8-(formyloxy)-4,7,9,12-tetramethyl-3-)oxo-7-vinyldecahydro-4,9a-propanocyclopenta[8]annulen-5-yl)oxy)-2-oxoethoxy)-1-hydroxy-8-methylbenzo[d][1,2,3]diazaborinine-2(1H)-carboxylate (360.00 mg, crude) as white solid and used directly.

To a solution of methyl 7-(2-(((2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl)oxy)-2-oxoethoxy)-1-hydroxy-8-methylbenzo[d][1,2,3]diazaborinine-2(1H)-carboxylate (360.0 mg, 562.1 umol, 1.0 eq) in MeOH (50 mL) was added NaHCO$_3$ (236.1 mg, 2.8 mmol, 5.0 eq). The mixture was stirred at 50° C. for 4 hours. The mixture was filtered and washed with MeOH 50 mL, the filtrate was concentrated in pressure to afford crude product. The crude product was purified by Prep-HPLC. The solvent was concentrated until water left and freeze-dried by lyophilizer to give methyl 7-(2-(((2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl)oxy)-2-oxoethoxy)-1-hydroxy-8-methylbenzo[d][1,2,3]diazaborinine-2(1H)-carboxylate (40.0 mg, 65.3 umol, 11.6% yield) as white solid. $^1$H NMR (DMSO-d$_6$, 400 MHz) δ 9.12 (s, 1H), 8.03 (s, 1H), 7.65-7.55 (m, 1H), 7.39-7.28 (m, 1H), 6.09 (dd, J=11.2, 17.6 Hz, 1H), 5.59 (d, J=8.0 Hz, 1H), 5.14-4.83 (m, 6H), 4.68 (d, J=6.4 Hz, 3H), 3.91 (s, 3H), 2.64 (s, 3H), 2.15-1.12 (m, 10H), 1.03 (m, 4H), 0.83 (d, J=6.4 Hz, 3H), 0.66 (d, J=6.4 Hz, 3H). MS (ESI): mass calcd. for C$_{32}$H$_{42}$BFN$_2$O$_8$ 612.5, m/z found 629.4 (M+H₂O—H)⁻. HPLC: 100.0% (220 nm), 100.0% (254 nm).

96. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate

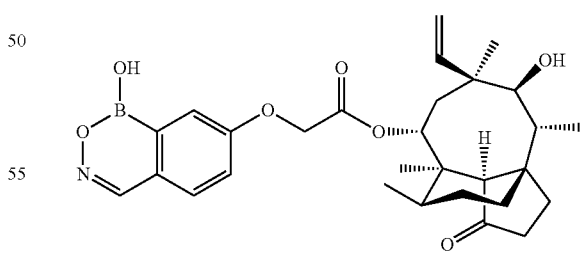

To a solution of (2-formyl-5-hydroxyphenyl)boronic acid (200.0 mg, 1.2 mmol, 1.0 eq) in EtOH (20 mL) was stirred at 50° C. for 12 hours. The mixture was filtered to give 1H-benzo[d][1,2,6]oxazaborinine-1,7-diol (150.0 mg, 909.4 umol, 75.2% yield) as brown solid.

A solution of Tos-pleuromutilin (200.0 mg, 375.5 umol, 1.0 eq), 1H-benzo[d][1,2,6]oxazaborinine-1,7-diol (61.1 mg, 375.5 umol, 1.00 eq) and K$_2$CO$_3$ (155.7 mg, 1.1 mmol, 3.0 eq) in DMF (15 mL) was stirred at 50° C. for 3 hours. Water was added to the mixture and acidified with 2N HCl (aq), white solid was precipitated and filtered, the crude product purified by prep-HPLC (Instrument: Gilson 281 semi-preparative HPLC system. Column: Synergi Max-RP C12 100×30 4 u. Mobile phase: A: TFA/H$_2$O=0.075% v/v; B: ACN Gradient: B % 35-100, 16 min. Flow rate: 20 ml/min. Monitor wavelength: 220&254 nm) to give (3aR, 4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate (10.0 mg, 19.1 umol, 5.1% yield) as white solid. $^1$H NMR (DMSO-d$_6$, 400 MHz) δ 9.29 (s, 1H), 8.54 (s, 1H), 7.71 (d, J=8.2 Hz, 1H), 7.49 (s, 1H), 7.37 (d, J=6.0 Hz, 1H), 6.13-6.04 (m, 1H), 5.60 (d, J=7.8 Hz, 1H), 5.11-4.96 (m, 2H), 4.87 (d, J=7.2 Hz, 1H), 4.53 (d, J=6.2 Hz, 1H), 3.41 (m, 1H), 2.41 (s, 1H), 2.05 (m, 4H), 1.71-1.44 (m, 4H), 1.40-1.20 (m, 7H), 1.04 (s, 4H), 0.81 (d, J=6.8 Hz, 3H), 0.65 (d, J=7.0 Hz, 3H). MS (ESI): mass calcd. for C$_{29}$H$_{38}$BNO$_7$ 523.3, m/z found 522.3 (M−H)$^-$. HPLC: 97.5% in 220 nm; 94.3% in 254 nm.

97. (3aR,4R,5R,7S,8S,9R,9aS,12R)-8-hydroxy-4,7, 9,12-tetramethyl-3-oxo-7-vinyldecahydro-4,9a-propanocyclopenta[8]annulen-5-yl 2-((8-fluoro-1-hydroxy-1H-benzo[d][1,2,6]oxazaborinin-7-yl)oxy) acetate

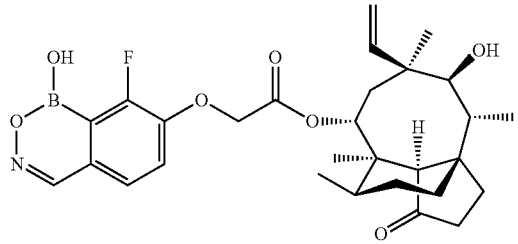

BCl$_3$ (1 M, 22.44 mL) was added to a solution of 4-(benzyloxy)-3-fluoro-2-(4,4,5,5-tetramethyl-1,3,2-dioxaborolan-2-yl)benzaldehyde (2.0 g, 5.6 mmol) in DCM (50 mL) at 0° C. The mixture was stirred at 0° C. for 3 hours. Water (50 mL) was added to quench the reaction, the mixture was extracted with EtOAc (50 mL) twice, the combined organic layers were concentrated to give (2-fluoro-6-formyl-3-hydroxyphenyl)boronic acid (1.0 g, 82.4% yield) as green solid. $^1$H NMR (DMSO-d$_6$, 400 MHz) δ 10.82 (s, 1H), 9.74 (d, J=2.8 Hz, 1H), 8.17 (s, 2H), 7.58 (d, J=8.4 Hz, 1H), 7.03 (t, J=8.4 Hz, 1H).

(2-fluoro-6-formyl-3-hydroxyphenyl)boronic acid (300.0 mg, 1.6 mmol), NH$_2$OH.HCl (124.6 mg, 1.8 mmol) and KOAc (191.9 mg, 1.9 mmol) in H$_2$O (5 mL) and EtOH (5 mL) were stirred at 50° C. for 2 hours. The mixture was filtered to give 8-fluoro-1H-benzo[d][1,2,6]oxazaborinine-1,7-diol (190.0 mg, crude). $^1$H NMR (DMSO-d$_6$, 400 MHz) δ 10.70 (s, 1H), 8.48 (d, J=2.8 Hz, 1H), 7.46-7.43 (m, 1H), 7.40-7.34 (m, 1H).

A solution of 8-fluoro-1H-benzo[d][1,2,6]oxazaborinine-1,7-diol (190.0 mg, 1.1 mmol) and pleuromutilitosylate (559.4 mg, 1.1 mmol) and K$_2$CO$_3$ (435.4 mg, 3.2 mmol) in DMF (5 mL) was stirred at 50° C. for 2 hours. Water was added to the mixture and filtered to give crude product, which was purified by pre-HPLC (column: Waters Xbridge 150×25 mm, 5 m; liquid phase: [A-10 mM NH$_4$HCO$_3$ in H$_2$O; B-ACN] B %: 1%-25%, 12 min]) to give (3aR,4R, 5R,7S,8S,9R,9aS,12R)-8-hydroxy-4,7,9,12-tetramethyl-3-oxo-7-vinyldecahydro-4,9a-propanocyclopenta[8]annulen-5-yl2-((8-fluoro-1-hydroxy-1H-benzo[d][1,2,6] oxazaborinin-7-yl)oxy)acetate (6.0 mg, 1.00% yield) as beige solid. $^1$H NMR (DMSO-d$_6$, 400 MHz) δ 9.44-9.27 (m, 1H), 8.55 (brs, 1H), 7.54 (brs, 2H), 6.10 (dd, J=11.2, 17.6 Hz, 1H), 5.59 (d, J=8.8 Hz, 1H), 5.23-4.90 (m, 4H), 4.54 (brs, 1H), 2.40 (brs, 1H), 2.24-1.97 (m, 4H), 1.72-1.19 (m, 10H), 1.10-0.94 (m, 3H), 0.81 (d, J=6.4 Hz, 3H), 0.64 (d, J=7.2 Hz, 3H). MS (ESI): mass calcd. for C$_{29}$H$_{37}$BFNO$_7$ 541.4, m/z found 558.3 (M+H$_2$O—H)$^-$. HPLC: 94.9% (220 nm), 95.8% (254 nm).

98. (2S,3aR,4R,5R,7S,8S,9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy) acetate

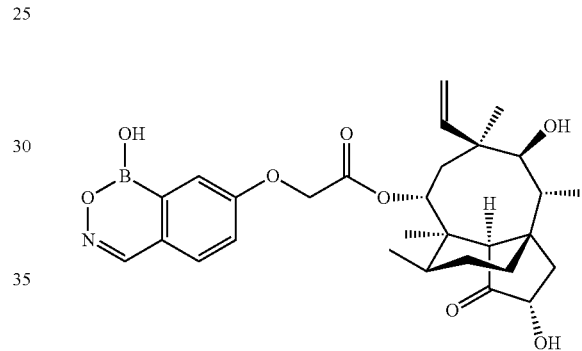

A solution of (2S,3aR,4R,5R,7S,8S,9R,9aS,12R)-2,8-dihydroxy-4,7,9,12-tetramethyl-3-oxo-7-vinyldecahydro-4, 9a-propanocyclopenta[8]annulen-5-yl 2-(tosyloxy) acetate (500.0 mg, 911.2 umol, 1.0 eq), 1H-benzo[d][1,2,6]oxazaborinine-1,7-diol (148.4 mg, 911.2 umol, 1.0 eq) and K$_2$CO$_3$ (377.8 mg, 2.7 mmol, 3.0 eq) in DMF (15 mL) was stirred at 50° C. for 2 hours. Water was added to the mixture and acidified with 2N HCl (aq), white solid was precipitated and filtered to give the crude product, which was purified by prep-HPLC (Instrument: Gilson 281 semi-preparative HPLC system. Column: Synergi Max-RP C12 100×30 4 u. Mobile phase: A: TFA/H$_2$O=0.075% v/v; B: ACN Gradient: B % 30-100, 16 min. Flow rate: 25 ml/min. Monitor wavelength: 220&254 nm) to give (2S,3aR,4R,5R,7S,8S, 9R,9aS,12R)-2,8-dihydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy) acetate (12.0 mg, 22.3 umol, 2.4% yield) as white solid. $^1$H NMR (DMSO-d$_6$, 400 MHz) δ 8.51 (s, 1H), 7.70 (d, J=8.4 Hz, 1H), 7.46 (d, J=2.8 Hz, 1H), 7.34 (dd, J=2.8, 8.4 Hz, 1H), 6.09 (dd, J=11.2, 17.6 Hz, 1H), 5.55 (d, J=8.4 Hz, 1H), 5.09-5.01 (m, 2H), 4.85 (d, J=6.8 Hz, 1H), 4.52 (s, 2H), 3.75-3.71 (m, 1H), 3.30 (d, J=5.6 Hz, 1H), 2.31 (s, 1H), 2.14-1.93 (m, 2H), 1.87-1.69 (m, 2H), 1.45-1.16 (m, 8H), 1.09-0.97 (m, 4H), 0.81 (d, J=7.0 Hz, 3H), 0.67-0.57 (m, 3H). MS (ESI): mass calcd. for $C_{29}H_{38}BNO_8$ 539.3, m/z found 540.3 (M+H)$^+$. HPLC: 95.8% in 220 nm; 98.8% in 254 nm.

99. (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate

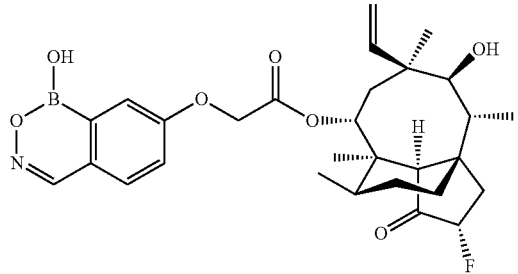

A solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-(tosyloxy) acetate (800.0 mg, 1.3 mmol, 1.0 eq), 1H-benzo[d][1,2,6]oxazaborinine-1,7-diol (225.3 mg, 1.3 mmol, 1.0 eq) and $K_2CO_3$ (572.2 mg, 4.1 mmol, 3.0 eq) in DMF (25 mL) was stirred at 50° C. for 2 hours. Water was added to the mixture and acidified with 2N HCl (aq), white solid was precipitated and filtered to give the crude product (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate (620.0 mg, crude) as yellow solid and used directly.

A solution of (2S,3aR,4R,5R,7S,8S,9R,9aS,12R)-2-fluoro-8-(formyloxy)-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate (620.0 mg, 1.1 mmol, 1.0 eq) and $K_2CO_3$ (752.0 mg, 5.5 mmol, 5.0 eq) in MeOH (100 mL) was stirred at room temperature for 2 hours. The mixture was filtered and the solvent was evaporated to give crude product, which was purified by prep-HPLC (Instrument: Gilson 281 semi-preparative HPLC system. Column: Synergi Max-RP C12 100×30 4 u. Mobile phase: A: TFA/$H_2O$=0.075% v/v; B: ACN Gradient: B % 40-100, 16 min. Flow rate: 25 ml/min. Monitor wavelength: 220&254 nm) to give (2S,3aR,4R,5R,7S,8S,9R,9aS,12R)-2-fluoro-8-hydroxy-4,7,9,12-tetramethyl-3-oxo-7-vinyldecahydro-4,9a-propanocyclopenta[8]annulen-5-yl 2-((1-hydroxy-1H-benzo[d][1,2,6]oxazaborinin-7-yl)oxy)acetate (18.0 mg, 33.3 umol, 3.1% yield) as white solid. $^1$H NMR (DMSO-$d_6$, 400 MHz) δ 8.54 (s, 1H), 7.71 (d, J=8.8 Hz, 1H), 7.50 (s, 1H), 7.38 (dd, J=2.4, 8.2 Hz, 1H), 6.07 (dd, J=11.0, 17.6 Hz, 1H), 5.58 (d, J=7.8 Hz, 1H), 5.11-4.89 (m, 5H), 2.61 (s, 1H), 2.25-1.96 (m, 4H), 1.81 (d, J=14.0 Hz, 1H), 1.46-1.19 (m, 9H), 1.10-0.96 (m, 4H), 0.84 (d, J=7.0 Hz, 3H), 0.66 (d, J=6.6 Hz, 3H). MS (ESI): mass calcd. for $C_{29}H_{37}BFNO_7$ 541.3, m/z found 540.0 (M−H). HPLC: 92.0% in 220 nm; 94.0% in 254 nm.

100. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydro-[1,2]oxaborolo[4,3-c]pyridin-6-yl)oxy)acetate

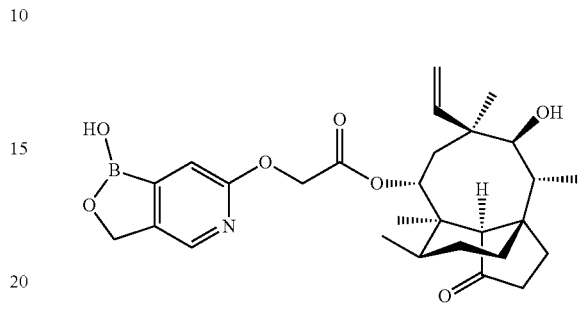

To a solution of benzyl alcohol (8.20 mL, 79.4 mmol) in DMF (100 mL) cooled in ice-water bath was added NaH (3.46 g, 86.6 mmol) in portions. The reaction was stirred for 30 min at 0° C. Then 6-chloronicotinonitrile (10.00 g, 72.2 mmol) was added. The mixture was stirred for 30 min at room temperature. Then the reaction was quenched by ice water (200 mL), white solid precipitated. The mixture was filtered and the cake was washed with cold water, dried to give 6-(benzyloxy)nicotinonitrile (15.9 g, yield 100%) as white solid. $^1$H NMR (MeOD, 400 MHz) δ 8.55 (s, 1H), 7.97 (d, J=8.0 Hz, 1H), 7.44-7.31 (m, 5H), 6.96 (d, J=8.0 Hz, 1H), 5.45 (s, 2H).

To a solution of 6-(benzyloxy)nicotinonitrile (14.8 g, 70.5 mmol) in anhydrous THF (700 mL) was added LDA (42 mL, 82 mmol) dropwise at −78° C. The reaction mixture was stirred at −78° C. for 30 min. Then triisopropyl borate (32.3 mL, 140 mmol) was added to the mixture dropwise. The reaction was gradually warmed to room temperature and stirred for 30 min at this temperature. The reaction was quenched by adding water (300 mL) and extracted with MTBE (200 mL) twice. Then the pH of the aqueous layer was adjusted to 6-7 and extracted with EtOAc (300 mL) three times. The combined EtOAc layers were washed with brine, dried over $Na_2SO_4$ and concentrated. The residue was recrystallized by petroleum ether and EtOAc (~10:1) to give the desired product (2-(benzyloxy)-5-cyanopyridin-4-yl)boronic acid (11.2 g, yield 63%) as light yellow solid. $^1$H NMR (MeOD, 400 MHz) δ 8.46 (s, 1H), 7.44-7.30 (m, 5H), 7.08 (s, 1H), 5.41 (s, 2H).

A solution of (2-(benzyloxy)-5-cyanopyridin-4-yl)boronic acid (11.2 g, 44 mmol) in hydrochloride gas/methanol solution (100 mL, 4 mol/L) was stirred at 0° C. for 1 h. Then the solvent was evaporated and the residue was recrystallized by petroleum ether and EtOAc (10:1) to give (2-(benzyloxy)-5-(methoxycarbonyl)pyridin-4-yl)boronic acid (8.9 g, yield 70.6%) as milky solid. $^1$H NMR (MeOD, 400 MHz) δ 8.77 (s, 3H), 7.45-7.30 (m, 5H), 6.82 (s., 1H), 5.43 (s, 2H), 3.92 (s, 3H).

A solution of (2-(benzyloxy)-5-(methoxycarbonyl)pyridin-4-yl)boronic acid (1.0 g, 3.5 mmol) in MeOH (30 mL) was cooled with ice-water bath, to this solution was added NaBH$_4$ (1.3 g, 34.8 mmol) in portions. The reaction was quenched by adding of 3N aq.HCl solution (~10 mL). The mixture was then concentrated and the residue was partitioned between EtOAc and water. The pH the hydrous layer was adjusted to 6~7 and extracted with EtOAc for three times. The combined organic layer was washed with brine, dried over Na$_2$SO$_4$ and concentrated. The residue was purified by prep-HPLC to give the desired product 6-(benzyloxy)-[1,2]oxaborolo[4,3-c]pyridin-1(3H)-ol (630 mg, yield 75.1%) as yellow solid. $^1$H NMR (DMSO-d$_6$, 400 MHz) δ 8.28 (s, 1H), 7.45-7.31 (m, 5H), 7.12 (s, 1H), 5.37 (s, 2H), 5.02 (s, 2H) MS (ESI): mass calcd. for C$_{13}$H$_{12}$BNO$_3$ 241.1, m/z found 242.1 [M+1]$^+$. HPLC: 99.5% (220 nm), 99.2% (254 nm).

A suspension of 6-(benzyloxy)-[1,2]oxaborolo[4,3-c]pyridin-1(3H)-ol (300 mg, 1.2 mmol) and Pd/C (80 mg) in EtOAc (40 mL) was hydrogenated under 50 Psi of hydrogen pressure overnight at room temperature. The mixture was filtered through a pad of silica gel and the pad was washed with MeOH (20 mL). The combined filtrate was concentrated to dryness. The crude product was recrystallized with EtOAc to afford [1,2]oxaborolo[4,3-c]pyridine-1,6(3H)-diol (160 mg, yield 85%) as light brown solid. $^1$H NMR (DMSO-d$_6$, 400 MHz) δ 7.69 (s, 1H), 6.94 (s, 1H), 4.89 (s, 2H). MS (ESI): mass calcd. for C$_6$H$_6$BNO$_3$ 151.0, m/z found 152.1 [M+1]$^+$. HPLC: 95.0% (220 nm).

To a solution of [1,2]oxaborolo[4,3-c]pyridine-1,6(3H)-diol (60 mg, 0.4 mmol), Cs$_2$CO$_3$ (391 mg, 1.2 mmol) and a trace amount catalytic of water in DMF (10 mL) was added Iodo-pleuromutilin (200 mg, 0.4 mmol), the reaction mixture was bubbled with N$_2$ for 5 mins then sealed and heated in microwave at 60° C. for 45 min. The reaction was quenched by addition of water (20 mL). The pH of mixture was adjusted to 6-7 and extracted with EtOAc for three times. The combined organic layer was washed with brine, dried over Na$_2$SO$_4$ and concentrated. The residue was purified by prep-HPLC to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydro-[1,2]oxaborolo[4,3-c]pyridin-6-yl)oxy)acetate (41 mg, yield 19.6%) as off white solid. $^1$H NMR (DMSO-d$_6$, 400 MHz) δ 7.70 (s, 1H), 6.71 (s, 1H), 6.12 (dd, J$_{1,2}$=10.8 Hz, J$_{1,3}$=17.6 Hz, 1H), 5.51 (d, J=8.0 Hz, 1H), 5.14 (d, J=16.0 Hz, 1H), 5.02 (d, J=12.0 Hz, 1H), 4.88 (s, 2H), 4.61 (d, J=5.2 Hz, 2H), 3.42 (d, J=4.0 Hz, 1H), 2.39 (s, 1H), 2.17-2.00 (m, 4H), 1.67-1.60 (m, 2H), 1.47-1.26 (m, 9H), 1.06-0.95 (m, 4H), 0.81 (d, J=8.0 Hz, 3H), 0.66 (d, J=8.0 Hz, 3H). MS (ESI): mass calcd. for C$_{28}$H$_{38}$BNO$_7$ 511.3, m/z found 528.2 [M+H$_2$O−1]$^-$. HPLC: 99.4% (220 nm), 100% (254 nm).

101. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydro-[1,2]oxaborolo[4,3-b]pyridin-6-yl)oxy)acetate

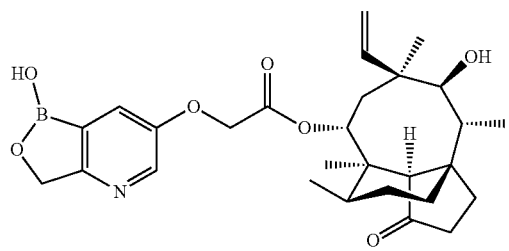

To a solution of benzyl alcohol (4.3 mL, 42.8 mmol) in DMF (100 mL) cooled in ice-water bath was added NaH (1.8 g, 45.6 mmol) in portions. The reaction was stirred for 1 h at 0° C. Then 3,5-dibromopicolinonitrile (10.0 g, 38.0 mmol) was added. The mixture was stirred for 30 min at room temperature. Then the reaction was quenched by ice water and extracted with EtOAc for three times. The combined organic layer was washed with brine, dried over Na$_2$SO$_4$ and concentrated. The residue was purified by column chromatography to give a mixture of 5-(benzyloxy)-3-bromopicolinonitrile and 3-(benzyloxy)-5-bromopicolinonitrile (5.13 g, yield 100%, ~1:1 in $^1$H NMR) as white solid. $^1$H NMR (CD$_3$OD, 400 MHz) δ 8.55 (d, J=2.0 Hz, 1H), 7.96-7.95 (m, 1H), 7.45-7.31 (m, 5H), 6.96 (d, J=8.8 Hz, 1H), 5.45 (s, 2H).

To a mixture of 5-(benzyloxy)-3-bromopicolinonitrile and 3-(benzyloxy)-5-bromopicolinonitrile (14.8 g, 17.3 mol) in water (100 mL) was added NaOH (3.5 g, 86.5 mmol) and the mixture was heated to reflux overnight. The pH of the reaction mixture was adjusted to 5-6 and extracted with EtOAc for three times. The combined organic layer was washed with brine, dried over Na$_2$SO$_4$ and concentrated to give a mixture of 5-(benzyloxy)-3-bromopicolinic acid and 3-(benzyloxy)-5-bromopicolinic acid (7.0 g, yield 100%, ~1:1 ratio).

A solution of 5-(benzyloxy)-3-bromopicolinic acid and 3-(benzyloxy)-5-bromopicolinic acid (7.00 g, 23 mmol) in HCl gas/MeOH (100 mL, 4 mol/L) was heated to reflux overnight. Then the solvent was evaporated and the residue was dissolved in water. The pH of the mixture was adjusted to 7-8 by adding aqueous NaHCO$_3$ solution, the resulting mixture was extracted with EtOAc for three times. The combined organic layer was washed with brine, dried over Na$_2$SO$_4$ and concentrated. The residue was purified by column chromatography give methyl 5-(benzyloxy)-3-bromopicolinate (2.0 g, yield 27.4%) as white solid. $^1$H NMR (CD$_3$OD, 400 MHz) δ 8.32 (d, J=2.4 Hz, 1H), 7.81 (d, J=2.4 Hz, 1H), 7.47-7.37 (m, 5H), 5.24 (s, 3H).

To a solution of methyl 5-(benzyloxy)-3-bromopicolinate (1.3 g, 4.0 mmol) in anhydrous THF (700 mL) was added DIBAL-H (20 mL, 20 mmol) dropwise at −78° C. The reaction mixture was stirred at room temperature for 2 hs then quenched by slowly adding water (10 mL). The resulting mixture was dried over Na$_2$SO$_4$ and concentrated to give (5-(benzyloxy)-3-bromopyridin-2-yl)methanol (1.1 g, yield 93.2%) as yellow oil. $^1$H NMR (CD$_3$OD, 400 MHz) δ 8.28 (d, J=2.8 Hz, 1H), 7.70 (d, J=2.8 Hz, 1H), 7.46-7.33 (m, 5H), 5.18 (s, 2H), 4.71 (s, 2H).

A suspension of (5-(benzyloxy)-3-bromopyridin-2-yl)methanol (1.8 g, 6.1 mmol) and DIEA (2.4 g, 18.3 mmol) in DCM (40 mL) cooled in ice-water bath was added MOMCl (1.0 g, 12.3 mmol) dropwise. The reaction was stirred at room temperature overnight. The reaction was quenched by water and extracted with DCM for three times. The combined organic layer was washed with brine, dried over Na$_2$SO$_4$ and concentrated. The residue was purified by column chromatography give the desired product (1.1 g, yield 53.4%).

A suspension of (5-(benzyloxy)-3-bromopyridin-2-yl)methanol (1.10 g, 3.3 mmol) in dioxane (100 ml) was bubbled with N$_2$ for 20 min. Then bis(pinacolato)dibarane (4.2 g, 16.5 mmol), PdCl$_2$(dppf)CH$_2$Cl$_2$ (0.2 g, 0.3 mmol), KOAc (0.7 g, 6.6 mmol) was added under N$_2$ protection. And the resulting solution was warmed at 70° C. overnight. The reaction mixture was then cooled and filtered through a celite pad. The filtrate was concentrated to provide the crude product (5-(benzyloxy)-2-((methoxymethoxy)methyl)pyridin-3-yl)boronic acid (6 g).

To a solution of (5-(benzyloxy)-2-((methoxymethoxy) methyl)pyridin-3-yl)boronic acid (6.0 g, crude) in THF (50 mL) was added hydrochloride acid (35 mL, 4 mol/L) and the mixture was stirred at 40° C. overnight. After cooled to room temperature, the mixture was poured into 50 mL of cold water and extracted with EtOAc (100 mL) three times, the combined organic layers were concentrated and residue was purified by prep-HPLC (column: Luna C18 100×30 mm, 5 µm; liquid phase: [A-TFA/H$_2$O=0.075% v/v; B-ACN] B %: 20%-55%, 25 min]) to give 6-(benzyloxy)-[1,2]oxaborolo[4,3-b]pyridin-1(3H)-ol (410 mg, yield 19.6%) as off-white solid. $^1$H NMR (DMSO-d$_6$, 400 MHz) δ 8.41 (s, 1H), 7.67 (s, 1H), 7.48-7.36 (m, 5H), 5.21 (s, 2H), 4.89 (s, 2H).

A suspension of 6-(benzyloxy)-[1,2]oxaborolo[4,3-b]pyridin-1(3H)-ol (200 mg, 0.83 mmol) and Pd/C (200 mg) in EtOAc/i-PrOH (50 mL, 1:1) was stirred at 25° C. overnight under hydrogen atmosphere (50 Psi). The mixture was filtered and washed with MeOH. The filtrate was concentrated. The crude product was washed with MeCN and Petroleum ether to give [1,2]oxaborolo[4,3-b]pyridine-1,6 (3H)-diol (120 mg, yield 96%). $^1$H NMR (DMSO-d$_6$, 400 MHz) δ 8.41 (s, 1H), 7.44 (s, 1H), 4.81 (s, 1H)

To a solution of [1,2]oxaborolo[4,3-b]pyridine-1,6(3H)-diol (50 mg, 0.33 mmol), Iodo-pleuromutilin (161 mg, 0.33 mmol), and Cs$_2$CO$_3$ (324 mg, 0.99 mol/L) in THF/H$_2$O (3 mL, 2:1) was sealed and heated under microwave at 60° C. for 45 min under N$_2$ protection. The mixture was adjusted pH to 5-6 and the solvent was evaporated. The residue was purified by prep-TLC (n-BuOH: AcOH:water=7:1:2) to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1,3-dihydro-[1,2]oxaborolo[4,3-b]pyridin-6-yl)oxy)acetate (14 mg, yield 8.3%) as light yellow solid. $^1$H NMR (DMSO-d$_6$, 400 MHz) δ 7.71-7.68 (m, 1H), 7.43-7.34 (m, 1H), 6.31-6.23 (m, 1H), 5.80 (d, J=7.6 Hz, 1H), 5.19-5.07 (m, 4H), 3.48 (d, J=4.4 Hz, 1H), 2.37-1.13 (m, 21H), 0.92 (d, J=6.4 Hz, 3H), 0.74 (d, J=6.4 Hz, 3H). MS (ESI): mass calcd. for C$_{28}$H$_{38}$BNO$_7$ 511.3, m/z found 528.2 [M+H$_2$O-1]$^-$. HPLC: 92.5% (220 nm), 92.4% (254 nm).

102. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydro-[1,2]oxaborolo[4,3-b]pyridin-6-yl)glycinate

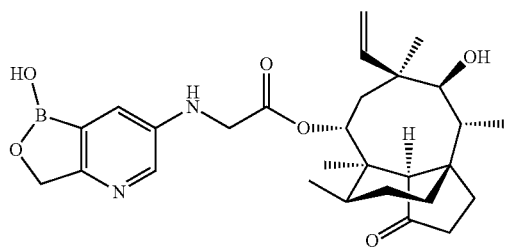

To a suspension of NaH (60% in mineral oil, 3.0 g, 75.6 mmol) in DMF (100 mL) at 0° C. was slowly added ethyl malonate (12 mL, 75.6 mmol) over 20 min. The mixture was allowed to stir for 20 min at room temperature, during which time the suspension became a solution. A solution of 3-bromo-2-chloro-5-nitropyridine (12.0 g, 50.4 mmol) in DMF (20 mL) was added slowly at 0° C. The resulting dark red mixture was allowed to stir at 40° C. for 2 h. The reaction mixture was then poured into 200 mL water and extracted with ethyl acetate (3×80 mL). The organic solutions were combined, washed with water and brine, dried over Na$_2$SO$_4$, filtered and concentrated. The residue was purified by silica gel column chromatography using petroleum ether:ethyl acetate: Et$_3$N=10:1:0.1 as eluent to give diethyl 2-(3-bromo-5-nitropyridin-2-yl)malonate (17.3 g, yield 95%) as a colorless oil. MS (ESI): mass calcd. for C$_{12}$H$_{13}$BrN$_2$O$_6$ 360.00, m/z found 361.0 [M+H]$^+$.

Diethyl 2-(3-bromo-5-nitropyridin-2-yl) malonate (17.3 g, 48.1 mmol) was refluxed in 150 mL 6M HCl for 5 h. The reaction mixture then cooled to room temperature and neutralized with NaOH in an ice bath to pH 10. The mixture was extracted with ethyl acetate (150 mL×2). The combined organic layers were washed with brine, dried over Na$_2$SO$_4$, filtered and concentrated under reduced pressure. The residue was purified by column chromatography on silica gel by elution with petroleum ether:ethyl acetate:Et$_3$N=10:1:0.1 to give 3-bromo-2-methyl-5-nitropyridine (8.37 g, yield 81%) as a white solid. MS (ESI): mass calcd. for C$_6$H$_5$BrN$_2$O$_2$ 215.95, m/z found 217.1 [M+H]$^+$.

To a solution of 3-bromo-2-methyl-5-nitropyridine (2.0 g, 9.26 mmol) and NBS (2.0 g, 11.24 mmol) in CCl$_4$ (35 mL) was added BPO (448 mg, 1.85 mmol). The reaction mixture was heated to reflux overnight. 100 mL water was added and extracted with DCM (30 mL×3). The combined organic layers were washed with brine, dried over Na$_2$SO$_4$, filtered and concentrated under reduced pressure to give 2.5 g of crude product 3-bromo-2-(bromomethyl)-5-nitropyridine. It was used in next step without further purification.

To a solution of crude 3-bromo-2-(bromomethyl)-5-nitropyridine (2.5 g, 8.4 mmol) in DMF (30 mL) was added NaOAc (1.48 g, 18.0 mmol). The reaction mixture was reacted at room temperature for 2 h, then ethyl acetate (150 mL) was added. The mixture was washed with water (50 mL×3). The solvent was removed and the residue was purified by silica gel column chromatography using petroleum ether: ethyl acetate=10:1 to give (3-bromo-5-nitropyridin-2-yl)methyl acetate (825 mg, yield 31% over two steps) as a white solid. MS (ESI): mass calcd. for C$_8$H$_7$BrN$_2$O$_4$ 273.96, m/z found 275.0 [M+H]$^+$.

To a solution of (3-bromo-5-nitropyridin-2-yl) methyl acetate (620 mg, 2.26 mmol), Pin$_2$B$_2$(1.15 g, 4.52 mmol) and KOAc (665 mg, 6.78 mmol) in 1,4-dioxane (5 mL) was added PdCl$_2$(dppf)$_2$ (83 mg, 0.11 mmol). The reaction mixture was stirred at 80° C. under argon atmosphere overnight. The solvent was removed and the residue was used in next step without further purification.

A mixture of (5-nitro-3-(4,4,5,5-tetramethyl-1,3,2-dioxaborolan-2-yl)pyridin-2-yl)methyl acetate (about 290 mg, 0.9 mmol), NaOH (700 mg, 17.5 mmol) in H$_2$O (1.5 mL) and THF (12 mL) was stirred at r.t for 4 h. Then the mixture was added HCl (6N) to pH=3 and continued to stir overnight. Water (10 mL) was added and the mixture was extracted with ethyl acetate (10 mL×2). The combined organic layers were dried over Na$_2$SO$_4$, filtered and concentrated under the reduced pressure. The residue was purified by prep-HPLC to give 6-nitro-[1,2]oxaborolo[4,3-b]pyridin-1(3H)-ol (110 mg, yield 27% over two steps) as a white solid. $^1$H NMR (400 MHz, DMSO-d$_6$) δ 9.83 (s, 1H), 9.44 (d, 1H), 8.82 (d, 1H), 5.12 (s, 2H). MS (ESI): mass calcd. for C$_6$H$_5$BN$_2$O$_4$ 180.03, m/z found 181.3 [M+H]$^+$.

A mixture of 6-nitro-[1,2]oxaborolo[4,3-b]pyridin-1(3H)-ol (50 mg, 0.27 mmol) and Pd/C (6 mg) in MeOH (6 mL) was stirred overnight at r.t under H$_2$ atmosphere. All insolubles were removed via filtration on Celite. The solvent was removed and the residue was used in next step without further purification. MS (ESI): mass calcd. for $C_6H_7BN_2O_2$ 150.06, m/z found 151.3 [M+H]$^+$.

A solution of crude 6-amino-[1,2]oxaborolo[4,3-b]pyridin-1 (3H)-ol (40 mg, 0.26 mmol) and I-Pleu (145 mg, 0.32 mmol) in DMF (2 mL) was stirred at 80° C. under argon atmosphere overnight. The mixture was purified by prep-HPLC under acid condition to (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (1-hydroxy-1,3-dihydro-[1,2]oxaborolo[4,3-b]pyridin-6-yl)glycinate TFA salt, 22 mg, yield 13% over two steps) as a white solid. $^1$H NMR (400 MHz, DMSO-$d_6$) δ 9.98 (s, 1H), 8.01 (d, 1H), 7.92 (d, 1H), 6.72 (s, 2H), 6.10 (q, 1H), 5.59-5.45 (m, 2H), 5.17-4.97 (m, 4H), 4.63 (d, 1H), 3.44-3.38 (m, 2H), 2.45 (s, 1H), 2.19-1.99 (m, 4H), 1.67-1.26 (m, 10H), 1.10-0.91 (m, 4H), 0.81 (d, 3H), 0.61 (d, 3H). HPLC purity: 100% (220 nm), 100% (254 nm); MS (ESI): mass calcd. for $C_{28}H_{39}BN_2O_6$ 510.29, m/z found 511.2 [M+H]$^+$.

103. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(4-(2-hydroxy-2,5-dihydro-1,2-oxaborol-3-yl)phenoxy)acetate

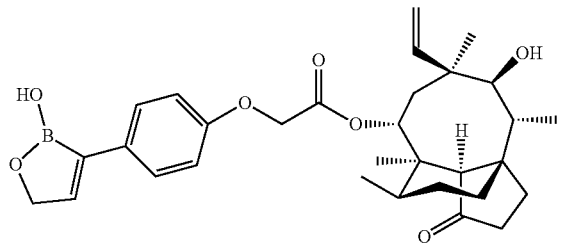

To a solution of 4-iodophenol (20.0 g, 90.9 mmol, 1.00 eq) and DIEA (41.1 g, 318.2 mmol, 3.5 eq) in DCM (200 mL) was added MOMCl (14.6 g, 181.80 mmol, 2.0 eq) drop-wise at 0° C. under $N_2$. The reaction mixture was warmed to 25° C. stirred for 1 hour. TLC (Petroleum ether/Ethyl acetate=3:1) showed the starting material was consumed completely. The reaction was quenched by ice slowly and then extracted with DCM (100 mL×2). The combined organic phase was washed with saturated brine (100 mL), dried over anhydrous $Na_2SO_4$ and concentrated in vacuo to give 1-iodo-4-(methoxymethoxy) benzene (18.0 g, 68.2 mmol, 75.0% yield) as light yellow oil. $^1$H NMR (DMSO-$d_6$, 400 MHz) δ 7.55-7.60 (m, 2H), 6.80-6.85 (m, 2H), 5.15 (s, 2H), 3.47 (s, 3H).

1-iodo-4-(methoxymethoxy)benzene (17.0 g, 64.3 mmol, 1.0 eq), prop-2-yn-1-ol (7.2 g, 128.8 mmol, 2.0 eq), TEA (16.3 g, 161.0 mmol, 2.5 eq), CuI (2.5 g, 12.9 mmol, 0.2 eq) and Pd(PPh$_3$)$_2$Cl$_2$ (2.3 g, 3.2 mmol, 0.05 eq) in THF (200 mL) was degassed and then heated to 50° C. for 1 hour under $N_2$. TLC (Petroleum ether/Ethyl acetate=3:1) showed the starting material was consumed completely. The reaction mixture was concentrated in vacuum to give a residue, which was pre-purified by column chromatography (Petroleum ether:EtOAc=5:1) to afford the pure 3-[4-(methoxymethoxy)phenyl]prop-2-yn-1-ol (10.0 g, 52.0 mmol, 80.8% yield) as yellow oil. $^1$H NMR (400 MHz, CDCl$_3$) δ 7.35-7.41 (m, 2H), 6.96-6.01 (m, 2H), 5.19 (s, 2H), 4.49 (s, 2H), 3.48 (s, 3H).

To a solution of LiAlH$_4$ (1.2 g, 31.2 mmol, 1.2 eq) and NaOMe (3.1 g, 57.2 mmol, 2.2 eq) in THF (100 mL) was added a solution of 3-[4-(methoxymethoxy)phenyl]prop-2-yn-1-ol (5.0 g, 26.0 mmol, 1.0 eq) in THF (25 mL) drop-wise at 0° C. The reaction mixture was stirred at 0° C. for 3 hours. Then I$_2$ (13.2 g, 52.0 mmol, 2.0 eq) in THF (25 mL) was added dropwise and the mixture was stirred at 25° C. for 12 hours. TLC (Petroleum ether/Ethyl acetate=3:1) showed the starting material was consumed completely. The reaction was quenched by ice slowly and then extracted with EtOAc (50 mL×2). The combined organic phase was washed with saturated brine (50 mL) and saturated sodium thiosulfate solution (50 mL), dried over anhydrous $Na_2SO_4$, filtered and concentrated in vacuo. The residue was purified by silica gel chromatography (Petroleum ether/Ethyl acetate=5/1) to give (Z)-3-iodo-3-[4-(methoxymethoxy)phenyl]prop-2-en-1-ol (5.0 g, 15.6 mmol, 60.1% yield) as light yellow oil. $^1$H NMR (DMSO-$d_6$, 400 MHz) δ 7.39-7.46 (m, 2H), 6.95-7.02 (m, 2H), 6.17 (t, J=5.6 Hz, 1H), 5.19 (s, 2H), 4.38 (d, J=5.6 Hz, 2H), 3.49 (s, 3H).

(Z)-3-iodo-3-[4-(methoxymethoxy)phenyl]prop-2-en-1-ol (2.0 g, 6.3 mmol, 1.0 eq), BPD (3.2 g, 12.5 mmol, 2.0 eq), KOAc (1.8 g, 18.7 mmol, 3.0 eq) and Pd(dppf)Cl$_2$.CH$_2$Cl$_2$ (255.1 mg, 312.4 umol, 0.05 eq) in dioxane (40 mL) was degassed and then heated to 100° C. for 12 hours under $N_2$. TLC (Petroleum ether/Ethyl acetate=3:1) showed the starting material was consumed completely. The reaction mixture was filtered, the filtrate was concentrated in vacuum to give a residue, which was purified by chromatography to afford 2-hydroxy-3-[4-(methoxymethoxy)phenyl]-5H-oxaborole (310.0 mg, 1.4 mmol, 22.5% yield) as light yellow solid. $^1$H NMR (DMSO-$d_6$, 400 MHz) δ 7.56-7.62 (m, 2H), 7.40 (s, 1H) 6.93-6.99 (m, 2H), 5.17 (s, 2H), 4.64 (d, J=1.6 Hz, 2H), 3.45 (s, 3H).

A mixture of 2-hydroxy-3-[4-(methoxymethoxy)phenyl]-5H-oxaborole (400.0 mg, 1.8 mmol, 1.0 eq) and HCl (4 M, 10.0 mL) in THF (10 mL) was stirred at 20° C. for 2 hours. The reaction mixture extracted with EtOAc (10 mL×2), washed with brine (20 mL), dried over $Na_2SO_4$, filtered and concentrated under reduced pressure to give 4-(2-hydroxy-5H-oxaborol-3-yl)phenol (280.0 mg, 1.6 mmol, 87.4% yield) as white solid. $^1$H NMR (CD$_3$OD, 400 MHz) δ 7.50 (d, J=8.4 Hz, 2H), 7.32 (s, 1H), 6.71 (d, J=8.8 Hz, 2H), 4.62 (s, 2H).

To a mixture of 4-(2-hydroxy-5H-oxaborol-3-yl)phenol (280.0 mg, 1.6 mmol, 1.0 eq) and [(19R,20R,21R,22S,23R,26S,27R,28S)-22-hydroxy-19,20,26,27-tetramethyl-24-oxo-26-vinyl-21-tricyclotetradecanyl] 2-(p-tolylsulfonyloxy)acetate (847.6 mg, 1.6 mmol, 1.0 eq) in DMF (10 mL), was added Cs$_2$CO$_3$ (1.0 g, 3.2 mmol, 2.0 eq) in one portion under $N_2$. The mixture was stirred at 25° C. for 16 hours. HPLC shown main peak as desired. Water (15 mL) was added and the mixture has a solid precipitation. The solid was collected, then purified by prep-HPLC (column: Luna 300×50.0 mm, 10 m; liquid phase: [A-H$_2$O+0.075% TFA; B-ACN] B %: 40%-70%, 20 min]) to afford (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl2-(4-(2-hydroxy-2,5-dihydro-1,2-oxaborol-3-yl)phenoxy)acetate (260.0 mg, 484.7 umol, 30.5% yield) as white solid. $^1$H NMR (CD$_3$CN, 400 MHz) δ 7.57 (d, J=6.8 Hz, 2H), 7.40 (s, 1H), 6.85 (d, J=7.0 Hz, 2H), 6.27 (dd, J=17.6, 11.2 Hz, 2H), 5.73 (d, J=8.4 Hz, 1H), 5.15 (s, 1H), 5.11 (m, 1H), 4.60 (s, 2H), 4.57 (s, 2H), 3.45 (d, J=7.0 Hz, 1H), 2.32-1.45 (m, 12H), 1.38 (s, 3H), 1.08 (s, 3H), 0.86 (d, J=7.2 Hz, 3H), 0.70 (d, J=7.2 Hz, 3H). MS (ESI): mass calcd. for $C_{31}H_{41}BO_7$ 536.3, m/z found 535.3 [M−H]$^-$. HPLC: 100% (220 nm), 100% (254 nm).

104. (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-methyl-1,2-dihydrobenzo[e][1,2]azaborinin-7-yl)oxy)acetate

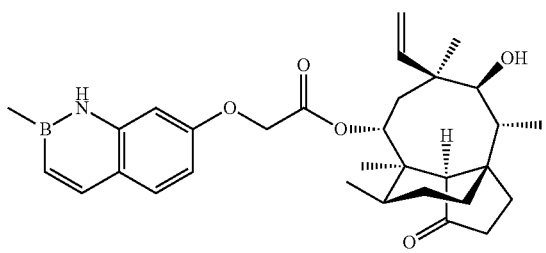

To a suspension of potassium vinyltrifluoroborate (1.24 g, 7.39 mmol, 1.1 equiv.), K$_3$PO$_4$ (4.27 g, 20.1 mmol, 3.0 equiv.), and Pd/C (10% w/w, 140 mg) in NMP (6.7 mL) was added 5-bromo-2-iodo-aniline (2.0 g, 6.7 mmol, 1.0 equiv.). The mixture was degassed with a stream of nitrogen gas for 5 min, sealed with a Teflon lined cap and stirred at 100° C. for 20 hours. HPLC indicated the reaction was completed. The reaction mixture was diluted with DCM (20 mL), filtered through a pad of Celite and the eluent concentrated under reduced pressure to give the crude product as a brown oil. The residue was purified by flash column chromatography (100% DCM) to give 5-bromo-2-vinyl-aniline (2) (1.10 g, 5.55 mmol, 83% yield) as a pale yellow oil. 1H NMR (CDCl3, 400 MHz) δ 7.12 (d, J=8.0 Hz, 1H), 6.88 (dd, J=1.6, 8.0 Hz, 1H), 6.85 (d, J=2.0, 1H), 6.67 (dd, J=11.2, 17.6 Hz, 1H), 5.63 (dd, J=1.2, 17.2 Hz, 1H), 5.35 (dd, J=1.2, 11.2 Hz, 1H), 4.10 (s, 2H).

To a microwave vial was added a stir bar, potassium trifluoromethylborate (128 mg, 1.05 mmol, 1.0 equiv.), and 5-bromo-2-vinyl-aniline (250 mg, 1.26 mmol, 1.2 equiv.). The vial was sealed with a Teflon lined crimp cap, and purged and back-filled with nitrogen gas three times. Toluene (1 mL) and CPME (1 mL) were added followed by SiCl4 (121 uL, 1.05 mmol, 1.0 equiv.) with stirring. After 3 minutes, TEA (215 uL, 1.58 mmol, 1.5 equiv.) was added and the reaction mixture was stirred at 45° C. for 20 hours. The reaction mixture was diluted with hexanes (5 mL) and purified by flash column chromatography (100% DCM) to give 7-bromo-2,1-borazaronaphthalene (3) (204 mg, 0.92 mmol, 87% yield) as a white solid. 1H NMR (CDCl3, 400 MHz) δ 7.85 (d, J=11.6 Hz, 1H), 7.55 (s, 1H), 7.42 (d, J=8.4 Hz, 1H), 7.35 (d, J=1.6, 1H), 7.22 (dd, J=2.0, 8.4 Hz, 1H), 6.80 (dd, J=2.0, 11.6 Hz, 1H).

To a screw-cap vial was added 7-bromo-2,1-borazaronaphthalene (10 mg, 0.045 mmol, 1.0 equiv.), (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-hydroxyacetate (51 mg, 0.13 mmol, 3.0 equiv.), NaOtBu (6 mg, 0.063 mmol, 1.4 equiv.), tBuBrettPhos (1.1 mg, 0.002 mmol, 0.05 equiv.) and tBuBrettPhos palladium G3 precatalyst (1.9 mg, 0.002 mmol, 0.05 equiv.). The vial was sealed and purged and back-filled with nitrogen gas three times. Subsequently, 1,4-dioxane (0.10 mL) was added and the mixture was stirred at 80° C. for 16 hours. The reaction mixture was quenched by addition of MeOH (0.5 mL), and purified by prep-HPLC (column: Phenomenex luna C18 250×50 mm×10 μm; liquid phase: [A-TFA/H2O=0.1% v/v; B-ACN] B %: 50%-95%, 25 min]). The combined fractions were concentrated under reduced pressure to give the product (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((2-methyl-1,2-dihydrobenzo[e][1,2]azaborinin-7-yl)oxy)acetate (1.6 mg, 0.003 mmol, 7% yield) as a light yellow solid. 1H NMR (CDCl3, 400 MHz) δ 7.84 (d, J=11.2 Hz, 1H), 7.51 (br s, 1H), 7.47 (d, J=8.8 Hz, 1H), 6.74 (dd, J=2.4, 8.8 Hz, 1H), 6.65 (dd, J=1.2, 11.2 Hz, 1H), 6.61 (d, J=2.4 Hz, 1H), 6.53 (dd, J=11.2, 17.6 Hz, 1H), 5.88 (d, J=8.0 Hz, 1H), 5.38 (dd, J=1.2, 11.2 Hz, 1H), 5.23 (dd, J=1.6, 17.6 Hz, 1H), 4.59 (s, 2H), 3.38 (d, J=6.8 Hz, 1H), 2.40-2.30 (m, 1H), 2.30-2.00 (m, 5H), 1.80-1.72 (m, 1H), 1.70-1.35 (m, 10H), 1.27-1.13 (m, 4H), 1.11 (s, 3H), 0.89 (d, J=6.8 Hz, 3H), 0.71 (s, 3H). MS (ESI): mass calcd. for C31H42BNO5 [M+AcO]− 578.33, found 578.4. HPLC: 99.0% (220 nm), 100.0% (254 nm).

Example 2

Antibacterial MIC Assays

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria that Grow Aerobically; Approved Standard—Tenth Edition, M07-A10; Performance Standards for Antimicrobial Susceptibility Testing; Twenty-fifth Informational Supplement, M100-S25).

Briefly, the microbroth dilution MIC method was used to quantitatively measure the in vitro antibacterial activity of a compound against a given bacterial isolate. The following bacterial strains were evaluated: *Staphylococcus aureus*, MRSA (ATCC 33591) and *Streptococcus pneumoniae* (ATCC 49619). Bacteria were grown in cation-adjusted Mueller-Hinton broth, with additions as required per species growth requirements (e.g. 3% lysed horse blood for fastidious organisms such as *S. pneumoniae*). A direct colony suspension in saline was prepared from colonies on an overnight agar plate to achieve a turbidity equivalent to 0.5 McFarland standard, which was subsequently diluted into the assay plate to achieve 5×10$^5$ CFU/mL. Assays plates were prepared by 2-fold dilution of compound across the plate and included a positive growth control. After incubation at 35° C. for 16-20 hours, the MIC was determined as the lowest concentration of compound that inhibits growth of the bacteria as detected by the unaided eye.

Anti-*Wolbachia* High-Content Assay

C6/36 cells (ECACC #89051705, derived from *Aedes albopictus* larvae) were infected with *Wolbachia pipientis* derived from the supernatant of cultured *A. albopictus* Aa23 cells to create a stably *Wolbachia*-infected cell line C6/36 (wAlbB). This cell line was subpassaged 6-8 days prior to plating out at a density of 2000 viable cells per well in a 384-well CellCarrier plate suspended in Liebovitz media supplemented with 20% fetal bovine serum, 2% tryptose phosphate broth and 1% non-essential amino acids. Compounds were dissolved and diluted in DMSO, and compound solution was added to each well to provide a final DMSO concentration <1% and a total volume of 100 μL per well.

Following 7 days of sterile incubation at 26° C., staining media containing SYTO 11 DNA dye was added to each well. After 15 minutes, all media was removed from each well and fresh media (no stain) was added. Imaging of each well was accomplished using a Perkin Elmer Operetta high-content imaging system. Five fields per well were imaged using a confocal 60× objective with the Fluorescein filter (excitation filter: 460-490 nm; emission filter: 500-550 nm). Images were analyzed using the Perkin Elmer Harmony software to score each intact cell on the basis of texture complexity of the cytoplasm. Full details can be found in: Clare, R. H. et al, J. Biomol. Screening, 2015, 20, 64-49.

Compound sample wells were analyzed and normalized (along with the positive controls) against the vehicle (untreated) control to give a percentage reduction of *Wolbachia*-infected cells. Using the cell number analysis, compounds with a host cell number amounting to less than 50% of the vehicle control were classified as toxic and retested at a reduced compound concentration. Dose-response curves were generated with percentage reduction of *Wolbachia*-infected cells versus compound concentration, using 5-10 compound serial dilutions. Data were analyzed and compound $EC_{50}$s determined using a 4 parameter logistic non-linear regression model. $EC_{50}$ is defined as the compound concentration producing a 50% reduction of *Wolbachia* in the C6/36 cell line.

Antibacterial testing results for exemplary compounds of the invention are provided below. Units for MIC are g/mL. Units for EC50 are μM. MIC of ≤0.25 is A, 0.5-2 is B, 4-32 is C, and ≥64 is D.

| Compound # | MIC *Staphylococcus aureus*, MRSA (ATCC 33591) | MIC *Streptococcus pneumoniae* (ATCC 49619) | EC50 *Wolbachia pipientis* in C6/36 cell line |
|---|---|---|---|
| 1. | A | A | 0.006 |
| 2. | A | B | 0.015 |
| 3. | A | A | 0.008 |
| 4. | A | B | 0.158 |
| 5. | A | A | |
| 6. | A | B | 0.032 |
| 7. | B | C | 0.428 |
| 8. | A | B | 0.05 |
| 9. | A | B | 0.052 |
| 10. | A | A | 0.011 |
| 11. | A | A | 0.1 |
| 12. | A | A | 0.064 |
| 13. | A | B | 0.081 |
| 14. | A | B | |
| 15. | A | A | |
| 16. | A | | |
| 17. | B | A | 0.623 |
| 18. | B | | >1 |
| 19. | A | B | 0.215 |
| 20. | A | B | >1 |
| 21. | B | A | 0.104 |
| 22. | B | B | >1 |
| 23. | B | B | 0.613 |
| 24. | A | B | >1 |
| 25. | B | B | >1 |
| 26. | A | B | >1 |
| 27. | A | A | 0.027 |
| 28. | B | B | >1 |
| 29. | B | B | >1 |
| 30. | B | C | >1 |
| 31. | B | B | 0.197 |
| 32. | A | B | >1 |
| 33. | A | B | 0.149 |
| 34. | A | B | 0.298 |
| 35. | A | B | 0.03 |
| 36. | A | B | 0.193 |
| 37. | A | B | 0.052 |
| 38. | A | B | 0.009 |
| 39. | A | B | 0.084 |
| 40. | A | B | 0.018 |
| 41. | B | B | 0.625 |
| 42. | C | | |
| 43. | B | B | 0.101 |
| 44. | A | B | >1 |
| 45. | A | B | 0.005 |
| 46. | A | B | 0.023 |
| 47. | B | C | 0.303 |
| 49. | B | | >1 |
| 49. | B | B | 0.257 |
| 50. | B | A | 0.409 |
| 51. | A | B | >1 |
| 52. | B | B | 0.228 |
| 53. | C | B | >1 |
| 54. | A | B | 0.106 |
| 55. | B | B | |
| 56. | A | B | 0.012 |
| 57. | A | B | 0.113 |
| 58. | A | B | 0.056 |
| 59. | B | C | >1 |
| 60. | B | C | >1 |
| 61. | A | A | 0.123 |
| 62. | A | B | |
| 63. | B | C | |
| 64. | A | B | |
| 65. | A | B | |
| 66. | B | C | |
| 67. | A | B | |
| 68. | A | B | |
| 69. | A | A | >1 |
| 70. | B | A | 0.012 |
| 71. | A | A | 0.001 |
| 72. | A | A | 0.003 |
| 73. | A | A | 0.001 |
| 74. | A | A | 0.004 |
| 75. | A | B | 0.009 |
| 76. | B | B | >1 |
| 77. | C | B | >1 |
| 78. | B | B | 0.013 |
| 79. | B | B | 0.056 |
| 80. | A | B | 0.239 |
| 81. | A | A | 0.034 |
| 82. | B | A | 0.036 |
| 83. | A | A | 0.015 |
| 84. | B | B | 0.078 |
| 85. | A | A | 0.172 |
| 86. | A | B | 0.001 |
| 87. | A | A | 0.004 |
| 88. | A | B | 0.004 |
| 89. | A | A | 0.107 |
| 90. | A | B | 0.003 |
| 91. | A | B | 0.001 |
| 92. | A | B | 0.003 |
| 93. | A | B | 0.164 |
| 94. | A | B | 0.026 |
| 95. | A | A | 0.046 |
| 96. | A | B | 0.014 |
| 97. | A | B | 0.329 |
| 98. | B | B | 0.063 |
| 99. | B | B | 0.013 |
| 100. | D | | >1 |
| 101. | B | C | >1 |
| 102. | D | D | >1 |
| 103. | A | A | 0.419 |
| 104. | A | B | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt or a hydrate or a solvate thereof, having a structure which is:

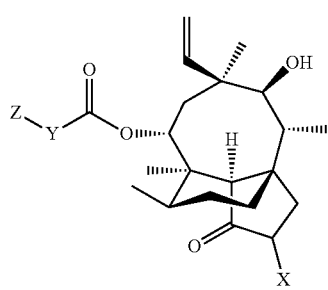

wherein
- X is H or F or OH;
- Y is selected from the group consisting of a bond, —O—, —S—, —NH—, alkylene, and heteroalkylene; and
- Z is a heterocyclic ring or ring system containing at least one endocyclic boron.

2. The compound of claim 1, or a salt or a hydrate or a solvate thereof, wherein said Y is *—OCH$_2$— or *—SCH$_2$— or *—NHCH$_2$— or *—CH$_2$NH— or *—C(O)NH—, wherein * represents the point of attachment to said Z.

3. The compound of claim 1, or a salt or a hydrate or a solvate thereof, wherein said Z is selected from the group consisting of benzoxaborole, pyridinyloxaborole, benzoxaborininol, benzoxazaborininol, benzodiazaborininol, oxaborole, and dihydrobenzoazaborinine.

4. The compound of claim 3, or a salt or a hydrate or a solvate thereof, wherein said Z is

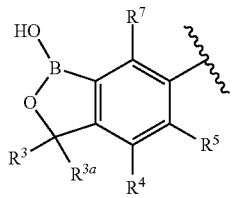

wherein
- $R^3$, $R^{3a}$, $R^4$, $R^5$, and $R^7$ are each independently selected from the group consisting of $R^{10}$, —OR$^{10}$, —NR$^{10}$R$^{11}$, —SR$^{10}$, —S(O)R$^{10}$, —S(O)$_2$R$^{10}$, —S(O)$_2$NR$^{10}$R$^{11}$, —C(O)R$^{10}$, —C(O)OR$^{10}$, and —C(O)NR$^{10}$R$^{11}$
wherein
- $R^{10}$ and $R^{11}$ are each independently selected from the group consisting of H, halogen, cyano, nitro, alkyl, heteroalkyl, cycloalkyl, heterocycloalkyl, aryl, and heteroaryl.

5. A selected from the group consisting of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((7-fluoro-1-hydroxy-1,3-dihydrobenzo[c][1,2]oxaborol-6-yl)oxy)acetate, (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl (7-fluoro-1-hydroxy-1,3-dihydrobenzo[c][1,2]oxaborol-6-yl)glycinate, (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl ((7-fluoro-1-hydroxy-1,3-dihydrobenzo[c][1,2] oxaborol-6-yl)methyl)carbamate, (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((1-hydroxy-1H-benzo [d][1,2,6] oxazaborinin-7-yl)oxy)acetate, and methyl 1-hydroxy-7-(2-(((3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl)oxy)-2-oxoethoxy)benzo[d][1,2,3]diazaborinine-2(1H)-carboxylate, or a salt or a hydrate or a solvate thereof.

6. The compound of claim 3, or a salt or a hydrate or a solvate thereof, wherein said Z is

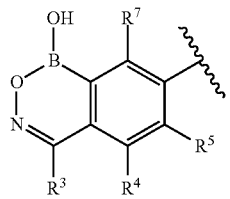

wherein
- $R^3$, $R^4$, $R^5$, and $R^7$ are each independently selected from the group consisting of $R^{10}$, —OR$^{10}$, —NR$^{10}$R$^{11}$, —SR$^{10}$, —S(O)R$^{10}$, —S(O)$_2$R$^{10}$, —S(O)$_2$NR$^{10}$R$^{11}$, —C(O)R$^{10}$, —C(O)OR$^{10}$, and —C(O)NR$^{10}$R$^{11}$
wherein
- $R^{10}$ and $R^{11}$ are each independently selected from the group consisting of H, halogen, cyano, nitro, alkyl, heteroalkyl, cycloalkyl, heterocycloalkyl, aryl, and heteroaryl.

7. The compound of claim 3, or a salt or a hydrate or a solvate thereof, wherein said Z is

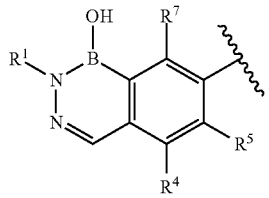

wherein
- $R^1$, $R^4$, $R^5$, and $R^7$ are each independently selected from the group consisting of $R^{10}$, —OR$^{10}$, —NR$^{10}$R$^{11}$, —SR$^{10}$, —S(O)R$^{10}$, —S(O)$_2$R$^{10}$, —S(O)$_2$NR$^{10}$R$^{11}$, —C(O)R$^{10}$, —C(O)OR$^{10}$, and —C(O)NR$^{10}$R$^{11}$
wherein
- $R^{10}$ and $R^{11}$ are each independently selected from the group consisting of H, halogen, cyano, nitro, alkyl, heteroalkyl, cycloalkyl, heterocycloalkyl, aryl, and heteroaryl.

8. A combination comprising the compound of claim 1, or a pharmaceutically acceptable salt or a hydrate or a solvate thereof, together with at least one other therapeutically active agent.

9. A pharmaceutical formulation comprising:
   a) the compound of claim 1, or a pharmaceutically acceptable salt or a hydrate or a solvate thereof; and
   b) a pharmaceutically acceptable excipient.

10. A method of inhibiting protein synthesis in a bacteria, the method comprising contacting the bacteria with the compound of claim 1, or a pharmaceutically acceptable salt or a hydrate or a solvate thereof, thereby inhibiting protein synthesis in the bacteria.

11. A method of inhibiting the growth of and/or killing a bacteria, the method comprising contacting the bacteria with the compound of claim 1, or a pharmaceutically acceptable salt or a hydrate or a solvate thereof, thereby inhibiting the growth of and/or killing the bacteria.

12. A method of treating a disease associated with a Gram-positive, Gram positive bacteria, and/or a worm in an animal, the method comprising administering to the animal a therapeutically effective amount of the compound of claim 1, or a pharmaceutically acceptable salt or a hydrate or a solvate thereof, thereby treating the disease.

13. The method of claim 12, wherein the disease is selected from the group consisting of pneumonia, hospital-acquired pneumonia, hospital-associated pneumonia, community-acquired pneumonia, acute bacterial skin and skin-structure infection (ABSSSI), bacteremia, endocarditis, osteomyelitis, gastroenteritis, toxic shock syndrome, meningitis, septic arthritis, urinary tract infection, skin and skin-structure infection, strep throat, necrotizing fasciitis, otitis media, sinusitis, actinomycosis, diptheria, anthrax, food poisoning, botulism, tetanus, gas gangrene, diarrhea, tuberculosis, leprosy, candidiasis, aspergillosis, coccidioidomycosis, cryptococcosis, histoplasmosis, blastomycosis, paracoccidioidomycosis, zygomycosis, phaeohyphomycosis, rhinosporidiosis, enterobiasis, filariasis, lymphatic filariasis, bancroftian filariasis, subcutaneous filariasis, serious cavity filariasis, elephantiasis, elephantiasis tropica, lymphadenitis, lymphangitis, lymphedema, and onchocerciasis.

* * * * *